US011274319B2

(12) United States Patent
Argyros et al.

(10) Patent No.: US 11,274,319 B2
(45) Date of Patent: Mar. 15, 2022

(54) METHODS FOR REGULATING NITROGEN METABOLISM DURING THE PRODUCTION OF ETHANOL FROM CORN BY METABOLICALLY ENGINEERED YEAST STRAINS

(71) Applicant: Lallemand Hungary Liquidity Management LLC, Budapest (HU)

(72) Inventors: Aaron Argyros, White River Junction, VT (US); Trisha Barrett, Bradford, VT (US)

(73) Assignee: Lallemand Hungary Liquidity Management LLC, Budapest (HU)

( * ) Notice: Subject to any disclaimer, the term of this patent is extended or adjusted under 35 U.S.C. 154(b) by 0 days.

(21) Appl. No.: 16/570,881

(22) Filed: Sep. 13, 2019

(65) Prior Publication Data

US 2020/0157578 A1 May 21, 2020

Related U.S. Application Data

(63) Continuation of application No. 14/771,831, filed as application No. PCT/US2014/025460 on Mar. 13, 2014, now Pat. No. 10,604,772.

(60) Provisional application No. 61/800,323, filed on Mar. 15, 2013.

(51) Int. Cl.

| | |
|---|---|
| ***C12P 7/06*** | (2006.01) |
| ***C12N 9/06*** | (2006.01) |
| ***C12N 9/00*** | (2006.01) |
| ***C12N 15/52*** | (2006.01) |
| ***C12N 9/60*** | (2006.01) |
| ***C12N 9/50*** | (2006.01) |
| ***C12N 9/02*** | (2006.01) |
| ***C12N 9/04*** | (2006.01) |
| ***C12N 9/10*** | (2006.01) |
| ***C12N 9/34*** | (2006.01) |
| ***C12P 7/10*** | (2006.01) |

(52) U.S. Cl.

CPC .............. *C12P 7/06* (2013.01); *C12N 9/0004* (2013.01); *C12N 9/0006* (2013.01); *C12N 9/0008* (2013.01); *C12N 9/0016* (2013.01); *C12N 9/1029* (2013.01); *C12N 9/2428* (2013.01); *C12N 9/50* (2013.01); *C12N 9/60* (2013.01); *C12N 9/93* (2013.01); *C12N 15/52* (2013.01); *C12Y 104/01002* (2013.01); *C12Y 104/01004* (2013.01); *C12Y 104/01014* (2013.01); *C12Y 603/01002* (2013.01); *C12Y 603/04006* (2013.01); *C12P 7/10* (2013.01); *C12Y 101/01001* (2013.01); *C12Y 101/01002* (2013.01); *C12Y 102/0101* (2013.01); *C12Y 197/01004* (2013.01); *C12Y 203/01054* (2013.01); *C12Y 302/01003* (2013.01); *C12Y 304/23041* (2013.01); *Y02E 50/10* (2013.01)

(58) Field of Classification Search

None

See application file for complete search history.

(56) References Cited

U.S. PATENT DOCUMENTS

| | | | |
|---|---|---|---|
| 7,018,829 | B1 | 3/2006 | Nielsen et al. |
| 7,935,514 | B2 | 5/2011 | Piatkowski et al. |
| 8,956,851 | B2 | 2/2015 | Argyros et al. |
| 2011/0129566 | A1 | 6/2011 | Van Vuuren et al. |
| 2011/0171709 | A1 | 7/2011 | Bardsley |

FOREIGN PATENT DOCUMENTS

| | | | |
|---|---|---|---|
| EP | 2 277 989 | A1 | 1/2011 |
| WO | 2005/093041 | A1 | 10/2005 |
| WO | 2011/140386 | A2 | 11/2011 |
| WO | 2012/138942 | A1 | 10/2012 |
| WO | 2014/081803 | A1 | 5/2014 |

OTHER PUBLICATIONS

Chinese Office Action for Application No. CN 201480028538.1, dated Jul. 25, 2017 (23 pages).

Bro, C., et al., "In silico aided metabolic engineering of *Saccharomyces cerevisiae* for improved bioethanol production," Metabolic Engineering 8:102-111, Elsevier Inc., United States (2006).

Coulon, J., et al., Metabolic Engineering of *Saccharomyces cerevisiae* to; Minimize the Production of Ethyl Carbamate in Wine. Am J Enol Vitic. 2006;57(2):113-124.

Dahabieh, M.S., et al., Functional Expression of the DUR3 Gene in a Wine Yeast Strain to Minimize Ethyl Carbamate in Chardonnay Wine. Am J Enol Vitic. 2009;60(4):537-541.

Guo, Z.P., et al., Expression of aspartic protease from Neurospora crassa in industrial ethanol-producing yeast and its application in ethanol production. Enzyme Microb Technol. Feb. 8, 2011;48(2):148-54. doi: 10.1016/j.enzmictec.2010.10.008. Epub Oct. 30, 2010.

(Continued)

*Primary Examiner* — Anand U Desai

(74) *Attorney, Agent, or Firm* — Nutter McClennen & Fish LLP

(57) ABSTRACT

The present invention provides for a mechanism to reduce glycerol production and increase nitrogen utilization and ethanol production of recombinant microorganisms. One aspect of this invention relates to strains of *S. cerevisiae* with reduced glycerol productivity that get a kinetic benefit from higher nitrogen concentration without sacrificing ethanol yield. A second aspect of the invention relates to metabolic modifications resulting in altered transport and/or intracellular metabolism of nitrogen sources present in corn mash.

21 Claims, 74 Drawing Sheets

Specification includes a Sequence Listing.

(56) References Cited

OTHER PUBLICATIONS

Guo, Z.P., et al., "Improving ethanol productivity by modification of glycolytic redox factor generation in glycerol-3-phosphate dehydrogenase mutants of an industrial ethanol yeast," J. Ind. Microbiol. Biotechnol. 38:935-43, Springer, Germany (2011).
Guo, Z.P., et al., Minimization of glycerol synthesis in industrial ethanol yeast without influencing its fermentation performance. Metabolic Engineering, Jan. 2011;13(1):49-59, Elsevier, Inc., United States.
Hahn-Hägerdal, B., et al., "Metabolic Engineering of *Saccharomyces cerevisiae* for Xylose Utilization," Adv. in Biochem. Eng. Biotechnol. 73:53-84, Springer-Veriag, Germany (2001).
Higgins, D.G., et al., Fast and sensitive multiple sequence alignments on a microcomputer, CABIOS, 5:151-153, Oxford University Press, UK (1989).
International Search Report and Written Opinion for Application No. PCT/US2014/025460, dated Sep. 24, 2014 (13 pages).
Kong, Q.X., et al., Overexpressing GLT1 in gpd1Delta mutant to improve the production of ethanol of *Saccharomyces cerevisiae*. Appl Microbiol Biotechnol. Jan. 2007;73(6):1382-6. Epub Oct. 5, 2006.
Ljungdahl, P.O., et al., Regulation of amino acid, nucleotide, and phosphate metabolism in *Saccharomyces cerevisiae*. Genetics. Mar. 2012;190(3):885-929. doi: 10.1534/genetics.111.133306.
Medina, V.G., et al.,Elimination of Glycerol Production in Anaerobic Cultures of a *Saccharomyces cerevisiae* Strain Engineered to Use Acetic Acid as an Electron Acceptor. Applied and Environmental Microbiology, Jan. 2010;76(1):190-195, American Societyfor Microbiology., United States.
Nissen, T.L., et al. "Optimization of Ethanol Production in *Saccharomyces cerevisiae* by Metabolic Engineering of the Ammonium Assimilation," Metab Eng. Jan. 2000; 2(1):69-77.
Roca, C., et al., Metabolic engineering of ammonium assimilation in xylose-fermenting *Saccharomyces cerevisiae* improves ethanol production. Appl Environ Microbiol. Aug. 2003;69(8):4732-6.
Salmon, J.M., et al., Improvement of nitrogen assimilation and fermentation kinetics under enological conditions by derepression of alternative nitrogen-assimilatory pathways in an industrial *Saccharomyces cerevisiae* strain. Appl Environ Microbiol. Oct. 1998;64(10):3831-7.
Sharp, P.M., et al., "The Codon Adaptation Index: A Measure of Directional Synonymous Codon Usage Bias, and Its Potential Applications" Nucleic Acids Res. 1987;15(3):1281-1295, IRL Press Limited, Oxford, England.
Van Maris, et al., Alcoholic fermentation of carbon souices in biomass hydrolysates by *Saccharomyces cerevisiae*: current status. Antonie Van Leeuwenhoek. Nov. 2006;90(4):391-418. Epub Oct. 11, 2006.
Welch, M., et al., "Designing Genes for Successful Protein Expression," Methods Enzymol. 2011;498:43-66. doi:10.1016/B978-0-12-385120-8. 00003-6.
Zhang, J., "Influence of Different Level of Assimilable Nitrogen on Alcoholic Fermentation by Yeasts," China Master's Thesis; China Excellent Master's Theses Full-Text Datatbase, Dec. 15, 2011 (7 pgs; abstract).

MA0631

Marked Deletion of GDH1 (just kan showed here – nat construct the same)

| MA0631 | | | |
|---|---|---|---|
| Fragment | Primers | Template | Expected Size |
| GDH1 5' Flank | X14961/X21291 | gDNA | 2065bp |
| AGTEF pro-kan/nat/tdk-HXT2 pro | X21289/X21290 | pMU2873/pMU2879 | 3820bp and 3583bp |
| GDH1 3' Flank | X21292/X14966 | gDNA | 2056bp |

MA0425

4 copy *S. cerevisiae* GDH2 integrated at GDH1 locus

MA0425

| Fragment | Primers | Template | Expected Size |
|---|---|---|---|
| GDH1 5' Flank | X14961/X19722 | gDNA | 2065bp |
| PGKpro-GDH2-ENO1ter | X19721/X15464 | pMU2908 | 5283bp |
| ADH1pro-GDH2-PDC1ter | X15465/X19727 | pMU2909 | 4546bp |
| GDH1 3' Flank | X19726/X14966 | gDNA | 2056bp |

MA0426

2 copy *S. cerevisiae* GLT1/GLN1 integrated at GDH1 locus

MA0426

| Fragment | Primers | Template | Expected Size |
|---|---|---|---|
| GDH1 5' Flank | X14961/X19722 | M2390 gDNA | 2065bp |
| PGKpro-GLT1-ENOter | X19721/X15464 | pMU2913 | 8442bp |
| ADH1pro-GLN1-PDC1ter | X15465/X19727 | pMU2911 | 2363bp |
| GDH1 3' Flank | X19726/X14966 | M2390 gDNA | 2056bp |

MA0426
18860 bp

MA0888

Clean deletion of GDH1

MA0888

| Fragment | Primers | Template | Expected Size |
|---|---|---|---|
| 5' Flank | X14961/X19949 | M2390 gDNA | 2065bp |
| 3' Flank | X19948/X14966 | M2390 gDNA | 2056bp |

MA0837

2 copy *N. crassa* GDH2 integrated at GDH1 locus

MA0837

| Fragment | Primers | Template | Expected Size |
|---|---|---|---|
| GDH1 5' Flank | X14961/X23320 | gDNA | 2065bp |
| ADH1pro-GDH2-PDC1 ter | X23319/X23322 | pMU3597 | 4403bp |
| GDH1 3' Flank | X23321/X14966 | gDNA | 2056bp |

MA0837
12458 bp

MA0616

GDH2 marked deletion

MA0616

| Fragment | Primers | Template | Expected Size |
|---|---|---|---|
| GDH2 5' Flank | X21123/X21124 | M2390 gDNA | 2024bp |
| AGTEFpro-kan/nat/tdk-HXT2pro | X21127/X21128 | pMU2873/pMU2879 | 3820bp and 3583bp |
| GDH2 3' Flank | X21125/X21126 | M2390 gDNA | 1990bp |

MA0616.1

GDH2 clean deletion

MA0616.1

| Fragment | Primers | Template | Expected Size |
|---|---|---|---|
| GDH2 5' Flank | X21123/X21507 | M2390 gDNA | 2024bp |
| GDH2 3' Flank | X21133/X21126 | M2390 gDNA | 1990bp |

MA0615

GDH3 marked deletion

MA0615

| Fragment | Primers | Template | Expected Size |
|---|---|---|---|
| GDH3 5' Flank | X21135/X21136 | M2390 gDNA | 1976bp |
| AGTEFpro-kan/nat/tdk-HXT2pro | X21139/X21140 | pMU2873/pMU2879 | 3820bp and 3583bp |
| GDH3 3' Flank | X21137/X21138 | M2390 gDNA | 2015bp |

MA0615.1

GDH3 clean deletion

MA0615.1

| Fragment | Primers | Template | Expected Size |
|---|---|---|---|
| GDH3 5' Flank | X21135/X21148 | M2390 gDNA | 1976bp |
| GDH3 3' Flank | X21147/X21138 | M2390 gDNA | 2015bp |

MA0622

URE2 marked deletion

MA0622

| Fragment | Primers | Template | Expected Size |
|---|---|---|---|
| URE2 5' Flank | X20022/X20023 | M2390 gDNA | 1968bp |
| AGTEF pro-kan/nat/tdk-HXT2 pro | X20028/X20029 | pMU2873, pMU2879 | 3820bp and 3583bp |
| URE2 3' Flank | X20024/X20025 | M2390 gDNA | 1885bp |

MA0622.1

URE2 clean deletion

MA0622.1

| Fragment | Primers | Template | Expected Size |
|---|---|---|---|
| URE2 5' Flank | X20022/X20027 | M2390 gDNA | 1968bp |
| URE2 3' Flank | X20026/X20025 | M2390 gDNA | 1885bp |

MA0580

DUR1,2,3 over expression at URE2 locus

MA0580

| Fragment | Primers | Template | Exp size |
|---|---|---|---|
| URE2 5' Flank | X20022/X21180 | M2390 gDNA | 1968bp |
| TEF2pro-DUR3-ADH3ter | X21179/X19513 | pMU3464 | 3208bp |
| ADH1pro-DUR1,2-PDC1ter | X19514/X21181 | pMU3411 | 6758bp |
| URE2 3' Flank | X21182/X20025 | M2390 gDNA | 1885bp |

MA0580
17966 bp

MA0581

MEP1 over expression at URE2 locus

MA0581

| Fragment | Primers | Template | Exp size |
|---|---|---|---|
| URE2 5' Flank | X20022/X21180 | M2390 gDNA | 1968bp |
| TEF2pro-MEP1-ADH3ter | X21179/X19513 | pMU3465 | 2479bp |
| ADH1pro-MEP1-PDC1ter | X19514/X21181 | pMU3460 | 2729bp |
| URE2 3' Flank | X21182/X20025 | M2390 gDNA | 1885bp |

MA0582

MEP2 over expression at URE2 locus

MA0582

| Fragment | Primers | Template | Exp size |
|---|---|---|---|
| URE2 5' Flank | X20022/X21180 | M2390 gDNA | 1968bp |
| TEF2pro-MEP2-ADH3ter | X21179/X19513 | pMU3465 | 2479bp |
| ADH1pro-MEP2-PDC1ter | X19514/X21181 | pMU3461 | 2750bp |
| URE2 3' Flank | X21182/X20025 | M2390 gDNA | 1885bp |

MA0583

GAP1 over expression at URE2 locus

MA0583

| Fragment | Primers | Template | Exp size |
|---|---|---|---|
| URE2 5' Flank | X20022/X21180 | M2390 gDNA | 1968bp |
| TEF2pro-GAP1-ADH3ter | X21179/X19513 | pMU3468 | 2809bp |
| ADH1pro-GAP1-PDC1ter | X19514/X21181 | pMU3463 | 3059bp |
| URE2 3' Flank | X21182/X20025 | M2390 gDNA | 1885bp |

MA0584

*S. cerevisiae* GDH2 over expression at URE2 locus

MA0584

| Fragment | Primers | Template | Exp size |
|---|---|---|---|
| URE2 5' Flank | X20022/X21320 | M2390 gDNA | 1968bp |
| ADH1pro-GDH2-PDC1ter | X21319/X15465 | pMU2909 | 4546bp |
| PGKpro-GDH2-ENO1ter | X15464/X21322 | pMU2908 | 5283bp |
| URE2 3' Flank | X21321/X20025 | M2390 gDNA | 1885bp |

MA0585

GLT1/GLN1 over expression at the URE2 locus

MA0585

| Fragment | Primers | Template | Exp size |
|---|---|---|---|
| URE2 5' Flank | X20022/X21320 | M2390 gDNA | 1968bp |
| ADH1pro-GLTI-PDC1ter | X21319/X15465 | pMU2911 | 2363bp |
| PGKpro-GLN1-ENO1ter | X15464/X21322 | pMU2913 | 8442bp |
| URE2 3' Flank | X21321/X20025 | M2390 gDNA | 1885bp |

MA0585
18794 bp

MA0617

AUA1 marked deletion

MA0617

| Fragment | Primers | Template | Expected Size |
|---|---|---|---|
| AUA1 5' Flank | X20620/X20621 | M2390 gDNA | 1947bp |
| AGTEFpro-kan/nat/tdk-HXT2pro | X20630/X20631 | pMU2873,pMU2879 | 3820bp and 3583bp |
| AUA1 3' Flank | X20622/X20623 | M2390 gDNA | 2015bp |

MA0617.1

AUA1 clean deletion

MA0617.1

| Fragment | Primers | Template | Expected Size |
|---|---|---|---|
| AUA1 5' Flank | X20620/X20633 | M2390 gDNA | 1947bp |
| AUA1 3' Flank | X20632/X20623 | M2390 gDNA | 2015bp |

MA0434

DUR3 over expression at FCY1 locus

| MA0434 | DUR3 | | |
|---|---|---|---|
| Fragment | Primers | Template | Exp Size |
| FCY 5' Flank | X21754/X18859 | gDNA | 2049bp |
| TP1pro-DUR3-FBA1ter | X18858/X18861 | pMU3471 | 3157bp |
| FCY 3' Flank | X18860/X18869 | gDNA | 2166bp |

MA0434 with DUR3
11157bp

MA0434.2

MEP1 over expression at FCY1 locus

| MA0434.2 | MEP1 | | |
|---|---|---|---|
| Fragment | Primers | Template | Exp Size |
| FCY 5' Flank | X21754/X18859 | gDNA | 2049bp |
| TP1pro-MEP1-FBA1ter | X18858/X18861 | pMU3472 | 2428bp |
| FCY 3' Flank | X18860/X18869 | gDNA | 2166bp |

MA0434.2 with MEP1
10428 bp

MA0434.3

MEP2 over expression at FCY1 locus

| MA0434.3 | MEP2 | | |
|---|---|---|---|
| Fragment | Primers | Template | Exp Size |
| FCY 5' Flank | X21754/X18859 | gDNA | 2049bp |
| TP1pro-MEP2-FBA1ter | X18858/X18861 | pMU3473 | 2449bp |
| FCY 3' Flank | X18860/X18869 | gDNA | 2166bp |

MA0434.3 with MEP2
10449 bp

MA0434.4

GAP1 over expression at FCY1 locus

| MA0434.4 | GAP1 | | |
|---|---|---|---|
| Fragment | Primers | Template | Exp Size |
| FCY 5' Flank | X21754/X18859 | gDNA | 2049bp |
| TP1pro-GAP1-FBA1ter | X18858/X18861 | pMU3475 | 2758bp |
| FCY 3' Flank | X18860/X18869 | gDNA | 2166bp |

MA0434.4 with GAP1
10758 bp

MA0434.5

MEP3 over expression at FCY1 locus

| MA0434.5 | MEP3 | | |
|---|---|---|---|
| Fragment | Primers | Template | Exp Size |
| FCY 5' Flank | X21754/X18859 | gDNA | 2049bp |
| TP1pro-MEP3-FBA1ter | X18858/X18861 | pMU3607 | 2420bp |
| FCY 3' Flank | X18860/X18869 | gDNA | 2166bp |

MA0434.5 with MEP3
10419 bp

MA0454.14

DUR1,2 over expression at FCY1 locus

MA0454.14

| Fragment | Primers | Template | Exp Size |
|---|---|---|---|
| FCY 5' Flank | X21754/X19552 | gDNA | 2018bp |
| pTEF2/ADH3t | X19551/X19968 | pMU3409 | 6508bp |
| pHXT7/PMA1trc | X19967/X19969 | pMU3410 | 6458bp |
| FCY3' Flank | X19970/X18869 | gDNA | 2159bp |

MA0464

DUR3 over expression at FCY1 locus

| MA0464 | DUR3 | | |
|---|---|---|---|
| Fragment | Primers | Template | Exp Size |
| FCY 5' Flank | X21754/X19552 | M2390 gDNA | 2018bp |
| TEF2pro-DUR3-ADH3ter | X19551/X20043 | pMU3464 | 3208bp |
| FCY 3' Flank | X20044/X18869 | M2390 gDNA | 2133bp |

MA0464.1

DUR1,2 over expression at FCY1 locus

| MA0464.1 | DUR1,2 | | |
|---|---|---|---|
| Fragment | Primers | Template | Exp Size |
| FCY 5' Flank | X21754/X19552 | M2390 gDNA | 2049bp |
| TEF2pro-DUR1,2-ADH3ter | X19551/X20043 | pMU3409 | 6508bp |
| FCY 3' Flank | X20044/X18869 | M2390 gDNA | 2166bp |

MA0464.1 with DUR1,2
14508 bp

MA0464.2

MEP1 over expression at FCY1 locus

| MA0464.2 | MEP1 | | |
|---|---|---|---|
| Fragment | Primers | Template | Exp Size |
| FCY 5' Flank | X21754/X19552 | M2390 gDNA | 2049bp |
| TEF2pro-MEP1-ADH3ter | X19551/X20043 | pMU3465 | 2479bp |
| FCY 3' Flank | X20044/X18869 | M2390 gDNA | 2166bp |

MA0464.2 with MEP1
10479 bp

MA0464.3

MEP2 over expression at FCY1 locus

| MA0464.3 | MEP2 | | |
|---|---|---|---|
| Fragment | Primers | Template | Exp Size |
| FCY 5' Flank | X21754/X19552 | M2390 gDNA | 2049bp |
| TEF2pro-MEP2-ADH3ter | X19551/X20043 | pMU3466 | 2500bp |
| FCY 3' Flank | X20044/X18869 | M2390 gDNA | 2166bp |

MA0464.4

GAP1 over expression at FCY1 locus

| MA0464.4 | GAP1 | | |
|---|---|---|---|
| Fragment | Primers | Template | Exp Size |
| FCY 5' Flank | X21754/X19552 | M2390 gDNA | 2049bp |
| TEF2pro-GAP1-ADH3ter | X19551/X20043 | pMU3468 | 2809bp |
| FCY 3' Flank | X20044/X18869 | M2390 gDNA | 2166bp |

MA0464.4 with GAP1
10809bp

MA0464.5

MEP3 over expression at FCY1 locus

| MA0464.5 | MEP3 | | |
|---|---|---|---|
| Fragment | Primers | Template | Exp Size |
| FCY 5' Flank | X21754/X19552 | M2390 gDNA | 2049bp |
| TEF2pro-DUR1,2-ADH3ter | X19551/X20043 | pMU3606 | 6508bp |
| FCY 3' Flank | X20044/X18869 | M2390 gDNA | 2166bp |

MA0464.5 with MEP3
10470 bp

MA0465.1

DUR1,2 over expression at FCY1

| MA0465.1 | DUR1,2 | | |
|---|---|---|---|
| Fragment | Primers | Template | Exp Size |
| FCY 5' Flank | X21754/X20283 | M2390 gDNA | 2049bp |
| HXT7pro-DUR1,2-PMA1ter | X20282/X20285 | pMU3410 | 6458bp |
| FCY 3' Flank | X20284/X18869 | M2390 gDNA | 2166bp |

MA0467

DUR3 over expression at FCY1 locus

| MA0467 | DUR3 | | |
|---|---|---|---|
| Fragment | Primers | Template | Exp Size |
| FCY 5' Flank | X21754/X21736 | M2390 gDNA | 2049bp |
| ADH1pro-DUR3-PDC1ter | X21735/X18847 | pMU3459 | 3458bp |
| FCY 3' Flank | X18846/X18869 | M2390 gDNA | 2166bp |

MA0467 with DUR3
11458 bp

MA0467.1

DUR1,2 over expression at FCY1 locus

| MA0467.1 | DUR1,2 | | |
|---|---|---|---|
| Fragment | Primers | Template | Exp Size |
| FCY 5' Flank | X21754/X21736 | M2390 gDNA | 2049bp |
| ADH1pro-DUR1,2-PDC1ter | X21735/X18847 | pMU3411 | 6758bp |
| FCY 3' Flank | X18846/X18869 | M2390 gDNA | 2166bp |

MA0467.2

MEP1 over expression at FCY1 locus

| MA0467.2 | MEP1 | | |
|---|---|---|---|
| Fragment | Primers | Template | Exp Size |
| FCY 5' Flank | X21754/X21736 | M2390 gDNA | 2049bp |
| ADH1pro-MEP1-PDC1ter | X21735/X18847 | pMU3460 | 2729bp |
| FCY 3' Flank | X18846/X18869 | M2390 gDNA | 2166bp |

MA0467.2 with MEP1
10729 bp

MA0467.3

MEP2 over expression at FCY1 locus

| MA0467.3 | MEP2 | | |
|---|---|---|---|
| Fragment | Primers | Template | Exp Size |
| FCY 5' Flank | X21754/X21736 | M2390 gDNA | 2049bp |
| ADH1pro-MEP2-PDC1ter | X21735/X18847 | pMU3461 | 2750bp |
| FCY 3' Flank | X18846/X18869 | M2390 gDNA | 2166bp |

MA0467.3 with MEP2
10750 bp

MA0467.4

GAP1 over expression at FCY1 locus

| MA0467.4 | GAP1 | | |
|---|---|---|---|
| Fragment | Primers | Template | Exp Size |
| FCY 5' Flank | X21754/X21736 | M2390 gDNA | 2049bp |
| ADH1pro-GAP1-PDC1ter | X21735/X18847 | pMU3463 | 3059bp |
| FCY 3' Flank | X18846/X18869 | M2390 gDNA | 2166bp |

MA0881

*S. cerevisiae* GDH2 over expression at FCY1 locus

MA0881

| Fragment | Primers | Template | Expected Size |
|---|---|---|---|
| 5' Flank | X21754/X23408 | M2390 gDNA | 2049bp |
| pPGK-GDH2-ENO1t | X23409/X15464 | pMU2908 | 5283bp |
| pADH-GDH2-PDC1trc | X15465/X18955 | pMU2909 | 4546bp |
| 3' Flank | X19950/X18869 | M2390 gDNA | 2166bp |

MA0881.1

GLT1/GLN1 over expression at FCY1 locus

MA0881.1

| Fragment | Primers | Template | Expected Size |
|---|---|---|---|
| 5' Flank | X21754/X23408 | M2390 gDNA | 2049bp |
| pPGK-GLT1-ENO1t | X23409/X15464 | pMU2913 | 8442bp |
| pADH-GLN1-PDC1trc | X15465/X18955 | pMU2911 | 2363bp |
| 3' Flank | X19950/X18869 | M2390 gDNA | 2166bp |

METHODS FOR REGULATING NITROGEN METABOLISM DURING THE PRODUCTION OF ETHANOL FROM CORN BY METABOLICALLY ENGINEERED YEAST STRAINS

CROSS REFERENCE TO RELATED APPLICATIONS

The present application is a continuation of U.S. Ser. No. 14/771,831 filed Sep. 1, 2015, which is a § 371 of PCT/US14/25460 filed Mar. 13, 2014, which claims priority to U.S. Provisional 61/800,323, filed Mar. 15, 2013, each of which application is hereby incorporated by reference in their entirety.

SEQUENCE LISTING

The contents of the attached sequence listing entitled "115235-265-seq_listing.txt" created on Sep. 13, 2019 (size 271 kb) is incorporated by reference in its entirety.

BACKGROUND OF THE INVENTION

Energy conversion, utilization and access underlie many of the great challenges of our time, including those associated with sustainability, environmental quality, security, and poverty. New applications of emerging technologies are required to respond to these challenges. Biotechnology, one of the most powerful of the emerging technologies, can give rise to important new energy conversion processes. Plant biomass and derivatives thereof are a resource for the biological conversion of energy to forms useful to humanity.

Among forms of plant biomass, both, grain-based biomass and lignocellulosic biomass collectively "biomass") are well-suited for energy applications. Each feedstock has advantages and disadvantages. For example, because of its large-scale availability, low cost, and environmentally benign production lignocellulosic biomass has gained attention as a viable feed source for biofuel production. In particular, many energy production and utilization cycles based on cellulosic biomass have near-zero greenhouse gas emissions on a life-cycle basis.

However, grain-based feed stocks are more readily converted to fuels by existing microorganisms, although grain-based feed stock is more expensive than lignocellulosic feed stock and conversion to fuel competes with alternative uses for the grain.

Biomass processing schemes involving enzymatic or microbial hydrolysis commonly involve four biologically mediated transformations: (1) the production of saccharolytic enzymes (cellulases and hemicellulases); (2) the hydrolysis of carbohydrate components present in pretreated biomass to sugars; (3) the fermentation of hexose sugars (e.g., glucose, mannose, and galactose); and (4) the fermentation of pentose sugars (e.g., xylose and arabinose). These four transformations can occur in a single step in a process configuration called consolidated bioprocessing ("CBP"), which is distinguished from other less highly integrated configurations in that it does not involve a dedicated process step for cellulose and/or hemicellulase production.

CBP offers the potential for lower cost and. higher efficiency than processes featuring dedicated cellulose production. The benefits result in part from avoided capital costs, substrate and other raw materials, and utilities associated with cellulase production. In addition, several factors support the realization of higher rates of hydrolysis, and hence reduced reactor volume and capital investment using CBP, including enzyme-microbe synergy and the use of thermophilic organisms and/or complexed cellulase systems. Moreover, cellulose-adherent cellulolytic microorganisms are likely to compete successfully for products of cellulose hydrolysis with non-adhered microbes, e.g., contaminants. Successful competition of desirable microbes increases the stability of industrial processes based on microbial cellulose utilization. P regress in developing CBP-enabling microorganisms is being made through two strategies: engineering naturally occurring cellulolytic microorganisms to improve product-related properties, such as yield and titer; and engineering non-cellulolytic organisms that exhibit high product yields and titers to express a heterologous cellulase and hemicellulase system enabling cellulose and hemicellulose utilization.

One way to meet the demand for ethanol production is to convert sugars found in biomass, i.e., materials such as agricultural wastes, corn hulls, corncobs, cellulosic materials, and the like to produce ethanol. Efficient biomass conversion in large-scale industrial applications requires a microorganism that is able to tolerate high concentrations of sugar and ethanol, and which is able to ferment more than one sugar simultaneously.

Bakers' yeast (*Saccharomyces cerevisiae*) is the preferred microorganism for the production of ethanol (Hahn-Hägerdal. B., et al., *Adv. Biochem. Eng. Biotechnol.* 73, 53-84 (2001)). Attributes in favor of this microbe are (i) high productivity at close to theoretical yields (0.51 g ethanol produced/g glucose used), (ii) high osmo- and ethanol tolerance, (iii) natural robustness in industrial processes, also (iv) being generally regarded as safe (GRAS) due to its long association with wine and bread making, and beer brewing. Furthermore, *S. cerevisiae* exhibits tolerance to inhibitors commonly found in hydrolysates resulting from biomass pretreatment. Exemplary metabolic pathways for the production of ethanol are depicted in FIG. 1. However, *S. cerevisiae* does not naturally break down components of cellulose, nor does it efficiently use pentose sugars.

Glycerol is a metabolic end-product of native yeast ethanolic fermentation (FIG. 1). During anaerobic growth on carbohydrates, production of ethanol and carbon dioxide is redox neutral, while the reactions that create cell biomass and associated carbon dioxide are more oxidized relative to carbohydrates. The production of glycerol, which is more reduced relative to carbohydrates, functions as an electron sink to off-set cell biomass formation, so that overall redox neutrality is conserved. This is essential from a theoretical consideration of conservation of mass, and in practice strains unable to produce glycerol are unable (or only very poorly able) to grow under anaerobic conditions.

There is a strong commercial incentive not to produce glycerol as a byproduct because it represents lost ethanol yield. In industrial corn ethanol fermentations, this yield loss can be up to 6% of theoretical, for a market of ~14 billion gallons/yr. At selling price of $2.50/gal, this is a total market value of $2 B/yr.

Strategies from the literature to address this problem include decreasing glycerol formation by engineering ammonia fixation to function with NADH instead of NADPH via up-regulation of GLN1, encoding glutamine synthetase, or GLT1, encoding glutamate synthase with deletion of GDH1, encoding the NADPH-dependent glutamate dehydrogenase. (Nissen, T. L., et al., *Metabolic Engineering* 2; 69-77 (2000)). Another strategy engineering cells to produce excess NADPH during glycolysis via expression of a NADPH linked glyceraldehyde-3-phosphate dehydrogenase (Bro, C, et al., *Metabolic Engineering* 8: 102-111 (2006)). Another strategy contained a deletion of GDH1, and over-expression of glutamate synthase (GLT1) and glutamine synthase (GLN1), which also resulted in reduced glycerol formation. However, growth rates and biomass formation were well below the control strain and improvements on the initial performance have not been demonstrated. Additionally, industrially relevant yields, titers and fermentation rates were never demonstrated (U.S. Pat. No. 7,018,829). Another strategy describes deletion of only GDH1 without overexpression of GDH2 or GLT1/GLN1. However, the strategy was dependent on the use of an industrial polyploid yeast strain capable of tolerating high ethanol concentrations. It is noted in the patent that GDH1 was the only deletion, and that there are no heterologous DNA sequences in the genome. Additionally, the maximum reduction in glycerol production seen was 12.04%, and the technology was not demonstrated on an industrially relevant substrate (U.S. Pat. No. 7,935,514). Most glycerol reduction strategies either only partially reduce the requirement for glycerol formation, or create a by-product other than ethanol. The present invention overcomes the shortcomings of these other strategies.

Corn mash contains free amino nitrogen. However the amount is too low to enable yeast biomass formation sufficient to meet the needs of the process. Nitrogen is added to industrial corn ethanol fermentations to promote yeast growth, most commonly in the form of urea and ammonia. Excess nitrogen can improve the fermentation kinetics of conventional yeasts; however ethanol yields are often lower due to excess biomass and glycerol formation. Typically, urea is added to industrial corn fermentations in concentrations that range from 500 ppm to 1000 ppm.

Yeast take up and assimilate ammonium as its preferred nitrogen source, followed by amino acids, and finally urea (FIGS. 2-4) (extensively reviewed by Lungdahl et al., *Genetics* 190: 885-929 (2012)). The mechanism of nitrogen catabolite repression (NCR) control is established by transcription factors which control the expression of ammonium, amino acid and urea transporters. These transcription factors also control expression of proteins responsible for degradation and assimilation of nitrogen containing molecules. It has been shown that de-repression of non-preferred nitrogen source assimilation pathways can improve fermentation kinetics (Salmon, J. M., and Barre, P., *Appl. Environ. Microbiol.* 64:3831-3837 (1998)); however, effects on ethanol productivity were not measured.

*S. cerevisiae* contains three known ammonium transporters. MEP1, MEP2 and MEP3. MEP1 and MEP2 are high affinity transporters while MEP3 is a low affinity transporter. *S. cerevisiae* breaks down urea through the enzymatic action of a urea-amido lyase (EC 6.3.4.6). This activity is encoded by the enzyme DUR1/2 in *S. cerevisiae* (FIGS. 2-4). Overexpression of DUR1/2 in wine yeasts has been shown to enhance urea degradation rates during fermentation of grape must (Coulon, J., el al., *Am. J. Enol. Vitic.* 57:2 (2006)). There are two known urea transporters in *S. cerevisiae*, DUR3 and DUR4 (FIGS. 2-4). It has been shown that overexpression of DUR3 resulted in improved urea degradation rates during wine fermentation (Dahabieh, M. S., et al., *Am. J. Enol. Vitic.* 60:4 (2009)). U.S. Patent Publ. No. 2011/0129566 describes the expression of DUR1/2 and DUR3 in wine yeasts.

Industrial corn mash substrates contain as much as 3% protein (w/v); however, much of the amino acid content contained in these proteins is unavailable to *S. cerevisiae*. Expression of one or more proteases would release amino acids that could serve as a nitrogen source for yeast. Additionally, the use of amino acids as a nitrogen source for *S. cerevisiae* in corn ethanol fermentations would improve yield through a reduction in the surplus NADH generated from in vivo amino acid synthesis during anaerobic growth.

Guo et al. engineered *S. cerevisiae* to express a heterologous protease for the purpose of improving ethanol yield (Guo, Z-p, et al., *Enzyme and Microbial Technology* 48: 148-154 (2011)). However, the work was conducted in a wild type yeast background that had not been previously engineered for reduced glycerol formation, and the activity of the expressed endoprotease primarily breaks protein into short polypeptides which are not transported by *S. cerevisiae.*

One aspect of the present invention relates to improved fermentation performance through co-expression of an exoprotease to release single amino acids. Additionally, corn kernel protein is primarily a class of storage proteins known as zeins. Zeins have been shown to be recalcitrant to hydrolysis by many proteases and it is possible that expression of zein specific proteases would result in improved proteolysis. Thus, another aspect of the present invention relates to expressing zein-specific proteases to improve corn protein hydrolysis and amino acid utilization by the yeast.

Amino acids are transported by a large family of amino acid permeases. One aspect of this invention relates to deregulation or over-expression of a specific or general amino acid permease to complement protease expression or metabolic engineering by improving the uptake rate of free amino acids released during proteolysis. For example, expression of the general amino acid permease GAP1 is negatively regulated by AUA1. One aspect of this invention relates to the deletion of AUA1 or over expression of GAP1 that could result in improved amino acid uptake rates.

PCT/US2012/032443, which is incorporated herein by reference, teaches a method of eliminating glycerol formation through the production of formate. The formate production pathway can also be combined with strains engineered for reduced activity of the native glycerol production pathway. These combinations can be designed such that strains are built with different degrees of glycerol reduction as shown in FIG. 5. Several embodiments of the current invention relate to a combination of those or related genetic modifications described in PCT/US2012/032443, with additional genetic modifications that are designed to alter nitrogen transport and assimilation.

One aspect of this invention relates to strains of *S. cerevisiae* with reduced glycerol production that get a kinetic benefit from higher nitrogen concentration without sacrificing ethanol yield. A second aspect of the invention relates to metabolic modifications resulting in altered transport and/or intracellular metabolism of nitrogen sources present in corn mash.

BRIEF SUMMARY OF THE INVENTION

Some embodiments are direct to a recombinant microorganism comprising: at least one engineered genetic modification that leads to the up-regulation or down-regulation of one or more native and/or heterologous enzymes that function in one or more ethanol production pathways; at least one engineered genetic modification that leads to the down-regulation of an enzyme in a glycerol-production pathway; and at least one engineered genetic modification that leads to the up-regulation or down-regulation of an enzyme in a nitrogen-assimilation pathway.

In some embodiments of the invention, the down-regulated enzyme in the nitrogen-assimilation pathway is glutamate dehydrogenase (Gdh) (EC 1.4.1.4).

In some embodiments of the invention, the microorganism further comprises least one genetic modification that leads to the up-regulation of an enzyme in a nitrogen-assimilation pathway.

In some embodiments of the invention, the up-regulated enzyme in the nitrogen-assimilation pathway is at least one enzyme selected from the group consisting of glutamate dehydrogenase (Gdh) (EC 1.4.1.2), glutamate synthase (Glt) (EC 1.4.1.14), and glutamine synthase (Gln) (EC 6.3.1.2). In some embodiments of the invention, the up-regulated enzyme in the nitrogen-assimilation pathway is a native ammonium transporter. In some embodiments of the invention, the up-regulated enzyme in the nitrogen-assimilation pathway is a MEP protein from the genus *Saccharomyces*. In some embodiments of the invention, the up-regulated enzyme in the nitrogen assimilation pathway is a urea-amido lyase (EC 6.3.4.6). In some embodiments of the invention, the up-regulated enzyme in the nitrogen assimilation pathway is a urea transporter. In some embodiments of the invention, the up-regulated enzyme in the nitrogen assimilation pathway is Gln3.

In some embodiments of the invention, the enzyme in the glycerol-production pathway is encoded by at least one enzyme selected from the group consisting of; a glycerol-3-phosphate dehydrogenase 1 polynucleotide (GPD1) (EC 1.1.1.8), a glycerol-3-phosphate dehydrogenase 1 polypeptide (Gpd1) (EC 1.1.1.8), a glycerol-3-phosphate dehydrogenase 2 polynucleotide (GPD2) (EC 1.1.1.8), a glycerol-3-phosphate dehydrogenase 2 polypeptide (Gpd2) (EC 1.1.1.8), a glycerol-3-phosphate phosphatase 1 polynucleotide (GPP1) (EC 3.1.3.21), a glycerol-3-phosphate phosphatase polypeptide 1 (Gpp1) (EC 3.1.3.21), a glycerol-3-phosphate phosphatase 2 polynucleotide (GPP2) (EC 3.1.3.21), and a glycerol-3-phosphate phosphatase polypeptide 2 (Gpp2) (EC 3.1.3.21).

In some embodiments of the invention, up-regulated enzyme that acts in an ethanol production pathway is pyruvate formate lyase (EC 2.3.1.54). In some embodiments of the invention, the up-regulated enzyme that acts in the ethanol production pathway is pyruvate formate lyase activating enzyme (EC 1.91.1.4).

In some embodiments of the invention, the up-regulated enzyme that acts in the ethanol production pathway is bifunctional acetaldehyde-alcohol dehydrogenase selected from a group of enzymes having both of the following Enzyme Commission Numbers: EC 1.2.1.10 and 1.1.1.1.

In some embodiments of the invention, the up-regulated enzyme that acts in the ethanol production pathway is an NADPH-dependent bifunctional acetaldehyde-alcohol dehydrogenase selected from a group of enzymes having both of the following Enzyme Commission Numbers: EC 1.2.1.10 and 1.1.1.2.

In some embodiments, the microorganism further comprises a down-regulation in one or more native enzymes encoded by a formate dehydrogenase enzyme selected from the group consisting of EC 1.2.1.43 and EC 1.2.1.2.

In some embodiments of the invention, the recombinant microorganism further comprises a heterologous GPD1 polynucleotide operably linked to a native GPD2 promoter. In some embodiments of the invention, the recombinant microorganism further comprises a heterologous GPD2 polynucleotide operably linked to a native GPD1 promoter.

In some embodiments of the invention, the microorganism further comprises an up-regulation or down-regulation of a regulatory element. In some embodiments the regulatory element is selected from the group consisting of: Ure2 and Aua1.

In some embodiments of the invention, the microorganism further comprises at least one additional up-regulated enzyme. In some embodiments of the invention, the additional up-regulated enzyme is a glucoamylase enzyme with EC number 3.2.1.3. In some embodiments of the invention, the additional up-regulated enzyme is a permease. In some embodiments of the invention, the additional up-regulated enzyme is a protease with EC number: 3.4.23.41.

In some embodiments of the invention, the up-regulated or down-regulated enzymes are under the control of a heterologous promoter. In some embodiments of the invention, the heterologous promoter is selected from a group consisting of: TEF2 (SEQ ID NO: 58), HXT7 (SEQ ID NO: 59), ADH1 (SEO ID NO: 60), and (SEQ ID NO: 61).

In some embodiments, the microorganism is a yeast. In some embodiments, the yeast is from the genus *Saccharomyces*. In some embodiments, the yeast is *Saccharomyces cerevisiae*. In some embodiments, the microorganism produces ethanol at a higher yield than an otherwise identical microorganism lacking the genetic modifications. In some embodiments, the microorganism produces an ethanol titer about 1% to about 10% more than an otherwise identical microorganism lacking the genetic modifications. In some embodiments, the microorganism produces an ethanol titer of at least about 125 g/L.

In some embodiments, the microorganism produces glycerol at a lower yield than an otherwise identical microorganism lacking the genetic modifications. In some embodiments, the microorganism produces a glycerol titer of about 10 to about 100% less than an otherwise identical microorganism lacking the genetic modifications.

In some embodiments, the invention relates to a composition comprising any recombinant microorganism herein, and a carbon-containing feedstock.

Some embodiments of the invention are directed to a method of producing a fermentation product using any composition herein, wherein the recombinant microorganism is capable of fermenting the carbon containing feedstock to yield the fermentation product.

Some embodiments of the invention are directed to a method of producing a fermentation product comprising: any composition provided herein; contacting the composition with a carbon containing feedstock, wherein the recombinant microorgan is capable of fermenting the carbon containing feedstock to yield the fermentation product; and, optionally recovering the fermentation production.

Some embodiments of the invention are directed to a method of producing ethanol comprising: providing any recombinant microorganism herein; culturing the recombinant microorganism in the presence of a carbon containing feedstock for sufficient time to produce ethanol; and optionally, extracting the ethanol.

Some embodiments of the invention are directed to a co-culture comprising at least two host cells, wherein one of the host cells comprises any recombinant microorganism herein; and another host cell that is genetically distinct from the recombinant microorganism.

Some embodiments of the invention are directed to a recombinant microorganism comprising, down-regulated Gpd1, down-regulated Gpd2, down-regulated Fdh1, down-regulated Fdh2, down-regulated Gdh1, up-regulated AdhE, up-regulated pyruvate formate lyase, an up-regulated pyruvate formate lyase-activating enzyme, GPD1 under the control of the GPD2 promoter, GPD2 under the control of the GPD1 promoter, and up-regulated Gdh2.

Some embodiments of the invention are directed to a recombinant microorganism comprising: down-regulated Gpd1, down-regulated Gpd2, down-regulated Fdh1, down-regulated Fdh2, down-regulated Gdh1, up-regulated AdhE, up-regulated pyruvate formate lyase, an up-regulated pyruvate formate lyase-activating enzyme. GPD1 under the control of the GPD2 promoter, GPD2 under the control of the GPD1 promoter, up-regulated Glt1 and up-regulated Gln1.

Some embodiments of the invention are directed to a recombinant microorganism comprising: down-regulated Gpd1, down-regulated Fdh1, down-regulated Fdh2, down-regulated Gdh1, up-regulated AdhE, up-regulated pyruvate formate lyase, an up-regulated pyruvate formate lyase-activated enzyme, GPD1 under the control of the GPD2 promoter, GPD2 under the control of the GPD1 promoter, up-regulated Glt1 and up-regulated Gln1.

Some embodiments of the invention are directed to a recombinant microorganism comprising: down-regulated Gpd2, down-regulated Fdh1, down-regulated Fdh2, down-regulated Gdh1, up-regulated AdhE, up-regulated pyruvate formate lyase, and an up-regulated pyruvate formate lyase-activating enzyme.

Some embodiments of the invention are directed to a recombinant microorganism comprising: down-regulated Gpd1, down-regulated Fdh1, down-regulated Fdh2, down-regulated Gdh1, up-regulated AdhE, up-regulated pyruvate formate lyase, an op-regulated pyruvate formate lyase-activating enzyme, and GPD2 under the control of the GPDL promoter.

Some embodiments of the invention are directed to a recombinant microorganism comprising, down-regulated Gpd1, down-regulated Fdh1, down-regulated Fdh2, down-regulated Gdh1, up-regulated AdhE, up-regulated pyruvate formate lyase, and an up-regulated pyruvate formate lyase-activating enzyme.

Some embodiments of the invention are directed to a recombinant microorganism comprising down-regulated Gpd1, down-regulated Fdh1, down-regulated Fdh2, up-regulated AdhE, up-regulated pyruvate formate lyase, an up-regulated pyruvate formate lyase-activating enzyme, upregulated-DUR/12, and GPD2 under the control of the GPD1 promoter.

Some embodiments of the invention are directed to a recombinant microorganism comprising, down-regulated Gpd1, down-regulated Fdh1, down-regulated Fdh2, up-regulated AdhE, up-regulated pyruvate formate lyase, an up-regulated pyruvate formate lyase-activating enzyme, and up-regulated-DUR/12.

Some embodiments of the invention are directed to a recombinant microorganism comprising, down-regulated Gpd1, down-regulated Gpd2, down-regulated Fdh1, down-regulated Fdh2, down-regulated Ure2, up-regulated AdhE, up-regulated pyruvate formate lyase, an up-regulated pyruvate formate lyase-activating enzyme, GPDL under the control of the GPD2 promoter, and GPD2 under the control of the GPD1 promoter.

Some embodiments of the invention are directed to a recombinant microorganism comprising: down-regulated Gpd1, down-regulated Gpd2, down-regulated Fdh1, down-regulated Fdh2, up-regulated AdhE, up-regulated pyruvate formate lyase, an up-regulated pyruvate formate lyase-activating enzyme, up-regulated GDH2, GPD1 under the control of the GPD2 promoter, and GPD2 under the control of the GPD1 promoter.

BRIEF DESCRIPTION OF THE DRAWINGS/FIGURES

FIG. 1 depicts simplified carbon and redox pathways utilized by wildtype *S. cerevisiae* during anaerobic growth. Ethanol formation is redox neutral while cell biomass formation generates net NADH which is balanced by glycerol formation.

FIG. 2 depicts urea transport and intracellular catabolism. The enzymes Dur3 and Dur4 are known transporters of urea. Once inside the cell, urea is broken down into 2 ammonia molecules and 2 carbon dioxide molecules in a reaction catalyzed by Dur1,2.

Figure 69:
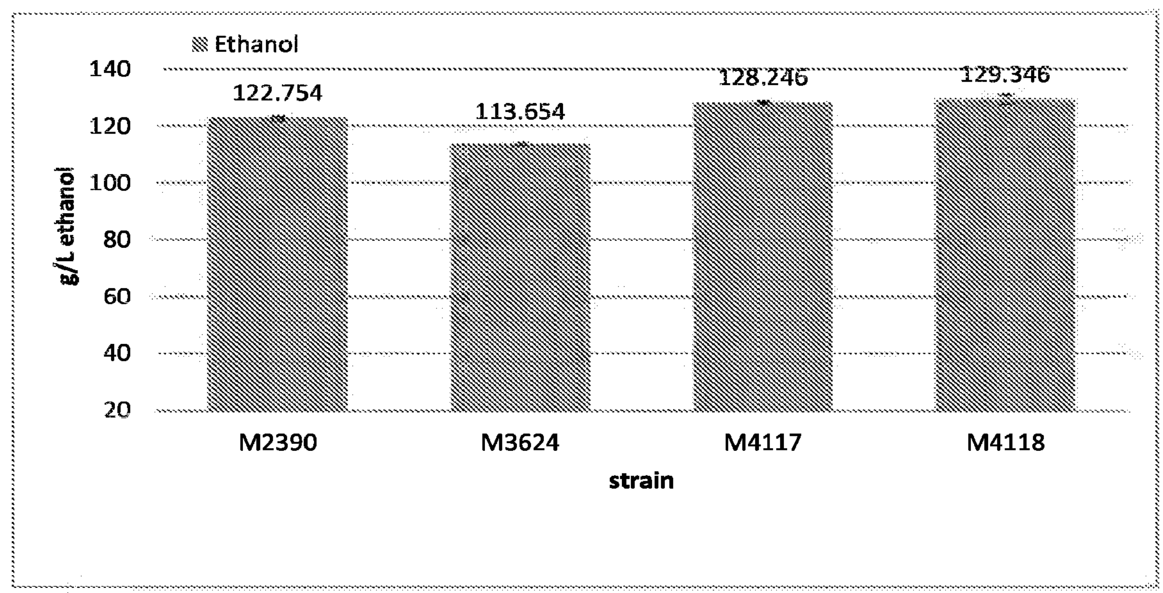

FIG. 69 depicts the final ethanol titers measured following fermentation of 31% solids corn mash in wildtype cells (M2390), a glycerol reduction strain containing the formate pathway (M3624), and 2 strains with modification of the ammonium assimilation pathway (M4117, which contains a deletion of gdh1 and an over-express ion of Gdh2, and M4118, which contains a deletion of gdh1 and an over-expression of Glt1 and Gln1).

Figure 70:
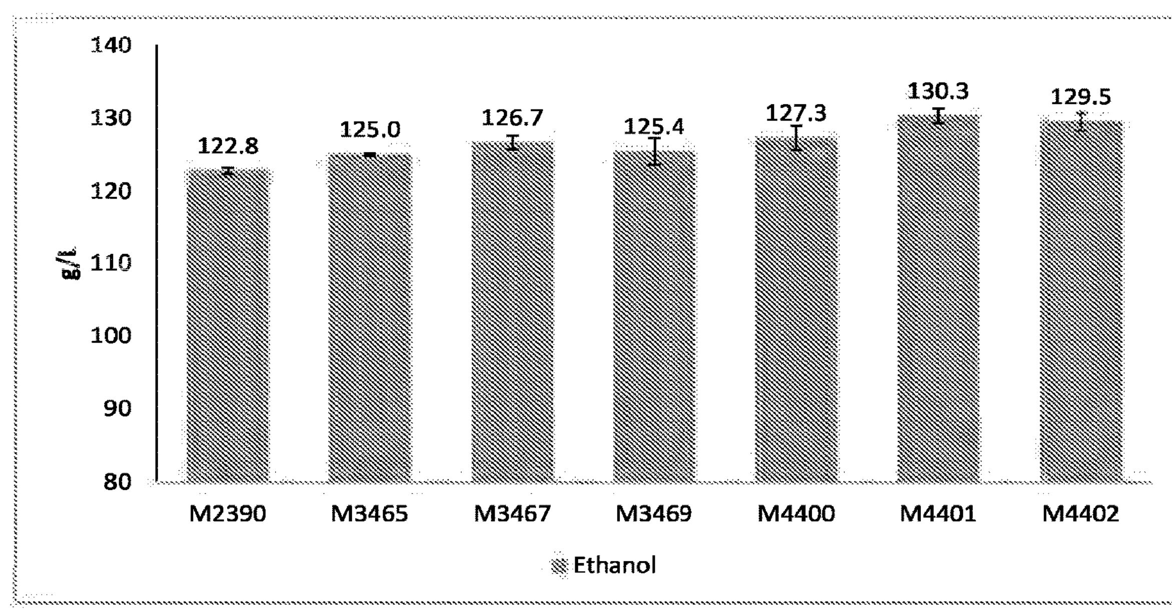
Figure 71:
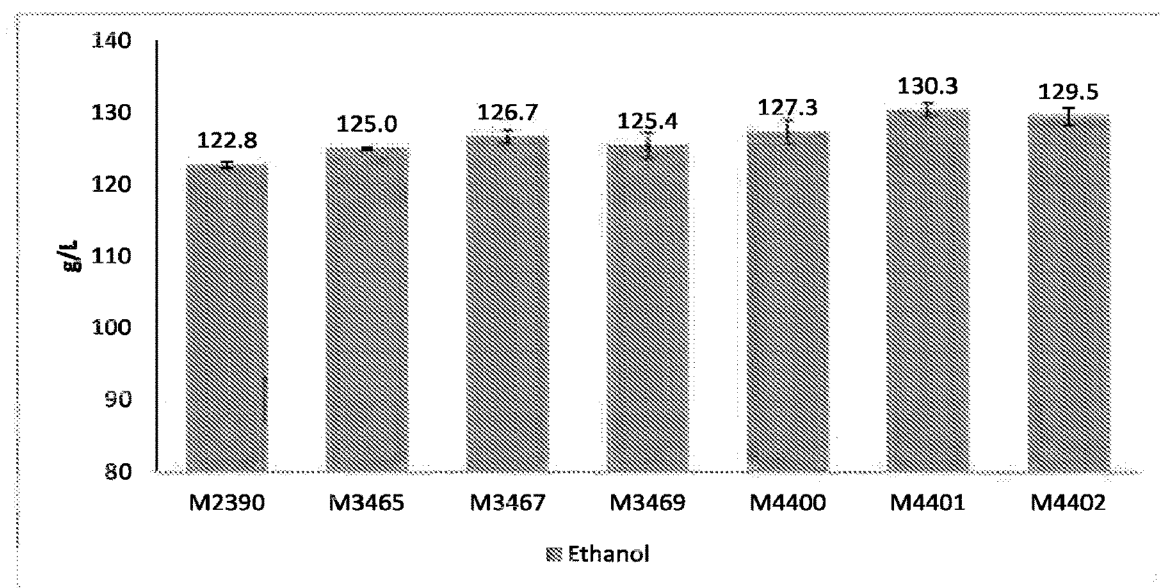

FIG. 70 depicts the ethanol titers measured following fermentation of 31% solids corn mash for glycerol reduction strains containing the formate pathway (M3465, M3467, M3469) that additionally have a deletion of gdh1 (M4400, M4401, M4402). M2390 was a parental control. FIG. 71 depicts the ethanol titers measured following fermentation of 31% solids corn mash for M2390, M3467, M3469, M4427 (M3467 parent strain: expression of DUR1/2 driven by the TEF2 promoter). M4428 (M3467 parent strain: expression of DUR1/2 driven by the HXT7 promoter), M4429 (M3467 parent strain, expression of DUR1/2 driven by the ADH1 promoter), M4430 (M3467 parent strain: expression of DUR1/2 driven by the HXT7/TEF2 promoters), M4431 (M3469 parent strain, expression of DUR1/2 driven by the TEF2 promoter), M4432 (M3469 parent strain: expression of DUR1/2 driven by the HXT7 promoter), M4433 (M3469 parent strain, expression of DUR1/2 driven by the ADH1 promoter), and M4434 (M3469 parent strain: expression of DUR1/2 driven by the HXT7/TEF2 promoters).

Figure 72:
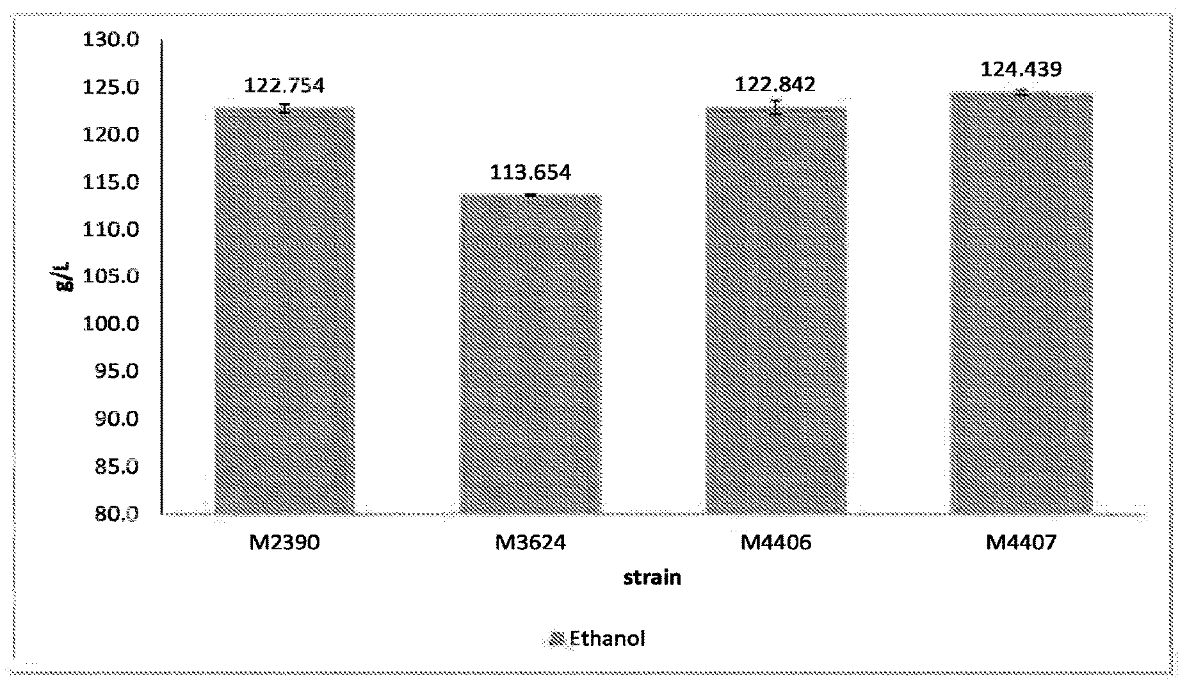

FIG. 72 depicts the ethanol titers measured following fermentation of 31% solids corn mash for M2390, M3624, M4406, and M4407.

Figure 73:
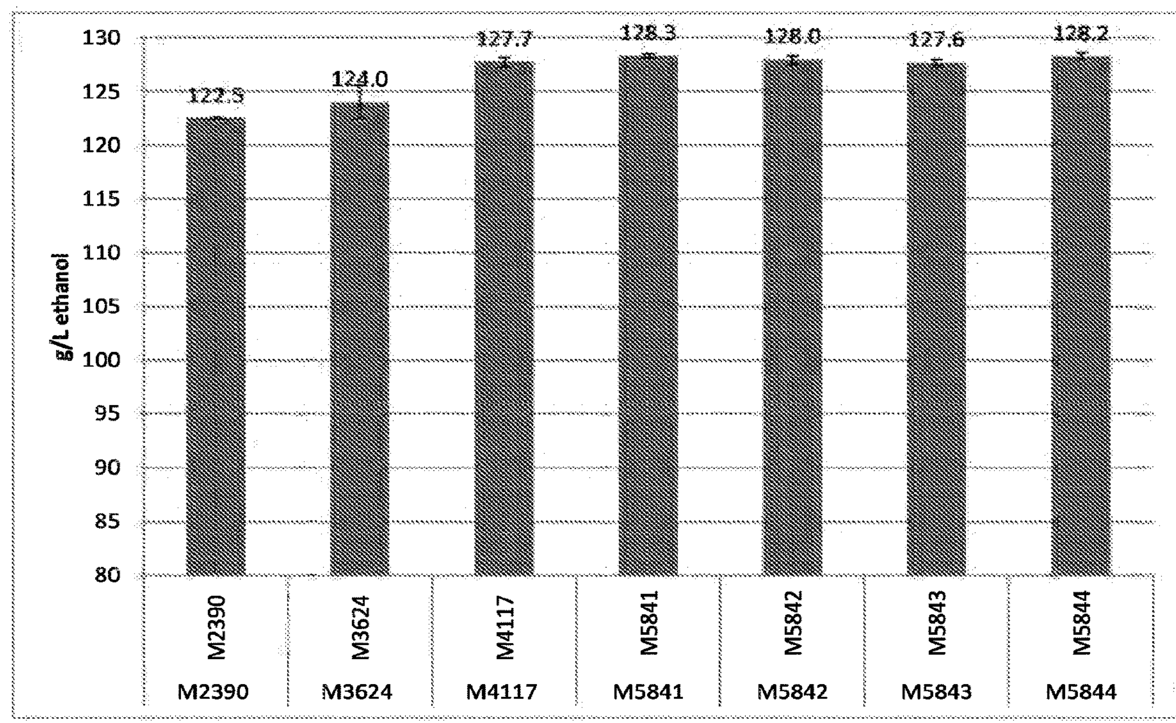

FIG. 73 depicts the ethanol titers produced after 68 hrs fermentation in mini-vials for strains M2390, M3624, M4117, M5841, M5842, M5843, and M5844.

Figure 74:
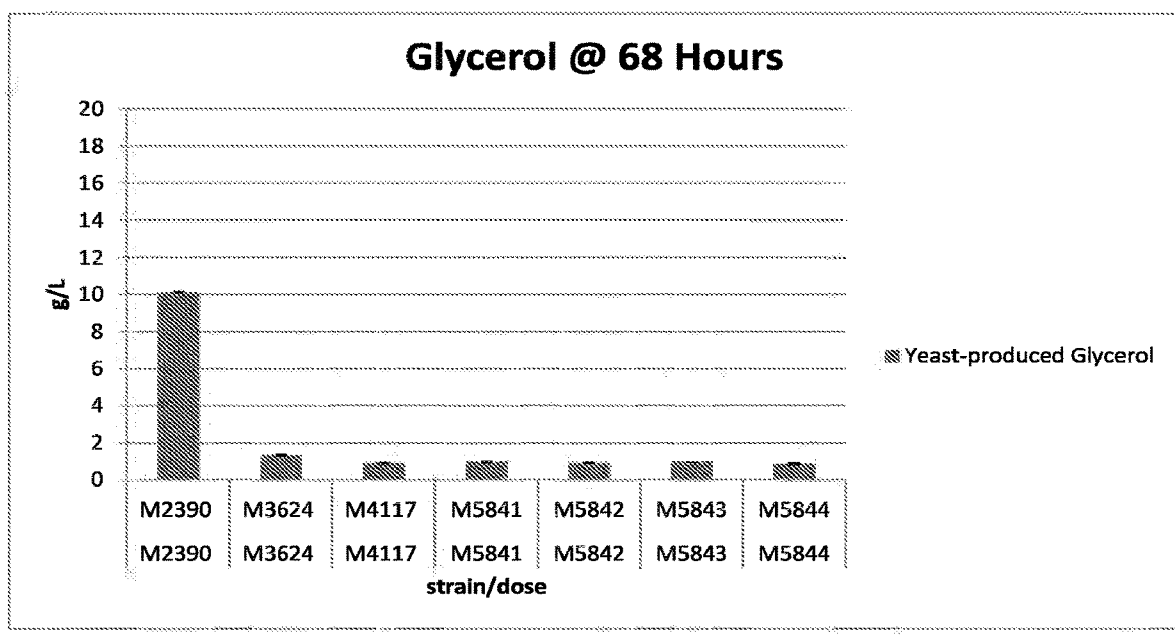

FIG. 74 depicts the glycerol titers produced after 68 hrs fermentation in mini-vials for strains M2390, M3624, M4117, M5841, M5842, M5843, and M5844.

DETAILED DESCRIPTION OF THE INVENTION

Definitions

Unless defined otherwise, all technical and scientific terms used herein have the same meaning as commonly understood to one of ordinary skill in the art of microbial metabolic engineering. Although methods and materials similar or equivalent to those described herein can be used in the practice of the disclosed methods and compositions, exemplary methods, devices and materials are described herein.

The embodiments described, and references in the specification to "one embodiment", "an embodiment", "an example embodiment", etc., indicate that the embodiments described can include a particular feature, structure, or characteristic, but every embodiment does not necessarily include the particular feature, structure, or characteristic. Moreover, such phrases ace not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

The description of "a" or "an" item herein may refer to a single item or multiple items. It is understood that wherever embodiments are described herein with the language "comprising," otherwise analogous embodiments described in terms of "consisting or" and/or "consisting essentially of" are also provided. Thus, for example, reference to "a polynucleotide" includes a plurality of such poly-nucleotides and reference to "the microorganism" includes reference to one or more microorganisms, and so forth.

The term "heterologous" is used in reference to a polynucleotide or a gene not normally found in the host organism, "Heterologous" includes up-regulated or down-regulated endogenous genes. "Heterologous" also includes a native coding region, or portion thereof, that is reintroduced into the source organism in a form that is different from the corresponding native gene, e.g., not in its natural location in the organism's genome. "Heterologous" also includes any gene that has been modified and placed into an organism. A heterologous gene may include a native coding region that is a portion of a chimeric gene including a non-native regulatory region that is reintroduced into the native host or modifications to the native regulatory sequences that affect the expression level of the gene. Foreign genes can comprise native genes inserted into a non-native organism, or chimeric genes. A heterologous polynucleotide, gene, polypeptide, or an enzyme may be derived or isolated from any source, eukaryotes, prokaryotes, viruses, or synthetic polynucleotide fragments, and includes up-regulated endogenous genes.

The terms "gene(s)" or "polynucleolide" or "nucleic acid" or "polynucleotide sequence(s)" are intended to include nucleic acid molecules, e.g., polynucleotides which include an open reading frame encoding a polypeptide, and can further include non-coding regulatory sequences, and introns. In addition, the terms are intended to include one or more genes that map to a functional locus. Also, the terms are intended to include a specific gene for a selected purpose. The gene may be endogenous to the host cell or may be recombinantly introduced into the host cell, e.g., as a plasmid maintained episomally or a plasmid (or fragment thereof) that is stably integrated into the genome. In addition to the plasmid form, a gene may, for example, be in the form of linear DNA or RNA. The ter "gene" is also intended to cover multiple copies of a particular gene, e.g., all of the DNA sequences in a cell encoding a particular gene product. A "gene" refers to an assembly of nucleotides that encode a polypeptide, and includes cDNA and genomic DNA nucleic acids. "Gene" also refers to a nucleic acid fragment that expresses a specific protein, including intervening sequences (introns) between individual coding segments (exons), as well as regulatory sequences preceding (5' non-coding sequences) and following (3' non-coding sequences) the coding sequence. "Native" or "endogenous" refers to a gene as found in nature with its own regulatory sequences.

A "nucleic acid," "polynucleotide," or "nucleic acid molecule" is a polymeric compound comprised of covalently linked subunits called nucleotides. Nucleic acid includes polyribonucleic acid (RNA) and polydeoxyribonucleic acid (DNA), both of which may be single-stranded or double-stranded. DNA includes cDNA, genomic DNA, synthetic DNA, and semi-synthetic DNA.

An "isolated nucleic acid molecule" or "isolated nucleic acid fragment" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA).

The term "expression" is intended to include the expression of a gene at least at the level of mRNA production, generally subsequently translated into a protein product. The term "expression," refers to the transcription and stable accumulation of sense (mRNA) or antisense RNA derived from the nucleic acid fragment of the invention. Expression may also refer to translation of mRNA into a polypeptide.

As used herein, an "expression vector" is a vector capable of directing the expression of genes to which it is operably linked.

A "vector," e.g., a "plasmid" or "YAC" (yeast artificial chromosome) refers to an extrachromosomal element often carrying one or more genes that are not part of the central metabolism of the cell, and is usually in the form of a circular double-stranded DNA molecule. Such elements may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. Preferably, the plasmids or vectors of the present invention are stable and self-replicating.

The term "integrated" as used herein refers to genetic elements that are placed, through molecular biology techniques, into a chromosome of a host cell. For example, genetic elements can be placed into the chromosomes of the host cell as opposed to in a vector such as a plasmid carried by the host cell. Methods for integrating genetic elements into the genome of a host cell are well known in the art and include homologous recombination.

The term "domain" as used herein refers to a part of a molecule or structure that shares common physical or chemical features, for example hydrophobic, polar, globular, helical domains or properties, e.g., a DNA binding domain or an ATP binding domain. Domains can be identified by their homology to conserved structural or functional motifs. Examples of cellobiohydrolase (CBH) domains include the catalytic domain (CD) and the cellulose binding domain (CBD).

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified, e.g., in Sambrook, J., Fritsch, E. F. and Maniatis, T. MOLECULAR CLONING: A LABORATORY MANUAL, Second Edition, Cold Spring Harbor Laboratory Press, Cold Spring Harbor (1989), particularly Chapter 11 and Table 11.1 therein (hereinafter "Maniatis", entirely incorporated herein by reference). The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of conditions uses a series of washes starting with 6×SSC, 0.5% SDS at room temperature for 15 min, then repeated with 2×SSC, 0.5% SDS at 45%, for 30 min, and then repeated twice with 0.2×SSC, 0.5% SDS at 50° C. for 30 min. For more stringent conditions, washes are performed at higher temperatures in which the washes are identical to those above except for the temperature of the final two 30 min washes in 0.2×SSC, 0.5% SDS are increased to 60° C. Another set of highly stringent conditions uses two final washes in 0.1×SSC, 0.1% SDS at 65° C. An additional set of highly stringent conditions are defined by hybridization at 0.1×SSC, 0.1% SDS, 65° C. and washed with 2×SSC, 0.1% SDS followed by 0.1×SSC, 0.1% SDS.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations tsar calculating Tm have been derived (see, e.g Maniatis at 9.50-9.51). For hybridizations with shorter nucleic acids, oligonucleotides, the position of mismatches becomes more important, and the length of the oligonucleotide determines its specificity (see, e.g., Maniatis, at 11.7-11.81. In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

The term "percent identity", as known in the an, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences.

As known in the art, "similarity" between two polypeptides is determined by comparing the amino acid sequence and conserved amino acid substitutes thereto of the polypeptide to the sequence of a second polypeptide.

"Identity" and "similarity" can be readily calculated by known methods, including but not limited to those described in: Computational Molecular Biology (Lesk, A. M., ed.) Oxford University Press, NY (1988); Biocomputing: Informatics and Genome Projects (Smith, D. W., ed.) Academic Press, NY (1993); Computer Analysis of Sequence Data, Part I (Griffin. A. M. and Griffin, H. G., eds.) Humana Press, NJ (1994); Sequence Analysis in Molecular Biology (von Heinje, G., ed.) Academic Press (1987); and Sequence Analysis Primer (Gribskov, M. and Devereux, J., eds.) Stockton Press. NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison. Wis.). Multiple alignments of the sequences disclosed herein were performed using the Clustal method of alignment (Higgins and Sharp (1989) CABIOS. 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

Suitable nucleic acid sequences or fragments thereof (isolated polynucleotides of the present invention) encode polypeptides that are at least about 70% to about 75% identical to the amino acid sequences reported herein, at least about 80%, about 85%, or about 90% identical to the amino acid sequences reported herein, or at least about 95%, about 96%, about 97%, about 98%, about 99%, or about 100% identical to the amino acid sequences reported herein. Suitable nucleic acid fragments are at least about 70%, about 75%, or about 80% identical to the nucleic acid sequences reported herein, at least about 80%, about 85%, or about 90% identical to the nucleic acid sequences reported herein, or at least about 95%, about 96%, about 97%, about 98%, about 99%, or about 100% identical to the nucleic acid sequences reported herein. Suitable nucleic acid fragments not only have the above identities/similarities but typically encode a polypeptide having at least 50 amino acids, at least 100 amino acids, at least 150 amino acids, at least 200 amino acids, or at least 250 amino acids.

A DNA or RNA "coding region" is a DNA or RNA molecule which is transcribed and/or translated into a polypeptide in a cell in vitro or in vivo when placed under the control of appropriate regulatory sequences. "Suitable regulatory regions" refer to nucleic acid regions located upstream (5' non-coding sequences), within, or downstream (3' non-coding sequences) of a coding region, and which influence the transcription, RNA processing or stability, or translation of the associated coding region. Regulatory regions may include promoters, translation leader sequences. RNA processing site, effector binding site and stem-loop structure. The boundaries of the coding region are determined by a start codon at the 5' (amino) terminus and a translation stop codon at the 3' (carboxyl) terminus. A coding region can include, but is not limited to, prokaryotic regions, cDNA from mRNA, genomic DNA molecules, synthetic DNA molecules, or RNA molecules. If the coding region is intended for expression in a eukaryotic cell, a polyadenylation signal and transcription termination sequence will usually be located 3' to the coding region.

An "isoform" is a protein that has the same function as another protein but which is encoded by a different gene and may have small differences in its sequence.

A "paralogue" is a protein encoded by a gene related by duplication within a genome.

An "orthologue" is gene from a different species that has evolved from a common ancestral gene by specification. Normally, orthologues retain the same function in the course of evolution as the ancestral gene.

"Open reading frame" is abbreviated ORF and means a length of nucleic acid, either DNA, cDNA or RNA, that comprises a translation start signal or initiation codon, such as an ATG or AUG, and a termination codon and can be potentially translated into a polypeptide sequence.

"Promoter" refers to a DNA fragment capable of controlling the expression of a coding sequence or functional RNA. In general, a coding region is located 3' to a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of cellular development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity. A promoter is generally bounded at its 3' terminus by the transcription initiation site and extends upstream (5' direction) to include the minimum number of bases or elements necessary to initiate transcription at levels detectable above background. Within the promoter will be found a transcription initiation site (conveniently defined for example, by mapping with nuclease S1), as well as protein binding domains (consensus sequences) responsible for the binding of RNA polymerase.

A coding region is "under the control" of transcriptional and translational control elements in a cell when RNA polymerase transcribes the coding region into mRNA, which is then trans-RNA spliced (if the coding region contains in irons) and translated into the protein encoded by the coding region.

"Transcriptional and translational control regions" are DNA regulatory regions, such as promoters, enhancers, terminators, and the like, that provide for the expression of a coding region in a host cell. In eukaryotic cells, polyadenylation signals are control regions.

The term "operably associated" refers to the association of nucleic acid sequences on a single nucleic acid fragment so that the function of one is affected by the other. For example, a promoter is operably associated with a coding region when it is capable of affecting the expression of that coding region (i.e., that the coding region is under the transcriptional control of the promoter). Coding regions can be operably associated to regulatory regions in sense or antisense orientation.

As used herein, the term "anaerobic" refers to an organism, biochemical reaction or process that is active or occurs under conditions of an absence of gaseous $O_2$.

"Anaerobic conditions" are defined as conditions under which the oxygen concentration in the fermentation medium is too low for the microorganism to use as a terminal electron acceptor. Anaerobic conditions may be achieved by sparging a fermentation medium with an inert gas such as nitrogen until oxygen is no longer available to the microorganism as a terminal electron acceptor. Alternatively, anaerobic conditions may be achieved by the microorganism consuming the available oxygen of fermentation until oxygen is unavailable to the microorganism as a terminal electron acceptor.

"Aerobic metabolism" refers to a biochemical process in which oxygen is used as a terminal electron acceptor to convert energy, typically in the form of ATP, from carbohydrates. Aerobic metabolism typically occurs, for example, via the electron transport chain in mitochondria in eukaryotes, wherein a single glucose molecule is metabolized completely into carbon dioxide in the presence of oxygen.

In contrast, "anaerobic metabolism" refers to a biochemical process in which oxygen is not the final acceptor of electrons generated. An aerobic metabolism can be divided into anaerobic respiration, in which compounds other than oxygen serve as the terminal electron acceptor, and substrate level phosphorylation, in which no exogenous electron acceptor is used and products of an intermediate oxidation state are generated via a "fermentative pathway."

"fermentative pathways", the amount of NAD(P)H generated by glycolysis is balanced by the consumption of the same amount of NAD(P)H in subsequent steps. For example, in one of the fermentative pathways of certain yeast strains, NAD(P)H generated through glycolysis donates its electrons to acetaldehyde, yielding ethanol. Fermentative pathways are usually active under anaerobic conditions but may also occur under aerobic conditions, under conditions where NADH is not fully oxidized via the respiratory chain.

As used herein, the term "end-product" refers to a chemical compound that is not or cannot be used by a cell, and so is excreted or allowed to diffuse into the extracellular environment. Common examples of end-products from anaerobic fermentation include, but are not limited to, ethanol, acetic acid, formic acid, lactic acid, hydrogen and carbon dioxide.

As used herein, "cofactors" are compounds involved in biochemical reactions that are recycled within the cells and remain at approximately steady state levels. Common examples of cofactors involved in anaerobic fermentation include, but are not limited to, $NAD^+$ and $NADP^+$. In metabolism, a cofactor can act in oxidation-reduction reactions to accept or donate electrons. When organic compounds are broken down by oxidation in metabolism, their energy can be transferred to $NAD^+$ by its reduction to NADH, to $NADP^+$ by its reduction to NADPH, or to another cofactor, $FAD^+$, by its reduction to $FADH_2$. The reduced cofactors can then be used as a substrate for a reductase.

As used herein, a "pathway" is a group of biochemical reactions that together can convert one compound into another compound in a step-wise process. A product of the first step in a pathway may be a substrate for the second step, and a product of the second step may be a substrate for the third, and so on. Pathways of the present invention include, but are not limited to, the pyruvate metabolism pathway the lactate production pathway, the ethanol production pathway, the glycerol-production pathway, the nitrogen assimilation pathway, and the ammonium assimilation pathway.

The term "recombination" or "recombinant" refers to the physical exchange of DNA between two identical (homologous), or nearly identical, DNA molecules. Recombination can be used for targeted gene deletion or to modify the sequence of a gene. The term "recombinant microorganism" and "recombinant host cell" are used interchangeably herein and refer to microorganisms that have been genetically modified to express or over-express endogenous polynucleotides, or to express heterologous polynucleotides, such as those included in a vector, or which have a modification in expression of an endogenous gene.

By "expression modification" it is meant that the expression of the gene, or level of a RNA molecule or equivalent RNA molecules encoding one or more polypeptides polypeptide subunits, or activity of one or more polypeptides or polypeptide, subunits is up regulated or down-regulated, such that expression, level, or activity, is greater than or less than that observed in the absence of the modification.

In one aspect of the invention, genes or particular polynucleotide sequences are partially, substantially, or completely deleted, silenced, inactivated, or down-regulated in order to inactivate the enzymatic activity they encode. Complete deletions provide maximum stability because there is no opportunity for a reverse mutation to restore function. Alternatively, genes can be partially, substantially, or completely deleted, silenced, inactivated, or down regulated by insertion, deletion, removal or substitution of nucleic acid sequences that disrupt the function and/or expression of the gene.

As used herein, the term "down-regulate" includes the deletion or mutation of a genetic sequence, or insertion of a disrupting genetic element, coding or non-coding, such that the production of a gene product is lessened by the deletion, mutation, or insertion it includes a decrease in the expression level (i.e., molecular quantity) of an mRNA car protein. "Delete" or "deletion" as used herein refers to a removal of a genetic element such that a corresponding gene is completely prevented from being expressed. In some embodiments, deletion refers to a complete gene deletion. Down-regulation can also occur by engineering the repression of genetic elements by chemical or other environmental means, for example by engineering a chemically-responsive promoter element for other type of conditional promoter) to control the expression of a desired gene product. Down-regulation can also occur through use of a weak promoter.

As used herein, the term "up-regulate" includes the insertion, reintroduction, mutation, or increased expression of a genetic sequence, such that the production of a gene product is increased by the insertion, reintroduction, or mutation. It includes an increase in the expression level (i.e., molecular quantity) of an mRNA or protein. "Insert" or "insertion" as used herein refers to an introduction of a genetic element such that a corresponding gene is expressed. Up-regulation can also occur by causing the increased expression of genetic elements through an alteration of the associated regulatory sequence. Up-regulation can occur by engineering the expression of genetic elements by chemical or oilier environmental means, for example by engineering a chemically-responsive promoter element (or other type of conditional promoter) to control the expression of a desired gene product. Up-regulation can also occur through use of a strong promoter.

As used herein, the term "glycerol-production pathway" refers to the collection of biochemical pathways that produce glycerol from DHAP. Components of the pathway consist of all substrates, cofactors, byproducts, intermediates, end-products, and enzymes in the pathway.

As used herein, the term "ethanol production pathway" refers the collection of biochemical pathways that produce ethanol from a carbohydrate source. Components of the pathway consist of all substrates, cofactors, byproducts, intermediates, end-products, and enzymes in the pathway.

As used herein, the term "nitrogen assimilation pathway" refers to the collection of biochemical pathways that result in the formation of organic nitrogen containing compounds from inorganic nitrogen compounds. Components of the pathway consist of ail substrates, cofactors, byproducts, intermediates, end-products, and enzymes in the pathway.

As used herein, the term "ammonium assimilation pathway" refers to the collection of biochemical pathways that assimilate ammonia or ammonium ($NH_4^+$) into glutamate and/or glutamine. The ammonium assimilation pathway is part of the larger nitrogen assimilation pathway. Components of the pathway consist of all substrates, cofactors, byproducts, intermediates, end-products, and enzymes in the pathway.

As used herein, the term "glycolysis" or "glycolytic pathway" refers to the canonical pathway of basic metabolism in which a sugar such as glucose is broken down into more oxidized products, converting energy and compounds required for cell growth. Components of the pathway consist of all substrates, cofactors, byproducts, intermediates end-products, and enzymes in the pathway.

As used herein, the term "alcohol dehydrogenase" or "ADH" is intended to include the enzymes that catalyze the conversion of ethanol into acetylaldehyde. Very commonly, the same enzyme catalyzes the reverse reaction from acetaldehyde to ethanol, which is the direction more relevant to fermentation. Alcohol dehydrogenase includes those enzymes that correspond to EC 1.1.1.1 and 1.1.1.2 and exemplified by the enzymes disclosed in GenBank Accession No. U49975.

As used herein, the term "aldehyde dehydrogenase", "ALD" or "ALDH" is intended to include the enzymes that catalyze the oxidation of aldehydes. Aldehyde dehydrogenase enzymes include "acetaldehyde dehydrogenase", which catalyzes the conversion of acetaldehyde into acetyl-CoA. Very commonly, the same enzyme catalyzes the reverse reaction from acetyl-CoA to acetaldehyde, which is the direction more relevant to fermentation. Aldehyde dehydrogenase includes those enzymes that correspond to EC 1.2.1.3, 1.2.1.4 and 1.2.1.10.

As used herein, the term "glycerol-3-phosphate dehydrogenase" or "GPD" is intended to include those enzymes capable of converting dihydroxyacetone phosphate to glycerol-3-phosphate. GPD includes those enzymes that correspond to EC 1.1.1.8. In some embodiments, the GPD is GPD1 and/or GPD2 from *S. cerevisiae* (GDP1: SEQ ID NO. 4 and 5, GDP2: SEQ ID NO: 6 and 7).

As used herein, the term "glycerol-3-phosphate phosphatase" or "GPP" is intended to include those enzymes capable of converting glycerol-1-phosphate to glycerol. Glycerol-3-phosphate is intended to include those enzymes that correspond to EC 3.1.3.21. (GPP1: SEQ ID NO: 158 and 159, GPP2: SEQ ID NO 160 and 161)

As used herein, the term "formate dehydrogenase" or "FDH" is intended to include those enzymes capable of converting formate to bicarbonate (carbon dioxide). Formate dehydrogenase includes those enzymes that correspond to EC 1.2.1.43 and EC 1.2.1.2. In some embodiments, the FDH is from *S. cerevisiae* (FDH1: SEQ ID NO: 1 and 2, FDH2: SEQ ID NO: 3).

As used herein, the term "bifunctional" is intended to include enzymes that catalyze more than one biochemical reaction step. A specific example of a bifunctional enzyme used herein is an enzyme (adhE) that catalyzes both the alcohol dehydrogenase and acetaldehyde dehydrogenase reactions, and includes those enzymes that correspond to EC 1.2.1.10 and 1.1.1.1. In some embodiments, the bifunctional acetaldehyde-alcohol dehydrogenase is from *B. adolescentis* (adhE: SEQ ID NO: 12, and 13). In some embodiments, the bifunctional enzyme is a NADPH specific bifunctional acetaldehyde-alcohol dehydrogenase, and includes those enzymes that correspond to EC L2.1.10 and 1.1.1.2. In some embodiments, the NADPH specific bifunctional acetaldehyde-alcohol dehydrogenase is from *L. mesenteroides* (SEQ ID NO: 14 and 15) or *O. oenii* (SEQ NO: 16 and 17).

As used herein, the term "pyruvate formate lyase" or "PFL" is intended to include the enzymes capable of converting pyruvate to formate and acetyl-CoA. PFL includes those enzymes that correspond to EC 2.3.1.54 and exemplified by SEQ ID NO: 8 and 9.

As used herein, the term "PFL-activating enzymes" is intended to include those enzymes capable of aiding in the activation of PFL. PFL-activating enzymes include those enzymes that correspond to EC 1.97.1.4 and are exemplified by SEQ ID NO: 10 and 11.

As used herein, the term "glutamate dehydrogenase", "GDH", or "GLDH" is intended to include those enzymes that convert glutamate to α-ketoglutarate, as well as those enzymes that catalyze the reverse reaction. The glutamate dehydrogenase can be NADPH-dependent (e.g. GDH1 or GDH3 in *S. cerevisiae*). The glutamate dehydrogenase can be NADH-dependent (e.g. GDH2 in *S. cerevisiae*). Glutamate dehydrogenases include those enzymes that correspond to EC 1.4.1.2 and EC 1.4.1.4. Glutamate dehydrogenases include those enzymes that correspond to accession numbers: M10590, S66436, S66039.1, U12980, NP_015020, NP_010066, S66039.1 and AAC04972. In some embodiments, the glutamate dehydrogenase is from *S. cerevisiae* (GDH1: SEQ ID NOs. 25 and 25; GDH2: SEQ ID NOs 26 and 27; GDH3: SEQ ID NOs. 30 and 31.) or *N. crassa* (GDH2: SEQ ID NOs: 28 29).

As used herein, the term "glutamate synthase" or "GLT" is intended to include those enzymes that convert L-glutamine and 2-oxoglutarate to L-glutamate, as well as those enzymes that catalyze the reverse reaction. Glutamate synthases include those enzymes that correspond to EC 1.4.1.14 and EC 1.4.1.13. In some embodiments, the glutamate synthase is GLT1 from *S. cerevisiae* (SEQ ID NOs: 32 and 33; accession numbers: X89221 and NP_010110.1).

As used herein, the term "glutamine synthase", "glutamine synthetase", or "GLN" is intended to include those enzymes that convert glutamate to glutamine. Glutamine synthases include those enzymes that correspond to EC 6.3.1.2. In some embodiments, the glutamine synthase is GLN1 from *S. cerevisiae* (SEQ ID NOs. 34 and 35; accession numbers: M65157 and NP_015360.2).

As used herein, the term "urea-amido lyase" is intended to include those enzymes that convert urea to urea-1-carboxylate. Urea-amido lyases include those enzymes that correspond to EC 6.3.4.6. In some embodiments, the urea-amido lyase is DUR1/2 (DUR1,2) from *S. cerevisiae* (SEQ ID NOs: 36 and 37; accession numbers: M64926 and NP_009767.1)

As used herein, the term "urea transporter" is a membrane protein that transports urea across a cellular membrane. In some embodiments, the urea transporter is Dur3 or Dur4 from *S. cerevisiae* (DUR3: SEQ ID NOs. 38 and 39; accession numbers: AY693170 and NP_011847.1).

As used herein, the term "protease" is any enzyme that hydrolyzes the peptide bonds between amino acids together in a protein. An exoprotease is a protease that breaks the peptide bonds of terminal amino acids in a protein. An endoprotease is a protease that breaks the peptide bonds of non-terminal amino acids in a protein. Proteases include those enzymes that correspond to EC 3.4.23.41. Proteases include those enzymes that correspond to accession numbers: NP_001151278, NP_001150196, NP_001148706, NCU00338, XP_001908191, XP_369812, EU9700941, NM_001156724, NM_001155234.1, XP_957809.2, XM_001908156.1, and XM_003717209.1. In some embodiments, the protease is from *Z. mays* (SEQ ID NOs: 40-45), *N. crassa* (SEQ ID NOs: 46-47), *P. anserine* (SEQ ID NOs: 48-49), or *M. oryzae* (SEQ ID NOs: 50-51).

As used herein, the term "glucoamylase" or "γ-amylase" refers to an amylase that acts on α-1,6-glycosidic bonds. Glucoamylases include those enzymes that correspond to EC 3.2.1.3. In some embodiments, the glucoamylase is *S. fibuligera* glucoamylase (glu-0111-CO) (SEQ ID NO: 162 and 163).

As used herein, the term "permease" refers to a membrane transport protein that facilitates the diffusion of a molecule through the use of passive transport in or out of a cell. In some embodiments, the permease is the amino acid permease GAP1 from *S. cerevisiae*. (SEQ ID NO: 52 and 53).

As used herein, the term "ammonium transporter" refers to permeases, and is intended to include the enzymes that are involved in the transport of ammonium and ammonia, and are exemplified by the *S. cerevisiae* MFP1, MEP2 and MEP3 enzymes (MEP 1: SEQ ID NOs: 18 and 19; MFP2 SEQ ID NOs: 20 and 21; MFP3 SEQ ID NOs: 22 and 23). Ammonium transporters include those enzymes that correspond to accession numbers: X77608, X83608, AY69277S, NP_011636.3, NP_014257.1, and NP_015464.1.

As used herein, the term "URE2" refers to transcription factor known in the an by that name that represses the nitrogen catabolism of glutamate by controlling the transcription factor. URE2 is a regulator of GLN3. In some embodiments, the URF2 is from *S. cerevisiae* (SEQ ID NOs: 54 and 55).

As used herein, "AUA1" refers to a transcription factor known in the art by that name which is required for the negative regulation of Gap1. In some embodiments, the AUA1 is from *S. cerevisiae* (SEQ ID NOs: 56 and 57).

As used herein, "GLN3" refers to a transcription factor known in the art by that name that activates genes that are regulated by nitrogen catabolite metabolism. In some embodiments, the GLN3 is from *S. cerevisiae* (SEQ ID NOs. 156 and 157). The term "feedstock" is defined as a raw material or mixture of raw materials supplied to a microorganism or fermentation process from which other products can be made. F or example, a carbon source, such as biomass or the carbon compounds derived from biomass are a feedstock for a microorganism that produces a product in a fermentation process. A feedstock can contain nutrients other than a carbon source.

Biomass can include any type of biomass known in the art or described herein. The terms "lignocellulosic material," "lignocellulosic substrate" and "cellulosic biomass" mean any type of carbon containing feed stock including woody biomass, such as recycled wood pulp fiber, sawdust, hardwood, softwood, grasses, sugar-processing residues, agricultural wastes, such as, but not limited to, rice straw, rice hulls, barley-straw, corn cobs, cereal straw, wheat straw, canola straw, oat straw, oat hulls, corn fiber, stover, succulents, agave, or any combination thereof.

The term "yield" is defined as the amount of product obtained per unit weight of raw material and may be expressed as gram product per gram substrate (g/g). Yield may be expressed as a percentage of the theoretical yield. "Theoretical yield" is defined as the maximum amount of product that can be generated per a given amount of substrate as dictated by the stoichemistry of the metabolic pathway used to make the product. For example, the theoretical yield for one typical conversion of glucose to ethanol is 0.51 g EtOH per 1 g, glucose. As such, a yield of 4.8 g ethanol from 10 g of glucose would be expressed as 94% of theoretical or 94% theoretical yield.

The term "titer" is defined as the strength of a solution or the concentration of a substance in solution. For example, the titer of a product in a fermentation broth is described as gram of product in solution per liter of fermentation broth or as g/kg broth.

As used herein, the term "flux" is the rate of flow of molecules through a metabolic pathway, akin to the flow of material in a process.

"Bacteria", or "eubacteria", refers to a domain of prokaryotic organisms. Bacteria include gram-positive (gram+) bacteria and gram-negative (gram−) bacteria.

"Yeast" refers to a domain of eukaryotic organisms that are unicellular fungi.

The terms "derivative" and "analog" refer to a polypeptide differing from the enzymes of the invention, but retaining essential properties thereof. Generally, derivatives and analogs are overall closely similar, and, in many regions, identical to the enzymes of the invention. The terms "derived from", "derivative" and "analog" when referring to enzymes of the invention include any polypeptides which retain at least some of the activity of the corresponding native polypeptide or the activity of its catalytic domain.

Derivatives of enzymes disclosed herein are polypeptides which may have been altered so as to exhibit features not found on the native polypeptide. Derivatives can be covalently modified by substitution (e.g. amino acid substitution), chemical, enzymatic, or other appropriate means with a moiety other than a naturally occurring amino acid (e.g., a detectable moiety such as an enzyme or radioisotope). Examples of derivatives include fusion proteins, or proteins which are based on a naturally occurring protein sequence, but which have been altered. F or example, proteins can be designed by knowledge of a particular amino acid sequence, and/or a particular secondary, tertiary, and quaternary structure. Derivatives include proteins that are modified based on the knowledge of a previous sequence, natural or synthetic, which is then optionally modified often, but not necessarily to confer some improved function. These sequences, or proteins, are then said to be derived from a particular protein or amino acid sequence. In some embodiments of the invention, a derivative must retain at least about 50% identity, at least about 60% identity, at least about 70% identity, at least about 80% identity, at least about 90% identity, at least about 95% identity, at least about 97% identity, or at least about 99% identity to the sequence the derivative is "derived from." In some embodiments of the invention, an enzyme is said to be derived from an enzyme naturally found in a particular species if, using molecular genetic techniques, the DNA sequence for part or all of the enzyme is amplified and placed into a new host cell.

"Isolated" from, as used herein, refers to a process whereby, using molecular biology techniques, genetic material is harvested from a particular organism often with the end goal of putting the general material into a non-native environment.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences.

As known in the art, "similarity" between two polypeptides is determined by comparing the amino acid sequence and conserved amino acid substitutes thereto of the polypeptide to the sequence of a second polypeptide.

"Identity" and "similarity" can be readily calculated b known methods, including but not limited to those described in: Computational Molecular Biology (Lesk, A. M., ed.) Oxford University Press NY (1988); Biocomputing: Informatics and Genome Projects (Smith, D. W., ed.) Academic Press, NY (1993); Computer Analysis of Sequence Data, Part I (Griffin, A. M., and Griffin, H. G., eds.) Humana Press, NJ (1994), Sequence Analysis in Molecular Biology (von Heinje, G., ed,) Academic Press (1987); and Sequence Analysis Primer (Gribskov, M. and Devereux, J., eds.) Stockton Press, NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignments of the sequences disclosed herein were performed using the Clustal method of alignment (Higgins and Sharp (1989) CABIOS. 5:151-153) with the default parameters (GAP PENALTY=10, GAP LENGTH PENALTY=10). Default parameters for pairwise alignments using the Clustal method were KTUPLE 1, GAP PENALTY=3. WINDOW=5 and DIAGONALS SAVED=5.

Suitable nucleic acid sequences or fragments thereof (isolated polynucleotides of the present invention) encode polypeptides that are at least about 70% to 75% identical to the amino acid sequences disclosed herein, at least about 80% at least about 85%, or at least about 90% identical to the amino acid sequences disclosed herein, or at least about 95%, at least about 96%, at least about 97%, at least about 98%, at least about 99%, or at least about 100% identical to the amino acid sequences disclosed herein. Suitable nucleic acid fragments are at least about 70%, at least about 75%, or at least about 80% identical to the nucleic acid sequences disclosed herein, at least about 80%, at least about 85%, or at least about 90% identical to the nucleic acid sequences disclosed herein, or at least about 95%, at least about 96%, at least about 97%, at least about 98%, at least about 99%, or at least about 100% identical to the nucleic acid sequences disclosed herein. Suitable nucleic acid fragments not only have the above identities/similarities but typically encode a polypeptide having at least about 50 amino acids, at least about 100 amino acids, at least about 150 amino acids, at least about 200 amino acids, or at least about 250 amino acids.

Codon Optimization

In some embodiments of the present invention, exogenous genes may be codon-optimized in order to express the polypeptide they encode most efficiently in the host cell. Methods of codon optimization are well known in the art. (See, e.g. Welch et al. "Designing genes for successful protein expression." *Methods Enzymol.* 2011, 498:43-66.)

In general, highly expressed genes in an organism are biased towards codons that are recognized by the most abundant tRNA species in that organism. One measure of this bias is the "codon adaptation index" or "CAI," which measures the extent to which the codons used to encode each amino acid in a particular gene are those which occur most frequently in a reference set of highly expressed genes from an organism. The Codon Adaptation Index is described in more detail in Sharp et al., "The Codon Adaptation Index, a Measure of Directional Synonymous Codon Usage Bias, and Its Potential Applications." *Nucleic Acids Research* (1987) 15: 1281-1295, which is incorporated by reference herein in its entirety.

A codon optimized sequence may be further modified for expression in a particular organism, depending on that organism's biological constraints. For example, large runs of "As" or "Ts" (e.g., runs greater than 3, 4, 5, 6, 7, 8, 9, or 10 consecutive bases) can effect transcription negatively. Therefore, it can be useful to remove a run by, for example, replacing at least one nucleotide in the run with another nucleotide. Furthermore, specific restriction enzyme sites may be removed for molecular cloning purposes by replacing at least one nucleotide in the restriction site with another nucleotide. Examples of such restriction enzyme sites include PasI, AscI, BamHI, BglII, ExoRI and XhoI. Additionally, the DNA sequence can be checked for direct repeals, inverted repeats and mirror repeats with lengths of about 5, 6, 7, 8, 9 or 10 bases or longer. Runs of "As" or "Ts", restriction sites and/or repeats can be modified by replacing at least one codon within the sequence with the "second best" codons, i.e. the codon that occurs at the second highest frequency for a particular amino acid within the particular organism for which the sequence is being optimized.

Deviations in the nucleotide sequence that comprise the codons encoding the amino acids of any polypeptide chain allow for variations in tire sequence coding for the gene. Since each codon consists of three nucleotides, and the nucleotides comprising DNA are restricted to four specific bases, there are 64 possible combinations of nucleotides, 61 of which encode amino acids (the remaining three codons encode signals ending translation). The "genetic code" which shows which codons encode which amino acids is reproduced herein as Table 1. As a result, many amino acids are designated by more than one codon. For example, the amino acids alanine and proline are coded for by four triplets, serine and arginine by six triplets each, whereas tryptophan and methionine are coded for by just one triplet. This degeneracy allows for DNA base composition to vary over a wide range without altering the amino acid sequence of the proteins encoded by the DNA.

TABLE 1

The Standard Genetic Code

| | T | C | A | G |
|---|---|---|---|---|
| T | TTT Phe(F) | TCT Ser(S) | TAT Tyr (Y) | TGT Cys(C) |
| | TTC" | TCC" | TAC" | TGC |
| | TTA Leu(L) | TCA" | TAA **Ter** | TGA **Ter** |
| | TTG" | TCG" | TAG **Ter** | TGG Trp(W) |
| C | CTT Leu(L) | CCT Pro(P) | CAT His(H) | CGT Arg(R) |
| | CTC" | CCC" | CAC" | CGC" |
| | CTA" | CCA" | CAA Gln(Q) | CGA" |
| | CTG" | CCG" | CAG" | CGG" |
| A | ATT Ile(I) | ACT Thr(T) | AAT Asn(N) | AGT Ser(S) |
| | ATC" | ACC" | AAC" | AGC" |
| | ATA" | ACA" | AAA Lys(K) | AGA Arg(R) |
| | **ATG** Met (M) | ACG" | AAG" | AGG" |
| G | GTT Val(V) | GCT Ala(A) | GAT Asp(D) | GGT Gly(G) |
| | GTC" | GCC" | GAC" | GGC" |
| | GTA" | GCA" | GAA Glu(E) | GGA" |
| | GTG" | GCG" | GAG" | GGG" |

Many organisms display a bias for use of particular codons to code for insertion of a particular amino acid in a growing peptide chain. Codon preference or codon bias, differences in codon usage between organisms, is afforded by degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

Host Cells

In some embodiments of the invention, the host cell is a eukaryotic microorganism. In some embodiments, the host cell is a yeast. In some embodiments, the host cell is able to digest and ferment cellulose. In some embodiments, the host cell is from the genus *Saccharomyces* In some embodiments, the host cell is *Saccharomyces cerevisiae.*

In some embodiments, the host cells of the invention are cultured at a temperature above about 20° C., above about 25° C., above about 27° C., above about 30° C., above about 33° C., above about 35'C, above about 37° C., above about 40° C., above about 43° C., above about 45° C., or above about 47° C. In some embodiments, the host cells of the invention contain genetic constructs that lead to the down-regulation of one or more genes encoding a polypeptide at least about 80%, at least about 85%, at least about 90%, at least about 95%, at least about 96%, at least about 97%, at least about 98%, at least about 99%, or about 100% identical to one or more of the polypeptides encoded. SEQ ID NOs: 2, 5, 7, 25, 31, 55, 57, 159 and 161, and the polynucleotide sequence encoded by SEQ ID NO: 3. In some embodiments, the host cells of the invention contain genetic constructs that lead to the expression or up-regulation of a polypeptide encoding the activity associated with EC Nos.: 1.1.1.8, 3.1.3.21, 1.2.1.43, 1.2.1.2, 1.4.1.2, and 1.4.1.4.

In some embodiments, the host cells of the invention contain genetic constructs that lead to the expression or up-regulation of one or more genes encoding a polypeptide at least about 80%, at least about 85%, at least about 90%, at least about 95%, at least about 96%, at least about 97%, at least about 98%, at least about 99%, or about 100% identical to one or more of the polypeptides encoded by SEQ ID NOs: 9, 11, 13, 15, 17, 19, 21, 23, 27, 33, 35, 37, 39, 41, 43, 45, 47, 49, 51, 53, 157, and 163. In some embodiments, the host cells of the invention contain genetic constructs that lead to the expression or up-regulation of a polypeptide encoding the activity associated with EC Nos.: 1.1.1.1, 1.1.1.2, 1.2.1.3, 1.2.1.4, 1.2.1.10, 2.3.1.54, 1.97.1.4, 1.4.1.2, 1.4.1.4, 1.1.1.14, 1.4.1.13, 6.3.1.2, 6.3.4.6, and 3.2.1.3.

In some embodiments, bifunctional acetaldehyde-alcohol dehydrogenase is un-regulated. In some embodiments, the up-regulated bifunctional acetaldehyde-alcohol dehydrogenase is from an enzyme that corresponds to an EC number selected from the group consisting of: EC 1.2.1.0 and 1.1.1.1. In some embodiments, the bifunctional acetaldehyde-alcohol dehydrogenase is a NADPH dependent bifunctional acetaldehyde-alcohol dehydrogenase selected from a group of enzymes having the following Enzyme Commission Numbers: EC 1.2.1.10 and 1.1.1.2. In some embodiments, the bifunctional acetaldehyde-alcohol dehydrogenase corresponds to a polypeptide selected from the group consisting of SEQ ID NOs: 13, 15, and 17. In some embodiments, the bifunctional acetaldehyde-alcohol dehydrogenase is adhE.

In some embodiments, pyruvate formate lyase is up-regulated. In some embodiments, the up-regulated pyruvate formate lyase is from an enzyme that corresponds to EC 2.3.1.54. In some embodiments, the pyruvate formate lyase corresponds to a polypeptide encoded by SEQ ID NO: 2. In some embodiments, pyruvate formate lyase activating enzyme is up-regulated. In some embodiments, the up-regulated pyruvate formate lyase activating enzyme is from an enzyme that corresponds to EC 1.97.1.4. In some embodiments, the pyruvate formate lyase activating enzyme corresponds to a polynucleotide encoded by SEQ ID NO: 3.

In some embodiments, glutamate dehydrogenase is up-regulated, in some embodiments, the glutamate dehydrogenase that is up-regulated is NADH-dependent. In some embodiments, the up-regulated glutamate dehydrogenase corresponds to EC 1.4.1.2. In some embodiments, glutamate dehydrogenase from *S. cerevisiae* is up-regulated. In some embodiments, the glutamate dehydrogenase that is up-regulated is from *S. cerevisiae* is GDH2 and corresponds to a polypeptide corresponding to SEQ ID NO: 29. In some embodiments, glutamate synthase is up-regulated. In some embodiments, the up-regulated glutamate synthase corresponds to EC 1.4.1.14. In some embodiments, glutamate synthase from *S. cerevisiae* is up-regulated. In some embodiments, the glutamate dehydrogenase that is up-regulated is from *S. cerevisiae* is GLT1 and corresponds to a polypeptide corresponding to SEQ ID NO: 33. In some embodiments, glutamine synthase is up-regulated. In some embodiments, the up-regulated glutamine synthase corresponds to EC 6.3.1.2. In some embodiments, glutamine synthase from *S. cerevisiae* is up-regulated. In some embodiments, the glutamine dehydrogenase that is up-regulated is from *S. cerevisiae* is GLN1 and corresponds to a polypeptide corresponding to SEQ ID NO: 35.

In some embodiments, a urea-amido lyase is up-regulated. In some embodiments, the up-regulated urea-amido lyase corresponds to EC 6.3.4.6. In some embodiments, urea-amido lyase from *S. cerevisiae* is up-regulated. In some embodiments, the urea-amido lyase that is up-regulated is from *S. cerevisiae* is DUR1/2 and corresponds to a polypeptide corresponding to SEQ ID NO: 37.

In some embodiments, a protease is up-regulated. In some embodiments, the up-regulated protease corresponds to EC 3.4.23.41. In some embodiments, the protease is an endoprotease. In some embodiments, the protease is an exoprotease. In some embodiments, a protease from *Z. mays, N. crassa, P. anserine*, or *M. oryzae* is up-regulated. In some embodiments, the protease that is up-regulated corresponds to a polypeptide corresponding to SEQ ID NOs: 41, 43, 45, 47, 49 or 51. In some embodiments, a permease is up-regulated. In some embodiments, a permease from *S. cerevisiae* is up-regulated. In some embodiments, the permease that is up-regulated is GAP1 and corresponds to a polypeptide corresponding to SEQ ID NO: 53.

In some embodiments, a glucoamylase is up-regulated. In some embodiments, the up-regulated glucoamylase corresponds to EC 3.2.1.3. In some embodiments, a glucoamylase from *S. fibuligera* is up-regulated. In some embodiments, the glucoamylase from *S. fibuligera* that is up-regulated corresponds to a polypeptide corresponding to SEQ ID NO: 163.

In some embodiments, an ammonium transporter is up-regulated. In some embodiments, an ammonium transporter from *S. cerevisiae* is up-regulated. In some embodiments, the ammonium transporter that is up-regulated is MEP1, MEP2, or MEP3 from *S. cerevisiae* and corresponds to a polypeptide corresponding to SEQ ID NOs: 19, 21, and 23. In some embodiments, a urea transporter is up-regulated. In some embodiments, a urea transporter from is from *S. cerevisiae*. In some embodiments, the urea transporter that is up-regulated is DUR3 or DUR4 from *S. cerevisiae* and corresponds to a polypeptide corresponding to SEQ ID NOs: 39.

In some embodiments, glycerol-3-phosphate dehydrogenase is down-regulated. In some embodiments, the down-regulated Gpd is from an enzyme that corresponds to EC 1.1.1.8. In some embodiments, the glycerol-3-phosphate dehydrogenase is selected from the group consisting of glycerol-3-phosphate dehydrogenase 1 ("Gpd1"), glycerol-3-phosphate dehydrogenase 2 ("Gpd2"), and combinations thereof. In some embodiments, the Gpd1 is from *S. cerevisiae* and corresponds to a polypeptide encoded by SEQ ID NO: 5. In some embodiments, the Gpd2 is from *S. cerevisiae* and corresponds to a polypeptide encoded by SEQ ID NO: 7. In some embodiments, formate dehydrogenase is down-regulated. In some embodiments, the down-regulated formate dehydrogenase corresponds to an EC number selected from the group consisting of: EC 1.2.1.43 and EC 1.2.1.2. In some embodiments, formate dehydrogenase from *S. cerevisiae* is down-regulated. In some embodiments, the formate dehydrogenase from *S. cerevisiae* corresponds to a polypeptide corresponding to SEQ ID NO: 2 or a polynucleotide corresponding to SEQ ID NO: 3. In some embodiments, glycerol-3-phosphate phosphatase is down-regulated. In some embodiments, the down-regulated glycerol-3-phosphate phosphatase corresponds to EC 3.1.3.21. In some embodiments, the down-regulated glycerol-3-phosphate phosphatase corresponds to a polynucleotide corresponding to SEQ ID NOs 158 or 160 or a polypeptide corresponding to SEQ ID NOs 159 or 161.

In some embodiments, glutamate dehydrogenase is down-regulated. In some embodiments, the glutamate dehydrogenase that is down-regulated is NADPH-dependent. In some embodiments, the down-regulated glutamate dehydrogenase corresponds to EC 1.4.1.4. In some embodiments, glutamate dehydrogenase that is down-regulated is from *S. cerevisiae*. In some embodiments, the glutamate dehydrogenase is from *S. cerevisiae* is GDH1 and corresponds to a polypeptide corresponding to SEQ ID NO. 25.

In some embodiments, a regulatory element is down-regulated. In some embodiments, the regulatory element that is down-regulated is from *S. cerevisiae*. In some embodiments, the regulatory element from *S. cerevisiae* is Ure2 and corresponds to a polypeptide corresponding to SEQ ID NO: 55. In some embodiments, the regulatory element from *S. cerevisiae* is Aua1 and corresponds to a polypeptide corresponding to SEQ ID NO: 57.

In some embodiments, bifunctional acetaldehyde-alcohol dehydrogenase (AdhE), *B. adolescentis* pyruvate formate lyase, and *B. adolescentis* pyruvate formate lyase activating enzyme are up-regulated, and Gpd1 and Gpd1 are down-regulated. In some embodiments, AdhE, *B. adolescentis* pyruvate formate lyase, and *B. adolescentis* pyruvate formate lyase activating enzyme are up-regulated, and Gpd1, Gpd2, Fdh1 and Fdh2 are down-regulated. In some embodiments. AdhE, *B. adolescentis* pyruvate formate lyase, and *B. adolescentis* pyruvate formate lyase activating enzyme are up-regulated. Gpd1, Gpd2, Fdh1 and Fdh2 are down-regulated, GPD1 is expressed under the control of the GPD2 promoter, and GPD2 is expressed under the control of the GPD1 promoter. In some embodiments, AdhE, *B. adolescentis* pyruvate formate lyase, and *B. adolescentis* pyruvate formate lyase activating enzyme are up-regulated, Gpd1, Gpd2, Fdh1, Fdh2, Gdh1 are down-regulated, GPD1 is expressed under the control of the GPD2 promoter, and GPD2 is expressed under the control of the GPD1 promoter. In some embodiments, AdhE, *B. adolescentis* pyruvate formate lyase, and *B. adolescentis* pyruvate formate lyase activating enzyme, and Glt1 are up-regulated. Gpd1, Gpd2, Fdh1, Fdh2, Gdh1 are down-regulated. GPD1 is expressed under the control of the GPD2 promoter, and GPD2 is expressed under the control of the GPD1 promoter. In some embodiments, AdhE, *B. adolescenlis* pyruvate formate lyase, and *B. adolescentis* pyruvate formate lyase activating enzyme, and Gln1 are up-regulated, Gpd1, Gpd2, Fdh1, Pdh2, Gdh1 are down-regulated, GPD1 is expressed under tire control of the GPD2 promoter, and GPD2 is expressed under the control of the GPD1 promoter. In some embodiments. AdhE, *B. adolescentis* pyruvate formate lyase, and *B. adolescentis* pyruvate formate lyase activating enzyme. Gln1 and Glt1 are up-regulated, Gpd1, Gpd2, Fdh1, Fdh2, Gdh1 are down-regulated, GPD1 is expressed under the control of the GPD2 promoter, and GPD2 is expressed under the control of the GPD1 promoter. In some embodiments, the regulatory element Ure2 is down-regulated. In some embodiments, the regulatory element Aua1 is down-regulated. In some embodiments, Gln3 is up-regulated.

In some embodiments, AdhE, *B. adolescentis* pyruvate formate lyase, and *B. adolescentis* pyruvate formate lyase activating enzyme are up-regulated, and Gpd2, Fdh1, and Fdh2 are down-regulated. In some embodiments, AdhE, *B. adolescentis* pyruvate formate lyase, and *B. adolescenlis* pyruvate formate lyase activating enzyme are up-regulated, and Gpd2, Fdh1, Fdh2, and Gdh1 are down-regulated. In some embodiments, AdhE, *B. adolescentis* pyruvate formate lyase, and *B. adolescentis* pyruvate formate lyase activating enzyme are up-regulated, and Gpd1, Fdh1, and Fdh2 are down-regulated. In some embodiments, AdhE, *B. adolescentis* pyruvate formate lyase, and *B. adolescentis* pyruvate formate lyase activating enzyme are up-regulated, and Gpd1, Fdh1, Fdh2, and Gdh1 are down-regulated. In some embodiments. Dur1/2 is additionally expressed. In some embodiments, Dur1/2 is expressed from the TEF2 promoter. In some embodiments, Dur1/2 is expressed from the HXT7 promoter. In some embodiments, Dur1/2 is expressed from the GPM1 promoter. In some embodiments. Dur1/2 is expressed from the ADH1 promoter. In some embodiments, Dur1/2 is expressed from the HXT7/TEF2 promoters. In some embodiments, Gln3 is up-regulated. In some embodiments, GPD1 is expressed from the GPD2 promoter, in some embodiments, GPD2 is expressed from a GPD1 promoter.

Ethanol Production

For a microorganism to produce ethanol most economically, it is desired to produce a high yield. In one embodiment, the only product produced is ethanol. Extra products lead to a reduction in product yield and an increase in capital and operating costs, particularly if the extra products have little or no value. Extra products also require additional capital and operating costs to separate these products from ethanol.

Ethanol production can be measured using any method known in the art. For example, the quantity of ethanol in fermentation samples can be assessed using HPLC analysis. Additionally, many ethanol assay kits are commercially available, for example, alcohol oxidase enzyme based assays. Methods of determining ethanol production are within the scope of those skilled in the art from the teachings herein.

In some embodiments of the invention where redirected carbon flux generates increased ethanol production, the ethanol output can be improved by growth-coupled selection. For example, continuous culture or serial dilution cultures can be performed to select for cells that grow faster and/or produce ethanol (or any desired product) more efficiently on a desired feedstock.

One embodiment of the present invention relates to a method of producing ethanol using a microorganism described herein wherein the microorganism is cultured in the presence of a carbon containing feedstock for sufficient time to produce ethanol and, optionally, extracting the ethanol. In some embodiments, nitrogen is added to the culture containing the recombinant microorganism and the feedstock.

Ethanol may be extracted by methods known in the art. (See, e.g., U.S. Appl. Pub. No. 2011/0171709, which is incorporated herein by reference in its entirety.)

Another embodiment of the present invention relates to a method of producing ethanol using a co-culture composed of at least two microorganisms in which at least one of the organisms is an organism described herein, and at least one of the organisms is a genetically distinct microorganism. In some embodiments, the genetically distinct microorganism is a yeast or bacterium. In some embodiments the genetically distinct microorganism is any organism from the genus *Issatchenkia, Pichia, Clavispora, Candida, Hansenula, Kluyveromyces, Saccharomyces, Trichoderma, Thermoascus, Escherichia, Clostridium, Caldicellulosiruptor, Thermoanaerobacter* and *Thermoanaerobacterium.*

In some embodiments, the recombinant microorganism produces about 2% to about 3% higher ethanol titer than a wildtype, non-recombinant organism; at least about 1% to at least about 2% higher ethanol titer than a wildtype, non-recombinant organism; at least about 1% to at least about 5% higher ethanol titer than a wildtype, non-recombinant organism; at least about 1% to at least about 7% higher ethanol titer than a wildtype, non-recombinant organism; at least about 1% to at least about 10% higher ethanol titer than a wildtype, non-recombinant organism; at least about 1% to at least about 15% higher ethanol titer than a wildtype, non-recombinant organism; at least about 1% to at least about 20% higher ethanol titer than a wildtype, non-recombinant organism; at least about 1% to at least about 30% higher ethanol titer than a wildtype, non-recombinant organism; at least about 1% to at least about 50% higher ethanol titer than a wildtype, non-recombinant organism; at least about 1% to at least about 75% higher ethanol titer than a wildtype, non-recombinant organism; at least about 1% to at least about 100% higher ethanol titer than a wildtype, non-recombinant organism. In some embodiments, the recombinant microorganism produces at least about 0.5 g/L ethanol to at least about 2 g/L ethanol, at least about 0.5 g/L ethanol to at least about 3 g/L, ethanol, at least about 0.5 g/L ethanol to at least about 5 g/L ethanol, at least about 0.5 g/L ethanol to at least about 7 g/L ethanol, at least about 0.5 g/L ethanol to at least about 10 g/L ethanol, at least about 0.5 g/L ethanol to at least about 15 g/L ethanol, at least about 0.5 g/L ethanol to at least about 20 g/L ethanol, at least about 0.5 g/L ethanol to at least about 30 g/L ethanol, at least about 0.5 g/L ethanol to at least about 40 g/L ethanol, at least about 0.5 g/L ethanol to at least about 50 g/L ethanol, at least about 0.5 g/L ethanol to at least about 75 g/L ethanol, at least about 0.5 g/L ethanol to at least about 99 g/L ethanol, at least about 0.5 g/L ethanol to at least about 125 g/L ethanol, or at least about 0.5 g/L to at least about 150 g/L ethanol per at least about 24 hour, at least about 48 hour, or at least about 72 hour incubation on a carbon-containing feed stock, such as corn mash.

In some embodiments, the recombinant microorganism produces ethanol at least about 55% to at least about 75% of theoretical yield, at least about 50% to at least about 80% of theoretical yield, at least about 45% to at least about 85% of theoretical yield, at least about 40% to at least about 90% of theoretical yield, at least about 35% to at least about 95% of theoretical yield, at least about 30% to at least about 99% of theoretical yield, or at least about 25% to at least about 99% of theoretical yield. In some embodiments, methods of producing ethanol can comprise contacting a biomass feedstock with a host cell or co-culture of the invention and additionally contacting the biomass feedstock with externally produced saccharolytic enzymes. In some embodiments, the host cells are genetically engineered transduced, transformed, or transfected) with the polynucleotides encoding saccharolytic enzymes.

An "amylolytic enzyme" can be any enzyme involved in amylase digestion, metabolism and/or hydrolysis. The term "amylase" refers to an enzyme that breaks starch down into sugar. Amylase is present in human saliva, where it begins the chemical process of digestion. Foods that contain much starch but little sugar, such as rice and potato, taste slightly sweet as they are chewed because amylase turns some of their starch into sugar in the mouth. The pancreas also makes amylase (α-amylase) to hydrolyse dietary starch into disaccharides and trisaccharides which are converted by other enzymes to glucose to supply the body with energy. Plants and some bacteria also produce amylase. All amylases are glycoside hydrolases and act on α-1,41-glycosidic bonds. Some amylases, such as γ-amylase (glucoamylase), also act on α-1,6-glycosidic bonds. Amylase enzymes include α-amylase (EC 3.2.1.1), β-amylase (EC 3.2.1.2), and γ-amylase (EC 3.2.1.3). The α-amylases are calcium metalloenzymes, unable to function in the absence of calcium. By acting at random locations along the starch chain, α-amylase breaks down long-chain carbohydrates, ultimately yielding maltotriose and maltose from amylose, or maltose, glucose and "limit dextrin" from amylopectin. Because it can act anywhere on the substrate, α-amylase tends to be faster-acting than β-amylase, in animals, it is a major digestive enzyme and its optimum pH is about 6.7-7.0. Another form of amylase, β-amylase is also synthesized by bacteria, fungi, and plants. Working from the non-reducing end, β-amylase catalyzes the hydrolysis of the second α-1,4 glycosidic bond, cleaving off two glucose units (maltose) at a time. Many microbes produce amylase to degrade extracellular starches. In addition to cleaving the last α(1-4) glycosidic linkages at the nonreducing end of amylose and amylopectin, yielding glucose, γ-amylase will cleave α(1-6) glycosidic linkages. Another amylolytic enzyme is alpha-glucosidase that acts on maltose and other short malto-oligosaccharides produced by alpha-, beta-, and gamma-amylases, converting them to glucose. Another amylolytic enzyme is pullulanase. Pullulanase is a specific kind of glucanase, an amylolytic exoenzyme, that degrades pullulan. Pullulan is regarded as a chain of maltotriose units linked by alpha-1,6-glycosidic bonds. Pullulanase (EC 3.2.1.41) is also known as pullulan-6-glucanohydrolase (debranching enzyme). Another amylolytic enzyme, isopullulanase, hydrolyses pullulan to isopanose (6-alpha-maltosylglucose). Isopullulanase (EC 3.2.1.57) is also known as pullulan 4-glucanohydrolase. An "amylase" can be any enzyme involved in amylase digestion, metabolism and/or hydrolysis, including α-amylase, β-amylase, glucoamylase, pullulanase, isopullulanase, and alpha-glucosidase.

In some embodiments, the recombinant microorganisms of the invention further comprise one or more native and/or heterologous enzymes which encodes a saccharolytic enzyme, including amylases, celluloses, hemicellulases, cellulolytic and amylolytic accessory enzymes, inulinases, levanases, and pentose sugar utilizing enzymes. In one aspect, the saccharolytic enzyme is an amylase, where the amylase is selected from *H. grisea, T. aurantiacus, T. emersonii, T. reesci, C. lacteus, C. formasamus, N. takasagoensis, C. acinaciformis, M. darwinensis, N. walkeri, S. fibuligera, C. luckowense R. speratus, Thermobfida fusca, Clostridum thermocellum, Clostridium cellulolyticum, Clostridum josui, Bacillus pumilis, Cellulomonas fimi, Saccharophagus degradans, Piromyces equii, Neocallimastix particarum* or *Arabidopsis thaliana*. In another aspect, the saccharolytic enzyme is a glucoamylase (glu-0111-CO) from *S. fibuligera.*

The term "xylanolytic activity" is intended to include the ability to hydrolyze glycosidic linkages in oligopentoses and polypentoses. The term "xylanase" is the name given to a class of enzymes which degrade the linear polysaccharide beta-1,4-xylan into xylose, thus breaking down hemicellulose, one of the major components of plant cell walls. As such, it plays a major role in micro-organisms thriving on plant sources (mammals, conversely, do not produce xylanase). Additionally, xylanases are present in fungi for the degradation of plant matter into usable nutrients. Xylanases include those enzymes that correspond to E.C. Number 3.2.1.8. A "xylose metabolizing enzyme" can be any enzyme involved in xylose digestion, metabolism and/or hydrolysis, including a xylose isomerase, xylulokinase, xylose reductase, xylose dehydrogenase, xylitol dehydrogenase, xylonate dehydratase, xylose transketolase, and a xylose transaldolase protein.

The term "pectinase" is a general term fir enzymes, such as pectolyase, pectozyme and polygalacturonase, commonly referred to in brewing as pectic enzymes. These enzymes break down pectin, a polysaccharide substrate that is found in the cell walls of plants. One of the most studied and widely used commercial pectinases is polygalacturonase. Pectinases are commonly used in processes involving the degradation of plant materials, such as speeding up the extraction of fruit juice from fruit, including apples and sapota. Pectinases have also been used in wine production since the 1960s.

A "saccharolytic enzyme" can be any enzyme involved in carbohydrate digestion, metabolism and/or hydrolysis, including amylases, cellulases, hemicellulases, cellulolytic and amylolytic accessory enzymes, inulinases, levanases, and pentose sugar utilizing enzymes.

"pentose sugar utilizing enzyme" can be any enzyme involved in pentose sugar digestion, metabolism and/or hydrolysis, including xylanase, arabinase, arabinoxylanase, arabinosidase, arabinofuranosidase, arabinoxylanase arabinosidase, and arabinofuranosidase, arabinose isomerase, ribulose-5-phosphate 4-epimerase, xylose isomerase, xylulokinase, xylose reductase, xylose dehydrogenase, xylitol dehydrogenase, xylonate dehydratase, xylose transketolase, and/or xylose transaldolase.

Glycerol Production

In some embodiments of the invention where redirected carbon flux generates increased ethanol production, the glycerol output can be decreased by growth-coupled selection. For example, continuous culture or serial dilution cultures can be performed to select for cells that produce less glycerol on a desired feedstock. Glycerol can be measured, for example, by HPLC analysis of metabolite concentrations.

In some embodiments, the recombinant microorganism produces at least about 20% to at least about 30% less glycerol than a wildtype, non-recombinant organism; at least about 30% to at least about 50% less glycerol than a wildtype, non-recombinant organism; at least about 40% to at least about 60% less glycerol than a wildtype, non-recombinant organism; at least about 50% to at least about 70% less glycerol than a wildtype, non-recombinant organism; at least about 60% to at least about 80% less glycerol than a wildtype, non-recombinant organism; at least about 70% to at least about 90% less glycerol than a wildtype, non-recombinant organism; at least about 75% to at least about 95% less glycerol than a wildtype, non-recombinant organism; at least about 70% to at least about 99% less glycerol than a wildtype, non-recombinant organism; at least about 15% to at least about 30% less glycerol than a wildtype, non-recombinant organism; at least about 10% to at least about 40% less glycerol than a wildtype, non-recombinant organism; at least about 10% to at least about 50% less glycerol than a wildtype, non-recombinant organism; at least about 10% to at least about 60% less glycerol than a wildtype, non-recombinant organism: at least about 10% to at least about 70% less glycerol than a wildtype, non-recombinant organism, at least about 10% to at least about 80% less glycerol than a wildtype, non-recombinant organism; at least about 10% to at least about 90% less glycerol than a wildtype, non-recombinant organism; at least about 10% to at least about 99% less glycerol than a wildtype, non-recombinant organism: at least about 10% to at least about 100% less glycerol than a wildtype, non-recombinant organism; at least about 5% to at least about 100% less glycerol than a wildtype, non-recombinant organism; a t least about 1% to at least about 100% less glycerol than, a wildtype, non-recombinant organism. In some embodiments, the recombinant microorganism produces no glycerol. In some embodiments, the recombinant microorganism has a growth rate at least about ½ to at least about equal to the growth rate of a wildtype, non-recombinant organism, at least about ¼ to at least about equal to the growth rate of a wildtype, non-recombinant organism, at least about ⅛ to at least about equal to the growth rate of a wildtype, non-recombinant organism, at least about 1/10 to at least about equal to the growth rate of a wildtype, non-recombinant organism, at least about 1/25 to at least about equal to the growth rate of a wildtype, non-recombinant organism, at least about 1/50 to at least about equal to the growth rate of a wildtype, non-recombinant organism or at least about 1/100th to at least about equal to the growth rate of a wildtype, non-recombinant organism.

A wildtype-non-recombinant organism produces glycerol at a rate of at least about 8-11 mM glycerol per gram dry cell weight (DCW) during anaerobic growth. In some embodiments, glycerol production is reduced to a rate of between 1-10 mM glycerol per gram dry cell weight during anaerobic growth.

EXAMPLES

Strains used in the follow ing examples were created using Mascoma Assemblies ("MAs"). Schematic diagrams of the MAs can be seen in FIGS. 6-44. Plasmids used to make the MAs can be seen in FIGS. 45-68 and Table 2. Primers used to create the MAs can be seen in Table 3 below and in SEQ ID NOs: 66-155. Strains used in the invention can be seen in Table 4 below. For a general description of molecular methods that could be used to create the strains, see U.S. Application No. 61/728,450 which is incorporated herein by reference.

TABLE 2

Plasmids used to make the MAs.

| Plasmid ID | Description |
|---|---|
| pMU2873 | AGTEF pro-KAN-AGTEF ter/HXT2 pro-TDK-ACT1 ter |
| pMU2819 | AGTEF pro-cloNAT-AGTEF ter/HXT2 pro-TDK-ACT1 ter |
| pMU2908 | PGK1 pro-*S. cerevisiae* GDH2-ENO1 ter |
| pMU2909 | ADH1 pro-*S. cerevisiae* GDH2-PDC1 ter |
| pMU2911 | ADH1 pro-GLN1-PDC1 ter |
| pMU2913 | PGK1 pro-GLT1-ENO1 ter |
| pMU3409 | TEF2 pro-DUR1,2-ADH3 ter |
| pMU3410 | HXT7 pro-DUR1,2-PMA1t |
| pMU3411 | ADH1 pro-DUR1,2-PDC1 ter |
| pMU3459 | ADH1 pro-DUR3-PDC1 ter |
| pMU3460 | ADH1 pro-MEP1-PDC1 ter |
| pMU3461 | ADH1 pro-MEP2-PDC1 ter |
| pMU3463 | ADH1 pro-GAP1-PDC1 ter |
| pMU3464 | TEF2 pro-DUR3-ADH3 ter |
| pMU3465 | TEF2 pro-MEP1-ADH3 ter |
| pMU3466 | TEF2 pro-MEP2-ADH3 ter |
| pMU2468 | TEF2 pro-GAP1-ADH3 ter |
| pMU3471 | TPI pro-DUR3-FBA1 ter |
| PMU3472 | TPI pro-MEP1-FBA1 ter |
| pMU3473 | TPI pro-MEP2-FBA1 ter |
| pMU3475 | TPI pro-GAP1-FBA1 ter |
| pMU3597 | ADH1 pro-*N. crassa* GDH2-PDC1 ter |
| pMU2605 | ADH1 pro-MEP3-PDC1 ter |
| pMU3606 | TEF2 pro-MEP3-ADH3ter |
| pMU3607 | TPI1 pro-MEP3-FBA1 ter |

TABLE 3

Primers used to create MAs.

| SEQ ID | Primer | Sequence 5' to 3' | Description |
|---|---|---|---|
| 66 | X14961 | gcagttaccttttagcacccaac | 5' GDH1 5' flank |
| 67 | X14966 | ggtgtaggtaagcagaatgaggag | 3' GDH1 3' flank |
| 68 | X15464 | GTCCATGTAAAATGATTGCTCCAATGATTGAAAGAGGTTTAGACATTGGCTCTTCATTG | ENOt + PDC1t |
| 69 | X15465 | ctaagctcaatgaagagccaatgtctaaacctctttcaatcattggagcaatcattta | PDC1t + ENOt |
| 70 | X18846 | gtccatgtaaaatgattgctccaatgattgaaaagcacgcagcacgctgtatttacgtat | FCY3' PDC1t |
| 71 | X18847 | AATTAAATACGTAAATACAGCGTGCTGCGTGCTTTTCAATCATTGGAGCAATCATTTTA | PDC1t + FCY3' |
| 72 | X18858 | agccagcttaaagagttaaaaatttcatagctactacttattcccttcgagattatatct | pTP1 + FCY5' |
| 73 | X18859 | GTTCCTAGATATAATCTCGAAGGGAATAAGTAGTAGCTATGAAATTTTTAACTCTTTAA | FCY5' + pTP1 |
| 74 | X18860 | acatcatcttttaacttgaatttattctctagcagcacgcagcacgctgtatttacgtat | FCY3' + FBA1t |
| 75 | X18861 | AATTAAATACGTAAATACAGCGTGCTGCGTGCTGCTAGAGAATAAATTCAAGTTAAAAG | FBA1t + FCY3' |
| 76 | X18869 | AGATCCTGTGGTAGTGCTGTCTGAACAGAA | FCY3' for 2kb |
| 77 | X18955 | ataaaattaaatacgtaaatacagcgtgctgcgtgctcgatttttttctaaaccgtgga | pADH1 + FCY3' rev |
| 78 | X19513 | acttggtgcggtccatgtaaaatgattgctccaatgattgaaaatgaggaagaaatccaa | ADH3t + PDC1t |
| 79 | X19514 | TGAAGGTCATTAGGATTTGGATTTCTTCCTCATTTTCAATCATTGGAGCAATCATTTTAC | PDC1t + ADH3t |

TABLE 3-continued

Primers used to create MAs.

| SEQ ID | Primer | Sequence 5' to 3' | Description |
|---|---|---|---|
| 80 | X19551 | agccagcttaaagagttaaaaatttcatagctagggcgccataaccaaggtatctatag | pTEF2 + FCY5' |
| 81 | X19552 | TGGCGGTCTATAGATACCTTGGTTATGGCGCCCTAGCTATGAAATTTTTAACTCTTTAAG | FCY5' + pTEF2 |
| 82 | X19721 | aaagaaatgtcagagccagaatttcaacaagctaagctttctaactgatctatccaaaa | pPGK + GDH15' |
| 83 | X19722 | TTTTCAGTTTTGGATAGATCAGTTAGAAAGCTTAGCTTGTTGAAATTCTGGCTCTGACAT | GDH15' + pPGK |
| 84 | X19726 | atccgaaatattccacggtttagaaaaaaatcggatgctatgtttgaccaaggtgatgta | GDH13' + pADH1 |
| 85 | X19727 | TTAAAATACATCACCTTGGTCAAACATAGCATCCGATTTTTTTCTAAACCGTGGAATATT | pADH1 + GDH13' |
| 86 | X19948 | aaagaaatgtcagagccagaatttcaacaagctgatgctatgtttgaccaaggtgatgta | GDH13' + GDH15' for deletion |
| 87 | x19949 | TTAAAATACATCACCTTGGTCAAACATAGCATCAGCTTGTTGAAATTCTGGCTCTGACAT | GDH15' + GDH13' for deletion |
| 88 | X19950 | atccgaaatattccacggtttagaaaaaaatcgagcacgcagcacgctgtatttacgtat | FCY3' + pADH1 |
| 89 | X19967 | tgaaggtcattaggatttggatttcttcctcataaattagtgtgtgtgcattatatatat | PMA1t + ADH3t |
| 90 | X19968 | TTTTTAATATATATAATGCACACACACTAATTTATGAGGAAGAAATCCAAATCCTAATGA | ADH3t + PMA1t |
| 91 | X19969 | AATTAAATACGTAAATACAGCGTGCTGCGTGCTCCAGAAAGGCAACGCAAAATTTTTTT | pHXT7 + FCY3' |
| 92 | X19970 | ccctggaaaaaaaattttgcgttgcctttctggagcacgcagcacgctgtatttacgtat | FCY3' + pHXT7 |
| 93 | X20022 | aggtagacgctacagtcacaggtgtcacaact | URE2 5' flank |
| 94 | X20023 | GGACGAGGCAAGCTAAACAGATCTCTAGACCTATTGGTGTACAACTTAATTTGCAGCTTA | URE2 5' flank |
| 95 | X20024 | ccgtttcttttctttggactatcatgtagtctcaggctgctttaaaaacaagaaagaaag | URE2 3' flank |
| 96 | X20025 | GAGTGGGATGCGCATATAGTGCATGAACCTAT | URE2 3' flank |
| 97 | X20026 | ttgttttaagctgcaaattaagttgtacaccaaaggctgctttaaaaacaagaaagaaag | URE2 3' + 5' for deletion |
| 98 | X20027 | CTTCTTCTTTCTTTCTTGTTTTTAAAGCAGCCTTTGGTGTACAACTTAATTTGCAGCTTA | URE2 5' + 3' for deletion |
| 99 | X20028 | ttgttttaagctgcaaattaagttgtacaccaataggtctagagatctgtttagcttgcc | pAGTEF + URE2 5' |
| 100 | X20029 | CTTCTTCTTTCTTTCTTGTTTTTAAAGCAGCCTGAGACTACATGATAGTCCAAAGAAAAG | pHXT2rc + URE2 3' |
| 101 | X20043 | ATAAAATTAAATACGTAAATACAGCGTGCTGCGTGCTATGAGGAAGAAATCCAAATCCT | ADH3 t tails for FCY1 3' flank |
| 102 | X20044 | tgaaggtcattaggatttggatttcttcctcatagcacgcagcacgctgtatttacgta | FCY 3' flank tails for ADH3t |
| 103 | X20282 | agccagcttaaagagttaaaaatttcatagctaccagaaaggcaacgcaaaattttttt | pHXT7 + FCY5' |
| 104 | X20283 | CCCTGGAAAAAAAATTTTGCGTTGCCTTTCTGGTAGCTATGAAATTTTTAACTCTTTAAG | FCY5' + pHXT7 |
| 105 | X20284 | tttttaatatatataatgcacacacactaatttagcacgcagcacgctgtatttacgtat | FCY3' + PMA1t |
| 106 | X20285 | AATTAAATACGTAAATACAGCGTGCTGCGTGCTAAATTAGTGTGTGTGCATTATATATAT | PMA1t + FCY3' |
| 107 | X20286 | agccagcttaaagagttaaaaatttcatagctatgtggtagaattcaaaagactatgtga | pGPM1 + FCY5' |
| 108 | X20287 | ATGGCATCACATAGTCTTTTGAATTCTACCACATAGCTATGAAATTTTTAACTCTTTAAG | FCY5' + pGPM1 |
| 109 | X20288 | ttttaatattgcttttcaattactgttattaaaagcacgcagcacgctgtatttacgtat | FCY3' + TPIt |
| 110 | X20289 | AATTAAATACGTAAATACAGCGTGCTGCGTGCTTTTAATAACAGTAATTGAAAAGCAATA | TPIt + FCY3' |
| 111 | X20620 | ggtgattggaatggttatggttccggaatcgc | AUA1 5' Flank |
| 112 | X20621 | GGACGAGGCAAGCTAAACAGATCTCTAGACCTATATACTACATAGAAAGCAATTAAAAGA | AUA15' + pAGTEF |
| 113 | X20622 | ccgtttcttttctttggactatcatgtagtctcctccacctaacaaacccgcaccaacac | AUA13' + pHXT2rc |
| 114 | X20623 | GTCATATGGCCTCTTAACGTGGTCCTTTGTGG | AUA1 3' Flank |

TABLE 3-continued

Primers used to create MAs.

| SEQ ID | Primer | Sequence 5' to 3' | Description |
|---|---|---|---|
| 115 | X20630 | tttttatcttttaattgctttctatgtagtatataggtctagagatctgtttagcttgcc | pAGTEF + AUA1 5' |
| 116 | X20631 | TACTTGGTGTTGGTGCGGGTTTGTTAGGTGGAGGAGACTACATGATAGTCCAAAGAAAAG | pHXT2rc + AUA13' |
| 117 | X20632 | tttttatcttttaattgctttctatgtagtatactccacctaacaaacccgcaccaacac | AUA13' + AUA15' |
| 118 | x20633 | TACTTGGTGTTGGTGCGGGTTTGTTAGGTGGAGTATACTACATAGAAAGCAATTAAAAGA | AUA15' + AUA13' |
| 119 | X21123 | gcgacatgtgatgagattgcatgcacctccacagaa | GDH2 5' Flank |
| 120 | X21124 | GGACGAGGCAAGCTAAACAGATCTCTAGACCTATCTTTATTCTTTTTATTGTTGTGAATT | GDH2 5' Flank + pAGTEF |
| 121 | X21125 | ccgtttcttttctttggactatcatgtagtctcgcttcaataaaattgttttgtataaat | GDH2 3' Flank + pHXT2rc |
| 122 | X21126 | GGCAGCTATCTCTACTATCCCGTTTAGTACTATCC | GDH2 3' Flank |
| 123 | X21127 | atattaaattcacaacaataaaaagaataaagataggtctagagatctgtttagcttgcc | pAGTEF + GDH2 5' |
| 124 | X21128 | GAACTAATTTATACAAAACAATTTTATTGAAGCGAGACTACATGATAGTCCAAAGAAAAG | pHXT2rc + GDH2 3' |
| 125 | X21133 | atattaaattcacaacaataaaaagaataaagagcttcaataaaattgttttgtataaa | GDH2 3' + GDH2 5' for deletion |
| 126 | X21135 | gcattgattgtctatcagagcatatcaaggtggt | GDH3 5' Flank |
| 127 | X21136 | GGACGAGGCAAGCTAAACAGATCTCTAGACCTACGGTGACTGTTGCTACTTCCCTATATA | GDH3 5' Flank + pAGTEF |
| 128 | X21137 | ccgtttcttttctttggactatcatgtagtctcccgtaagcgctattttctttttgttcg | GDH3 3' Flank + pHXT2rc |
| 129 | X21138 | GGCTAGGACCCCGTAAGGAGGAAAGAATAGGCAAG | GDH3 3' Flank |
| 130 | X21139 | tatatatatatagggaagtagcaacagtcaccgtaggtctagagatctgtttagcttgcc | pAGTEF + GDH3 5' |
| 131 | X21140 | TAGTTACGAACAAAAAGAAAATAGCGCTTACGGGAGACTACATGATAGTCCAAAGAAAAG | pHXT2rc + GDH3 3' |
| 132 | X21147 | tatatatatatagggaagtagcaacagtcaccgccgtaagcgctattttctttttgttcg | GDH3 3' + GDH3 5' |
| 133 | X21148 | TAGTTACGAACAAAAAGAAAATAGCGCTTACGGCGGTGACTGTTGCTACTTCCCTATATA | GDH3 5' + GDH3 3' |
| 134 | X21179 | ttgttttaagctgcaaattaagttgtacaccaagggcgccataaccaaggtatctataga | pTEF2 + URE2 5' |
| 135 | X21180 | TGGCGGTCTATAGATACCTTGGTTATGGCGCCCTTGGTGTACAACTTAATTTGCAGCTTA | URE2 5' + pTEF2 |
| 136 | X21181 | CTTCTTCTTTCTTTCTTGTTTTTAAAGCAGCCTCGATTTTTTTCTAAACCGTGGAATATT | pADH1rc + URE2 3' |
| 137 | X21182 | atccgaaatattccacggtttagaaaaaaatcgaggctgctttaaaaacaagaaagaaag | URE2 3' + pADH1rc |
| 138 | X21289 | aaagaaatgtcagagccagaatttcaacaagctaggtctagagatctgtttagcttgcct | pAGTEF + GDH1 5' |
| 139 | X21290 | TTAAAATACATCACCTTGGTCAAACATAGCATCGAGACTACATGATAGTCCAAAGAAAAG | pHXT2rc + GDH1 3' |
| 140 | X21291 | GGGACGAGGCAAGCTAAACAGATCTCTAGACCTAGCTTGTTGAAATTCTGGCTCTGACAT | GDH1 5' + pAGTEF |
| 141 | X21292 | ccgtttcttttctttggactatcatgtagtctcgatgctatgtttgaccaaggtgatgt | GDH1 3' + pHXT2rc |
| 142 | X21319 | ttgttttaagctgcaaattaagttgtacaccaacgatttttttctaaaccgtggaatatt | pADH1 + URE2 5' |
| 143 | X21320 | ATCCGAAATATTCCACGGTTTAGAAAAAAATCGTTGGTGTACAACTTAATTTGCAGCTTA | URE2 5' pADH1 |
| 144 | X21321 | ttttcagttttggatagatcagttagaaagcttaggctgctttaaaaacaagaaagaaag | URE2 3' + PGKprc |
| 145 | X21322 | CTTCTTCTTTCTTTCTTGTTTTTAAAGCAGCCTAAGCTTTCTAACTGATCTATCCAAAAC | PGKprc + URE2 3' |
| 146 | X21507 | GAACTAATTTATACAAAACAATTTTATTGAAGCTCTTTATTCTTTTTATTGTTGTGAATT | GDH25' + GDH23' for deletion |
| 147 | X21735 | agccagcttaaagagttaaaaatttcatagctacgatttttttctaaaccgtggaatatt | pADH1 + FCY5' |
| 148 | X21736 | ATCCGAAATATTCCACGGTTTAGAAAAAAATCGTAGCTATGAAATTTTTAACTCTTTAAG | FCY5' + pADH1 |
| 149 | X21754 | gccaaagtggattctcctactcaagctttgc | FCY5' Flank |

TABLE 3-continued

| SEQ ID | Primer | Sequence 5' to 3' | Description |
|---|---|---|---|
| Primers used to create MAs. | | | |
| 150 | X23319 | aaagaaatgtcagagccagaatttcaacaagctcgattttttttctaaaccgtggaatatt | pADH1 + GDH15' |
| 151 | X23320 | ATCCGAAATATTCCACGGTTTAGAAAAAAAATCGAGCTTGTTGAAATTCTGGCTCTGACAT | GDH1 5' + pADH1 |
| 152 | X23321 | gtccatgtaaaatgattgctccaatgattgaaagatgctatgtttgaccaaggtgatgta | GDH1 3' + PDC1t |
| 153 | X23322 | TTAAAATACATCACCTTGGTCAAACATAGCATCTTTCAATCATTGGAGCAATCATTTTAC | PDC1t + GDH13' |
| 154 | X23408 | TTTTCAGTTTTGGATAGATCAGTTAGAAAGCTTTAGCTATGAAATTTTTAACTCTTTAAG | FCY5' + pPGK |
| 155 | X23409 | agccagcttaaagagttaaaaatttcatagctaaagctttctaactgatctatccaaaac | pPGK + PCY5' |

TABLE 4

| Strain | Description | Genotype | Associated MA Cassette(s) |
|---|---|---|---|
| Strain genotypes. | | | |
| M2390 | Type Strain | WT | |
| M3465 | Glycerol Reduction Strain | Δfdh1::MA0608Δfdh2::MA0280Δgpd2::MA0289 | MA0280, MA0289, MA0608 |
| M3467 | Glycerol Reduction Strain | Δfdh1::MA0608Δfdh2::MA0280Δgpd1::MA0290 | MA0280, MA0290, MA0608 |
| M3469 | Glycerol Reduction Strain | Δfdh1::MA0608Δfdh2::MA0280Δgpd1::MA0293 | MA0280, MA0608, MA0293 |
| M3624 | Glycerol Reduction Strain | Δfdh1::MA0608Δfdh2::MA0280Δgpd1::MA0290Δgpd2::MA0286 | MA0286, MA0280, MA0290, MA0608 |
| M4076 | GDH1 marked deletion | Δfdh1::MA0608Δfdh2::MA0280Δgpd1::MA0290Δgpd2::MA0286Δgdh1::MA0631 | MA0286, MA0280, MA0290, MA0608, MA0631 |
| M4117 | *S. cerevisiae* GDH2 over expression | Δfdh1::MA0608Δfdh2::MA0280Δgpd1::MA0290Δgpd2::MA0286Δgdh1::MA0425 | MA0286, MA0280, MA0290, MA0608, MA0425 |
| M4118 | *S. cerevisiae* GLN1/GLT1 over expression | Δfdh1::MA0608Δfdh2::MA0280Δgpd1::MA0290Δgpd2::MA0286Δgdh1::MA0426 | MA0286, MA0280, MA0290, MA0608, MA0426 |
| M4312 | URE2 marked deletion | Δfdh1::MA0608Δfdh2::MA0280Δgpd1::MA0290Δgpd2::MA0286Δure2::MA0622 | MA0286, MA0280, MA0290, MA0608, MA0622 |
| M4373 | GDH1 marked deletion | Δfdh1::MA0608Δfdh2::MA0280Δgpd2::MA0289Δgdh1::MA0631 | MA0280, MA0289, MA0608, MA0631 |
| M4375 | GDH1 marked deletion | Δfdh1::MA0608Δfdh2::MA0280Δgpd1::MA0290Δgdh1::MA0631 | MA0280, MA0290, MA0608, MA0631 |
| M4377 | GDH1 marked deletion | Δfdh1::MA0608Δfdh2::MA0280Δgpd1::MA0293Δgdh1::MA0631 | MA0280, MA0608, MA0293, MA0631 |
| M4400 | GDH1 clean deletion | Δfdh1::MA0608Δfdh2::MA0280Δgpd2::MA0289Δgdh1::MA0888 | MA0280, MA0289, MA0608, MA0888 |
| M4401 | GDH1 clean deletion | Δfdh1::MA0608Δfdh2::MA0280Δgpd1::MA0290Δgdh1::MA0888 | MA0280, MA0290, MA0608, MA0888 |
| M4402 | GDH1 clean deletion | Δfdh1::MA0608Δfdh2::MA0280Δgpd1::MA0293Δgdh1::MA0888 | MA0280, MA0608, MA0293, MA0888 |
| M4406 | URE2 clean deletion | Δfdh1::MA0608Δfdh2::MA0280Δgpd1::MA0290Δgpd2::MA0286Δure2::MA0622.1 | MA0286, MA0280, MA0290, MA0608, MA0622.1 |
| M4427 | DUR1,2 over expression | Δfdh1::MA0608Δfdh2::MA0280Δgpd1::MA0290Δfcy1::MA0464.1 | MA0280, MA0290, MA0608, MA0464.1 |
| M4428 | DUR1,2 over expression | Δfdh1::MA0608Δfdh2::MA0280Δgpd1::MA0290Δfcy1::MA0465.1 | MA0280, MA0290, MA0608, MA0465.1 |
| M4429 | DUR1,2 over expression | Δfdh1::MA0608Δfdh2::MA0280Δgpd1::MA0290Δfcy1::MA0467.1 | MA0280, MA0290, MA0608, MA0467.1 |
| M4430 | DUR1,2 over expression | Δfdh1::MA0608Δfdh2::MA0280Δgpd1::MA0290Δfcy1::MA0454.14 | MA0280, MA0290, MA0608, MA0454.14 |
| M4431 | DUR1,2 over expression | Δfdh1::MA0608Δfdh2::MA0280Δgpd1::MA0293Δfcy1::MA0464.1 | MA0280, MA0293, MA0608, MA0464.1 |
| M4432 | DUR1,2 over expression | Δfdh1::MA0608Δfdh2::MA0280Δgpd1::MA0293Δfcy1::MA0465.1 | MA0280, MA0293, MA0608, MA0465.1 |
| M4433 | DUR1,2 over expression | Δfdh1::MA0608Δfdh2::MA0280Δgpd1::MA0293Δfcy1::MA0467.1 | MA0280, MA0290, MA0608, MA0467.1 |
| M4434 | DUR1,2 over expression | Δfdh1::MA0608Δfdh2::MA0280Δgpd1::MA0293Δfcy1::MA0454.14 | MA0280, MA0290, MA0608, MA0454.14 |
| M4469 | *S. cerevisiae* GDH2 over expression | Δfdh1::MA0608Δfdh2::MA0280Δgpd2::MA0289Δgdh1::MA0425 | MA0280, MA0289, MA0608, MA0425 |
| M4471 | *S. cerevisiae* GDH2 over expression | Δfdh1::MA0608Δfdh2::MA0280Δgpd1::MA0293Δgdh1::MA0425 | MA0280, MA0608, MA0293, MA0425 |
| M4507 | AUA1 marked deletion | Δfdh1::MA0608Δfdh2::MA0280Δgpd1::MA0290Δgpd2::MA0286Δaua1::MA0617 | MA0286, MA0280, MA0290, MA0608, MA0617 |
| M4538 | GDH1 marked deletion | Δgdh1::MA0631 | MA0631 |
| M4540 | AUA1 marked deletion | Δaua1::MA0617 | MA0617 |
| M4542 | URE2 marked deletion | Δfdh1::MA0608Δfdh2::MA0280Δgpd1::MA0293Δure2::MA0622 | MA0280, MA0608, MA0293, MA0622 |
| M4571 | AUA1 clean deletion | Δfdh1::MA0608Δfdh2::MA0280Δgpd1::MA0290Δgpd2::MA0286Δaua1::MA0617.1 | MA0286, MA0280, MA0290, MA0608, MA0617.1 |
| M4573 | GDH1 clean deletion | Δfdh1::MA0608Δfdh2::MA0280Δgpd1::MA0290Δgpd2::MA0286Δgdh1::MA0888 | MA0286, MA0280, MA0290, MA0608, MA0888 |

TABLE 4-continued

Strain genotypes.

| Strain | Description | Genotype | Associated MA Cassette(s) |
|---|---|---|---|
| M4590 | GDH1 clean deletion | Δgdh1::MA0888 | MA0888 |
| M4591 | AUA1 clean deletion | Δaua1::MA0617.1 | MA0617.1 |
| M4592 | URE2 clean deletion | Δfdh1::MA0608Δfdh2::MA0280Δgpd1::MA0293Δure2::MA0622.1 | MA0280, MA0608, MA0293, MA0622.1 |
| M4614 | URE2 marked deletion | Δfdh1::MA0608Δfdh2::MA0280Δgpd1::MA0290Δgpd2::MA0286Δgdh1::MA0425Δure2::MA0622 | MA0286, MA0280, MA0290, MA0608, MA0425, MA0622 |
| M4615 | URE2 marked deletion | Δfdh1::MA0608Δfdh2::MA0280Δgpd1::MA0290Δgpd2::MA0286Δgdh1::MA0426Δure2::MA0622 | MA0286, MA0280, MA0290, MA0608, MA0426, MA0622 |
| M4616 | URE2 marked deletion | Δure2::MA0622 | MA0622 |
| M4622 | *S. cerevisiae* GDH2 over expression | Δgdh1::MA0425 | MA0425 |
| M4623 | *S. cerevisiae* GLN1/GLT1 over expression | Δgdh1::MA0426 | MA0426 |
| M4624 | *S. cerevisiae* GLN1/GLT1 over expression | Δgdh1::MA0426 | MA0426 |
| M4625 | *S. cerevisiae* GLN1/GLT1 over expression | Δfdh1::MA0608Δfdh2::MA0280Δgpd2::MA0289Δgpd1::MA0426 | MA0280, MA0289, MA0608, MA0426 |
| M4625 | *S. cerevisiae* GLN1/GLT1 over expression | Δfdh1::MA0608Δfdh2::MA0280Δgpd1::MA0293Δgpd1::MA0426 | MA0280, MA0608, MA0293, MA0426 |
| M4626 | *S. cerevisiae* GLN1/GLT1 over expression | Δfdh1::MA0608Δfdh2::MA0280Δgpd1::MA0293Δgpd1::MA0426 | MA0280, MA0608, MA0293, MA0426 |
| M4654 | GDH3 marked deletion | Δgdh3::MA0615 | MA0615 |
| M4655 | GDH2 marked deletion | Δfdh1::MA0608Δfdh2::MA0280Δgpd1::MA0290Δgpd2::MA0286Δgdh1::MA0426Δgdh2::MA0616 | MA0286, MA0280, MA0290, MA0608, MA0426, MA0616 |
| M4656 | GDH3 marked deletion | Δfdh1::MA0608Δfdh2::MA0280Δgpd1::MA0290Δgpd2::MA0286Δgdh1::MA0426Δgdh3::MA0615 | MA0286, MA0280, MA0290, MA0608, MA0426, MA0615 |
| M4657 | GDH3 marked deletion | Δfdh1::MA0608Δfdh2::MA0280Δgpd1::MA0290Δgpd2::MA0286Δgdh1::MA0425Δgdh3::MA0615 | MA0286, MA0280, MA0290, MA0608, MA0425, MA0615 |
| M4674 | URE2 clean deletion | Δfdh1::MA0608Δfdh2::MA0280Δgpd1::MA0290Δgpd2::MA0286Δgdh1::MA0425Δure2::MA0622.1 | MA0286, MA0280, MA0290, MA0608, MA0425, MA0622.1 |
| M4675 | URE2 clean deletion | Δfdh1::MA0608Δfdh2::MA0280Δgpd1::MA0290Δgpd2::MA0286Δgdh1::MA0426Δure2::MA0622.1 | MA0286, MA0280, MA0290, MA0608, MA0426, MA0622.1 |
| M4676 | URE2 clean deletion | Δure2::MA0622.1 | MA0622.1 |
| M4677 | GDH2 marked deletion | Δgdh2::MA0616 | MA0616 |
| M4690 | GDH3 clean deletion | Δgdh3::MA0615.1 | MA0615.1 |
| M4691 | GDH2 clean deletion | Δfdh1::MA0608Δfdh2::MA0280Δgpd1::MA0290Δgpd2::MA0286Δgdh1::MA0426Δgdh2::MA0616.1 | MA0286, MA0280, MA0290, MA0608, MA0426, MA0616.1 |
| M4692 | GDH3 clean deletion | Δfdh1::MA0608Δfdh2::MA0280Δgpd1::MA0290Δgpd2::MA0286Δgdh1::MA0426Δgdh3::MA0615.1 | MA0286, MA0280, MA0290, MA0608, MA0426, MA0615.1 |
| M4693 | GDH3 clean deletion | Δfdh1::MA0608Δfdh2::MA0280Δgpd1::MA0290Δgpd2::MA0286Δgdh1::MA0425Δgdh3::MA0615.1 | MA0286, MA0280, MA0290, MA0608, MA0425, MA0615.1 |
| M4694 | GDH2 clean deletion | Δgdh2::MA0616.1 | MA0616.1 |
| M4748 | DUR3 over expression | Δfcy1::MA0464 | MA0464 |
| M4749 | GAP1 over expression | Δfcy1::MA0464.4 | MA0464.4 |
| M4750 | MEP1 over expression | Δfcy1::MA0464.2 | MA0464.2 |
| M4751 | DUR1,2 over expression | Δfcy1::MA0465.1 | MA0465.1 |
| M4752 | MEP1 over expression | Δfcy1::MA0434.2 | MA0434.2 |
| M4753 | MEP2 over expression | Δfcy1::MA0434.3 | MA0434.3 |
| M4754 | DUR3 over expression | Δfcy1::MA0434 | MA0434 |
| M4755 | GAP1 over expression | Δfcy1::MA0434.4 | MA0434.4 |
| M4756 | MEP2 over expression | Δfcy1::MA0464.2 | MA0464.2 |
| M4810 | DUR3 over expression | Δfcy1::MA0467 | MA0467 |
| M4811 | DUR3 over expression | Δfcy1::MA0467 | MA0467 |
| M4812 | MEP1 over expression | Δfcy1::MA0467.2 | MA0467.2 |
| M4813 | MEP1 over expression | Δfcy1::MA0467.2 | MA0467.2 |
| M4814 | GAP1 over expression | Δfcy1::MA0467.4 | MA0467.4 |
| M4815 | GAP1 over expression | Δfcy1::MA0467.4 | MA0467.4 |
| M5841 | *N. crassa* GDH2 over expression | Δfdh1::MA0608Δfdh2::MA0280Δgpd1::MA0290Δgpd2::MA0286Δgdh1::MA0837 | MA0280, MA0608, MA0286, MA0290, MA0837 |
| M5842 | *N. crassa* GDH2 over expression | Δfdh1::MA0608Δfdh2::MA0280Δgpd1::MA0290Δgpd2::MA0286Δgdh1::MA0837 | MA0280, MA0608, MA0286, MA0290, MA0837 |
| M5843 | *N. crassa* GDH2 over expression | Δfdh1::MA0608Δfdh2::MA0280Δgpd1::MA0290Δgpd2::MA0286Δgdh1::MA0837 | MA0280, MA0608, MA0286, MA0290, MA0837 |
| M5844 | *N. crassa* GDH2 over expression | Δfdh1::MA0608Δfdh2::MA0280Δgpd1::MA0290Δgpd2::MA0286Δgdh1::MA0837 | MA0280, MA0608, MA0286, MA0290, MA0837 |

Example 1

Deletion of GDH1 and Overexpression of GDH2 or GLT1/GLN1

M3624 (Δgpd1::GPD2-*B. adolescentis*pf1A/pF1B/adhEΔgpd2::GPD1 *B. adolescentis*pf1A/pf1B/adhEΔfdh1Δfdh2::*B. adolescentis*pf1A/pf1B/adhE) has an approximately 85% reduction in glycerol formation when grown on >30% solids corn mash. However, the strain is unable to complete the fermentation even after extended incubation periods. Two modifications of the ammonium assimilation pathway were constructed in M3624 and evaluated for fermentation performance. The modifications were a deletion of GDH1 and over-expression of Gdh2, resulting in strain M4117 (M3634 Gdh2; Δgdh1). The second modification was a deletion of GDH1 and overexpression of GLT1 and GLN1, resulting in strain M4118 (M3634 Glt1: Gln1; Δgdh1). These strains were compared to M3624 and the conventional yeast control (M2390 (a wild type unmodified strain isolated from industrial sources)) following fermentation of 31% solids corn mash.

An industrial corn mash was prepared to a final solids concentration of 31% supplemented with penicillin (0.006 mg/mL) and urea (0.5 g/l). Glucoamylase was added at a concentration of 0.6 AGU/gTS. Fermentation was stopped by addition of each strain to an final starting concentration of 0.1 g/l. Vials were capped with a rubber stopper and sealed. A 23-gauge needle was inserted through die stopper to vent and for the safety of the experiment. Vials were incubated at 35° C. with shaking at 125 rpm. At the termination of the experiment samples were prepared for HPLC analysis of ethanol and residual sugars.

The results in FIG. 69 illustrate that both M4117 and M4118 reach a much higher final ethanol titer than M3624, which was unable to complete the fermentation. Relative to M2390 both M4117 and M4118 had ethanol titers that were 4.2% and 5.2% higher respectively.

Example 2

Deletion of GDH1

Figure 1:
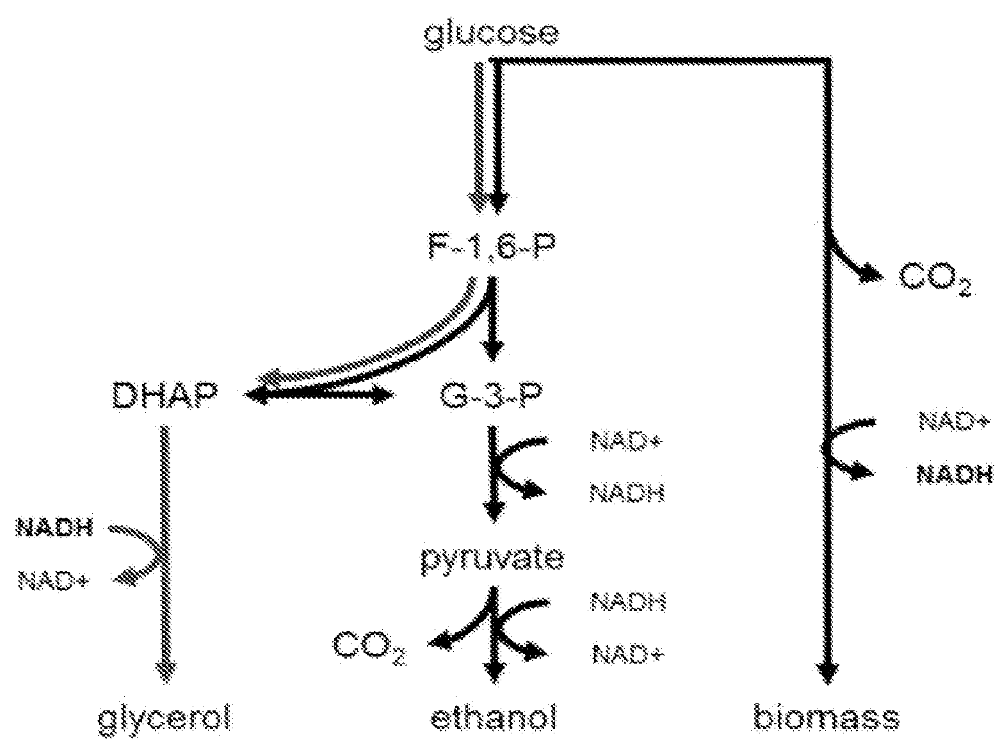
Figure 2:
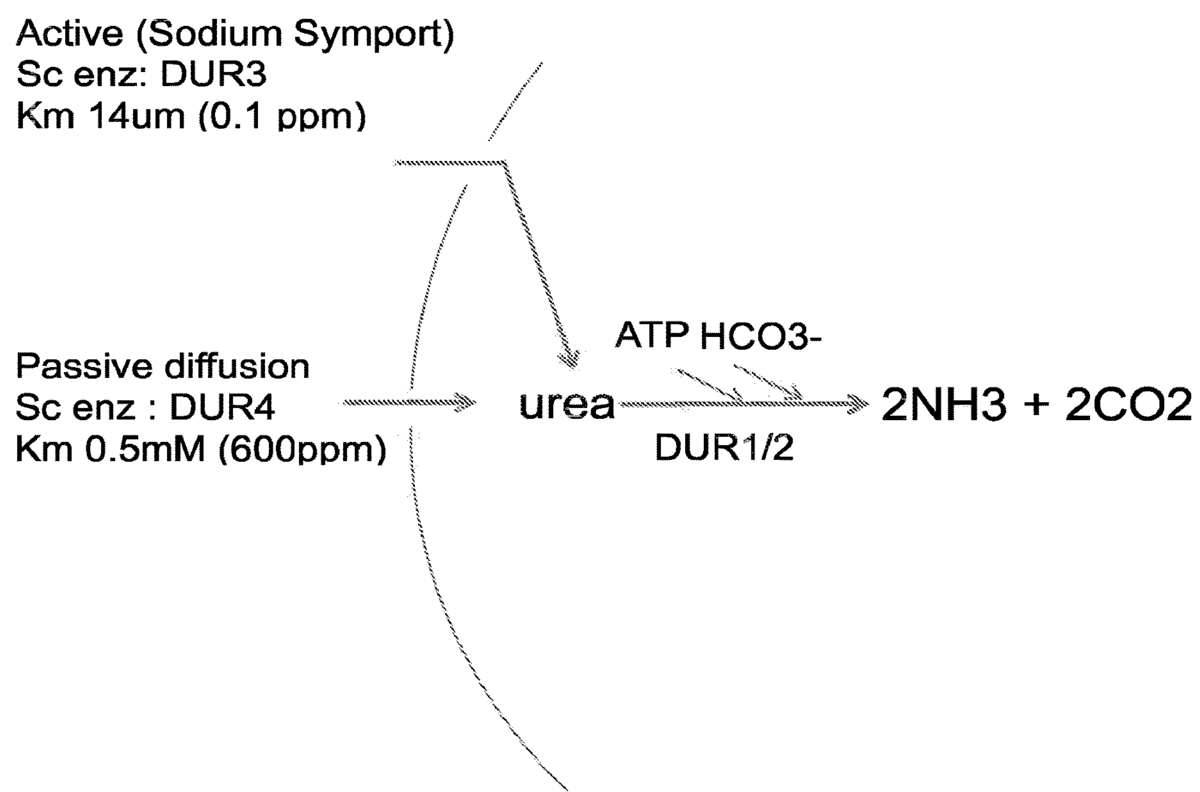
Figure 3:
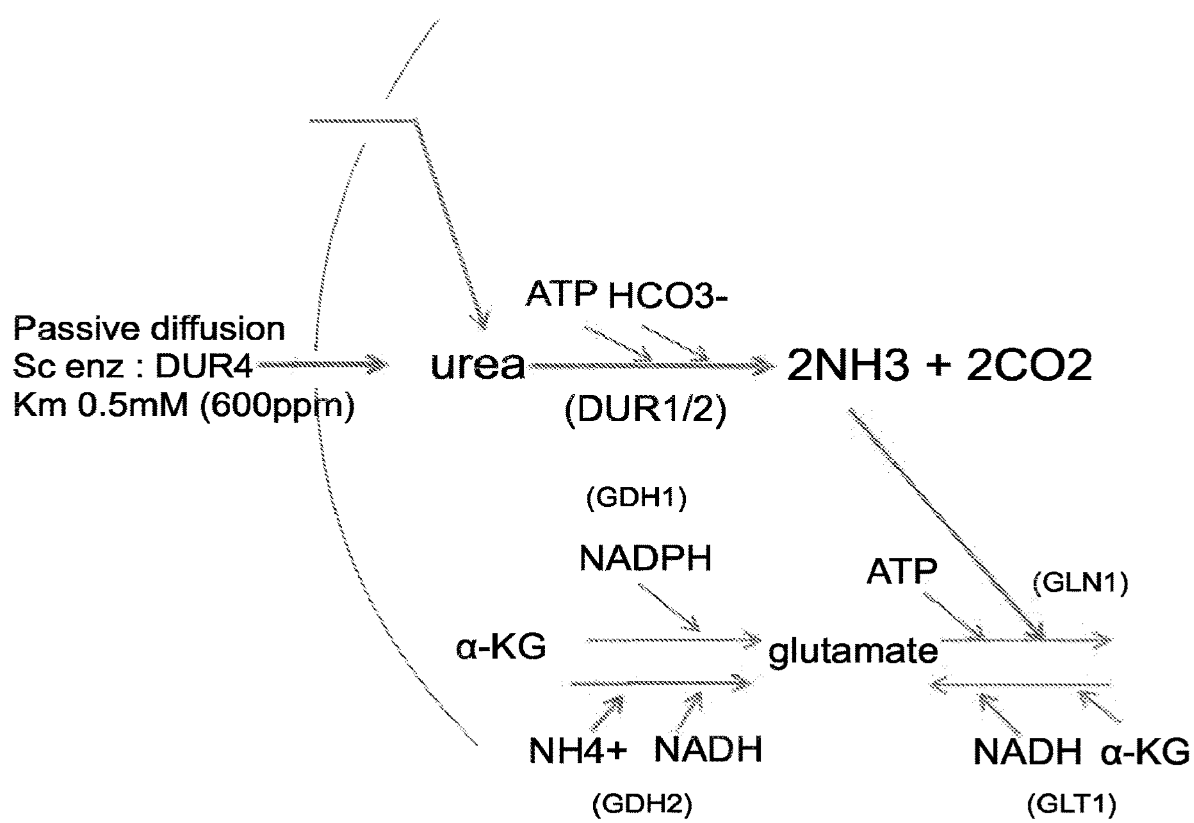
FIG. 3 depicts the process by which an unmodified *S. cerevisiae* assimilates urea.
Figure 4:
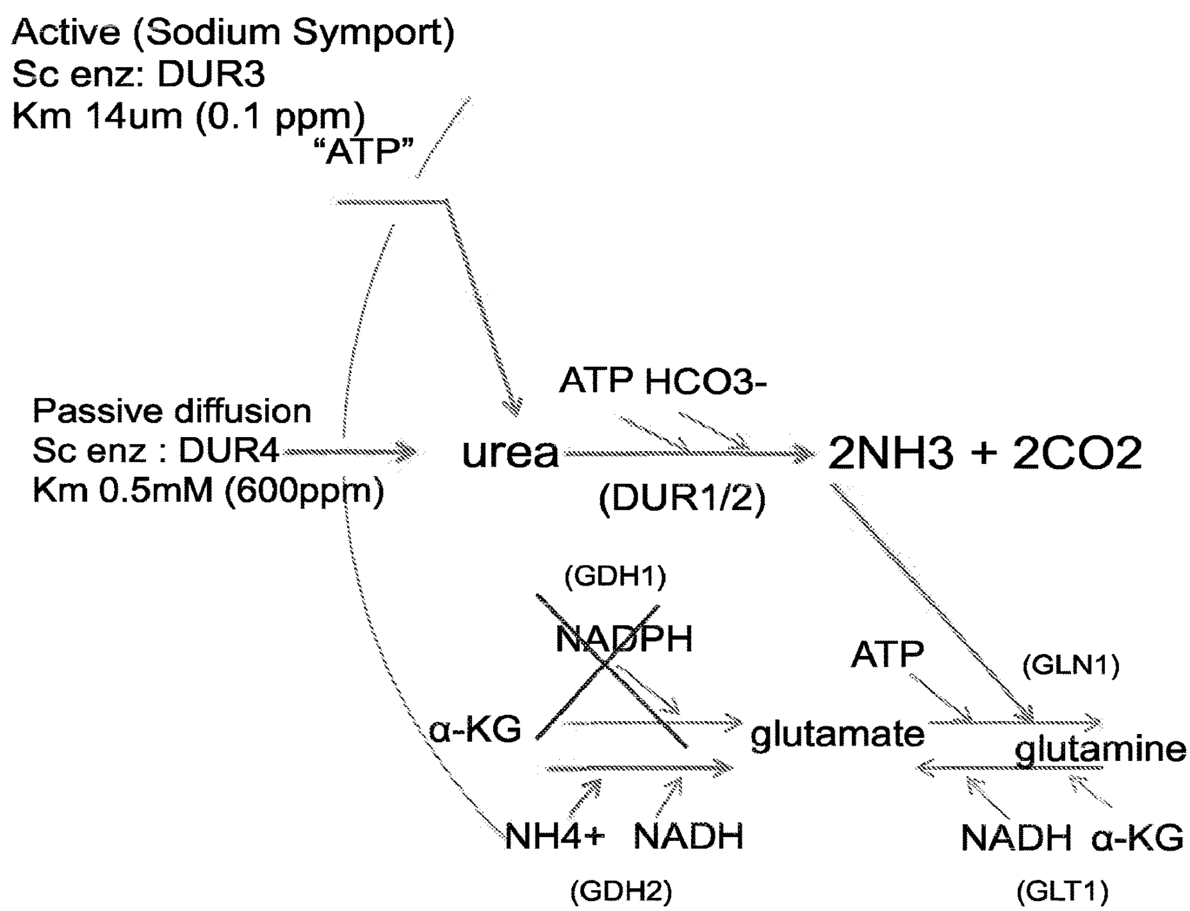
FIG. 4 depicts process by which a genetically modified glycerol reduction strain which contains a deletion of Gdh1 assimilates urea.
Figure 5:
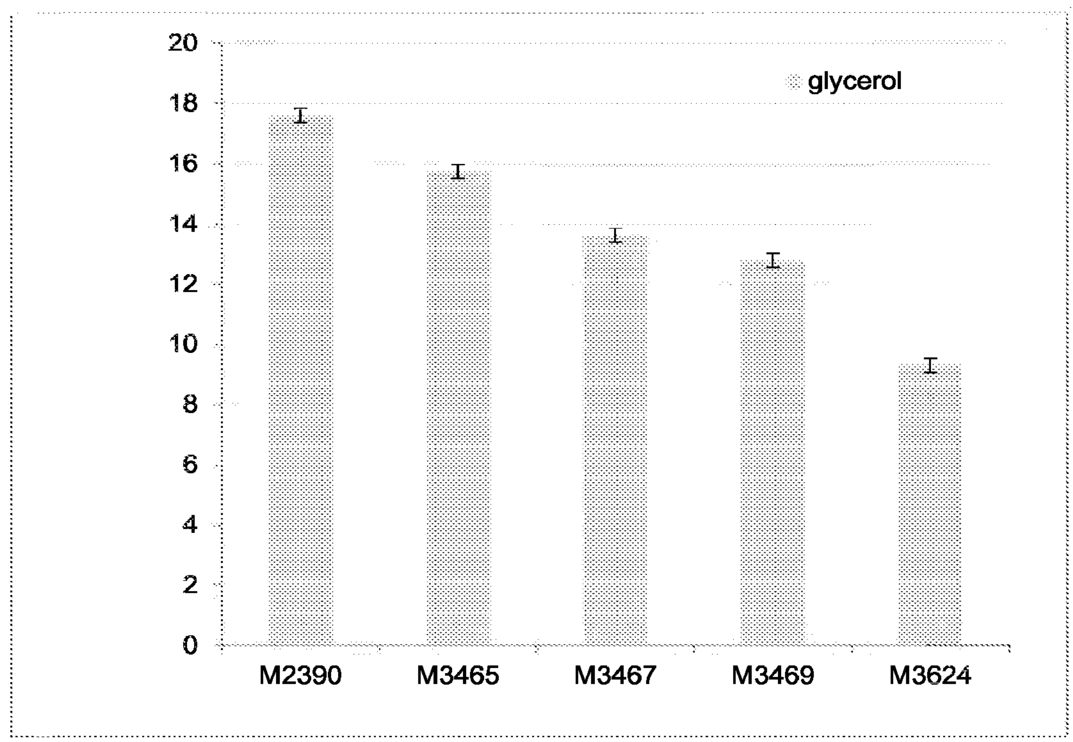
FIG. 5 depicts the glycerol titers of the wild type and glycerol reduction strains containing the formate pathway (M2390 (wildtype), M3465, M3467, M3469, and M3624 are depicted). This data shows total glycerol present in corn mash which contained 7 g/l glycerol prior to fermentation.
Figure 6:
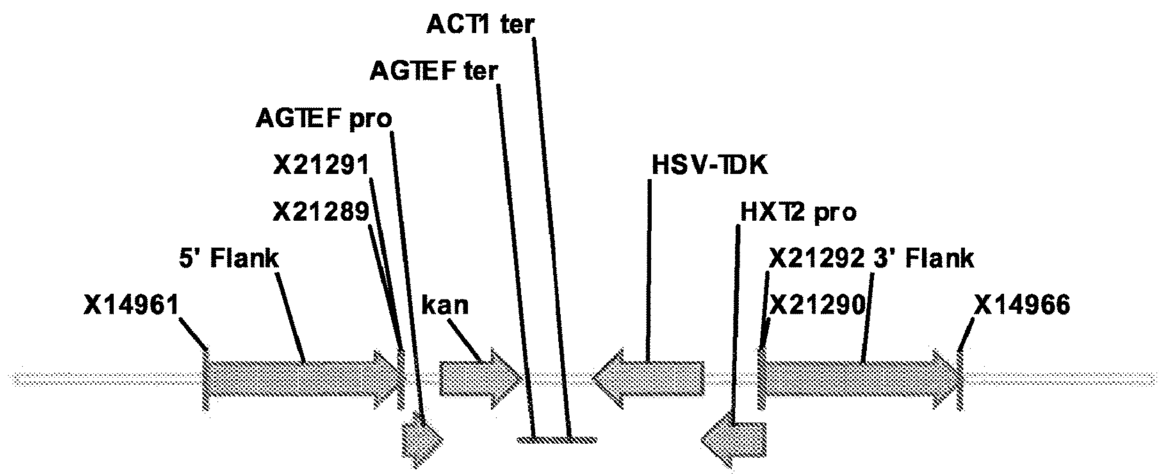
FIG. 6 depicts a schematic diagram of the MA0631 insertion cassette.
Figure 7:
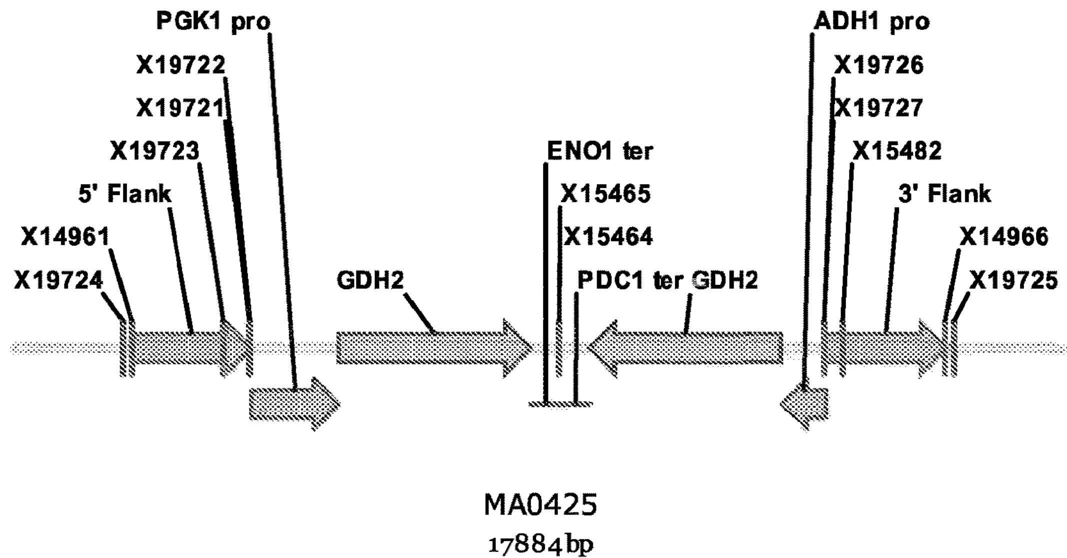
FIG. 7 depicts a schematic diagram of the MA0425 insertion cassette.
Figure 8:
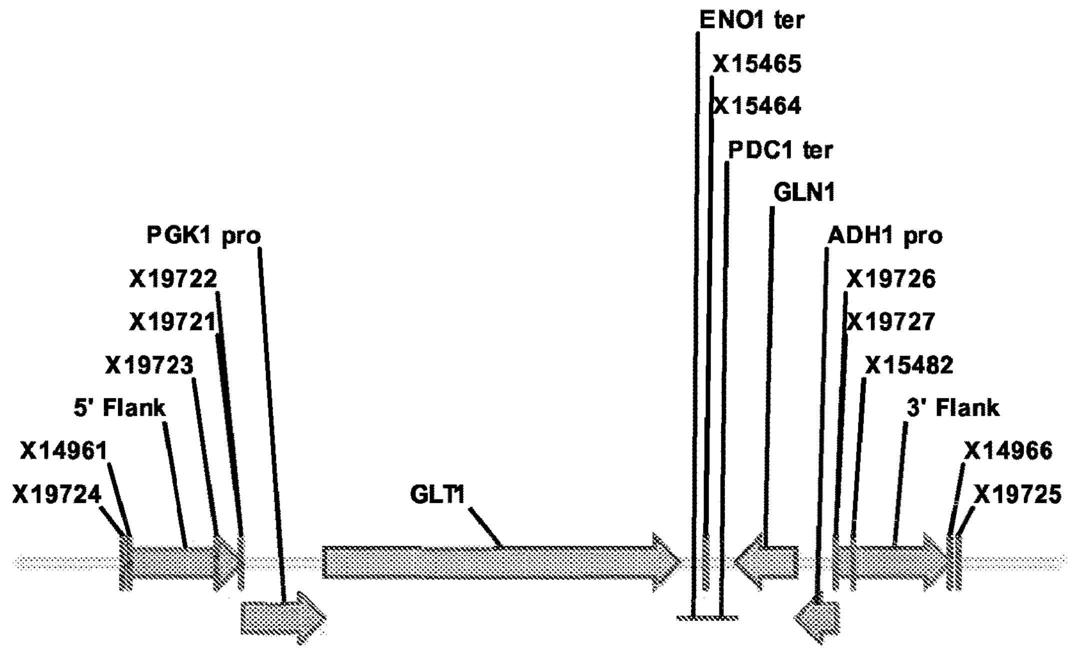
FIG. 8 depicts a schematic diagram of the MA0426 insertion cassette.
Figure 9:
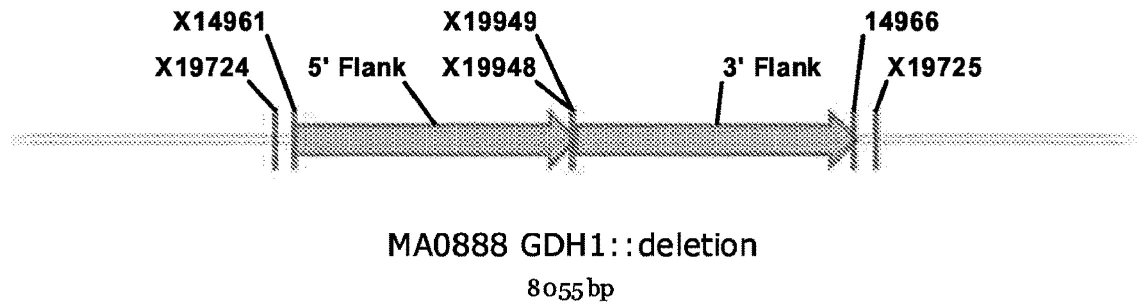
FIG. 9 depicts a schematic diagram of the MA0888 insertion cassette.

As shown in FIG. 5, M3465 (Δgpd2::*B. adolescentis*pf1A/pf1B/adhEΔfdh1Δfdh2::*B. adolesentis*pf1A/pf1B/adhE), M3467 (Δfdh1Δfdh2::PFK-pro-adhE-HXT-ter ENO1-pro-pf1B-ENO1-ter ADH1-pro-adhE-PDC10-ter TPI-pro-pf1A-FBA-ter Δgpd1::GPD2::PFK-pro-adhE-HXT-ter ENO1-pro-pf1B-ENO1-ter ADH1-pro-adhE-PDC10-ter TPI-pro-pf1A-FBA-ter) and M3469 (Δgpd1::*B. adolescentis* pf1A/pf1B/adhE fdh1Δfdh2Δ::*B. adolescentis*pf1A/pf1B/adhE) have degrees of glycerol reduction ranging from 20% to ~45% relative to the control strain M2390. A clean deletion of GDH1 was constructed in each of these backgrounds resulting in M4400 (M3465 Δgdh1), M4401(M3467 Δgdh1) and M4402 (M3469 ΔgdhI) and compared to the conventional yeast control (M2390) following fermentation of 31% solids corn mash (The fermentation was performed as described in Example 1). As shown in FIG. 70, all three glycerol reduction strains engineered with a deletion of GDH1 reached a higher ethanol titer than their respective parent strain.

Example 3

Overexpression of DUR1/2

Four different DUR1/2 expression cassettes were constructed in both M3467 Δfdh1Δfdh2::PFK-pro-adhE-HX7-ter ENO1-pro-pf1B-ENO1-ter ADH1-pro-adhE-PDC10-ter TPI-pro-pf1A-FBA-ter Δgpd1::GPD2::PFK-pro-adhE-HXT-ter ENO1-pro-pf1B-ENO1-ter ADH1-pro-adhE-PDC10-ter TPI-pro-pf1A-FBA-ter) and M3469 (Δgpd1::*B. adolescentis* pf1A/pf1B/adhE fdh1Δfdh2Δ::*B. adolescentis*pf1A/pf1B/adhE) resulting in strains M4427-M3343 (Table 5). These strains were compared to their parent strain and the conventional yeast control (M2390) following fermentation of 31% solids corn mash (The fermentation was performed as described in Example 1). As shown in FIG. 71, all strains containing an overexpression of DUR1/2 reached the same or higher ethanol titers than their respective parent strain but the TEF2 and ADH1 promoter appeared particularly affective. Promoters and terminators used and that could be used include: *S. cerevisiae* TEF 2 promoter: SEQ ID NO: 58, *S. cerevisiae* HXT7 promoter: SEQ ID NO: 59, *S. cerevisiae, S. cerevisiae* ADH1 promoter: SEQ ID NO: 60, *S. cerevisiae* TP1 promoter: SEQ ID NO: 61, *S. cerevisiae* FBA1 terminator: SEQ ID NO: 62, *S. cerevisiae* PDC1 terminator: SEQ ID NO: 63, *S. cerevisiae* PMA1 terminator: SEQ IS NO: 64, and *S. cerevisiae* ADH3 terminator: SEQ ID NO: 65.

TABLE 5

Description of constructions and strain designations containing over-expression of DUR1/2

| Parent strain | Strain desinnation | Genetic modification |
|---|---|---|
| M3467 | M4427 | MA0464.1: expression of DUR1,2 from the TEF2 promoter |
| M3467 | M4428 | MA0405.1: expression of DUR1,2 from the HXT7 promoter |
| M3467 | M4429 | MA467.1: expression of DUR1,2 from the ADH1 promoter |
| M3467 | M4430 | MA454.14: expression of DUR1,2 from the HXT7/TEF2 promoters |
| M3469 | M4431 | MA0464.1: expression of DUR1,2 from the TEF2 promoter |
| M3469 | M4432 | MA0465.1: expression of DUR1,2 from the HXT7 promoter |
| M3469 | M4433 | MA4671: expression of DUR1,2 from the ADH1 promoter |
| M3469 | M4434 | MA454.14: expression of DUR1,2 from the HXT7/TEF2 promoters |

Example 4

Deletion of URE2

To evaluate an alteration in the *S. cerevisiae* nitrogen catabolite repression system in glycerol reduction backgrounds, a deletion of URE2 was constructed in M3624 (Example 1), creating strain M4406 (M3624 Δure2). This strain was compared to M3624 and the conventional yeast control (M2390) following fermentation of 31% solids corn mash (The fermentation teas performed as described in Example 1). As shown in FIG. 72, M4406 reached a higher titer than M3624 however a yield increase over the conventional strain was not observed and there was ~15 g/l residual glucose. This is an and c a ti on that additional modifications to the NCR system may give improved performance or that an adaptation of M4406 may be required to obtain the potential yield increase.

Example 5

Regulation of Nitrogen Utilization

Preferred nitrogen sources generally repress transcription of genes required to utilize non-preferred nitrogen sources. Urea is added as a supplemental nitrogen source in corn mash fermentation; however, there are significant quantities of amino acids and ammonia, both of which are preferred nitrogen sources over urea. Expression of the urea transporter (Dur3) and the urea:amido lyase responsible for intracellular degradation (Dur1/2) may be repressed in the presence amino acids and ammonia as part of a phenomenon referred to as Nitrogen Catabolite Repression (NCR). This repression could slow the rate of urea uptake or require larger quantities to be added. It would be an economic benefit to a corn ethanol producer if constitutive expression of Dur3 and Dur1,2 allowed them to either reduce the amount of urea needed or accelerate fermentation rate.

The NCR is controlled by Ure2 and four transcription factors known as Gln3, Gat1, Dal80, and Gzf3. Ure2 participates in repressing gene expression in the presence of non-preferred nitrogen source. It has been observed that deletion of URE2 activates the expression of genes involved in the uptake of non-preferred nitrogen sources inactivation of Ure2 results in dephosphorylation and nuclear localization of the transcription factor Gln3.

Example 5A

Deletion of URE2 Deletion of URE2 Results in Nuclear Localization of GLN3 and Activation of NCR Sensitive Genes To evaluate an alteration in the *S. cerevisiae* nitrogen catabolite repression system in glycerol reduction backgrounds, a deletion of Ure2 is constructed as in Example 4. A deletion of URE2 will be constructed in M3624 (Example 1). Strains in which URE2 is deleted show a nuclear localization of Gln3, and an activation of NCR sensitive genes, including; Dur3 and Dur1/2.

Example 5B

Overexpression GLN3 Results in Activation of NCR Sensitive Genes

To evaluate an alteration in the *S. cerevisiae* nitrogen catabolite repression system in glycerol reduction backgrounds, Gln3 (SEQ ID NOs: 156 and 157) is overexpressed. Strains in which Gln3 is overexpressed show an activation of NCR sensitive genes, including Dur3 and Dur1/2.

Example 6

Deletion of GDH1 and Expression of *S. cerevisiae* GDH2

The results show that strain M3624 (Example 1) was able to reach a slightly higher titer than strain M2390 (WT), producing 1.5 g/l more ethanol (FIG. 73). To create strain M4117 (M3634 Gdh2; Δgdh1), the GDH1 gene was deleted and replaced with 4 copies of the *S. cerevisiae* GDH2 gene expression cassette. The results in FIG. 73 below demonstrate that when compared to M3624, M4117 had a clear improvement of 3.7 g/l more ethanol. The data shown in FIG. 74 shows that M3624 makes 1.3 g/l glycerol which is 87% less than the wild type strain M2390, which made 10 g/l. The deletion of GDH1 and addition of the *S. cerevisiae* GDH2 expression cassette decreased the glycerol titers to around 1 g/l. These results illustrate that the combination of glycerol reduction through formate production is synergistic with modifications to the ammonium assimilation pathway.

Example 7

Deletion of GDH1 and Expression of *N. crassa* GDH2

Figure 10:
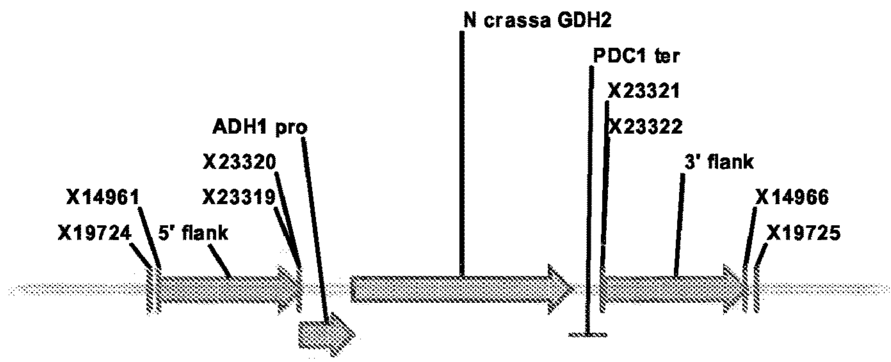
FIG. 10 depicts a schematic diagram of the MA0837 insertion cassette.
Figure 11:
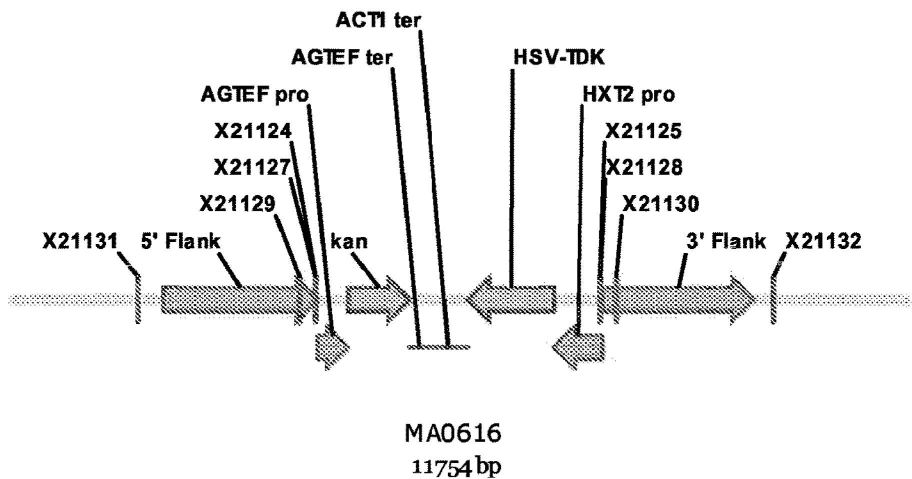
FIG. 11 depicts a schematic diagram of the MA0616 insertion cassette.
Figure 12:
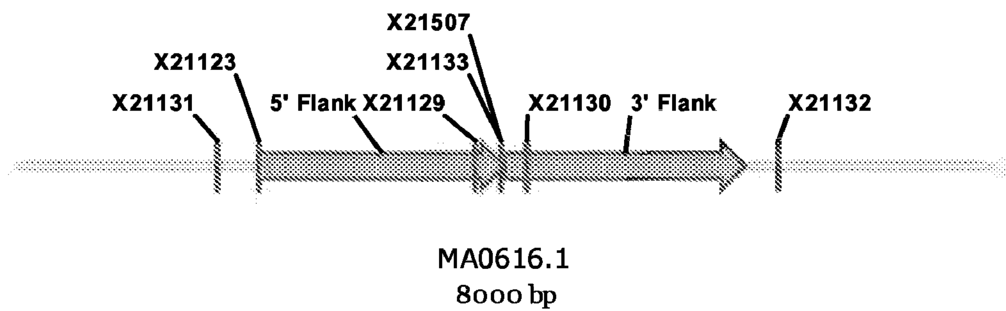
FIG. 12 depicts a schematic diagram of the MA0616.1 insertion cassette.
Figure 13:
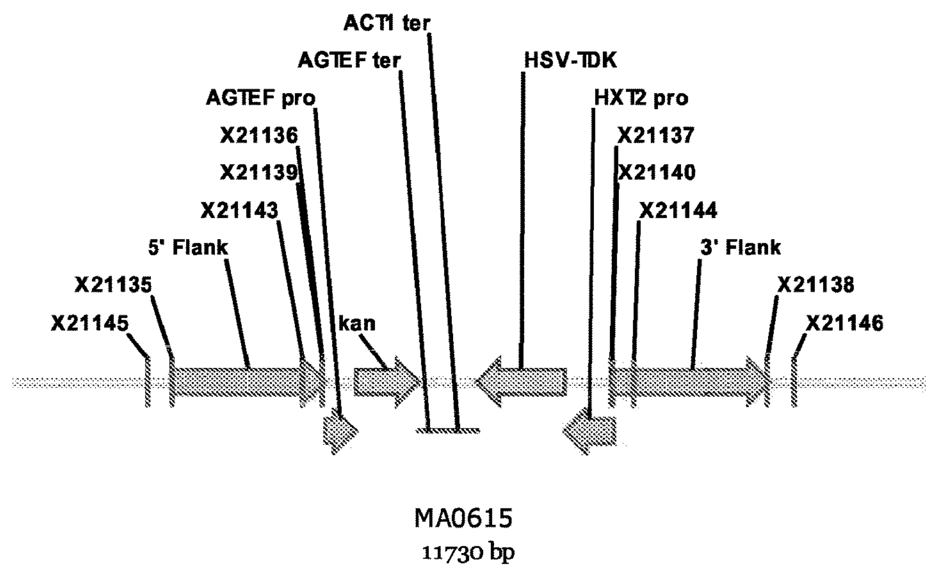
FIG. 13 depicts a schematic diagram of the MA0615 insertion cassette.
Figure 14:
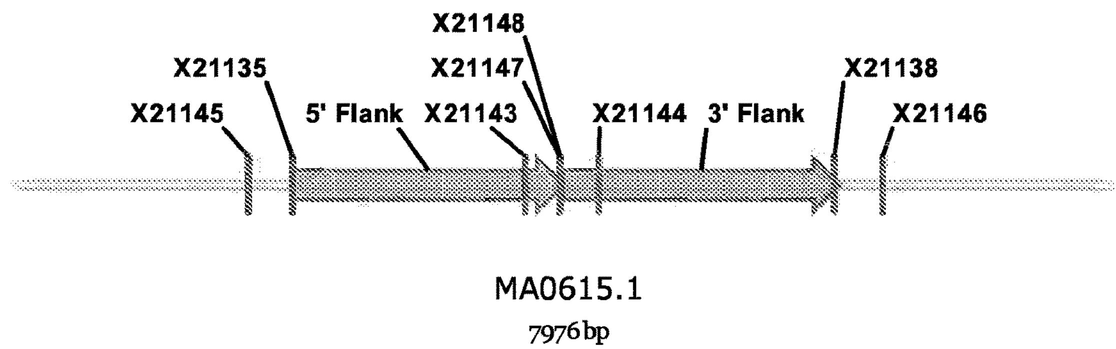
FIG. 14 depicts a schematic diagram of the MA0615.1 insertion cassette.
Figure 15:
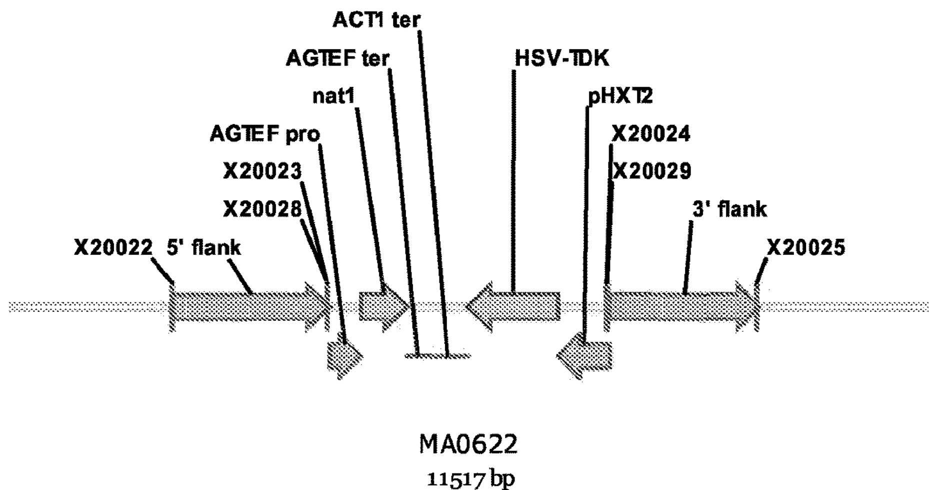
FIG. 15 depicts a schematic diagram of the MA0622 insertion cassette.
Figure 16:
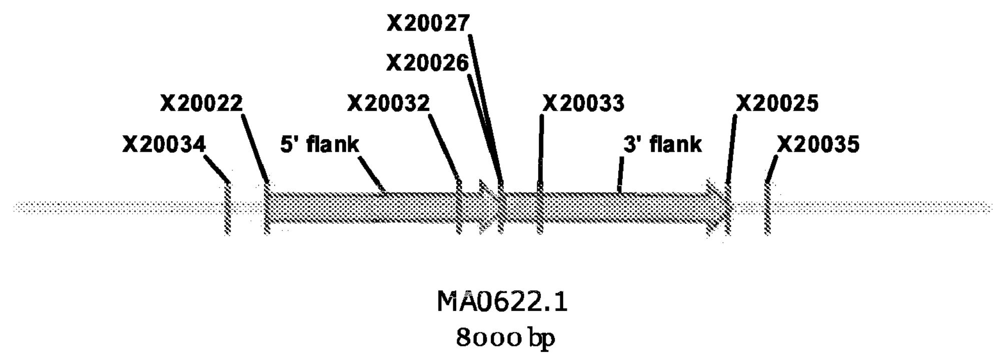
FIG. 16 depicts a schematic diagram of the MA0622.1 insertion cassette.
Figure 17:
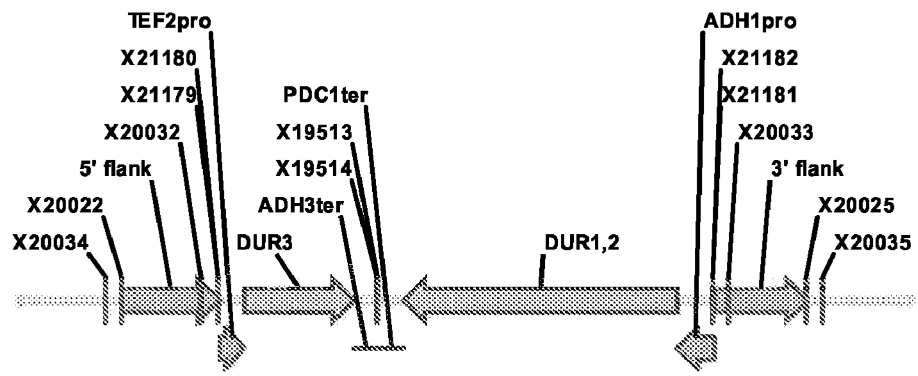
FIG. 17 depicts a schematic diagram of the MA0580 insertion cassette.
Figure 18:
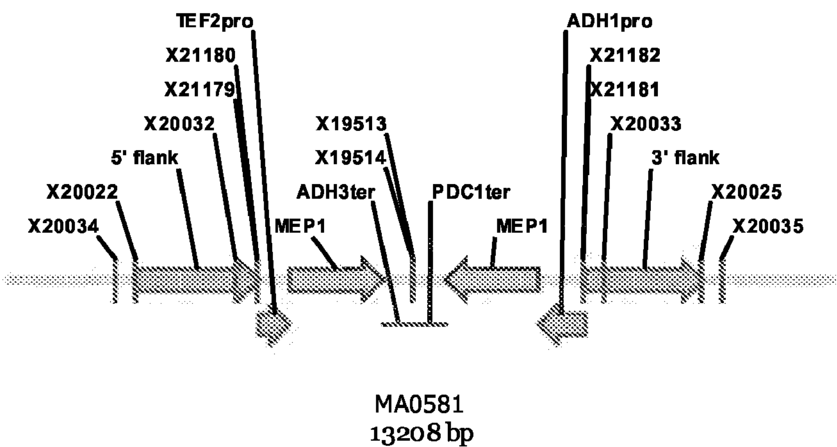
FIG. 18 depicts a schematic diagram of the MA0581 insertion cassette.
Figure 19:
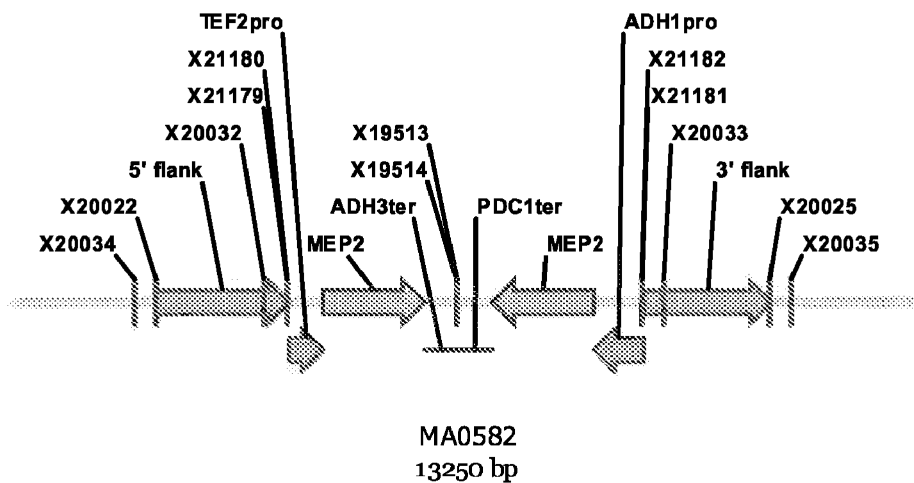
FIG. 19 depicts a schematic diagram of the MA0582 insertion cassette.
Figure 20:
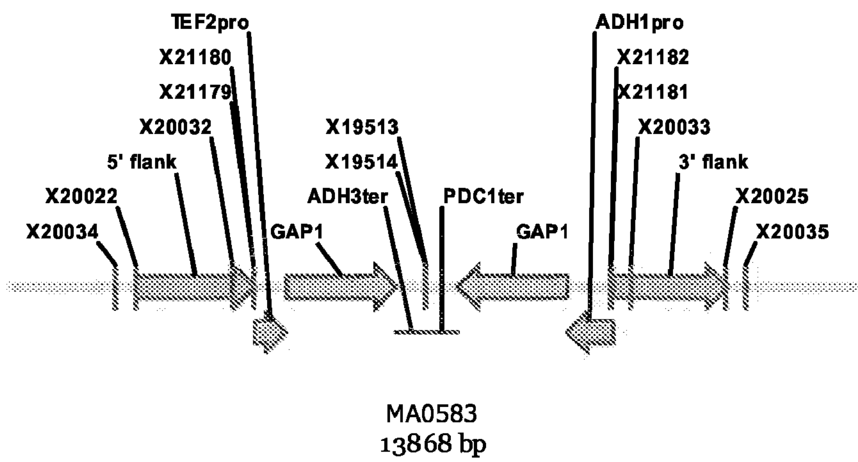
FIG. 20 depicts a schematic diagram of the MA0583 insertion cassette.
Figure 21:
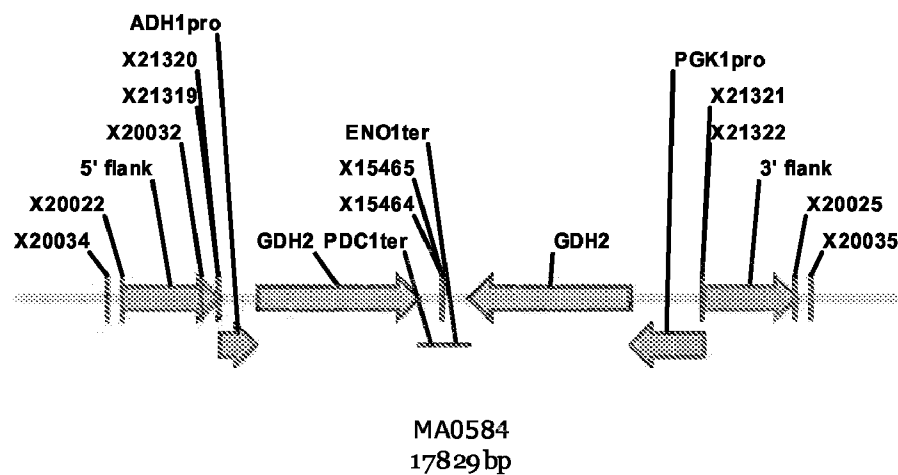
FIG. 21 depicts a schematic diagram of the MA0584 insertion cassette.
Figure 22:
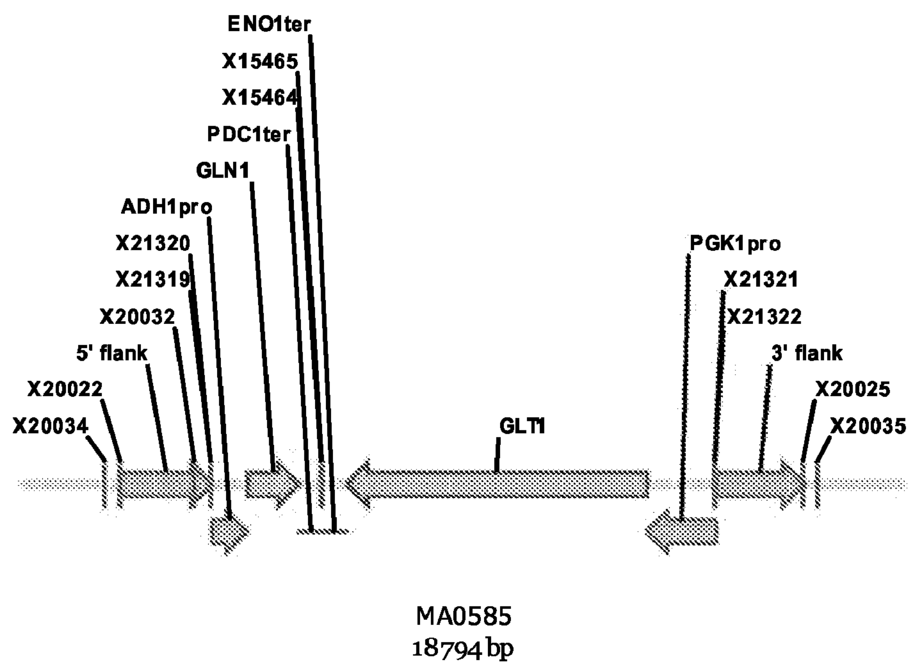
FIG. 22 depicts a schematic diagram of the MA0585 insertion cassette.
Figure 23:
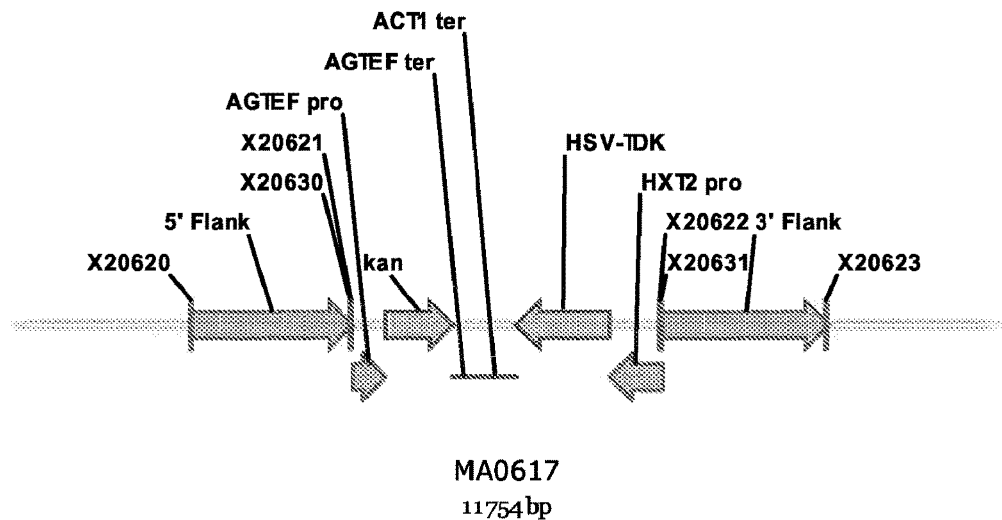
FIG. 23 depicts a schematic diagram of the MA0617 insertion cassette.
Figure 24:
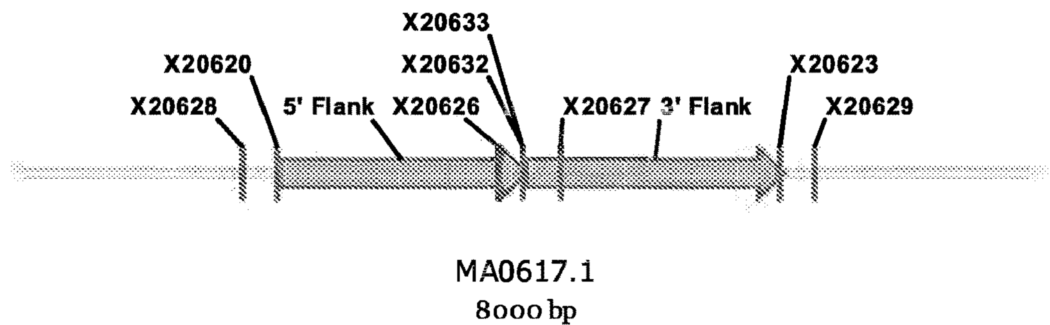
FIG. 24 depicts a schematic diagram of the MA0617.1 insertion cassette.
Figure 25:
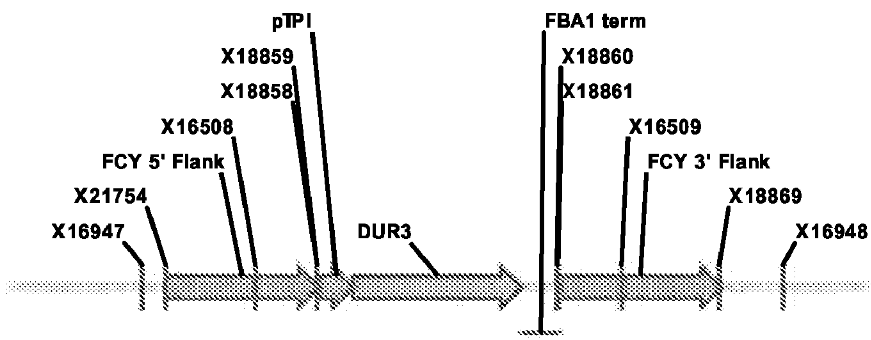
FIG. 25 depicts a schematic diagram of the MA0434 insertion cassette.
Figure 26:
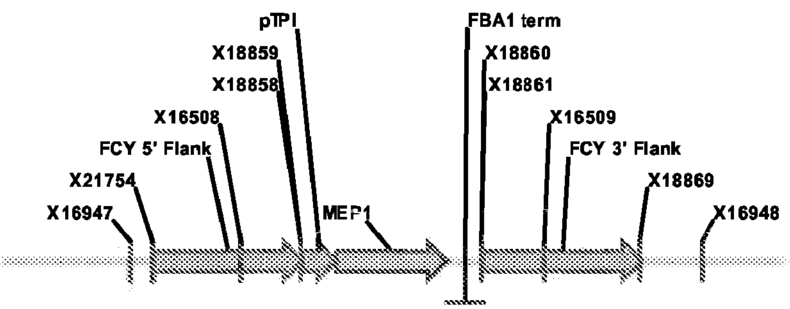
FIG. 26 depicts a schematic diagram of the MA0434.2 insertion cassette.
Figure 27:
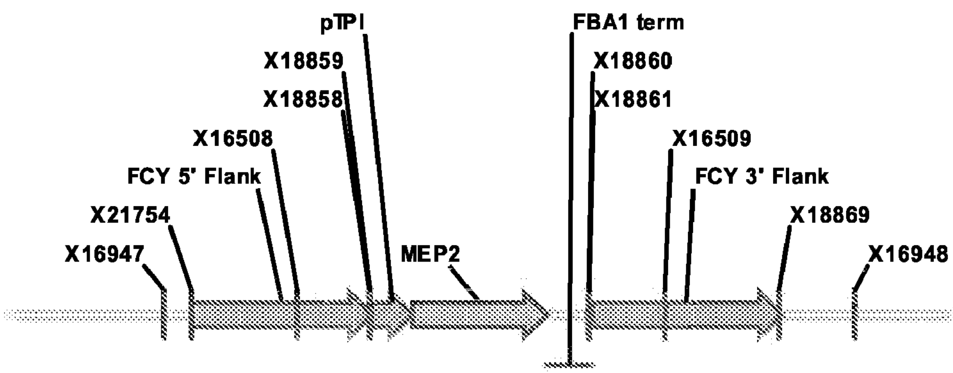
FIG. 27 depicts a schematic diagram of the MA0434.3 insertion cassette.
Figure 28:
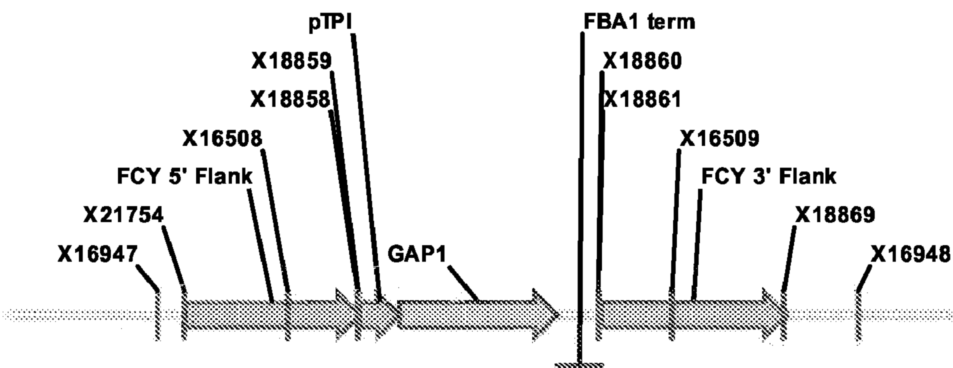
FIG. 28 depicts a schematic diagram of the MA0434.4 insertion cassette.
Figure 29:
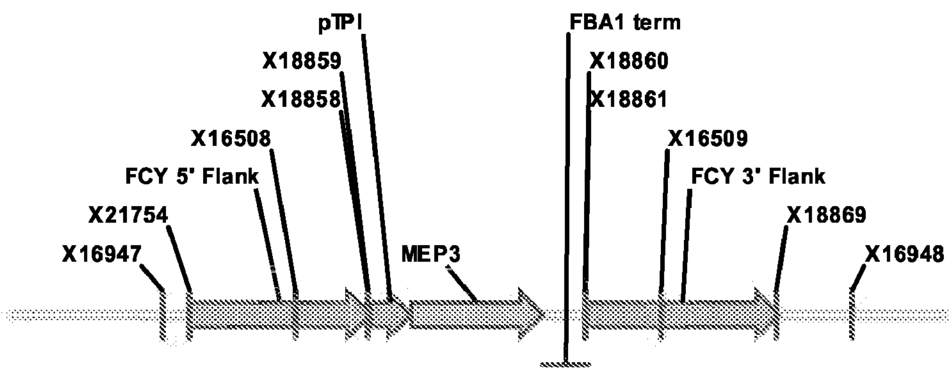
FIG. 29 depicts a schematic diagram of the MA0434.5 insertion cassette.
Figure 30:
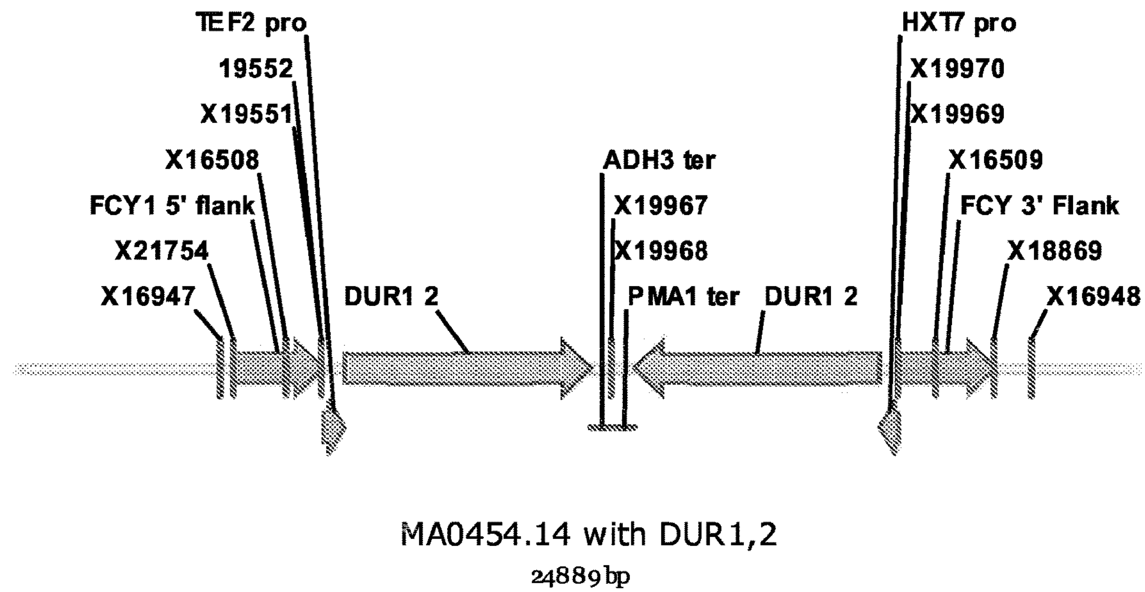
FIG. 30 depicts a schematic diagram of the MA0454.14 insertion cassette.
Figure 31:
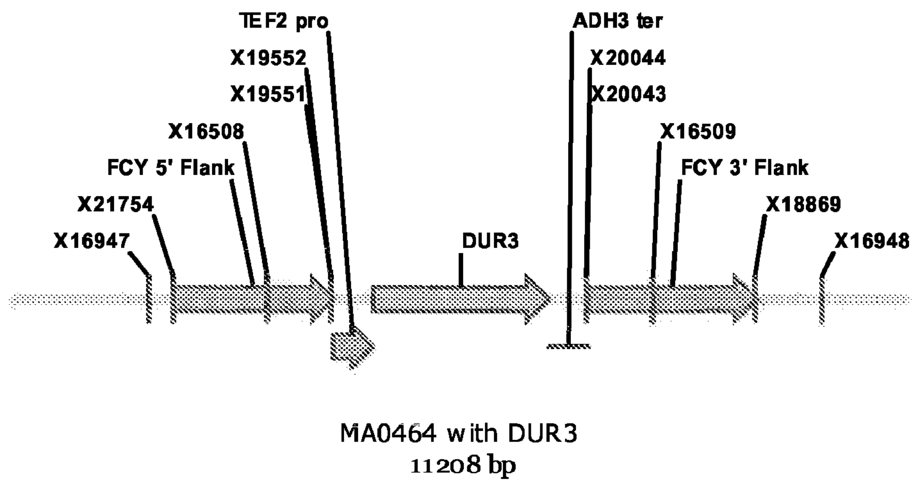
FIG. 31 depicts a schematic diagram of the MA0464 insertion cassette.
Figure 32:
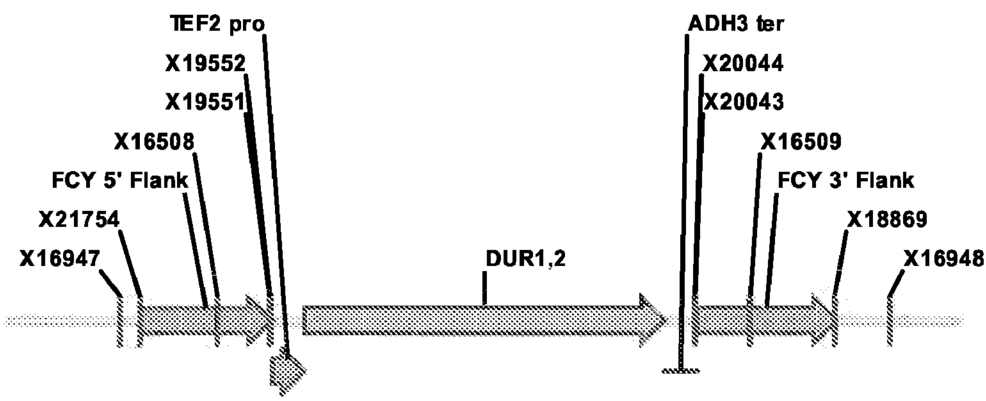
FIG. 32 depicts a schematic diagram of the MA0464.1 insertion cassette.
Figure 33:
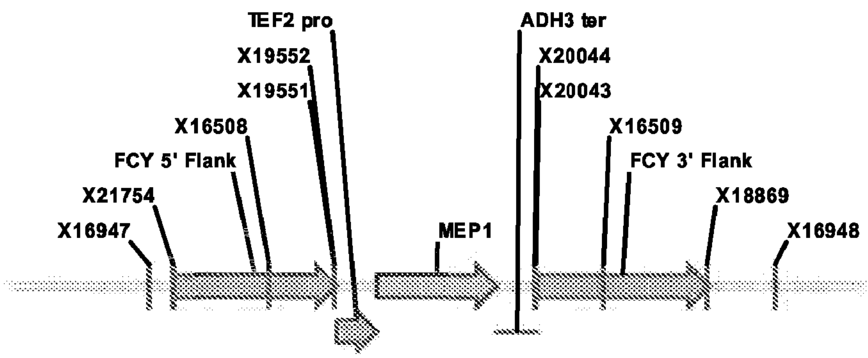
FIG. 33 depicts a schematic diagram of the MA0464.2 insertion cassette.
Figure 34:
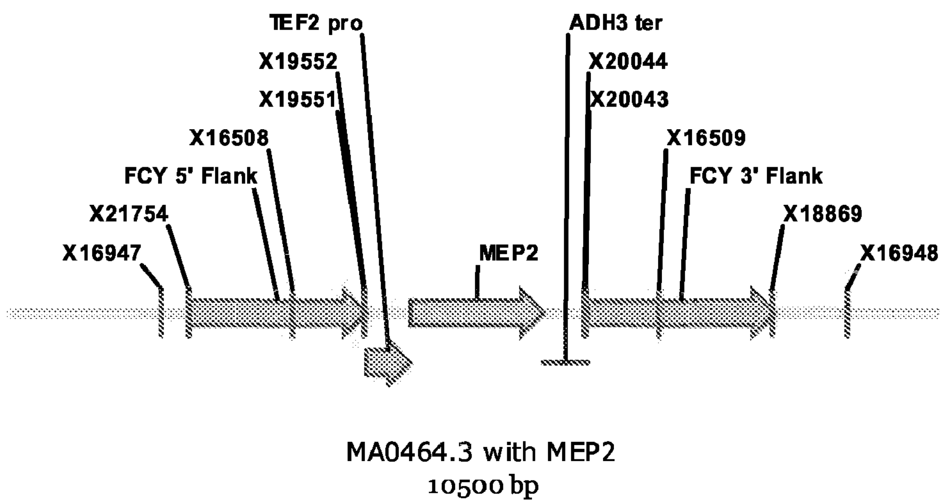
FIG. 34 depicts a schematic diagram of the MA0464.3 insertion cassette.
Figure 35:
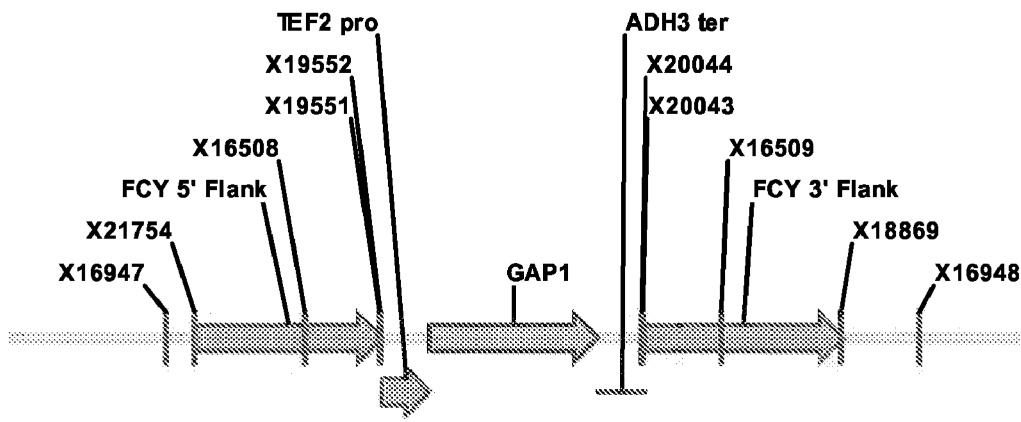
FIG. 35 depicts a schematic diagram of the MA0464.4 insertion cassette.
Figure 36:
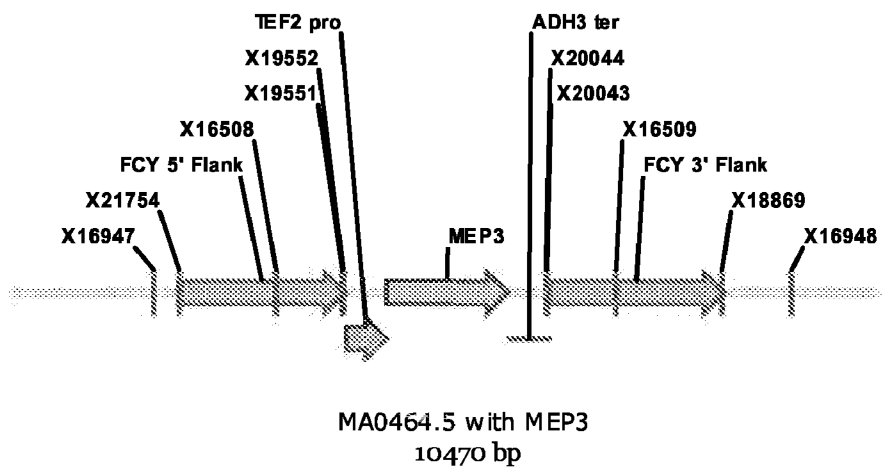
FIG. 36 depicts a schematic diagram of the MA0464.5 insertion cassette.
Figure 37:
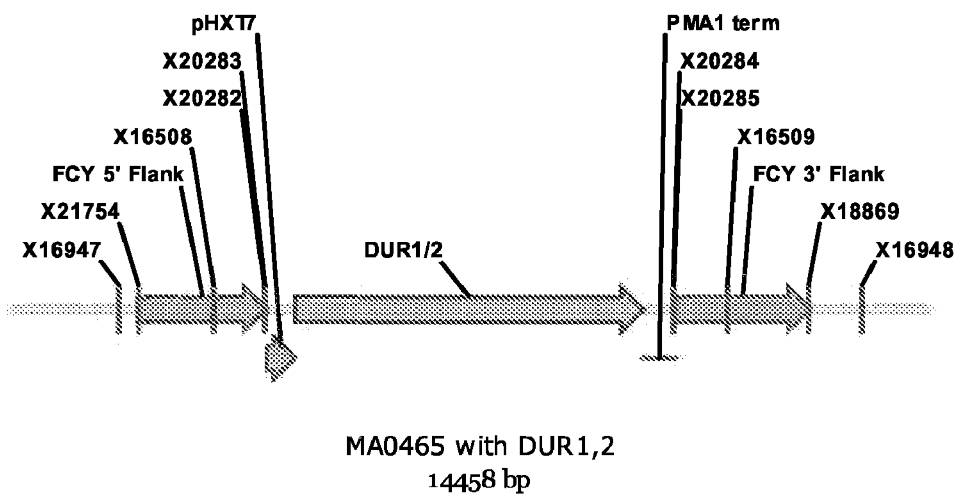
FIG. 37 depicts a schematic diagram of the MA0465.1 insertion cassette.
Figure 38:
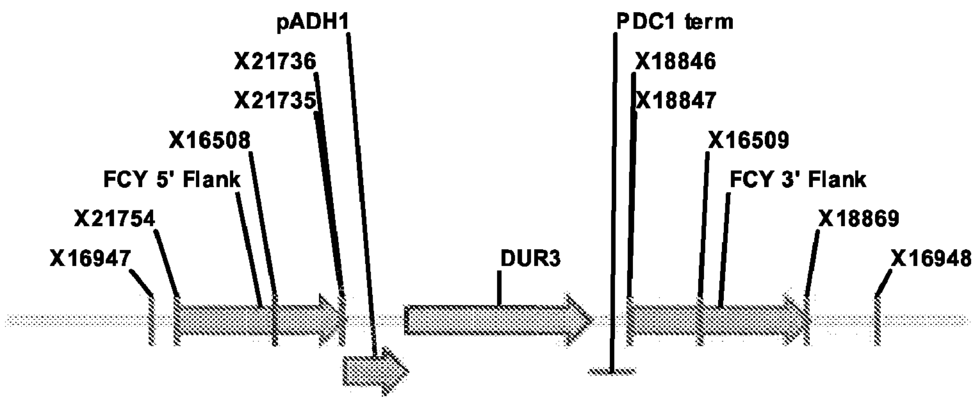
FIG. 38 depicts a schematic diagram of the MA0467 insertion cassette.
Figure 39:
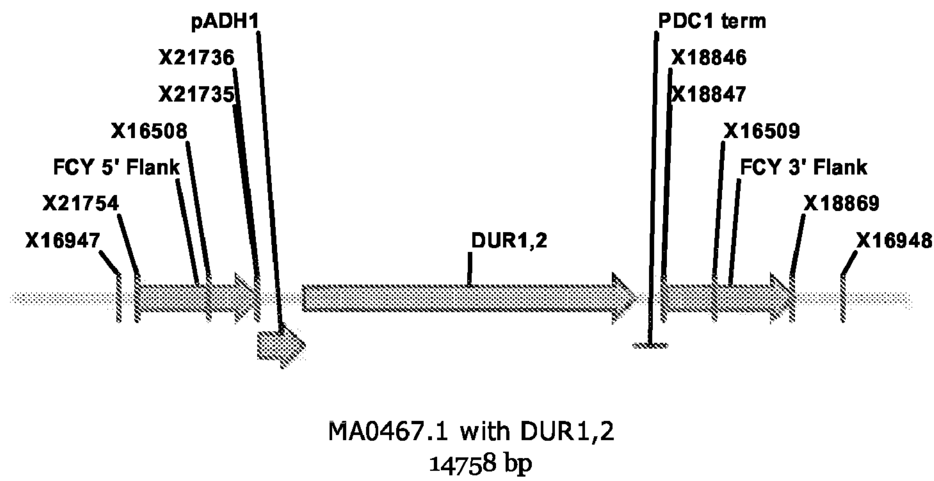
FIG. 39 depicts a schematic diagram of the MA0467.1 insertion cassette.
Figure 40:
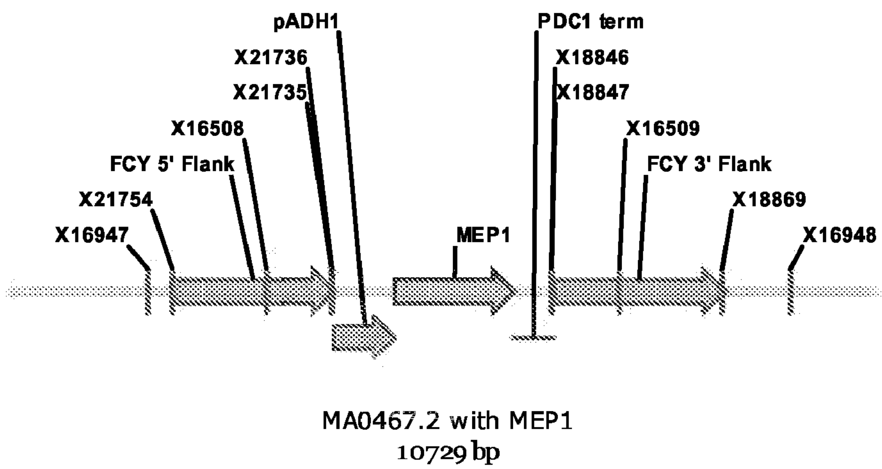
FIG. 40 depicts a schematic diagram of the MA0467.2 insertion cassette.
Figure 41:
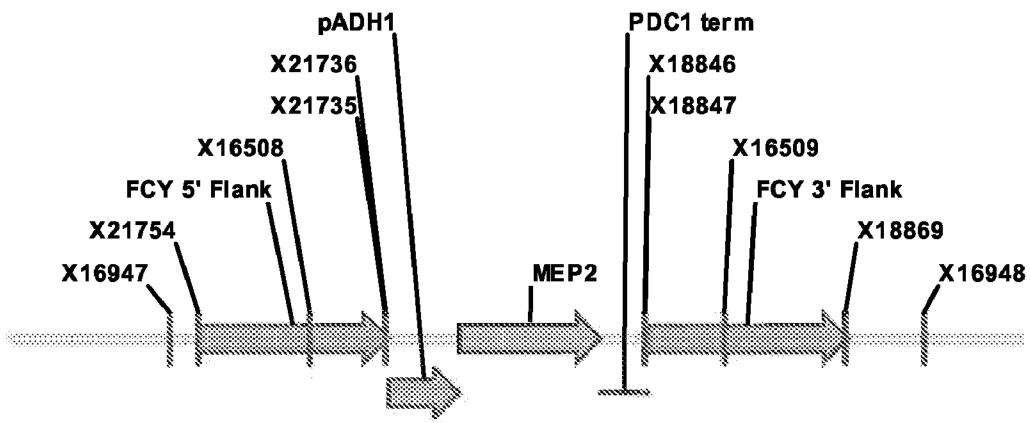
FIG. 41 depicts a schematic diagram of the MA0467.3 insertion cassette.
Figure 42:
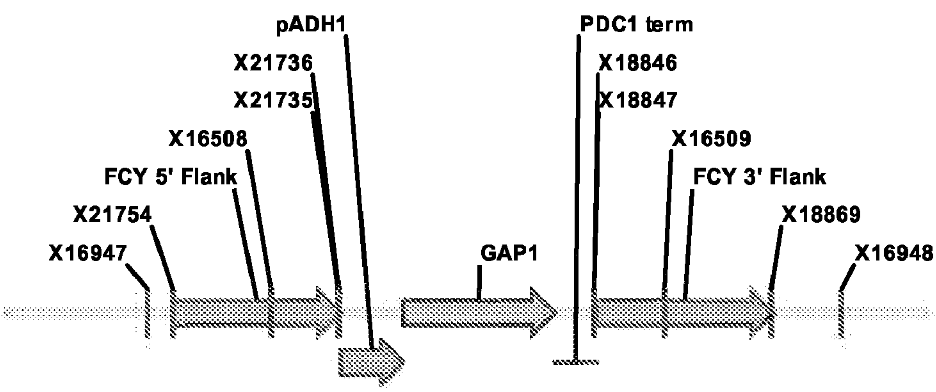
FIG. 42 depicts a schematic diagram of the MA0467.4 insertion cassette.
Figure 43:
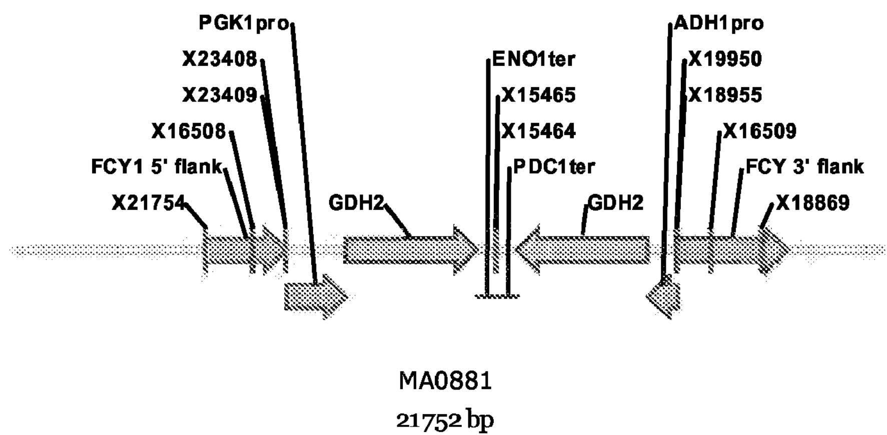
FIG. 43 depicts a schematic diagram of the MA0881 insertion cassette.
Figure 44:
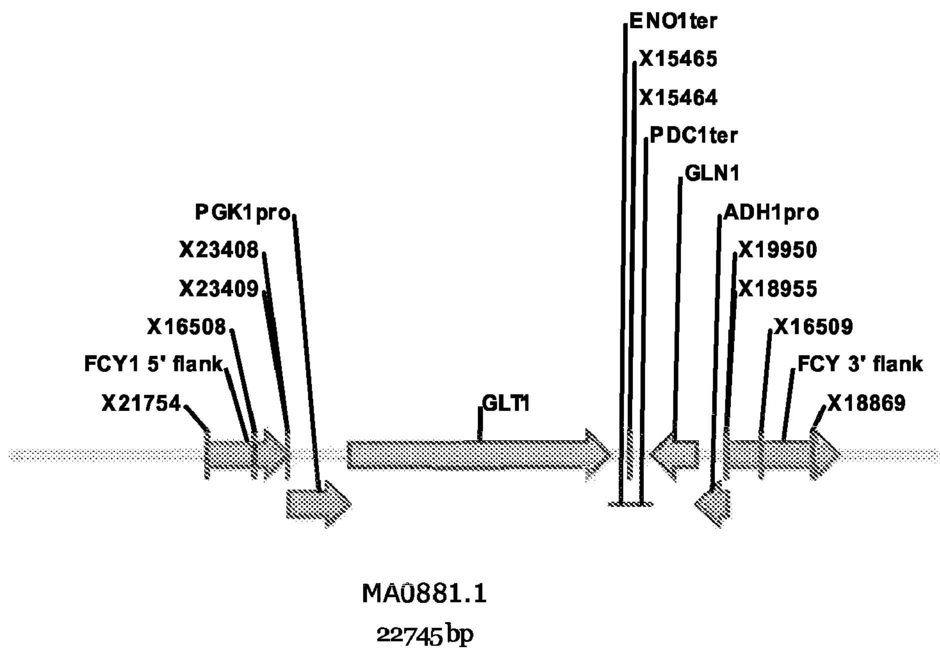
FIG. 44 depicts a schematic diagram of the MA0881.1 insertion cassette.
Figure 45:
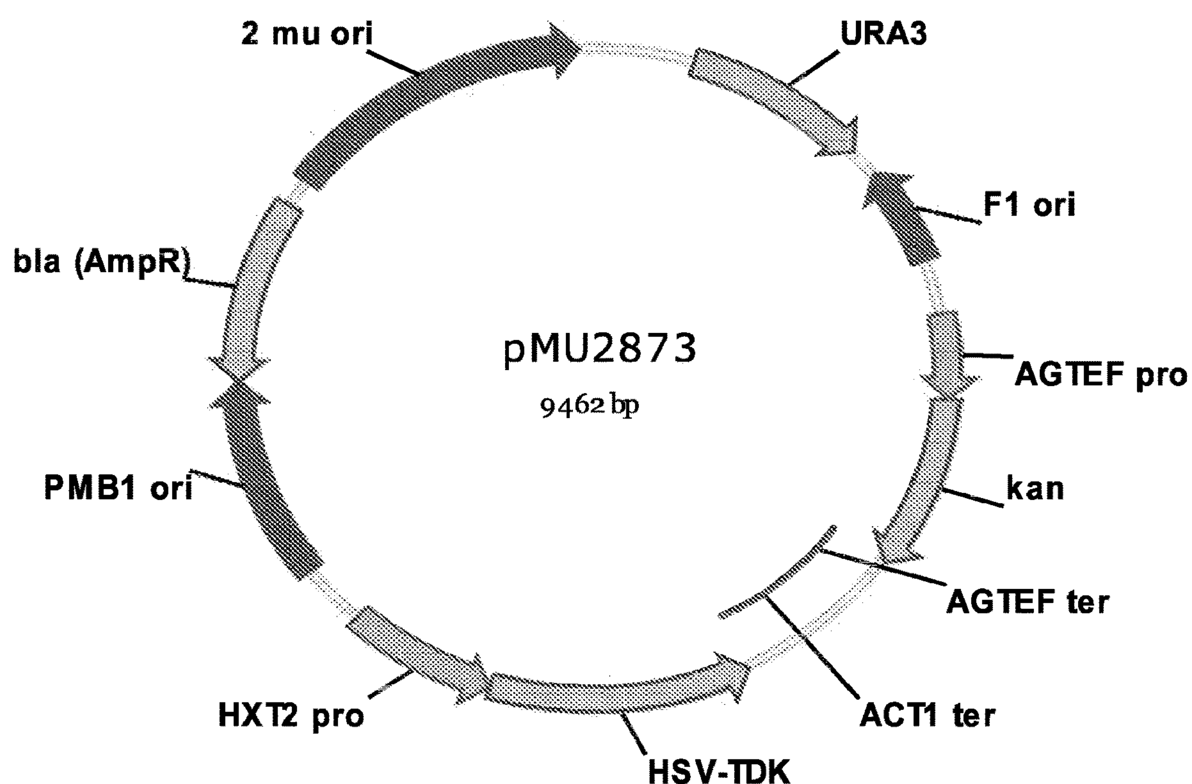
FIG. 45 depicts a plasmid map for pMU2873.
Figure 46:
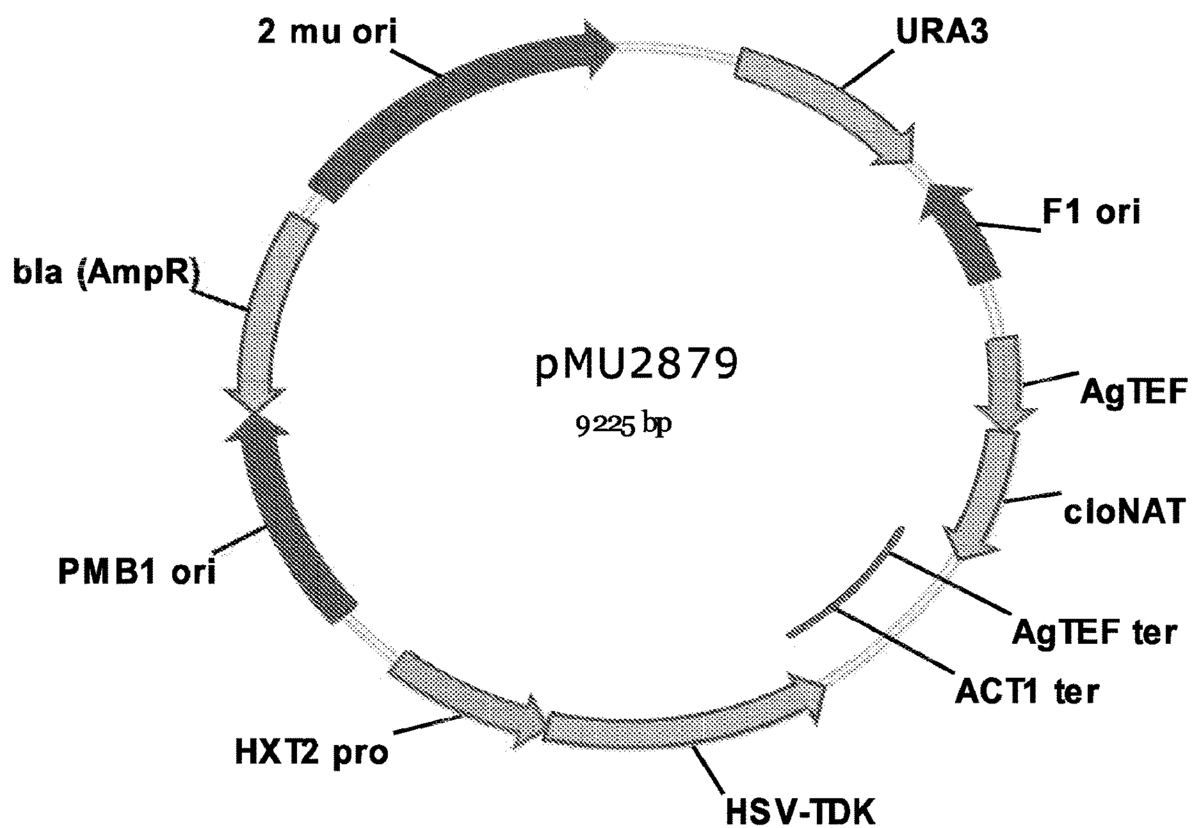
FIG. 46 depicts a plasmid map for pMU2879.
Figure 47:
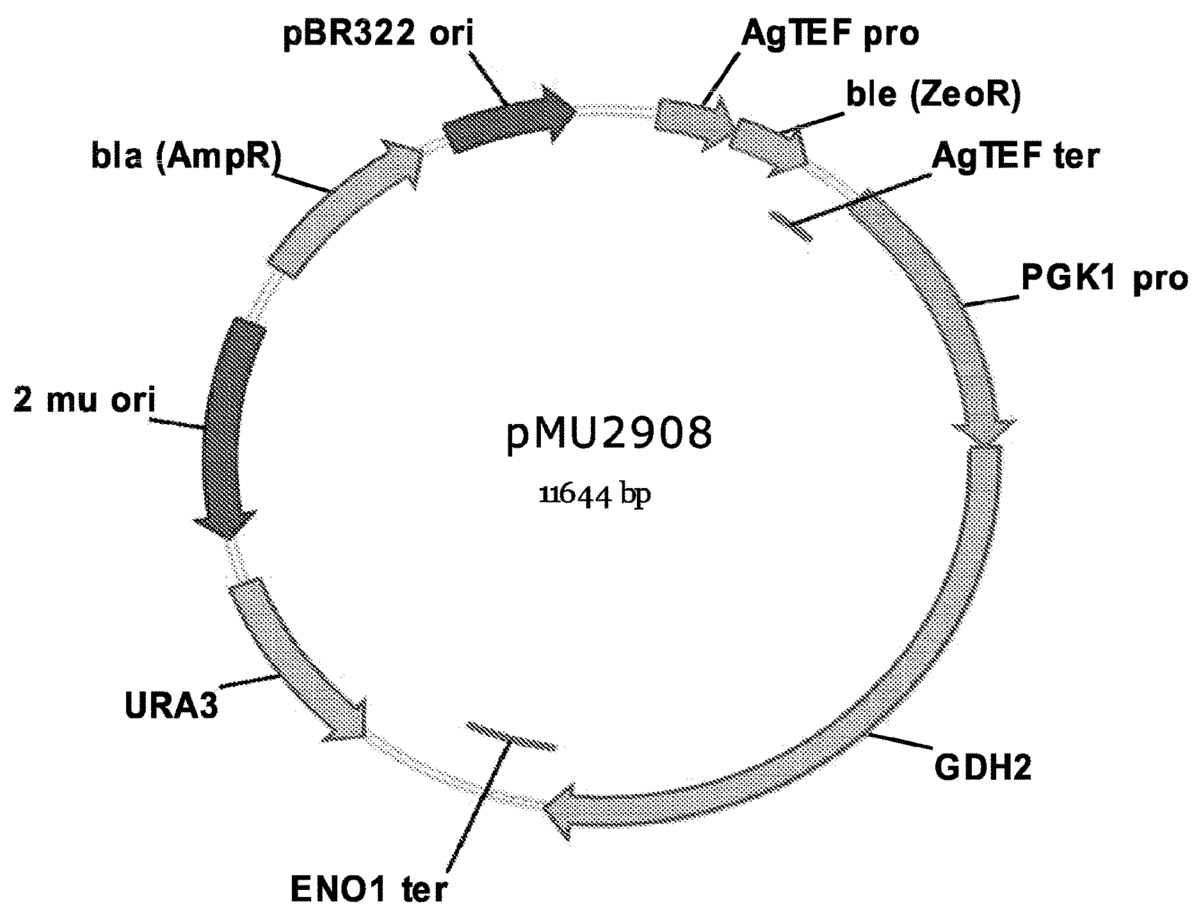
FIG. 47 depicts a plasmid map for pMU2908.
Figure 48:
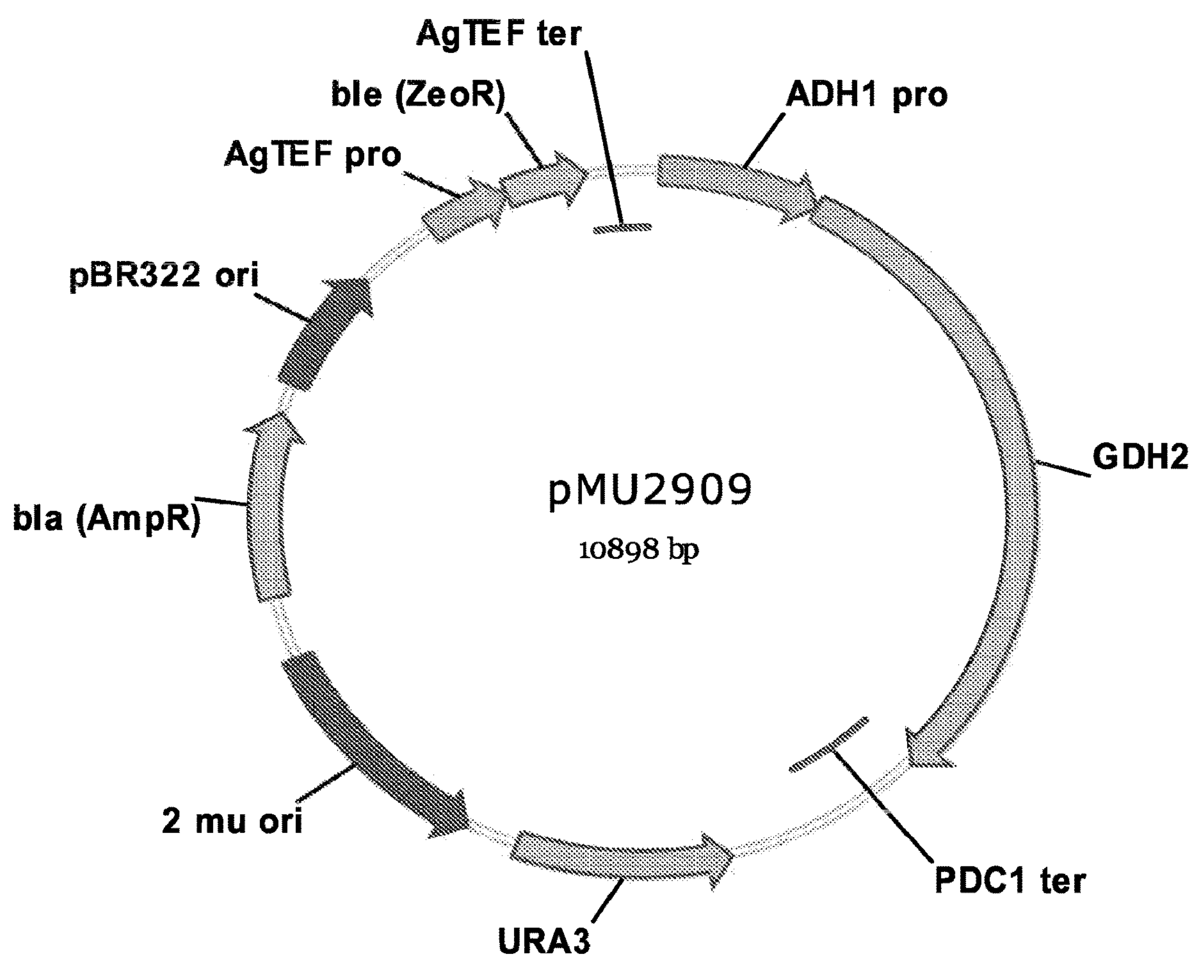
FIG. 48 depicts a plasmid map for pMU2909.
Figure 49:
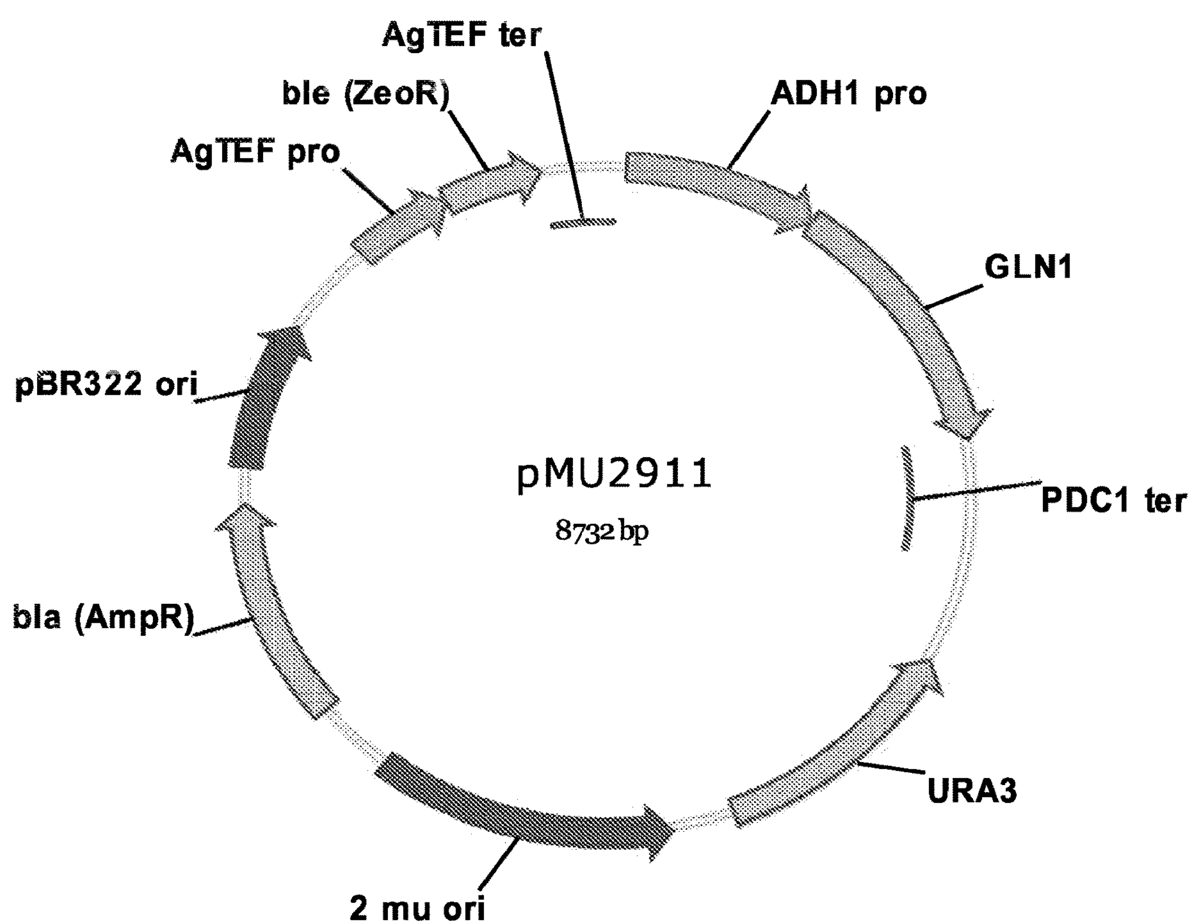
FIG. 49 depicts a plasmid map for pMU2911.
Figure 50:
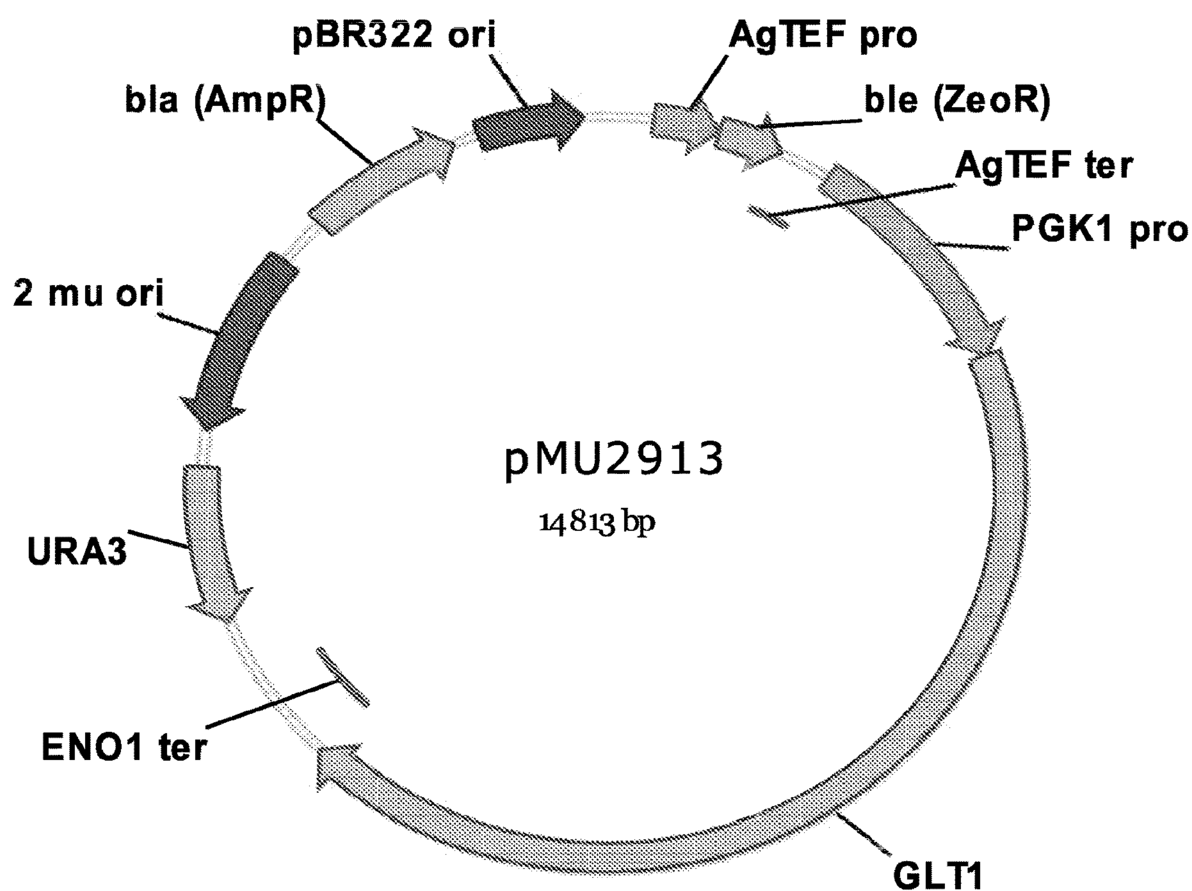
FIG. 50 depicts a plasmid map for pMU2913.
Figure 51:
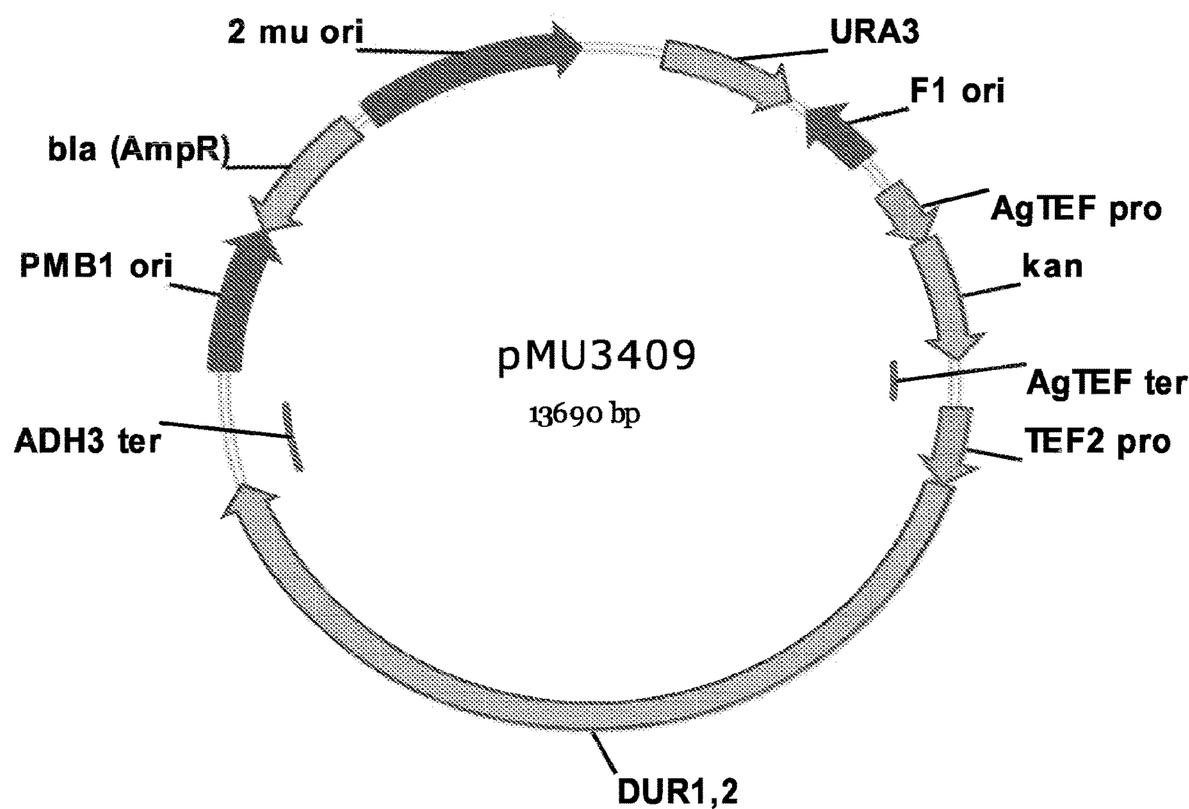
FIG. 51 depicts a plasmid map for pMU3409.
Figure 52:
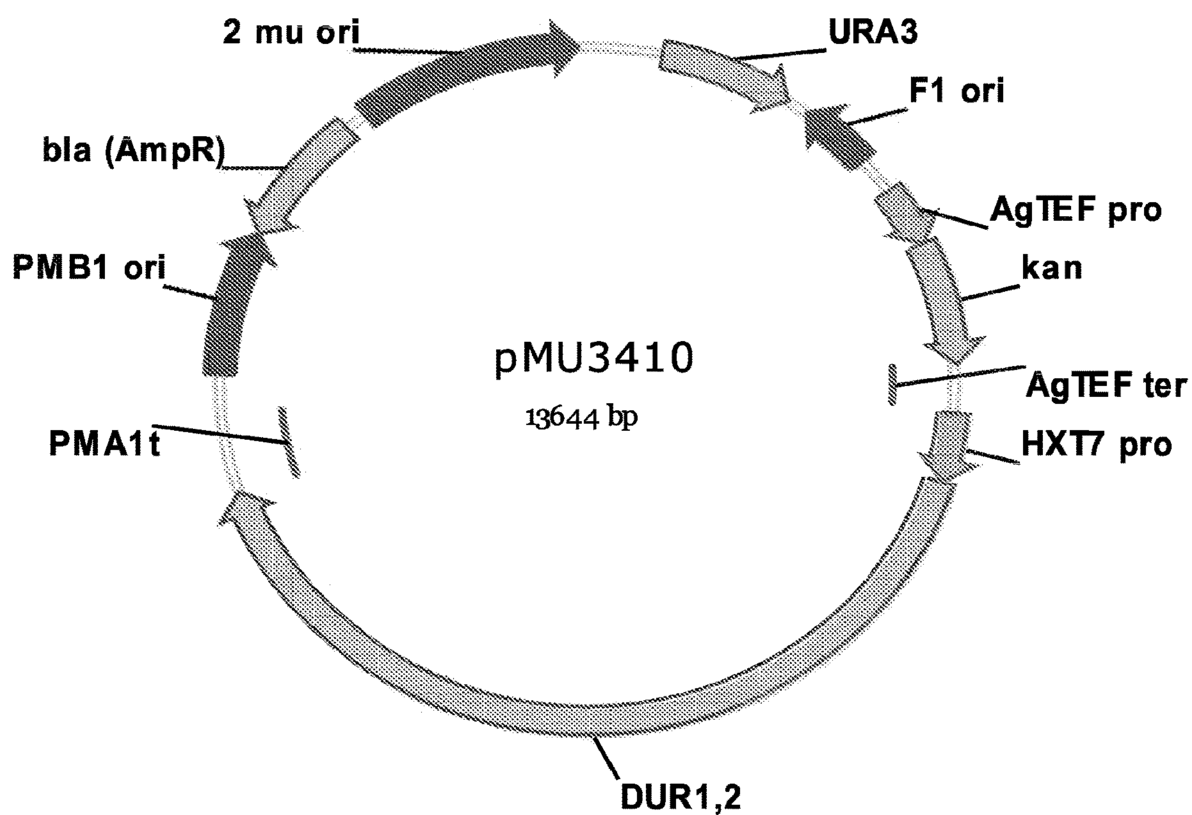
FIG. 52 depicts a plasmid map for pMU3410.
Figure 53:
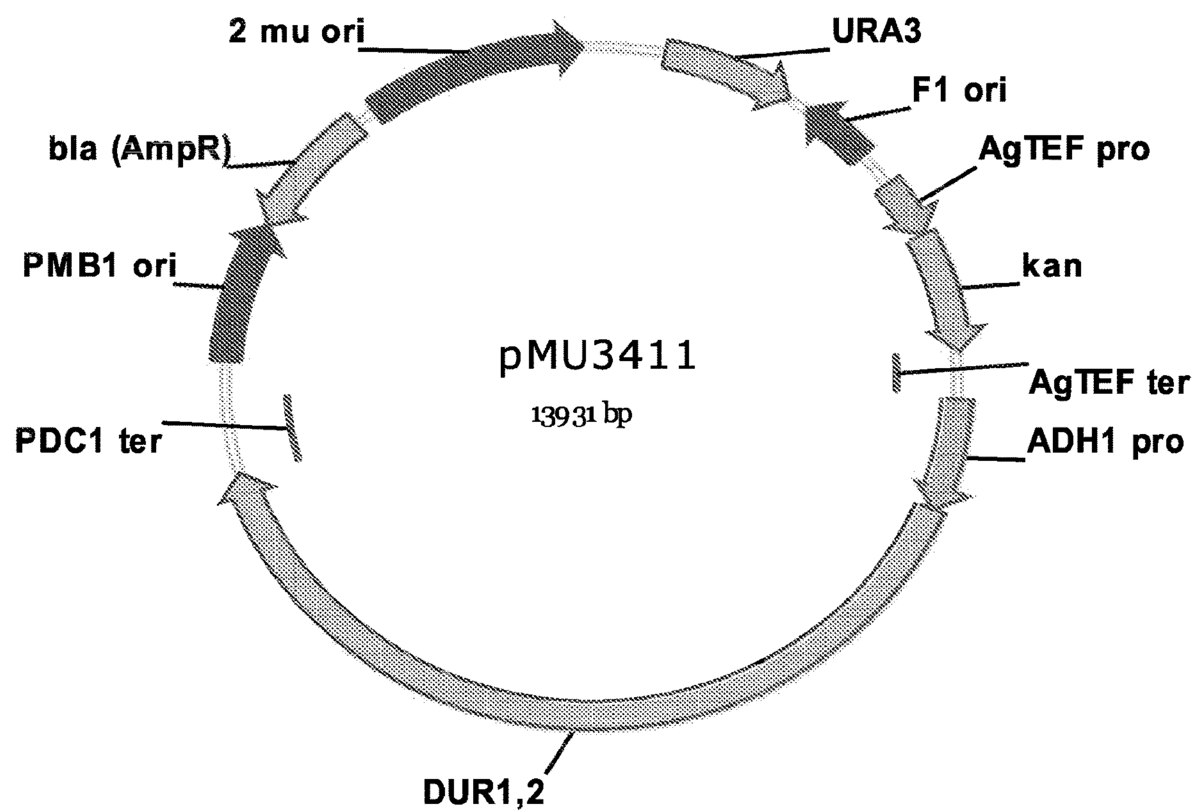
FIG. 53 depicts a plasmid map for pMU3411.
Figure 54:
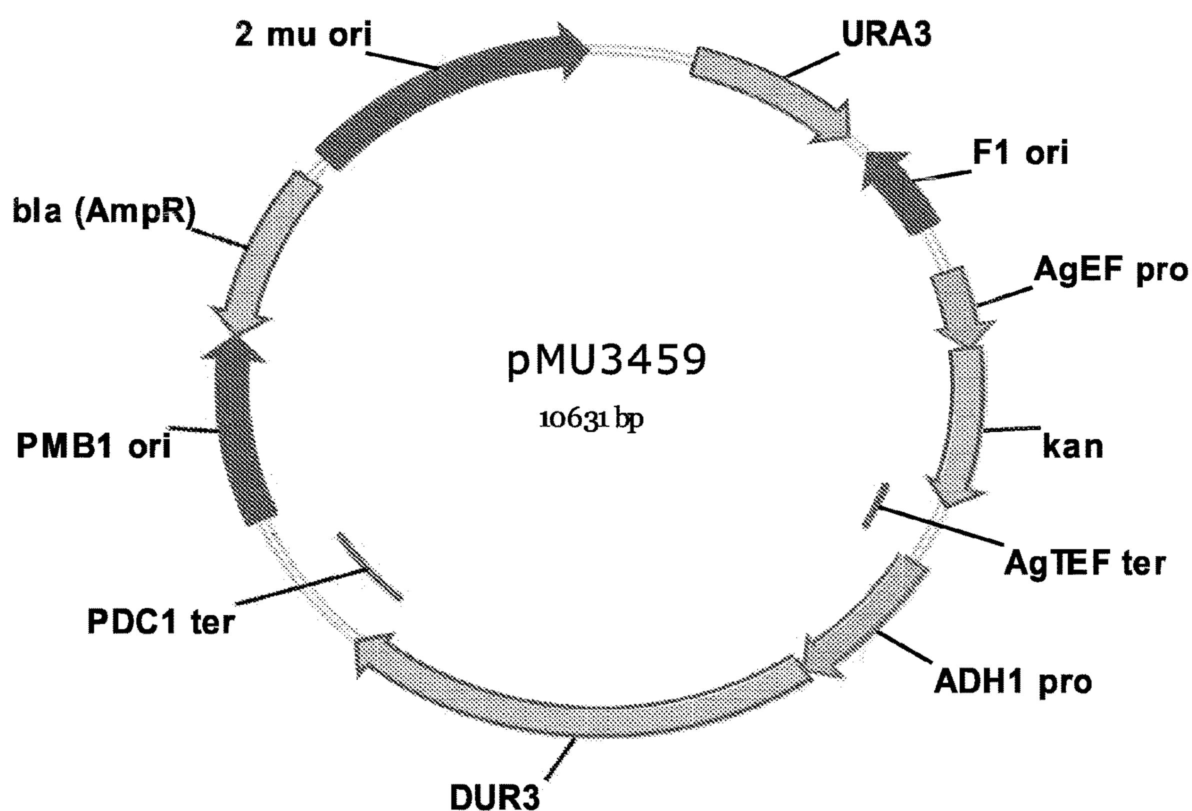
FIG. 54 depicts a plasmid map for pMU3459.
Figure 55:
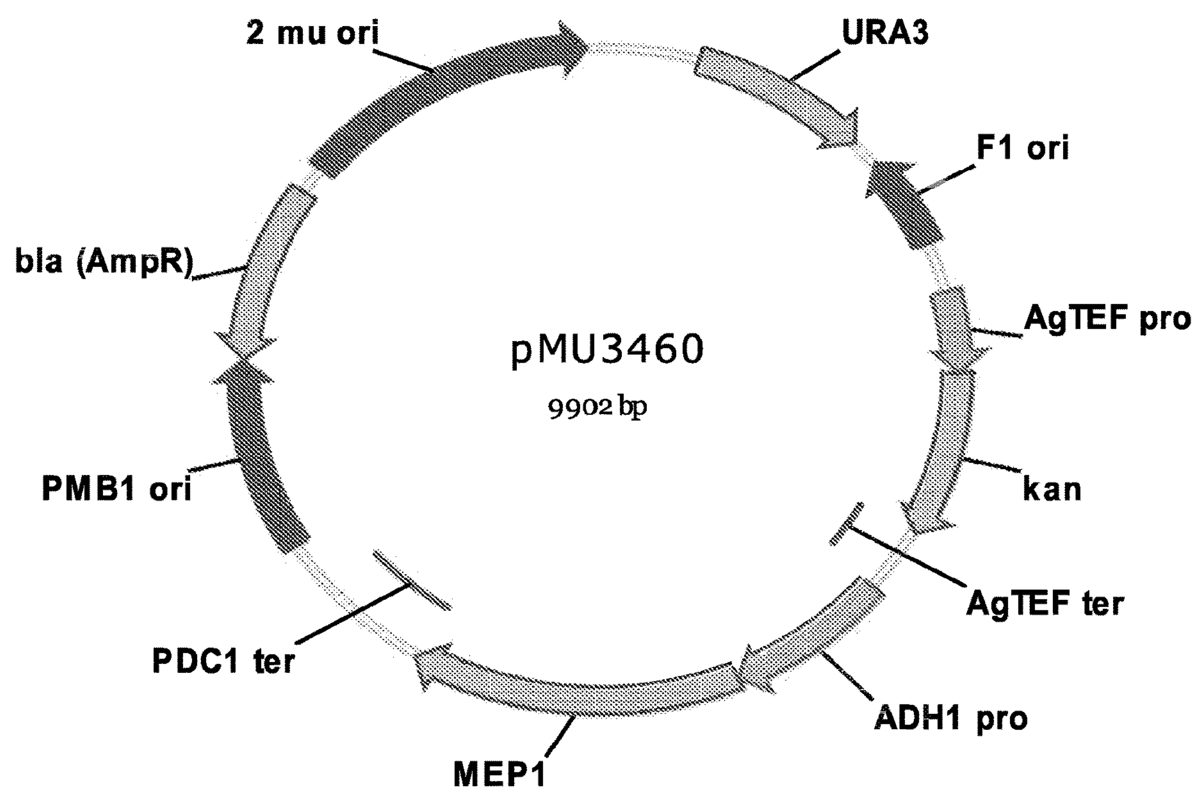
FIG. 55 depicts a plasmid map for pMU3460.
Figure 56:
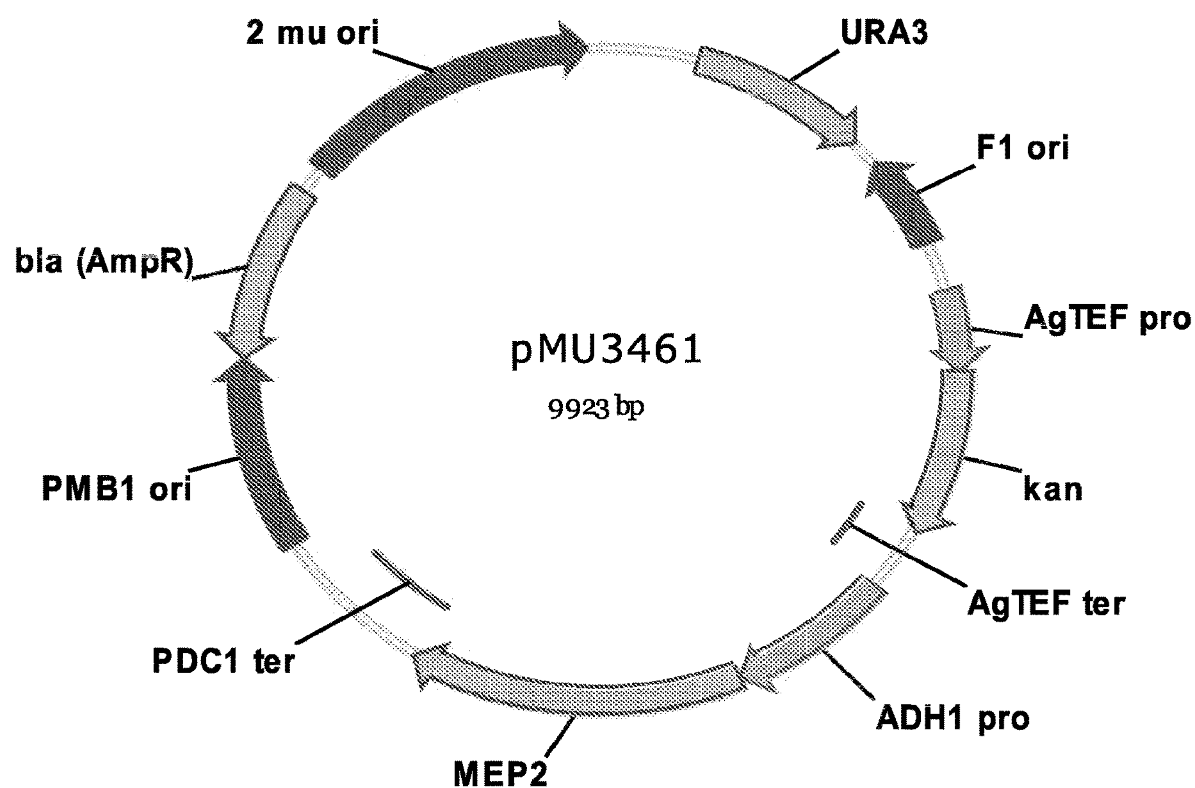
FIG. 56 depicts a plasmid map for pMU3461.
Figure 57:
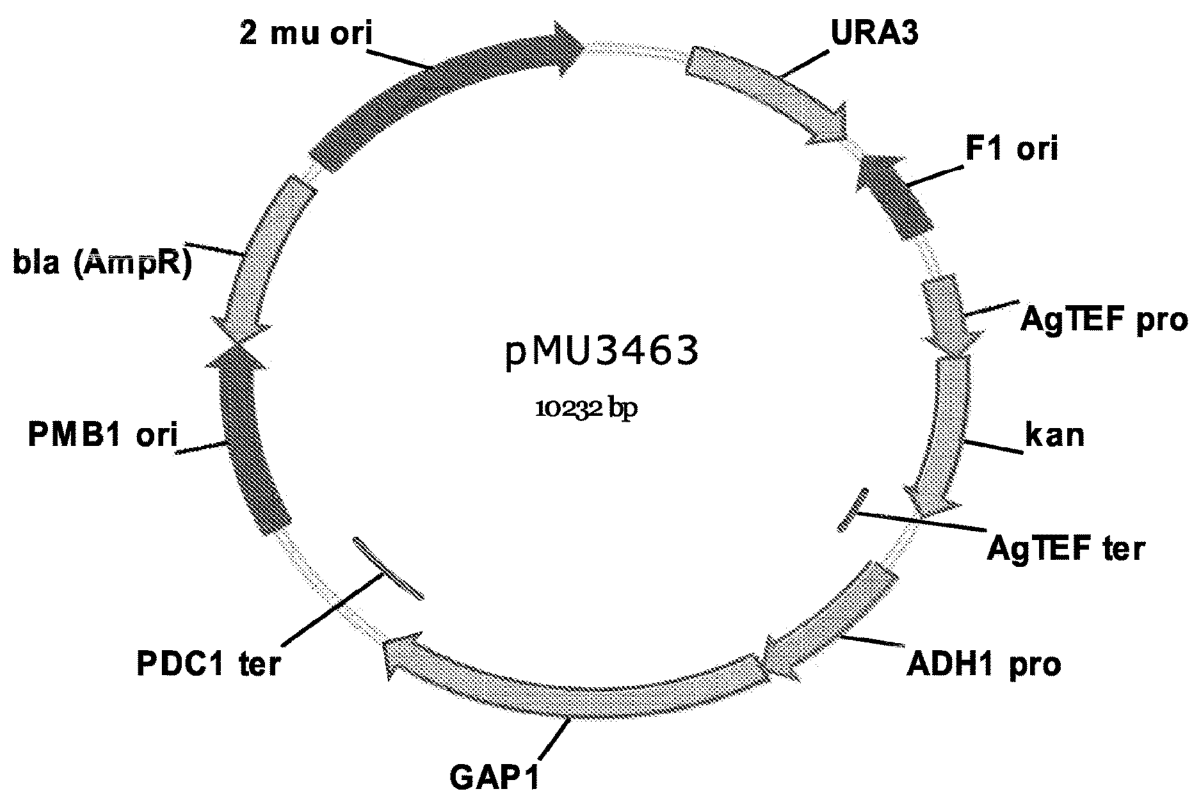
FIG. 57 depicts a plasmid map for pMU3463.
Figure 58:
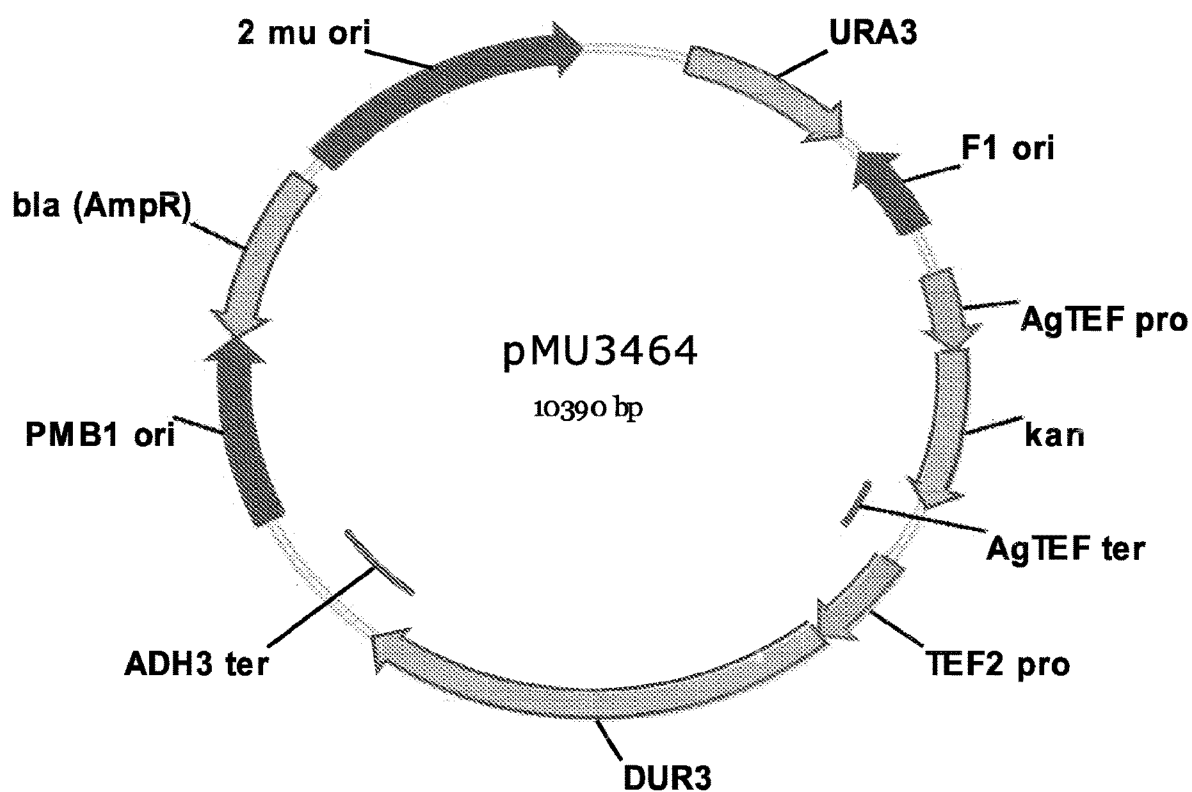
FIG. 58 depicts a plasmid map for pMU3464.
Figure 59:
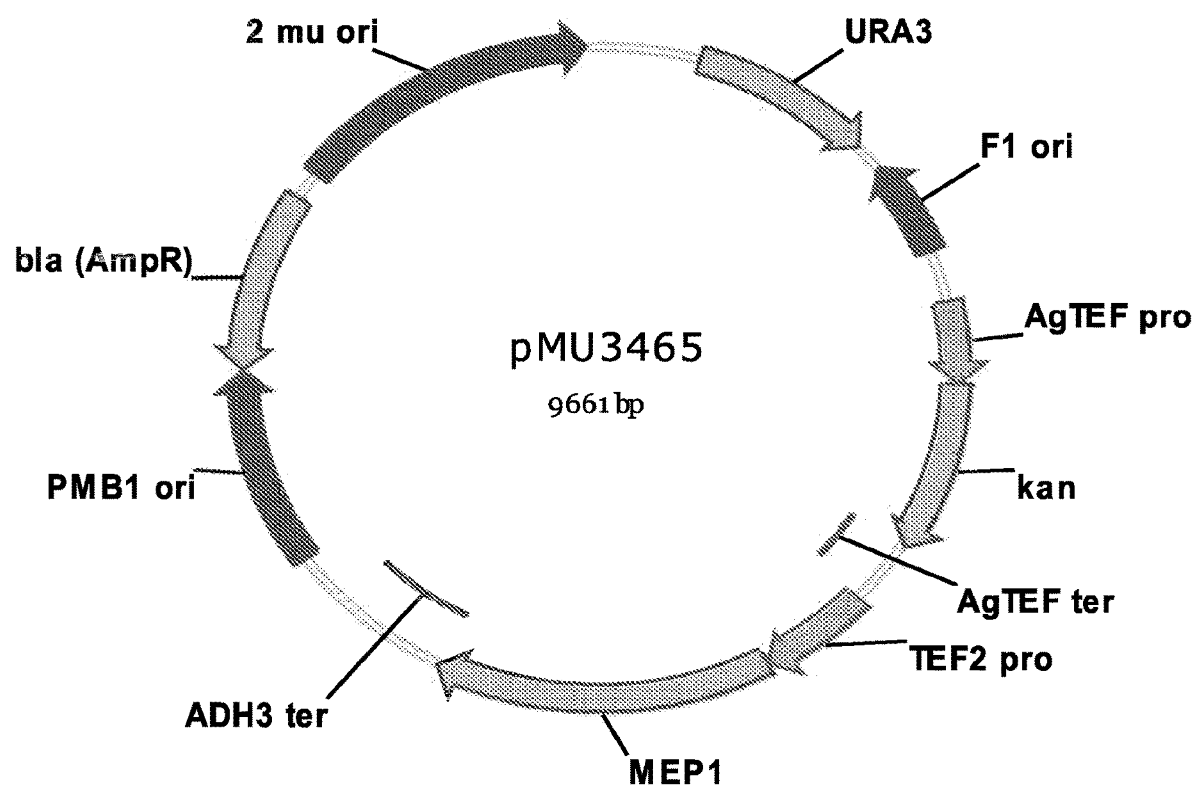
FIG. 59 depicts a plasmid map for pMU3465.
Figure 60:
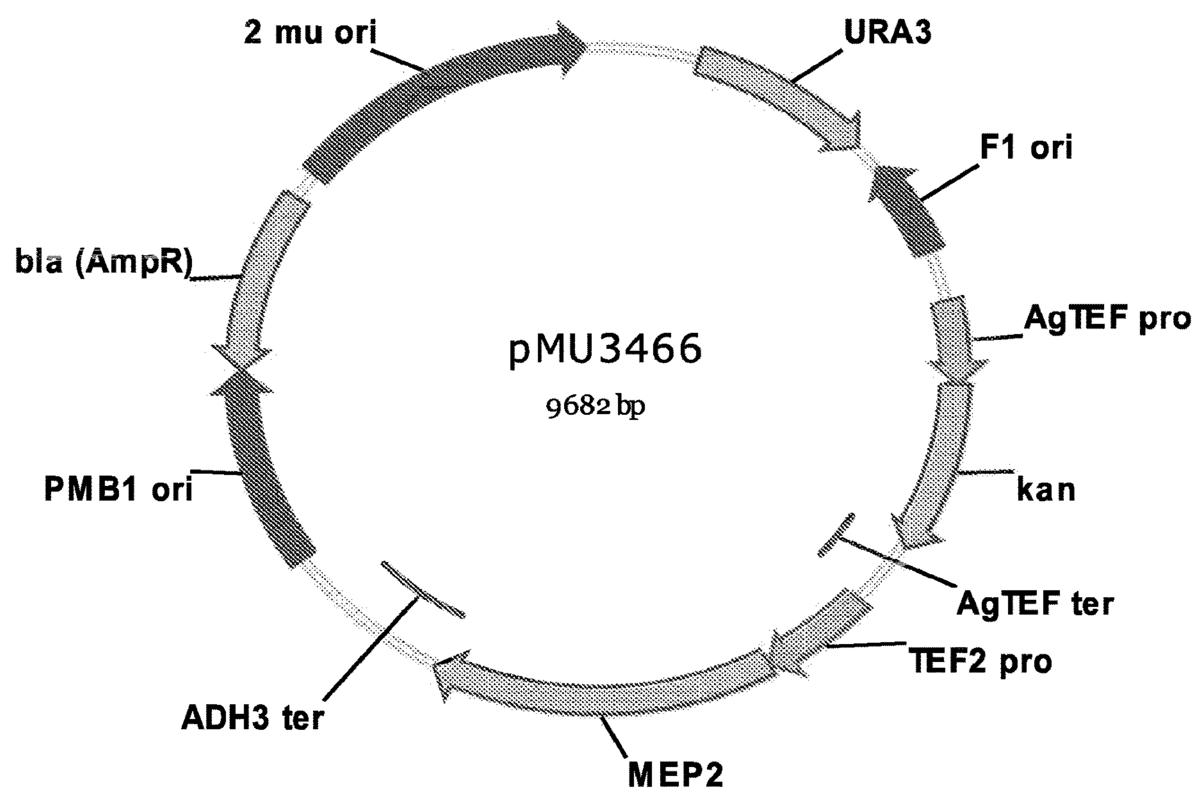
FIG. 60 depicts a plasmid map for pMU3466.
Figure 61:
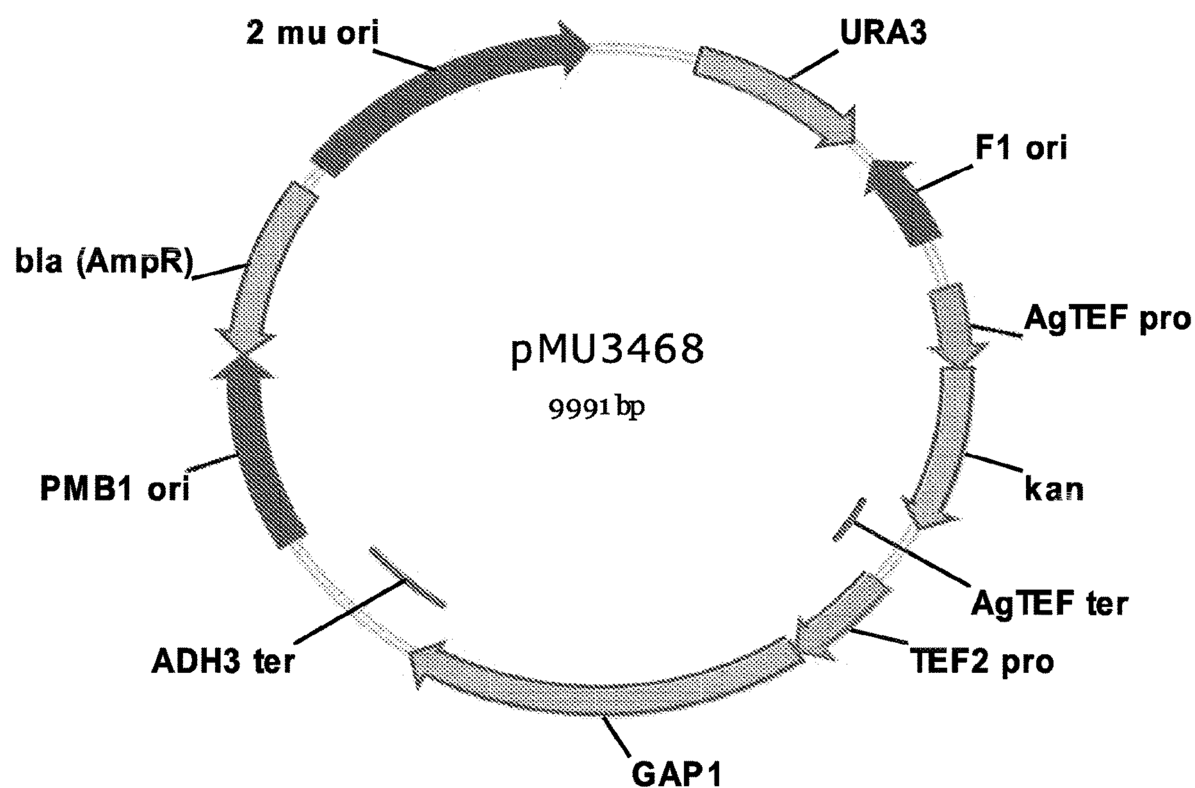
FIG. 61 depicts a plasmid map for pMU3468.
Figure 62:
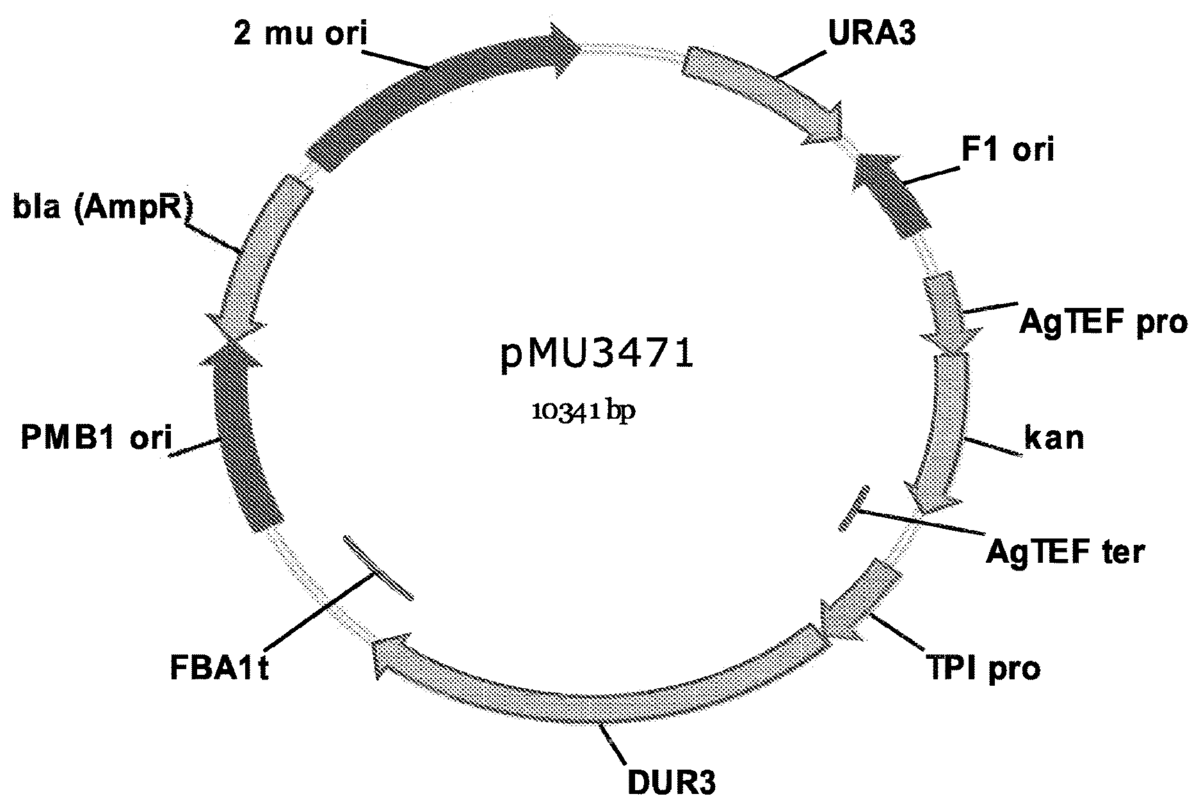
FIG. 62 depicts a plasmid map for pMU3471.
Figure 63:
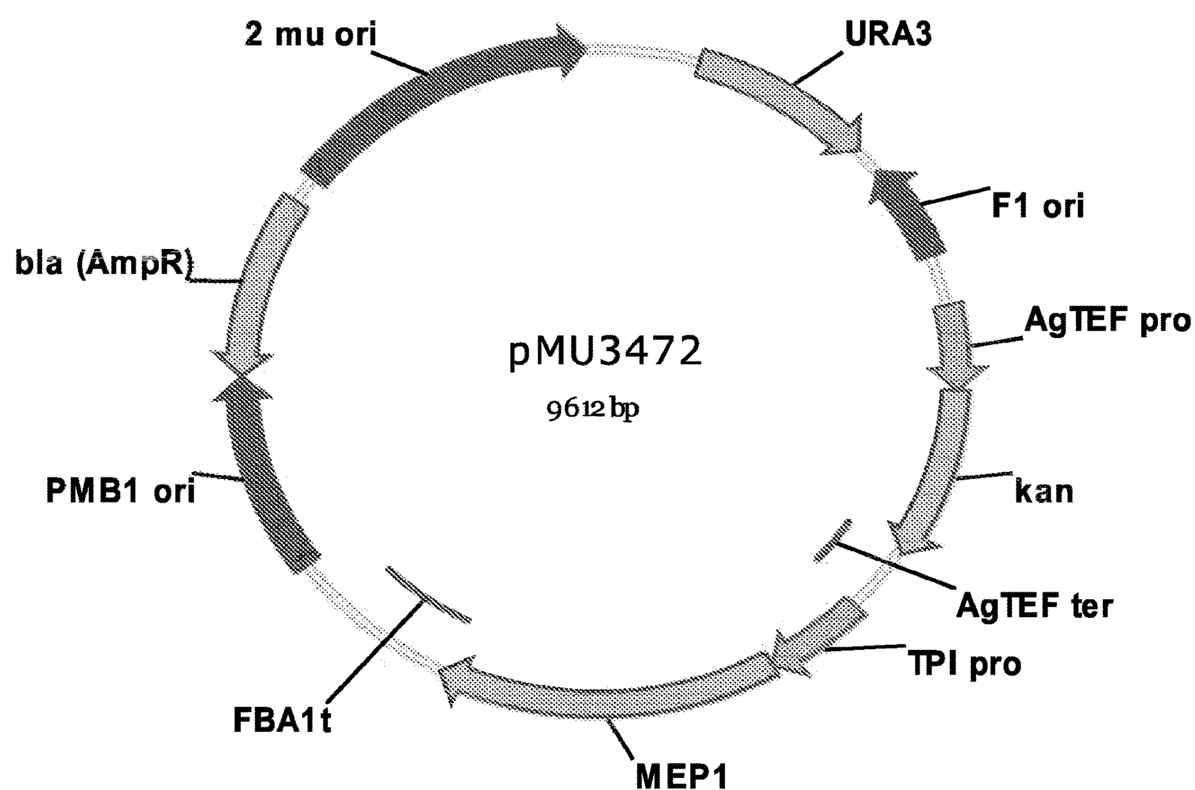
FIG. 63 depicts a plasmid map for pMU3472.
Figure 64:
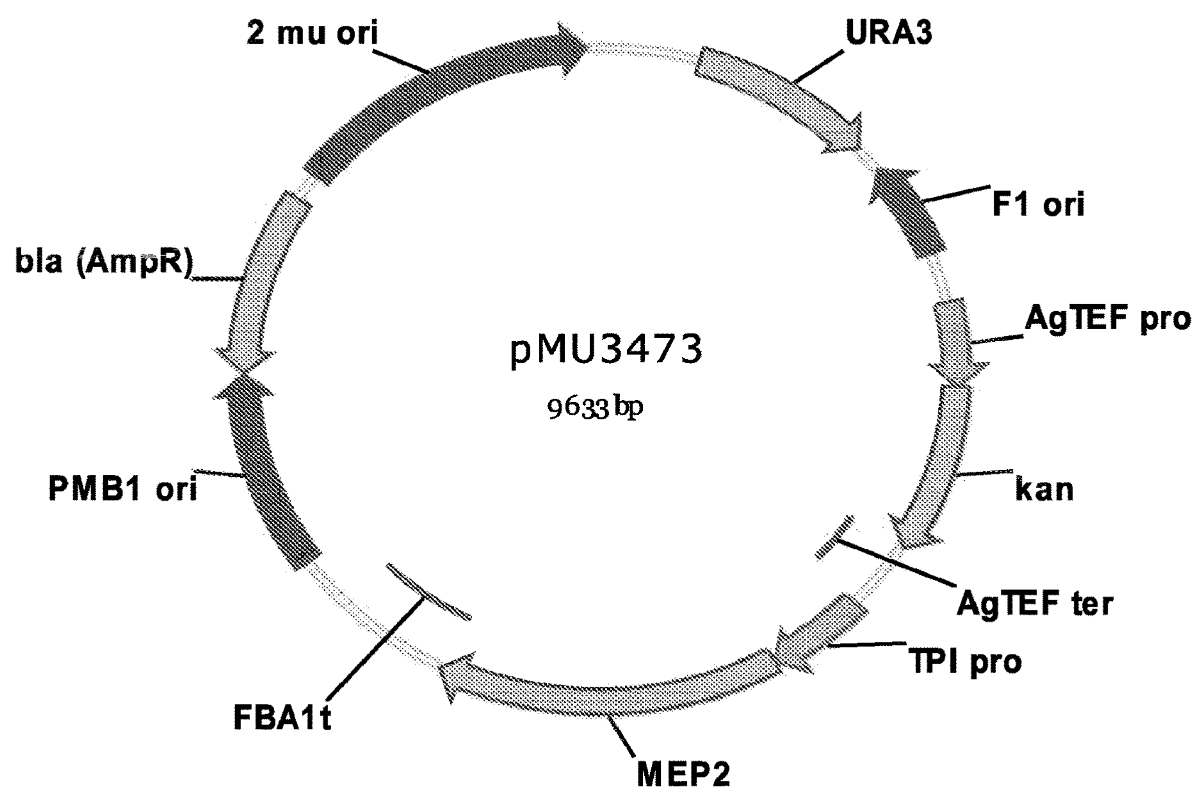
FIG. 64 depicts a plasmid map for pMU3473.
Figure 65:
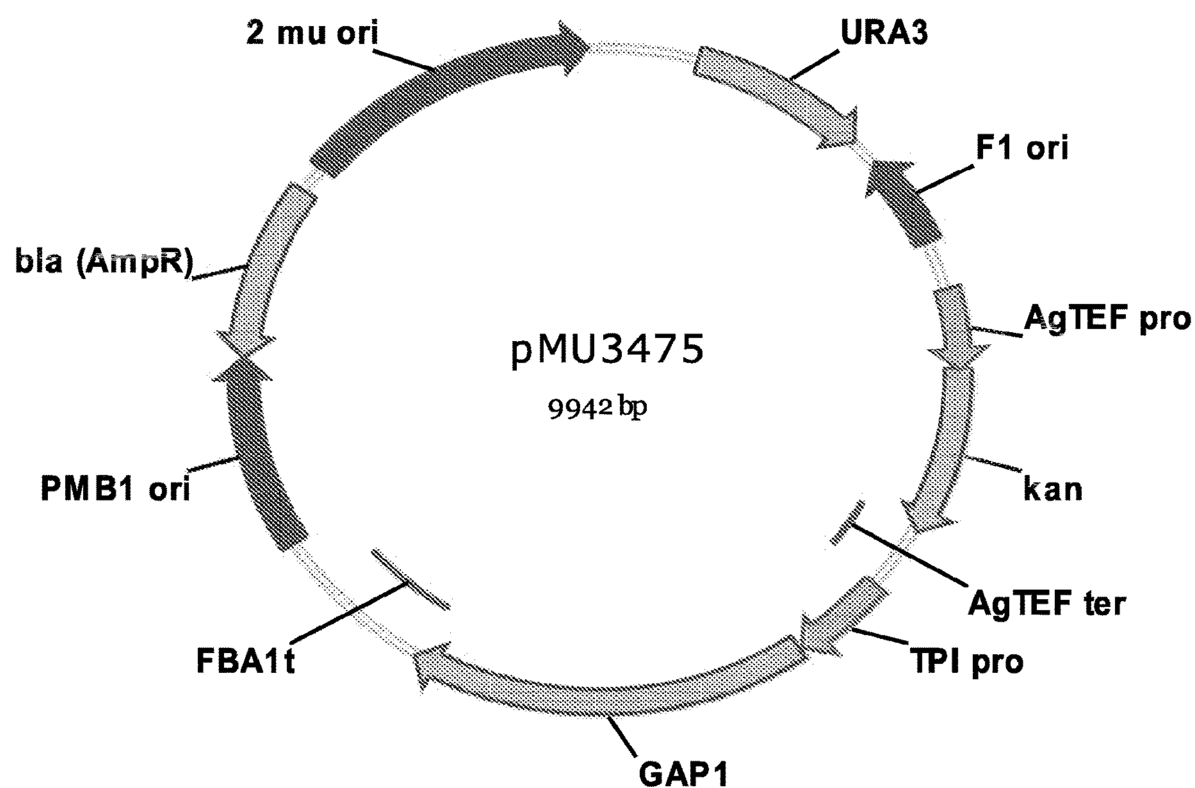
FIG. 65 depicts a plasmid map for pMU3475.
Figure 66:
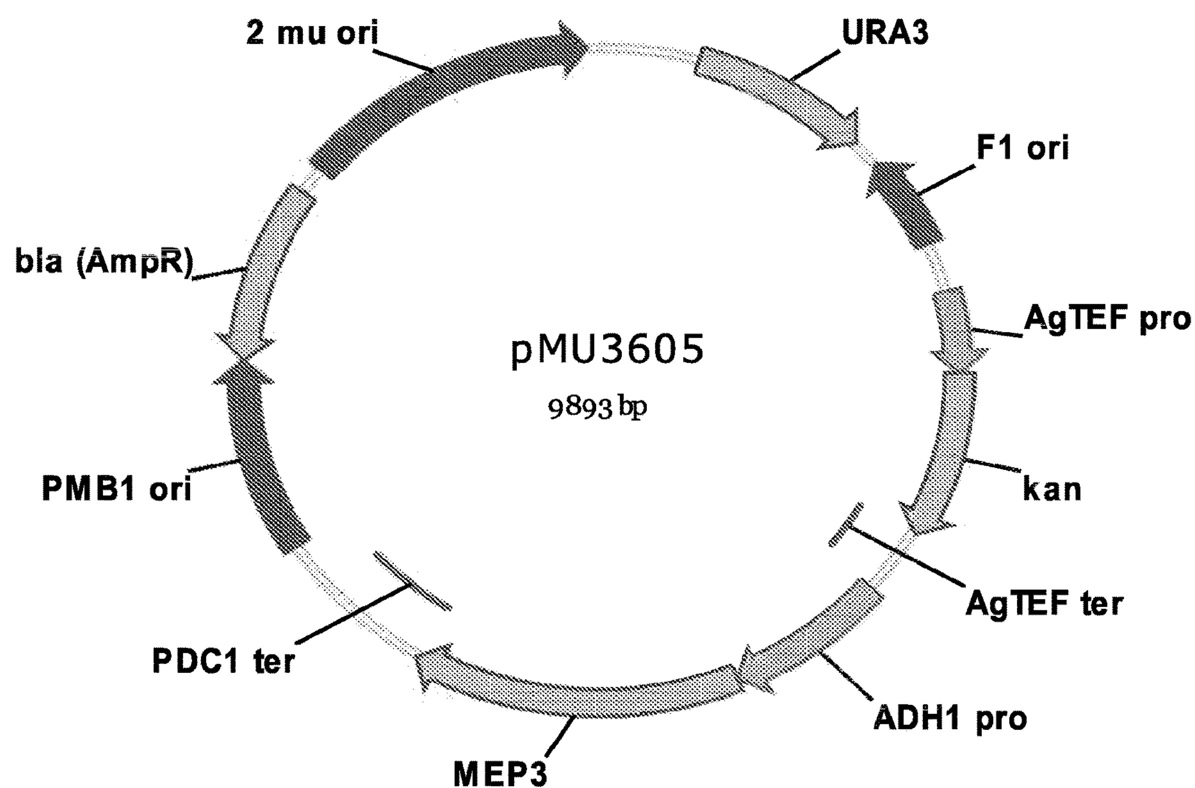
FIG. 66 depicts a plasmid map for pMU3605.
Figure 67:
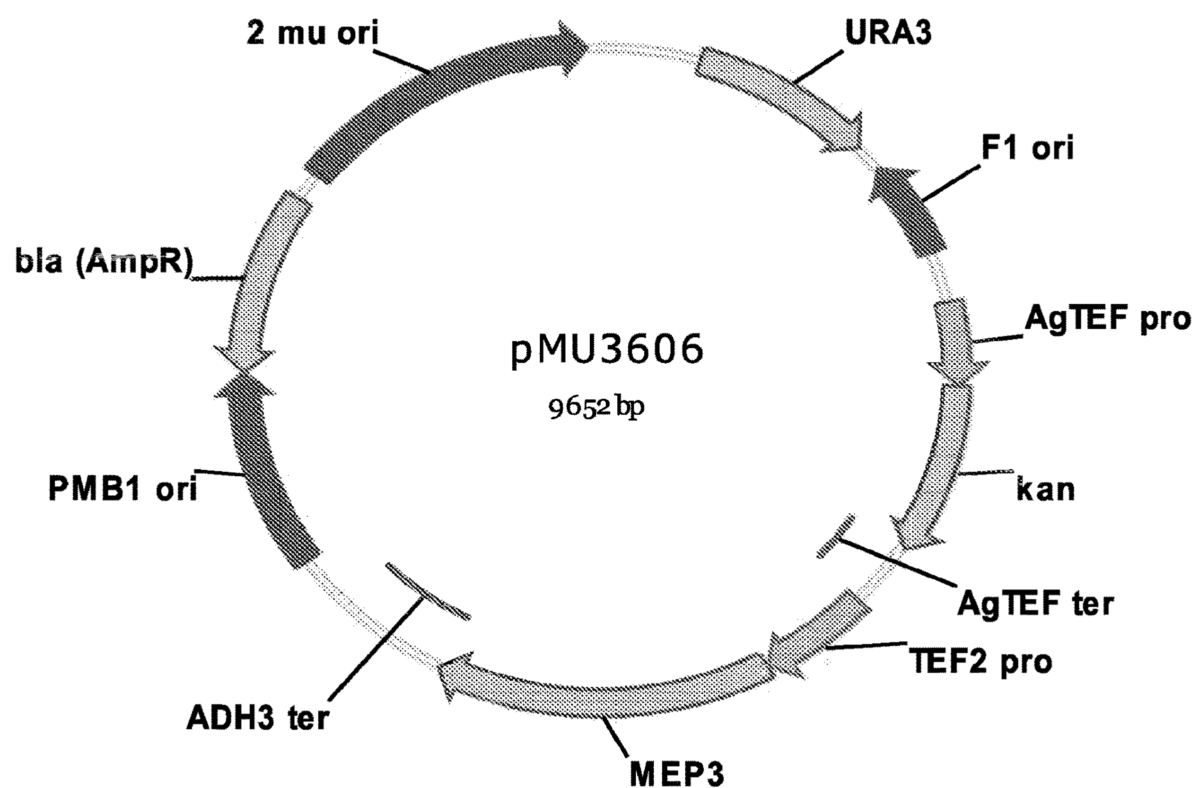
FIG. 67 depicts a plasmid map for pMU3606.
Figure 68:
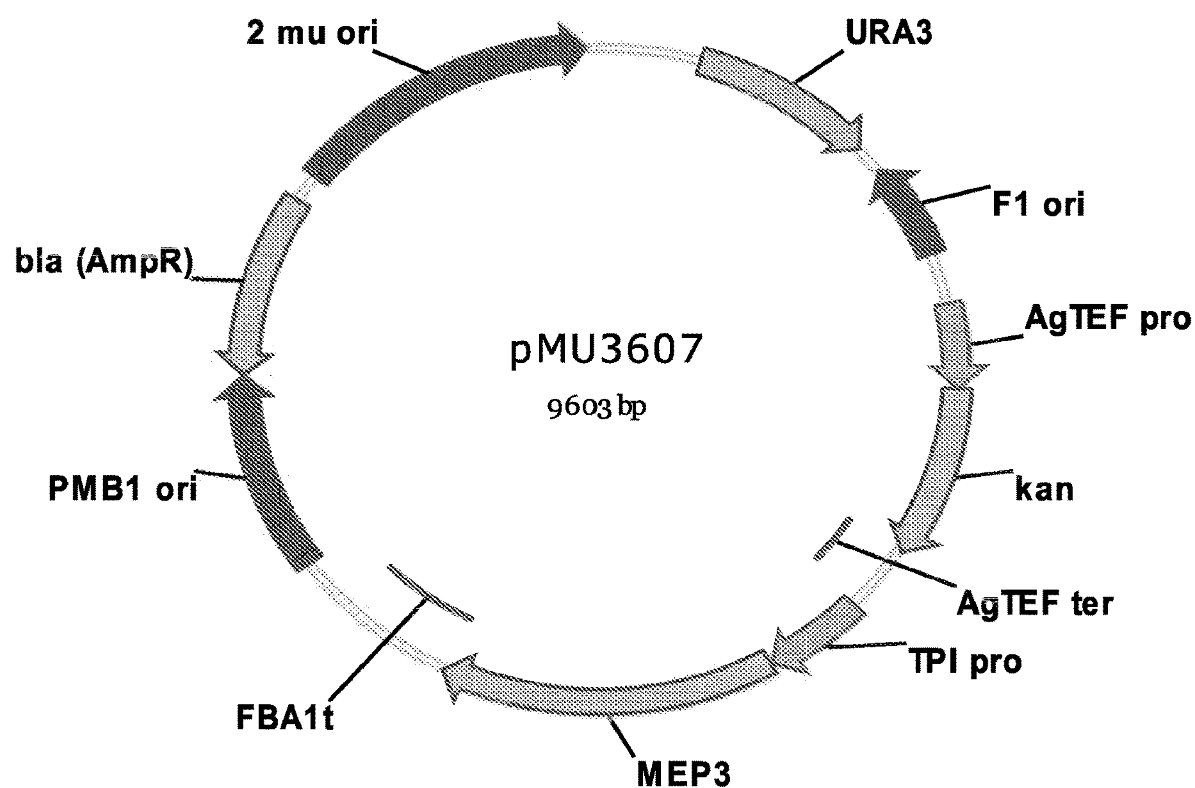
FIG. 68 depicts a plasmid map for pMU3607.

To create strains M5841-M5844, the GDH1 gene was deleted and replaced with 4 copies of the *N. crassa* GDH2 gene expression cassette in FIG. 10. Each strain resulted from independent colonies and have the same genotype (Table 6). The results shown in FIG. 73 demonstrate that the addition of the *N. crassa* GDH2 to M3624 resulted in titers that were between 3.6 g/l and 4.3 g/l higher than M3624. The data shown in FIG. 74 shows that M3624 makes 1.3 g/l glycerol which is 87% less than the wild type strain M2390, which made 10 g/l. The deletion of GDH1 and addition of the *N. crassa* GDH2 expression cassette decreased the glycerol titers to around 1 g/l. These results support the conclusion that a combination of glycerol reduction through formate production is synergistic with modifications to the ammonium assimilation pathway, even when using a heterologous expression of GDH2.

TABLE 6

Glycerol deletion strains which further comprise a deletion of gdh1 and an expression of Gdh2.

| Strain | Genotype |
|---|---|
| M2390 | WT |
| M3624 | Δfdh1Δfdh2::4a2pΔgpd1::gpd24a2pΔgpd2::gpd14a2p |
| M4117 | Δfdh1Δfdh2::4a2pΔgpd1::gpd24a2pΔgpd2::gpd14a2pΔScgdh1::4gdh2 |
| M5841 | Δfdh1Δfdh2::4a2pΔgpd1::gpd24a2pΔgpd2::gpd14a2pΔNcrassagdh1::4gdh2 |
| M5842 | Δfdh1Δfdh2::4a2pΔgpd1::gpd24a2pΔgpd2::gpd14a2pΔNcrassagdh1::4gdh2 |
| M5843 | Δfdh1Δfdh2::4a2pΔgpd1::gpd24a2pΔgpd2::gpd14a2pΔNcrassagdh1::4gdh2 |
| M5844 | Δfdh1Δfdh2::4a2pΔgpd1::gpd24a2pΔgpd2::gpd14a2pΔNcrassagdh1::4gdh2 |

The strains in Table 6 were inoculated in vials containing 4 ml industrial corn mash (mini-vials). The fermentation was allowed to proceed for 68 hrs and samples were run on an HPLC to obtain ethanol and glycerol values.

All documents cited herein, including journal articles or abstracts, published or corresponding U.S. or foreign patent applications, issued or foreign patents, or any other documents, are each entirely incorporated by reference herein, including all data, tables, figures, and text presented in the cited documents.

Those skilled in the art will recognize, or be able to ascertain using no more than routine experimentation, many equivalents to the specific embodiments of the invention described herein. Such equivalents are intended to be encompassed by the following claims.

The strains shown in examples are M2390, M3465, M3467, M3469, M3624, M4117, M4118, M4400, M4401, M4402, M4406, M4427, M4428, M4429, M4430, M4431, M4432, M4433 and M4434. The details of the aforesaid strains such as description, genotype and associated MA cassettes are listed in Table 4.

The invention claimed is:

1. A method of producing a fermentation product comprising:

a) providing a recombinant yeast comprising:

(i) at least one engineered genetic modification that leads to the up-regulation of one or more native and/or heterologous enzymes that function in one or more ethanol production pathways;

(ii) and, at least one engineered genetic modification that leads to the down-regulation of an enzyme in a glycerol-production pathway; and, (iii) at least one engineered genetic modification that leads to the up-regulation or down-regulation of an enzyme in a nitrogen-assimilation pathway;

wherein the upregulated enzyme that acts in the ethanol production pathway is selected from the group consisting of pyruvate formate lyase (EC 2.3.1.54), pyruvate formate lyase activating enzyme (EC 1.91.1.4), bifunctional acetaldehyde-alcohol dehydrogenase selected from a group of enzymes having both of the following Enzyme Commission Numbers: EC 1.2.1.10 and 1.111; and an NADPH-dependent bifunctional acetaldehyde-alcohol dehydrogenase selected from a group of enzymes having both of the following Enzyme Commission Numbers: EC 1.2.1.10 and 1.1.1.2;

wherein the down-regulated enzyme in the glycerol-production pathway is selected from the group consisting of glycerol-3-phosphate dehydrogenase 1 polynucleotide (GPD1) (EC 1.1.1.8), glycerol-3-phosphate dehydrogenase 1 polypeptide (Gpd1) (EC 1.1.1.8), glycerol-3-phosphate dehydrogenase 2 polynucleotide (GPD2) (EC 1.1.1.8), glycerol-3-phosphate dehydrogenase 2 polypeptide (Gpd2) (EC 1.1.1.8), glycerol-3-phosphate phosphatase 1 polynucleotide (GPP1) (EC 3.1.3.21), a glycerol-3-phosphate phosphatase polypeptide 1 (Gpp1) (EC 3.1.3.21), a glycerol-3-phosphate phosphatase 2 polynucleotide (GPP2) (EC 3.1.3.21), and glycerol-3-phosphate phosphatase polypeptide 2 (Gpp2) (EC 3.1.3.21); and wherein the down-regulated enzyme in the nitrogen-assimilation pathway is glutamate dehydrogenase (Gdh) (EC 1.4.1.4); or wherein the up-regulated enzyme in the nitrogen-assimilation pathway is at least one enzyme selected from the group consisting of glutamate dehydrogenase (Gdh) (EC 1.4.1.2), glutamate synthase (Glt) (EC 1.4.1.14), and glutamine synthase (Gln) (EC 6.3.1.2); an ammonium transporter; a urea-amido lyase (EC 6.3.4.6); and a urea transporter;

b) contacting the composition with a carbon containing feedstock, wherein the recombinant yeast is capable of fermenting the carbon containing feedstock to yield the fermentation product; and, c) optionally recovering the fermentation production.

2. The method of claim 1, wherein the fermentation product is ethanol.

3. The method of claim 1, wherein the recombinant yeast produces glycerol at a lower yield than an otherwise identical yeast lacking the genetic modifications.

4. The method of claim 1, wherein the up-regulated enzyme in the nitrogen-assimilation pathway is a Gdh7 isolated from an organism from a genus selected from the group consisting of *Saccharomyces* and *Neurospora* (Gdh2); a Glt1 isolated from an organism from the genus *Saccharomyces* (Glt1); a Gln1 isolated from an organism from the genus *Saccharomyces* (Gln1'); a MEP protein selected from the group consisting of; Mep1, Mep2, and Mep3 and isolated from an organism from a genus selected from the genus *Saccharomyces*; a urea-amido lyase isolated from an organism from the germs *Saccharomyces*; a Dur3 or a Dur4 isolated from an organism from the genus *Saccharomyces*; or a Gln 3 isolated from the genus *Saccharomyces*.

5. The method of claim 1, wherein the down-regulated enzyme in the nitrogen-assimilation pathway is encoded by a polypeptide sequence at least 80%, 90%, 95%, or 100% identical to a polypeptide sequence selected from the group consisting of: SEQ ID NOs: 25 and 31 (*S. cerevisiae* Gdh1 and Gdh3).

6. The method of claim 1, wherein the up-regulated enzyme in the nitrogen-assimilation pathway is encoded by a polypeptide sequence at least 80%, 90%, 95% or 100% identical to a polypeptide sequence selected from the group consisting of: SEQ ID NOs: 27 and 29 (Gdh2); a polypeptide sequence at least 80%, 90%, 95% or 100% identical to a polypeptide sequence encoded by SEQ ID NO: 33 (Glt1); a polypeptide sequence at least 80%, 90%, 95% or 100% identical to a polypeptide sequence encoded by SEQ ID NO: 35 (Gln1); a polypeptide sequence at least 80%, 90%, 95% or 100% identical to a polypeptide sequence encoded by SEQ ID NO: 19 (Mep1); a polypeptide sequence at least 80%, 90%, 95% or 100% identical to a polypeptide sequence encoded by SEQ ID NO: 21 (Mep2); a polypeptide sequence at least 80%, 90%, 95% or 100% identical to a polypeptide sequence encoded by SEQ ID NO: 23 (Mep3); a polypeptide sequence at least 80%, 90%, 95% or 100% identical to a polypeptide sequence encoded by SEQ ID NO: 37 (Dur1/2); a polypeptide sequence at least 80%, 90%, 95% or 100% identical to a polypeptide sequence encoded by: SEQ ID NO: 39 (Dur3); or a polypeptide sequence at least 80%, 90%, 95% or 100% identical to a polypeptide sequence encoded by SEQ ID NO: 156 (Gln3).

7. The method of claim 1, wherein the enzyme in the glycerol production pathway is encoded by a polypeptide sequence at least 80%, 90%, 95% or 100% identical to the polypeptide sequence encoded by: SEQ ID NO: 5 (Gpd1); a polypeptide sequence at least 80%, 90%, 95% or 100% identical to the polypeptide sequence encoded by: SEQ ID NO: 7 (Gpd2); a polypeptide sequence at least 80%, 90%, 95% or 100% identical to the polypeptide sequence encoded by: SEQ ID NO: 159 (Gpp1); or a polypeptide sequence at least 80%, 90%, 95% or 100% identical to the polypeptide sequence encoded by: SEQ ID NO: 161 (Gpp2).

8. The method of claim 1, wherein the enzyme that acts in the ethanol production pathway is encoded by a polypeptide sequence at least 80%, 90%, 95% or 100% identical to the polypeptide sequence encoded by SEQ ID NO: 9 (*B. adolescentis* Pf1); encoded by a polypeptide sequence at least 80%, 90%, 95% or 100% identical to the polypeptide sequence encoded by SEQ ID NO: 11 (*B. adolescentis* Pf1-activating enzyme); encoded by a polypeptide sequence at least 80%, 90%, 95% or 100% identical to the polypeptide sequence encoded by SEQ ID NO: 13 (*B. adolescentis* AdhE); or encoded by a polypeptide sequence at least 80%, 90%, 95% or 100% identical to a polypeptide sequence selected from a group consisting of SEQ ID NOs: 15 and 17.

9. The method of claim 1, wherein the recombinant yeast further comprises a down-regulation in one or more native enzymes encoded by a formate dehydrogenase enzyme selected from the group consisting of: EC 1.2.1.43 and EC 1.2.1.2; and/or a heterologous GPD1 polynucleotide operably linked to a native GPD2 promoter; and/or a heterologous GPD2 polynucleotide operably linked to a native GPD1 promoter; and/or an up-regulation or down-regulation of a regulatory element.

10. The method of claim 1, wherein the down-regulated enzyme is encoded by a polypeptide sequence at least 80%, 90%, 95% or 100% identical to a polypeptide sequence encoded by SEQ ID NO: 2 (Fdh1); or a polypeptide sequence at least 80%, 90%, 95% or 100% identical to a polypeptide sequence encoded by the polynucleotide sequence of SEQ ID NO: 3 (Fdh2).

11. The method of claim 9, wherein the regulatory element is selected from the group consisting of Ure2 and Aua1.

12. The method of claim 1, wherein the recombinant yeast further comprises at least one additional up-regulated enzyme, wherein the at least one additional up-regulated enzyme is a glucoamylase enzyme with an EC number 3.2.1.3; a permease; or a protease with EC number: 3.4.23.41.

13. The method of claim 12, wherein the up-regulated enzyme is encoded by a polypeptide sequence at least 80%, 90%, 95% or 100% identical to a polypeptide sequence encoded by SEQ ID NO: 163 (glucoamylase); a polypeptide sequence at least 80%, 90%, 95% or 100% identical to a polypeptide sequence encoded by SEQ ID NO: 53 (Gap); or a polypeptide sequence at least 80%, 90%, 95% or 100% identical to a polypeptide sequence selected from a group consisting of SEQ ID NOs: 41, 43, 45, 47, 49, and 51 (protease).

14. The method of claim 1, wherein the up-regulated enzymes are under the control of a heterologous promoter.

15. The method of claim 1, wherein the recombinant yeast produces ethanol at a higher yield than an otherwise identical yeast lacking the genetic modifications, or the recombinant yeast produces an ethanol titer from about 1% to about 10% more than an otherwise identical yeast lacking the genetic modifications, or the recombinant yeast produces an ethanol titer of at least 125 g/L, or the recombinant yeast produces a glycerol titer of from about 10 to about 100% less than an otherwise identical microorganism lacking the genetic modification.

16. The method of claim 11, wherein the regulatory element is encoded by polypeptide sequence at least 80%, 90%, 95% or 100% identical to a polypeptide sequence encoded by a polynucleotide, sequence of SEQ ID NO: 55 (Ure2) or a polypeptide sequence at least 80%, 90%, 95% or 100% identical to a polypeptide sequence encoded by a polynucleotide sequence of SEQ ID NO: 57 (Aua1).

17. The method of claim 12, wherein the at least one additional up-regulated enzyme is a glucoamylase enzyme with an EC number 3.2.1.3 isolated from the genus *Saccharomycopsis*; a permease isolated from the genus *Saccharomyces* (permease); or a protease with EC number: 3.4.23.41 isolated from a genus selected from the group consisting of: *Zea, Neurospora, Podospora* and *Magnaporthe*.

18. The method of claim 14, wherein the heterologous promoter is selected from a group consisting of: TEF2 (SEQ ID NO: 58), HXT7 (SEQ ID NO: 59), ADH1 (SEQ ID NO: 60), and TP1 (SEQ ID NO: 61).

19. The method of claim 1, wherein nitrogen is added to the culture containing the recombinant yeast and the carbon-containing feedstock.

20. The method of claim 1, wherein the carbon-containing feedstock is selected from the group, consisting of woody biomass, grasses, sugar-processing residues, municipal waste, agricultural wastes, wood pulp fiber, sawdust, hardwood, softwood, rice straw, rice hulls, barley straw, corn cobs, cereal straw, wheat straw, canola straw, oaf straw, oat hulls, corn fiber, stover, succulents, agave, cane bagasse, switchgrass, *miscanthus*, paper sludge, or any combination thereof.

21. The method of claim 1, wherein the carbon-containing feedstock is from corn.

* * * * *

UNITED STATES PATENT AND TRADEMARK OFFICE

CERTIFICATE OF CORRECTION

PATENT NO. : 11,274,319 B2
APPLICATION NO. : 16/570881
DATED : March 15, 2022
INVENTOR(S) : Aaron Argyros et al.

It is certified that error appears in the above-identified patent and that said Letters Patent is hereby corrected as shown below:

In the Claims

At Column 239, Claim number 1, Line number 22, please replace “1.111” with --1.1.1.1--

At Column 240, Claim number 4, Line number 3, please replace “;” with --:--

At Column 240, Claim number 4, Line number 4, please remove “a genus selected from”

At Column 240, Claim number 4, Line number 6, please replace “germs” with --genus--

At Column 242, Claim number 15, Line number 2, please remove “of” after “titer”

Signed and Sealed this
Nineteenth Day of July, 2022

Katherine Kelly Vidal

Katherine Kelly Vidal
*Director of the United States Patent and Trademark Office*

SEQUENCE LISTING

```
<160> NUMBER OF SEQ ID NOS: 163

<210> SEQ ID NO 1
<211> LENGTH: 1131
<212> TYPE: DNA
<213> ORGANISM: Saccharomyces cerevisiae

<400> SEQUENCE: 1

atgtcgaagg gaaaggtttt gctggttctt tacgaaggtg gtaagcatgc tgaagagcag     60

gaaaagttat tggggtgtat tgaaaatgaa cttggtatca gaaatttcat tgaagaacag    120

ggatacgagt tggttactac cattgacaag gaccctgagc caacctcaac ggtagacagg    180

gagttgaaag acgctgaaat tgtcattact acgccctttt tccccgccta catctcgaga    240

aacaggattg cagaagctcc taacctgaag ctctgtgtaa ccgctggcgt cggttcagac    300

catgtcgatt tagaagctgc aaatgaacgg aaaatcacgg tcaccgaagt tactggttct    360

aacgtcgttt ctgtcgcaga gcacgttatg gccacaattt tggttttgat aagaaactat    420

aatggtggtc atcaacaagc aattaatggt gagtgggata ttgccggcgt ggctaaaaat    480

gagtatgatc tggaagacaa aataatttca acggtaggtg ccggtagaat tggatatagg    540

gttctggaaa gattggtcgc atttaatccg aagaagttac tgtactacga ctaccaggaa    600

ctacctgcgg aagcaatcaa tagattgaac gaggccagca agcttttcaa tggcagaggt    660

gatattgttc agagagtaga gaaattggag gatatggttg ctcagtcaga tgttgttacc    720

atcaactgtc cattgcacaa ggactcaagg ggtttattca ataaaaagct tatttcccac    780

atgaaagatg gtgcatactt ggtgaatacc gctagaggtg ctatttgtgt cgcagaagat    840

gttgccgagg cagtcaagtc tggtaaattg gctggctatg gtggtgatgt ctgggataag    900

caaccagcac caaaagacca tccctggagg actatggaca ataaggacca cgtgggaaac    960

gcaatgactg ttcatatcag tggcacatct ctggatgctc aaaagaggta cgctcaggga   1020

gtaaagaaca tcctaaatag ttacttttcc aaaaagtttg attaccgtcc acaggatatt   1080

attgtgcaga atggttctta tgccaccaga gcttatggac agaagaaata a            1131

<210> SEQ ID NO 2
<211> LENGTH: 376
<212> TYPE: PRT
<213> ORGANISM: Saccharomyces cerevisiae

<400> SEQUENCE: 2

Met Ser Lys Gly Lys Val Leu Leu Val Leu Tyr Glu Gly Gly Lys His
1               5                   10                  15

Ala Glu Glu Gln Glu Lys Leu Leu Gly Cys Ile Glu Asn Glu Leu Gly
            20                  25                  30

Ile Arg Asn Phe Ile Glu Glu Gln Gly Tyr Glu Leu Val Thr Thr Ile
        35                  40                  45
```

```
Asp Lys Asp Pro Glu Pro Thr Ser Thr Val Asp Arg Glu Leu Lys Asp
    50                  55                  60

Ala Glu Ile Val Ile Thr Thr Pro Phe Phe Pro Ala Tyr Ile Ser Arg
65                  70                  75                  80

Asn Arg Ile Ala Glu Ala Pro Asn Leu Lys Leu Cys Val Thr Ala Gly
                85                  90                  95

Val Gly Ser Asp His Val Asp Leu Glu Ala Ala Asn Glu Arg Lys Ile
            100                 105                 110

Thr Val Thr Glu Val Thr Gly Ser Asn Val Val Ser Val Ala Glu His
        115                 120                 125

Val Met Ala Thr Ile Leu Val Leu Ile Arg Asn Tyr Asn Gly Gly His
    130                 135                 140

Gln Gln Ala Ile Asn Gly Glu Trp Asp Ile Ala Gly Val Ala Lys Asn
145                 150                 155                 160

Glu Tyr Asp Leu Glu Asp Lys Ile Ile Ser Thr Val Gly Ala Gly Arg
                165                 170                 175

Ile Gly Tyr Arg Val Leu Glu Arg Leu Val Ala Phe Asn Pro Lys Lys
            180                 185                 190

Leu Leu Tyr Tyr Asp Tyr Gln Glu Leu Pro Ala Glu Ala Ile Asn Arg
        195                 200                 205

Leu Asn Glu Ala Ser Lys Leu Phe Asn Gly Arg Gly Asp Ile Val Gln
    210                 215                 220

Arg Val Glu Lys Leu Glu Asp Met Val Ala Gln Ser Asp Val Val Thr
225                 230                 235                 240

Ile Asn Cys Pro Leu His Lys Asp Ser Arg Gly Leu Phe Asn Lys Lys
                245                 250                 255

Leu Ile Ser His Met Lys Asp Gly Ala Tyr Leu Val Asn Thr Ala Arg
            260                 265                 270

Gly Ala Ile Cys Val Ala Glu Asp Val Ala Glu Ala Val Lys Ser Gly
        275                 280                 285

Lys Leu Ala Gly Tyr Gly Gly Asp Val Trp Asp Lys Gln Pro Ala Pro
    290                 295                 300

Lys Asp His Pro Trp Arg Thr Met Asp Asn Lys Asp His Val Gly Asn
305                 310                 315                 320

Ala Met Thr Val His Ile Ser Gly Thr Ser Leu Asp Ala Gln Lys Arg
                325                 330                 335

Tyr Ala Gln Gly Val Lys Asn Ile Leu Asn Ser Tyr Phe Ser Lys Lys
            340                 345                 350

Phe Asp Tyr Arg Pro Gln Asp Ile Ile Val Gln Asn Gly Ser Tyr Ala
        355                 360                 365

Thr Arg Ala Tyr Gly Gln Lys Lys
    370                 375
```

<210> SEQ ID NO 3
<211> LENGTH: 1129
<212> TYPE: DNA
<213> ORGANISM: Saccharomyces cerevisiae

<400> SEQUENCE: 3

```
atgtcgaagg gaaaggtttt gctggttctt tatgaaggtg gtaagcatgc tgaagagcag      60

gaaaagttat tggggtgtat tgaaaatgaa cttggtatca gaaatttcat tgaagaacag     120

ggatacgagt tggttactac cattgacaag gaccctgagc caacctcaac ggtagacagg     180

gagttgaaag acgctgaaat tgtcattact acgccctttt tccccgccta catctcgaga     240
```

```
aacaggattg cagaagctcc taacctgaag ctctgtgtaa ccgctggcgt cggttcagac    300

catgtcgatt tagaagctgc aaatgaacgg aaaatcacgg tcaccgaagt tactggttct    360

aacgtcgttt ctgtcgcaga gcacgttatg gccacaattt tggttttgat aagaaactat    420

aatggtggtc atcaataagc aattaatggt gagtgggata ttgccggcgt ggctaaaaaa    480

tgagtatgat ctggaagaca aaataatttc aacggtaggt gccggtagaa ttggatatag    540

ggttctggaa agattggtcg catttaatcc gaagaagtta ctgtactacg actaccagga    600

actacctgcg gaagcaatca atagattgaa cgaggccagc aagcttttca atggcagagg    660

tgatattgtt cagagagtag agaaattgga ggatatggtt gctcagtcag atgttgttac    720

catcaactgt ccattgcaca aggactcaag ggtttattc aataaaaagc ttatttccca     780

catgaaagat ggtgcatact tggtgaatac cgctagaggt gctatttgtg tcgcagaaga    840

tgttgccgag gcagtcaagt ctggtaaatt ggctggctat ggtggtgatg tctgggataa    900

gcaaccagca ccaaaagacc atccctggag gactatggac aataaggacc acgtgggaaa    960

cgcaatgact gttcatatca gtggcacatc tctgcatgct caaaagaggt acgctcaggg   1020

agtaaagaac atcctaaata gttacttttc caaaaagttt gattaccgtc cacaggatat   1080

tattgtgcag aatggttctt atgccaccag agcttatgga cagaagaaa              1129
```

<210> SEQ ID NO 4
<211> LENGTH: 1176
<212> TYPE: DNA
<213> ORGANISM: Saccharomyces cerevisiae

<400> SEQUENCE: 4

```
atgtctgctg ctgctgatag attaaactta acttccggcc acttgaatgc tggtagaaag     60

agaagttcct cttctgtttc tttgaaggct gccgaaaagc ctttcaaggt tactgtgatt    120

ggatctggta actggggtac tactattgcc aaggtggttg ccgaaaattg taagggatac    180

ccagaagttt tcgctccaat agtacaaatg tgggtgttcg aagaagagat caatggtgaa    240

aaattgactg aaatcataaa tactagacat caaaacgtga aatacttgcc tggcatcact    300

ctacccgaca atttggttgc taatccagac ttgattgatt cagtcaagga tgtcgacatc    360

atcgttttca acattccaca tcaatttttg ccccgtatct gtagccaatt gaaaggtcat    420

gttgattcac acgtcagagc tatctcctgt ctaaagggtt ttgaagttgg tgctaaaggt    480

gtccaattgc tatcctctta catcactgag gaactaggta ttcaatgtgg tgctctatct    540

ggtgctaaca ttgccaccga agtcgctcaa gaacactggt ctgaaacaac agttgcttac    600

cacattccaa aggatttcag aggcgagggc aaggacgtcg accataaggt tctaaaggcc    660

ttgttccaca gaccttactt ccacgttagt gtcatcgaag atgttgctgg tatctccatc    720

tgtggtgctt tgaagaacgt tgttgcctta ggttgtggtt tcgtcgaagg tctaggctgg    780

ggtaacaacg cttctgctgc catccaaaga gtcggtttgg gtgagatcat cagattcggt    840

caaatgtttt tcccagaatc tagagaagaa acatactacc aagagtctgc tggtgttgct    900

gatttgatca ccacctgcgc tggtggtaga aacgtcaagg ttgctaggct aatggctact    960

tctggtaagg acgcctggga atgtgaaaag gagttgttga atggccaatc cgctcaaggt   1020

ttaattacct gcaaagaagt tcacgaatgg ttggaaacat gtggctctgt cgaagacttc   1080

ccattatttg aagccgtata ccaaatcgtt tacaacaact acccaatgaa gaacctgccg   1140

gacatgattg aagaattaga tctacatgaa gattag                             1176
```

```
<210> SEQ ID NO 5
<211> LENGTH: 391
<212> TYPE: PRT
<213> ORGANISM: Saccharomyces cerevisiae

<400> SEQUENCE: 5

Met Ser Ala Ala Ala Asp Arg Leu Asn Leu Thr Ser Gly His Leu Asn
1               5                   10                  15

Ala Gly Arg Lys Arg Ser Ser Ser Ser Val Ser Leu Lys Ala Ala Glu
            20                  25                  30

Lys Pro Phe Lys Val Thr Val Ile Gly Ser Gly Asn Trp Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380
```

Glu Leu Asp Leu His Glu Asp
385 390

<210> SEQ ID NO 6
<211> LENGTH: 1320
<212> TYPE: DNA
<213> ORGANISM: Saccharomyces cerevisiae

<400> SEQUENCE: 6
atgcttgctg tcagaagatt aacaagatac acattcctta agcgaacgca tccggtgtta 60
tatactcgtc gtgcatataa aattttgcct tcaagatcta ctttcctaag aagatcatta 120
ttacaaacac aactgcactc aaagatgact gctcatacta atatcaaaca gcacaaacac 180
tgtcatgagg accatcctat cagaagatcg gactctgccg tgtcaattgt acatttgaaa 240
cgtgcgccct tcaaggttac agtgattggt tctggtaact gggggaccac catcgccaaa 300
gtcattgcgg aaaacacaga attgcattcc catatcttcg agccagaggt gagaatgtgg 360
gtttttgatg aaaagatcgg cgacgaaaat ctgacggata tcataaatac aagacaccag 420
aacgttaaat atctacccaa tattgacctg ccccataatc tagtggccga tcctgatctt 480
ttacactcca tcaagggtgc tgacatcctt gttttcaaca tccctcatca atttttacca 540
aacatagtca aacaattgca aggccacgtg gcccctcatg taagggccat ctcgtgtcta 600
aaagggttcg agttgggctc caagggtgtg caattgctat cctcctatgt tactgatgag 660
ttaggaatcc aatgtggcgc actatctggt gcaaacttgg caccggaagt ggccaaggag 720
cattggtccg aaaccaccgt ggcttaccaa ctaccaaagg attatcaagg tgatggcaag 780
gatgtagatc ataagatttt gaaattgctg ttccacagac cttacttcca cgtcaatgtc 840
atcgatgatg ttgctggtat atccattgcc ggtgccttga agaacgtcgt ggcacttgca 900
tgtggtttcg tagaaggtat gggatggggt aacaatgcct ccgcagccat tcaaaggctg 960
ggtttaggtg aaattatcaa gttcggtaga atgtttttcc cagaatccaa agtcgagacc 1020
tactatcaag aatccgctgg tgttgcagat ctgatcacca cctgctcagg cggtagaaac 1080
gtcaaggttg ccacatacat ggccaagacc ggtaagtcag ccttggaagc agaaaaggaa 1140
ttgcttaacg gtcaatccgc ccaagggata atcacatgca gagaagttca cgagtggcta 1200
caaacatgtg agttgaccca agaattccca ttattcgagg cagtctacca gatagtctac 1260
aacaacgtcc gcatggaaga cctaccggag atgattgaag agctagacat cgatgacgaa 1320

<210> SEQ ID NO 7
<211> LENGTH: 440
<212> TYPE: PRT
<213> ORGANISM: Saccharomyces cerevisiae

<400> SEQUENCE: 7

Met Leu Ala Val Arg Arg Leu Thr Arg Tyr Thr Phe Leu Lys Arg Thr
1 5 10 15

His Pro Val Leu Tyr Thr Arg Arg Ala Tyr Lys Ile Leu Pro Ser Arg
20 25 30

Ser Thr Phe Leu Arg Arg Ser Leu Leu Gln Thr Gln Leu His Ser Lys
35 40 45

Met Thr Ala His Thr Asn Ile Lys Gln His Lys His Cys His Glu Asp
50 55 60

His Pro Ile Arg Arg Ser Asp Ser Ala Val Ser Ile Val His Leu Lys
65 70 75 80

Arg Ala Pro Phe Lys Val Thr Val Ile Gly Ser Gly Asn Trp Gly Thr

```
                85                  90                  95

Thr Ile Ala Lys Val Ile Ala Glu Asn Thr Glu Leu His Ser His Ile
            100                 105                 110

Phe Glu Pro Glu Val Arg Met Trp Val Phe Asp Glu Lys Ile Gly Asp
        115                 120                 125

Glu Asn Leu Thr Asp Ile Ile Asn Thr Arg His Gln Asn Val Lys Tyr
    130                 135                 140

Leu Pro Asn Ile Asp Leu Pro His Asn Leu Val Ala Asp Pro Asp Leu
145                 150                 155                 160

Leu His Ser Ile Lys Gly Ala Asp Ile Leu Val Phe Asn Ile Pro His
                165                 170                 175

Gln Phe Leu Pro Asn Ile Val Lys Gln Leu Gln Gly His Val Ala Pro
            180                 185                 190

His Val Arg Ala Ile Ser Cys Leu Lys Gly Phe Glu Leu Gly Ser Lys
        195                 200                 205

Gly Val Gln Leu Leu Ser Ser Tyr Val Thr Asp Glu Leu Gly Ile Gln
    210                 215                 220

Cys Gly Ala Leu Ser Gly Ala Asn Leu Ala Pro Glu Val Ala Lys Glu
225                 230                 235                 240

His Trp Ser Glu Thr Thr Val Ala Tyr Gln Leu Pro Lys Asp Tyr Gln
                245                 250                 255

Gly Asp Gly Lys Asp Val Asp His Lys Ile Leu Lys Leu Leu Phe His
            260                 265                 270

Arg Pro Tyr Phe His Val Asn Val Ile Asp Asp Val Ala Gly Ile Ser
        275                 280                 285

Ile Ala Gly Ala Leu Lys Asn Val Val Ala Leu Ala Cys Gly Phe Val
    290                 295                 300

Glu Gly Met Gly Trp Gly Asn Asn Ala Ser Ala Ala Ile Gln Arg Leu
305                 310                 315                 320

Gly Leu Gly Glu Ile Ile Lys Phe Gly Arg Met Phe Phe Pro Glu Ser
                325                 330                 335

Lys Val Glu Thr Tyr Tyr Gln Glu Ser Ala Gly Val Ala Asp Leu Ile
            340                 345                 350

Thr Thr Cys Ser Gly Gly Arg Asn Val Lys Val Ala Thr Tyr Met Ala
        355                 360                 365

Lys Thr Gly Lys Ser Ala Leu Glu Ala Glu Lys Glu Leu Leu Asn Gly
    370                 375                 380

Gln Ser Ala Gln Gly Ile Ile Thr Cys Arg Glu Val His Glu Trp Leu
385                 390                 395                 400

Gln Thr Cys Glu Leu Thr Gln Glu Phe Pro Leu Phe Glu Ala Val Tyr
                405                 410                 415

Gln Ile Val Tyr Asn Asn Val Arg Met Glu Asp Leu Pro Glu Met Ile
            420                 425                 430

Glu Glu Leu Asp Ile Asp Asp Glu
        435                 440


<210> SEQ ID NO 8
<211> LENGTH: 2376
<212> TYPE: DNA
<213> ORGANISM: Bifidobacterium adolescentis

<400> SEQUENCE: 8

atggcagcag ttgatgcaac ggcggtctcc caggaggaac ttgaggctaa ggcttgggaa      60

ggcttcaccg agggcaactg gcagaaggac attgatgtcc gcgacttcat ccagaagaac     120
```

```
tacacgccat atgagggcga cgagtccttc ctggctgacg ccaccgacaa gaccaagcac    180

ctgtggaagt atctggacga caactatctg tccgtggagc gcaagcagcg cgtctacgac    240

gtggacaccc acaccccggc gggcatcgac gccttcccgg ccggctacat cgattccccg    300

gaagtcgaca atgtgattgt cggtctgcag accgatgtgc cgtgcaagcg cgccatgatg    360

ccgaacggcg gctggcgtat ggtcgagcag gccatcaagg aagccggcaa ggagcccgat    420

ccggagatca agaagatctt caccaagtac cgcaagaccc acaacgacgg cgtcttcggc    480

gtctacacca agcagatcaa ggtagctcgc cacaacaaga tcctcaccgg cctgccggat    540

gcctacggcc gtggccgcat catcggcgat taccgtcgtg tggccctgta cggcgtgaac    600

gcgctgatca agttcaagca gcgcgacaag gactccatcc cgtaccgcaa cgacttcacc    660

gagccggaga tcgagcactg gatccgcttc cgtgaggagc atgacgagca gatcaaggcc    720

ctgaagcagc tgatcaacct cggcaacgag tacggcctcg acctgtcccg cccggcacag    780

accgcacagg aagccgtgca gtggacctac atgggctacc tcgcctccgt caagagccag    840

gacggcgccg ccatgtcctt cggccgtgtc tccaccttct tcgacgtcta cttcgagcgc    900

gacctgaagg ccggcaagat caccgagacc gacgcacagg agatcatcga taacctggtc    960

atgaagctgc gcatcgtgcg cttcctgcgc accaaggatt acgacgcgat cttctccggc   1020

gatccgtact gggcgacttg gtccgacgcc ggcttcggcg acgacggccg taccatggtc   1080

accaagacct cgttccgtct gctcaacacc ctgaccctcg agcacctcgg acctggcccg   1140

gagccgaaca tcaccatctt ctgggatccg aagctgccgg aagcctacaa gcgcttctgc   1200

gcccgaatct ccatcgacac ctcggccatc cagtacgagt ccgataagga aatccgctcc   1260

cactggggcg acgacgccgc catcgcatgc tgcgtctccc cgatgcgcgt gggcaagcag   1320

atgcagttct tcgccgcccg tgtgaactcc gccaaggccc tgctgtacgc catcaacggc   1380

ggacgcgacg agatgaccgg catgcaggtc atcgacaagg gcgtcatcga cccgatcaag   1440

ccggaagccg atggcacgct ggattacgag aaggtcaagg ccaactacga gaaggccctc   1500

gaatggctgt ccgagaccta tgtgatggct ctgaacatca tccattacat gcatgataag   1560

tacgcttacg agtccatcga gatggctctg cacgacaagg aagtgtaccg caccctcggc   1620

tgcggcatgt ccggcctgtc gatcgcggcc gactccctgt ccgcatgcaa gtacgccaag   1680

gtctacccga tctacaacaa ggacgccaag accacgccgg gccacgagaa cgagtacgtc   1740

gaaggcgccg atgacgatct gatcgtcggc taccgcaccg aaggcgactt cccgctgtac   1800

ggcaacgatg atgaccgtgc cgacgacatc gccaagtggg tcgtctccac cgtcatgggc   1860

caggtcaagc gtctgccggt gtaccgcgac gccgtcccga cccagtccat cctgaccatc   1920

acctccaatg tggaatacgg caaggccacc ggcgccttcc cgtccggcca caagaagggc   1980

accccgtacg ctccgggcgc caacccggag aacggcatgg actcccacgg catgctgccg   2040

tccatgttct ccgtcggcaa gatcgactac aacgacgctc ttgacggcat ctcgctgacc   2100

aacaccatca cccctgatgg tctgggccgc gacgaggaag agcgtatcgg caacctcgtt   2160

ggcatcctgg acgccggcaa cggccacggc ctgtaccacg ccaacatcaa cgtgctgcgc   2220

aaggagcagc tcgaggatgc cgtcgagcat ccggagaagt acccgcacct gaccgtgcgc   2280

gtctccggct acgcggtgaa cttcgtcaag ctcaccaagg aacagcagct cgacgtgatc   2340

tcccgtacgt tccaccaggg cgctgtcgtc gactga                             2376
```

<210> SEQ ID NO 9

<211> LENGTH: 791
<212> TYPE: PRT
<213> ORGANISM: Bifidobacterium adolescentis

<400> SEQUENCE: 9

```
Met Ala Ala Val Asp Ala Thr Ala Val Ser Gln Glu Glu Leu Glu Ala
1               5                   10                  15

Lys Ala Trp Glu Gly Phe Thr Glu Gly Asn Trp Gln Lys Asp Ile Asp
            20                  25                  30

Val Arg Asp Phe Ile Gln Lys Asn Tyr Thr Pro Tyr Glu Gly Asp Glu
        35                  40                  45

Ser Phe Leu Ala Asp Ala Thr Asp Lys Thr Lys His Leu Trp Lys Tyr
    50                  55                  60

Leu Asp Asp Asn Tyr Leu Ser Val Glu Arg Lys Gln Arg Val Tyr Asp
65                  70                  75                  80

Val Asp Thr His Thr Pro Ala Gly Ile Asp Ala Phe Pro Ala Gly Tyr
                85                  90                  95

Ile Asp Ser Pro Glu Val Asp Asn Val Ile Val Gly Leu Gln Thr Asp
            100                 105                 110

Val Pro Cys Lys Arg Ala Met Met Pro Asn Gly Gly Trp Arg Met Val
        115                 120                 125

Glu Gln Ala Ile Lys Glu Ala Gly Lys Glu Pro Asp Pro Glu Ile Lys
    130                 135                 140

Lys Ile Phe Thr Lys Tyr Arg Lys Thr His Asn Asp Gly Val Phe Gly
145                 150                 155                 160

Val Tyr Thr Lys Gln Ile Lys Val Ala Arg His Asn Lys Ile Leu Thr
                165                 170                 175

Gly Leu Pro Asp Ala Tyr Gly Arg Gly Arg Ile Ile Gly Asp Tyr Arg
            180                 185                 190

Arg Val Ala Leu Tyr Gly Val Asn Ala Leu Ile Lys Phe Lys Gln Arg
        195                 200                 205

Asp Lys Asp Ser Ile Pro Tyr Arg Asn Asp Phe Thr Glu Pro Glu Ile
    210                 215                 220

Glu His Trp Ile Arg Phe Arg Glu Glu His Asp Glu Gln Ile Lys Ala
225                 230                 235                 240

Leu Lys Gln Leu Ile Asn Leu Gly Asn Glu Tyr Gly Leu Asp Leu Ser
                245                 250                 255

Arg Pro Ala Gln Thr Ala Gln Glu Ala Val Gln Trp Thr Tyr Met Gly
            260                 265                 270

Tyr Leu Ala Ser Val Lys Ser Gln Asp Gly Ala Ala Met Ser Phe Gly
        275                 280                 285

Arg Val Ser Thr Phe Phe Asp Val Tyr Phe Glu Arg Asp Leu Lys Ala
    290                 295                 300

Gly Lys Ile Thr Glu Thr Asp Ala Gln Glu Ile Ile Asp Asn Leu Val
305                 310                 315                 320

Met Lys Leu Arg Ile Val Arg Phe Leu Arg Thr Lys Asp Tyr Asp Ala
                325                 330                 335

Ile Phe Ser Gly Asp Pro Tyr Trp Ala Thr Trp Ser Asp Ala Gly Phe
            340                 345                 350

Gly Asp Asp Gly Arg Thr Met Val Thr Lys Thr Ser Phe Arg Leu Leu
        355                 360                 365

Asn Thr Leu Thr Leu Glu His Leu Gly Pro Gly Pro Glu Pro Asn Ile
    370                 375                 380

Thr Ile Phe Trp Asp Pro Lys Leu Pro Glu Ala Tyr Lys Arg Phe Cys
```

```
385                 390                 395                 400

Ala Arg Ile Ser Ile Asp Thr Ser Ala Ile Gln Tyr Glu Ser Asp Lys
                405                 410                 415

Glu Ile Arg Ser His Trp Gly Asp Asp Ala Ala Ile Ala Cys Cys Val
            420                 425                 430

Ser Pro Met Arg Val Gly Lys Gln Met Gln Phe Phe Ala Ala Arg Val
        435                 440                 445

Asn Ser Ala Lys Ala Leu Leu Tyr Ala Ile Asn Gly Gly Arg Asp Glu
    450                 455                 460

Met Thr Gly Met Gln Val Ile Asp Lys Gly Val Ile Asp Pro Ile Lys
465                 470                 475                 480

Pro Glu Ala Asp Gly Thr Leu Asp Tyr Glu Lys Val Lys Ala Asn Tyr
                485                 490                 495

Glu Lys Ala Leu Glu Trp Leu Ser Glu Thr Tyr Val Met Ala Leu Asn
            500                 505                 510

Ile Ile His Tyr Met His Asp Lys Tyr Ala Tyr Glu Ser Ile Glu Met
        515                 520                 525

Ala Leu His Asp Lys Glu Val Tyr Arg Thr Leu Gly Cys Gly Met Ser
    530                 535                 540

Gly Leu Ser Ile Ala Ala Asp Ser Leu Ser Ala Cys Lys Tyr Ala Lys
545                 550                 555                 560

Val Tyr Pro Ile Tyr Asn Lys Asp Ala Lys Thr Thr Pro Gly His Glu
                565                 570                 575

Asn Glu Tyr Val Glu Gly Ala Asp Asp Asp Leu Ile Val Gly Tyr Arg
            580                 585                 590

Thr Glu Gly Asp Phe Pro Leu Tyr Gly Asn Asp Asp Asp Arg Ala Asp
        595                 600                 605

Asp Ile Ala Lys Trp Val Val Ser Thr Val Met Gly Gln Val Lys Arg
    610                 615                 620

Leu Pro Val Tyr Arg Asp Ala Val Pro Thr Gln Ser Ile Leu Thr Ile
625                 630                 635                 640

Thr Ser Asn Val Glu Tyr Gly Lys Ala Thr Gly Ala Phe Pro Ser Gly
                645                 650                 655

His Lys Lys Gly Thr Pro Tyr Ala Pro Gly Ala Asn Pro Glu Asn Gly
            660                 665                 670

Met Asp Ser His Gly Met Leu Pro Ser Met Phe Ser Val Gly Lys Ile
        675                 680                 685

Asp Tyr Asn Asp Ala Leu Asp Gly Ile Ser Leu Thr Asn Thr Ile Thr
    690                 695                 700

Pro Asp Gly Leu Gly Arg Asp Glu Glu Glu Arg Ile Gly Asn Leu Val
705                 710                 715                 720

Gly Ile Leu Asp Ala Gly Asn Gly His Gly Leu Tyr His Ala Asn Ile
                725                 730                 735

Asn Val Leu Arg Lys Glu Gln Leu Glu Asp Ala Val Glu His Pro Glu
            740                 745                 750

Lys Tyr Pro His Leu Thr Val Arg Val Ser Gly Tyr Ala Val Asn Phe
        755                 760                 765

Val Lys Leu Thr Lys Glu Gln Gln Leu Asp Val Ile Ser Arg Thr Phe
    770                 775                 780

His Gln Gly Ala Val Val Asp
785                 790

<210> SEQ ID NO 10
```

<211> LENGTH: 879
<212> TYPE: DNA
<213> ORGANISM: Bifidobacterium adolescentis

<400> SEQUENCE: 10
atgtctgaac atattttccg ttccacgacc agacacatgc tgagggattc caaggactac 60
gtcaatcaga cgctgatggg aggcctgtcc ggattcgaat cgccaatcgg cttggaccgt 120
ctcgaccgca tcaaggcgtt gaaaagcggc gatatcggtt tcgtgcactc gtgggacatc 180
aacacttccg tggatggtcc tggcaccaga atgaccgtgt tcatgagcgg atgccctctg 240
cgctgccagt actgccagaa tccggatact tggaagatgc gcgacggcaa gcccgtctac 300
tacgaagcca tggtcaagaa aatcgagcgg tatgccgatt tattcaaggc caccggcggc 360
ggcatcactt tctccggcgg cgaatccatg atgcagccgg ctttcgtgtc acgcgtgttc 420
catgccgcca agcagatggg agtgcatacc tgcctcgaca cgtccggatt cctcggggcg 480
agctacaccg atgacatggt ggatgacatc gacctgtgcc tgcttgacgt caaatccggc 540
gatgaggaga cctaccataa ggtgaccggc ggcatcctgc agccgaccat cgacttcgga 600
cagcgtctgg ccaaggcagg caagaagatc tgggtgcgtt tcgtgctcgt gccgggcctc 660
acatcctccg aagaaaacgt cgagaacgtg gcgaagatct gcgagacctt cggcgacgcg 720
ttggaacata tcgacgtatt gcccttccac cagcttggcc gtccgaagtg gcacatgctg 780
aacatcccat acccgttgga ggaccagaaa ggcccgtccg cggcaatgaa acaacgtgtg 840
gtcgagcagt tccagtcgca cggcttcacc gtgtactaa 879

<210> SEQ ID NO 11
<211> LENGTH: 292
<212> TYPE: PRT
<213> ORGANISM: Bifidobacterium adolescentis

<400> SEQUENCE: 11

Met Ser Glu His Ile Phe Arg Ser Thr Thr Arg His Met Leu Arg Asp
1 5 10 15

Ser Lys Asp Tyr Val Asn Gln Thr Leu Met Gly Gly Leu Ser Gly Phe
20 25 30

Glu Ser Pro Ile Gly Leu Asp Arg Leu Asp Arg Ile Lys Ala Leu Lys
35 40 45

Ser Gly Asp Ile Gly Phe Val His Ser Trp Asp Ile Asn Thr Ser Val
50 55 60

Asp Gly Pro Gly Thr Arg Met Thr Val Phe Met Ser Gly Cys Pro Leu
65 70 75 80

Arg Cys Gln Tyr Cys Gln Asn Pro Asp Thr Trp Lys Met Arg Asp Gly
85 90 95

Lys Pro Val Tyr Tyr Glu Ala Met Val Lys Lys Ile Glu Arg Tyr Ala
100 105 110

Asp Leu Phe Lys Ala Thr Gly Gly Gly Ile Thr Phe Ser Gly Gly Glu
115 120 125

Ser Met Met Gln Pro Ala Phe Val Ser Arg Val Phe His Ala Ala Lys
130 135 140

Gln Met Gly Val His Thr Cys Leu Asp Thr Ser Gly Phe Leu Gly Ala
145 150 155 160

Ser Tyr Thr Asp Asp Met Val Asp Asp Ile Asp Leu Cys Leu Leu Asp
165 170 175

Val Lys Ser Gly Asp Glu Glu Thr Tyr His Lys Val Thr Gly Gly Ile
180 185 190

```
Leu Gln Pro Thr Ile Asp Phe Gly Gln Arg Leu Ala Lys Ala Gly Lys
        195                 200                 205

Lys Ile Trp Val Arg Phe Val Leu Val Pro Gly Leu Thr Ser Ser Glu
    210                 215                 220

Glu Asn Val Glu Asn Val Ala Lys Ile Cys Glu Thr Phe Gly Asp Ala
225                 230                 235                 240

Leu Glu His Ile Asp Val Leu Pro Phe His Gln Leu Gly Arg Pro Lys
                245                 250                 255

Trp His Met Leu Asn Ile Pro Tyr Pro Leu Glu Asp Gln Lys Gly Pro
            260                 265                 270

Ser Ala Ala Met Lys Gln Arg Val Val Glu Gln Phe Gln Ser His Gly
        275                 280                 285

Phe Thr Val Tyr
    290


<210> SEQ ID NO 12
<211> LENGTH: 2733
<212> TYPE: DNA
<213> ORGANISM: Bifidobacterium adolescentis

<400> SEQUENCE: 12

atggcagacg caaagaagaa ggaagagccg accaagccga ctccggaaga gaagctcgcc     60

gcagccgagg ctgaggtcga cgctctggtc aagaagggcc tgaaggctct tgatgaattc    120

gagaagctcg atcagaagca ggttgaccac atcgtggcca aggcttccgt cgcagccctg    180

aacaagcact tggtgctcgc caagatggcc gtcgaggaga cccaccgtgg tctggtcgaa    240

gacaaggcca ccaagaacat cttcgcctgc gagcatgtca ccaactacct ggctggtcag    300

aagaccgtcg gcatcatccg cgaggacgac gtgctgggca tcgacgaaat cgccgagccg    360

gttggcgtcg tcgctggcgt gaccccggtc accaacccga cctccaccgc catcttcaag    420

tcgctgatcg cactgaagac ccgctgcccg atcatcttcg gcttccaccc gggcgcacag    480

aactgctccg tcgcggccgc caagatcgtt cgcgatgccg ctatcgcagc aggcgctcct    540

gagaactgta ttcagtggat cgagcatccg tccatcgagg ccactggcgc cctgatgaag    600

catgatggtg tcgccaccat cctcgccacc ggtggtccgg gcatggtcaa ggccgcatac    660

tcctccggca agccggccct gggcgtcggc gcgggcaatg ctccggcata cgttgacaag    720

aacgtcgacg tcgtgcgtgc agccaacgat ctgattcttt ccaagcactt cgattacggc    780

atgatctgcg ctaccgagca ggccatcatc gccgacaagg acatctacgc tccgctcgtt    840

aaggaactca agcgtcgcaa ggcctatttc gtgaacgctg acgagaaggc caagctcgag    900

cagtacatgt tcggctgcac cgcttactcc ggacagaccc cgaagctcaa ctccgtggtg    960

ccgggcaagt ccccgcagta catcgccaag gccgccggct tcgagattcc ggaagacgcc   1020

accatccttg ccgctgagtg caaggaagtc ggcgagaacg agccgctgac catggagaag   1080

cttgctccgg tccaggccgt gctgaagtcc gacaacaagg aacaggcctt cgagatgtgc   1140

gaagccatgc tgaagcatgg cgccggccac accgccgcca tccacaccaa cgaccgtgac   1200

ctggtccgcg agtacggcca gcgcatgcac gcctgccgta tcatctggaa ctccccgagc   1260

tccctcggcg gcgtgggcga catctacaac gccatcgctc cgtccctgac cctgggctgc   1320

ggctcctacg gcggcaactc cgtgtccggc aacgtccagg cagtcaacct catcaacatc   1380

aagcgcatcg ctcggaggaa caacaacatg cagtggttca agattccggc caagacctac   1440

ttcgagccga acgccatcaa gtacctgcgc gacatgtacg gcatcgaaaa ggccgtcatc   1500
```

```
gtgtgcgata aggtcatgga gcagctcggc atcgttgaca agatcatcga tcagctgcgt   1560

gcacgttcca accgcgtgac cttccgtatc atcgattatg tcgagccgga gccgagcgtg   1620

gagaccgtcg aacgtggcgc cgccatgatg cgcgaggagt tcgagccgga taccatcatc   1680

gccgtcggcg gtggttcccc gatggatgcg tccaagatta tgtggctgct gtacgagcac   1740

ccggaaatct ccttctccga tgtgcgtgag aagttcttcg atatccgtaa gcgcgcgttc   1800

aagattccgc cgctgggcaa gaaggccaag ctggtctgca ttccgacttc ttccggcacc   1860

ggttccgaag tcacgccgtt cgctgtgatt accgaccaca agaccggcta taagtacccg   1920

atcaccgatt acgcgctgac cccgtccgtc gctatcgtcg atccggtgct ggcacgtact   1980

cagccgcgca agctggcttc cgatgctggt ttcgatgctc tgacccacgc ttttgaggct   2040

tatgtgtccg tgtatgccaa cgacttcacc gatggtatgg cattgcacgc tgccaagctg   2100

gtttgggaca acctcgctga gtccgtcaat ggcgagccgg gtgaggagaa gacccgtgcc   2160

caggagaaga tgcataatgc cgccaccatg gccggcatgg ctttcggctc cgccttcctc   2220

ggcatgtgcc acggcatggc ccacaccatt ggtgcactgt gccacgttgc ccacggtcgt   2280

accaactcca tcctcctgcc gtacgtgatc cgttacaacg gttccgtccc ggaggagccg   2340

accagctggc cgaagtacaa caagtacatc gctccggaac gctaccagga gatcgccaag   2400

aaccttggcg tgaacccggg caagactccg gaagagggcg tcgagaacct ggccaaggct   2460

gttgaggatt accgtgacaa caagctcggt atgaacaaga gcttccagga gtgcggtgtg   2520

gatgaggact actattggtc catcatcgac cagatcggca tgcgcgccta cgaagaccag   2580

tgcgcaccgg cgaacccgcg tatcccgcag atcgaggata tgaaggatat cgccattgcc   2640

gcctactacg gcgtcagcca ggcggaaggc cacaagctgc gcgtccagcg tcagggcgaa   2700

gccgctacgg aggaagcttc cgagcgcgcc tga                                2733
```

```
<210> SEQ ID NO 13
<211> LENGTH: 910
<212> TYPE: PRT
<213> ORGANISM: Bifidobacterium adolescentis

<400> SEQUENCE: 13

Met Ala Asp Ala Lys Lys Lys Glu Glu Pro Thr Lys Pro Thr Pro Glu
1               5                   10                  15

Glu Lys Leu Ala Ala Ala Glu Ala Glu Val Asp Ala Leu Val Lys Lys
            20                  25                  30

Gly Leu Lys Ala Leu Asp Glu Phe Glu Lys Leu Asp Gln Lys Gln Val
        35                  40                  45

Asp His Ile Val Ala Lys Ala Ser Val Ala Ala Leu Asn Lys His Leu
    50                  55                  60

Val Leu Ala Lys Met Ala Val Glu Glu Thr His Arg Gly Leu Val Glu
65                  70                  75                  80

Asp Lys Ala Thr Lys Asn Ile Phe Ala Cys Glu His Val Thr Asn Tyr
                85                  90                  95

Leu Ala Gly Gln Lys Thr Val Gly Ile Ile Arg Glu Asp Asp Val Leu
            100                 105                 110

Gly Ile Asp Glu Ile Ala Glu Pro Val Gly Val Val Ala Gly Val Thr
        115                 120                 125

Pro Val Thr Asn Pro Thr Ser Thr Ala Ile Phe Lys Ser Leu Ile Ala
    130                 135                 140

Leu Lys Thr Arg Cys Pro Ile Ile Phe Gly Phe His Pro Gly Ala Gln
```

```
145                 150                 155                 160

Asn Cys Ser Val Ala Ala Ala Lys Ile Val Arg Asp Ala Ala Ile Ala
                165                 170                 175

Ala Gly Ala Pro Glu Asn Cys Ile Gln Trp Ile Glu His Pro Ser Ile
            180                 185                 190

Glu Ala Thr Gly Ala Leu Met Lys His Asp Gly Val Ala Thr Ile Leu
        195                 200                 205

Ala Thr Gly Gly Pro Gly Met Val Lys Ala Ala Tyr Ser Ser Gly Lys
    210                 215                 220

Pro Ala Leu Gly Val Gly Ala Gly Asn Ala Pro Ala Tyr Val Asp Lys
225                 230                 235                 240

Asn Val Asp Val Val Arg Ala Ala Asn Asp Leu Ile Leu Ser Lys His
                245                 250                 255

Phe Asp Tyr Gly Met Ile Cys Ala Thr Glu Gln Ala Ile Ile Ala Asp
            260                 265                 270

Lys Asp Ile Tyr Ala Pro Leu Val Lys Glu Leu Lys Arg Arg Lys Ala
        275                 280                 285

Tyr Phe Val Asn Ala Asp Glu Lys Ala Lys Leu Glu Gln Tyr Met Phe
    290                 295                 300

Gly Cys Thr Ala Tyr Ser Gly Gln Thr Pro Lys Leu Asn Ser Val Val
305                 310                 315                 320

Pro Gly Lys Ser Pro Gln Tyr Ile Ala Lys Ala Ala Gly Phe Glu Ile
                325                 330                 335

Pro Glu Asp Ala Thr Ile Leu Ala Ala Glu Cys Lys Glu Val Gly Glu
            340                 345                 350

Asn Glu Pro Leu Thr Met Glu Lys Leu Ala Pro Val Gln Ala Val Leu
        355                 360                 365

Lys Ser Asp Asn Lys Glu Gln Ala Phe Glu Met Cys Glu Ala Met Leu
    370                 375                 380

Lys His Gly Ala Gly His Thr Ala Ala Ile His Thr Asn Asp Arg Asp
385                 390                 395                 400

Leu Val Arg Glu Tyr Gly Gln Arg Met His Ala Cys Arg Ile Ile Trp
                405                 410                 415

Asn Ser Pro Ser Ser Leu Gly Gly Val Gly Asp Ile Tyr Asn Ala Ile
            420                 425                 430

Ala Pro Ser Leu Thr Leu Gly Cys Gly Ser Tyr Gly Gly Asn Ser Val
        435                 440                 445

Ser Gly Asn Val Gln Ala Val Asn Leu Ile Asn Ile Lys Arg Ile Ala
    450                 455                 460

Arg Arg Asn Asn Asn Met Gln Trp Phe Lys Ile Pro Ala Lys Thr Tyr
465                 470                 475                 480

Phe Glu Pro Asn Ala Ile Lys Tyr Leu Arg Asp Met Tyr Gly Ile Glu
                485                 490                 495

Lys Ala Val Ile Val Cys Asp Lys Val Met Glu Gln Leu Gly Ile Val
            500                 505                 510

Asp Lys Ile Ile Asp Gln Leu Arg Ala Arg Ser Asn Arg Val Thr Phe
        515                 520                 525

Arg Ile Ile Asp Tyr Val Glu Pro Glu Pro Ser Val Glu Thr Val Glu
    530                 535                 540

Arg Gly Ala Ala Met Met Arg Glu Glu Phe Glu Pro Asp Thr Ile Ile
545                 550                 555                 560

Ala Val Gly Gly Gly Ser Pro Met Asp Ala Ser Lys Ile Met Trp Leu
                565                 570                 575
```

```
Leu Tyr Glu His Pro Glu Ile Ser Phe Ser Asp Val Arg Glu Lys Phe
            580                 585                 590

Phe Asp Ile Arg Lys Arg Ala Phe Lys Ile Pro Pro Leu Gly Lys Lys
        595                 600                 605

Ala Lys Leu Val Cys Ile Pro Thr Ser Ser Gly Thr Gly Ser Glu Val
    610                 615                 620

Thr Pro Phe Ala Val Ile Thr Asp His Lys Thr Gly Tyr Lys Tyr Pro
625                 630                 635                 640

Ile Thr Asp Tyr Ala Leu Thr Pro Ser Val Ala Ile Val Asp Pro Val
                645                 650                 655

Leu Ala Arg Thr Gln Pro Arg Lys Leu Ala Ser Asp Ala Gly Phe Asp
            660                 665                 670

Ala Leu Thr His Ala Phe Glu Ala Tyr Val Ser Val Tyr Ala Asn Asp
        675                 680                 685

Phe Thr Asp Gly Met Ala Leu His Ala Ala Lys Leu Val Trp Asp Asn
    690                 695                 700

Leu Ala Glu Ser Val Asn Gly Glu Pro Gly Glu Glu Lys Thr Arg Ala
705                 710                 715                 720

Gln Glu Lys Met His Asn Ala Ala Thr Met Ala Gly Met Ala Phe Gly
                725                 730                 735

Ser Ala Phe Leu Gly Met Cys His Gly Met Ala His Thr Ile Gly Ala
            740                 745                 750

Leu Cys His Val Ala His Gly Arg Thr Asn Ser Ile Leu Leu Pro Tyr
        755                 760                 765

Val Ile Arg Tyr Asn Gly Ser Val Pro Glu Glu Pro Thr Ser Trp Pro
    770                 775                 780

Lys Tyr Asn Lys Tyr Ile Ala Pro Glu Arg Tyr Gln Glu Ile Ala Lys
785                 790                 795                 800

Asn Leu Gly Val Asn Pro Gly Lys Thr Pro Glu Glu Gly Val Glu Asn
                805                 810                 815

Leu Ala Lys Ala Val Glu Asp Tyr Arg Asp Asn Lys Leu Gly Met Asn
            820                 825                 830

Lys Ser Phe Gln Glu Cys Gly Val Asp Glu Asp Tyr Tyr Trp Ser Ile
        835                 840                 845

Ile Asp Gln Ile Gly Met Arg Ala Tyr Glu Asp Gln Cys Ala Pro Ala
    850                 855                 860

Asn Pro Arg Ile Pro Gln Ile Glu Asp Met Lys Asp Ile Ala Ile Ala
865                 870                 875                 880

Ala Tyr Tyr Gly Val Ser Gln Ala Glu Gly His Lys Leu Arg Val Gln
                885                 890                 895

Arg Gln Gly Glu Ala Ala Thr Glu Glu Ala Ser Glu Arg Ala
            900                 905                 910
```

<210> SEQ ID NO 14
<211> LENGTH: 2703
<212> TYPE: DNA
<213> ORGANISM: Leuconostoc mesenteroides

<400> SEQUENCE: 14

```
atggcagaag caattgcaaa gaaacccgca aaaagggttt tgacccctga agaaaaagcg      60

gaattacaaa cacaagctga gaagatgact gaggtattga ttgaaaaatc acaaaaggca     120

ttgtctgaat tttcaacatt ttcgcaagaa caagttgata aaattgttgc agctatggcc     180

ttggcaggtt ctgagaattc acttctgtta gcccatgctg ctcacgacga gactggacgt     240
```

```
ggggttgtgg aagataagga tacgaaaaat cgtttcgcct cagaatcagt ttataacgct    300
attaagtttg ataagactgt gggtgttatt agtgaagaca agattcaagg taaggtagaa    360
ttagcagccc cacttggtat tttggctgga atcgtcccaa cgacaaatcc aacgtcgaca    420
actattttca aatcaatgtt gacagcaaag acacgtaaca caattatctt tgctttccat    480
ccccaggctc aaaaagcatc ggttcttgct gcaaaaattg tttatgatgc tgctgttaaa    540
gcaggcgcac cggaaaactt tatccaatgg attgaaaagc cttcacttta tgcaacaagt    600
gcgctgatac aaaatcctca cattgcttca attctagcta ctggtgggcc atcaatggtt    660
aatgcagctt tgaagtcagg aaatccatcc atgggtgtcg gtgctggaaa cggtgcagtt    720
tatattgatg caactgttga cacagatcgt gccgtgtccg atttgttgtt atcaaagcgt    780
ttcgataatg gcatgatttg tgccacagaa aactcagccg ttattcaagc accaatctat    840
gacgaaattt taactaagtt acaagaacaa ggtgcatacc ttgttcctaa gaaagactac    900
aaaaaaattg ctgattatgt atttaagcct aacgcagagg gatttggtat tgctggtcct    960
gttgctggta tgtcaggacg ttggattgct gagcaagcag gcgtaaagat tcctgatggt   1020
aaagatgtac ttttgttcga attagatcag aagaacatag gtgaagcgtt atcttctgaa   1080
aagttatcgc cattactttc aatttataaa gttgagaagc gtgaagaagc tattgagact   1140
gttcaatcct tgttaaacta tcaaggcgcg gggcacaacg cagcaattca aattggttca   1200
caagatgatc cattcattaa agagtatgct gacgctattg gtgcatcacg tattttggtt   1260
aaccaacctg actcaatcgg tggtgttgga gatatttaca cagatgctat gcgtccatcg   1320
ttgacacttg gtaccggatc atgggggaag aattcattgt ctcataactt atcaacatac   1380
gacttactta atattaagac cgtggctcgc cgccgtaatc gtcctcaatg ggttcgttta   1440
cctaaggaag tttactacga agccaatgcc attacttact tacaagactt gcctactata   1500
aaccgtgcat ttattgtcgc tgatcctggt atggttcagt tcggatttgt tggcagagta   1560
ctaggtcaac ttgagttacg tcaagaacag gttgaaacaa atatctatgg ttcagttaag   1620
cctgacccaa ctttgtcaca agctgttgaa attgctcgcc aaatggcaga cttcaaacca   1680
gatacagtta ttttacttgg cggtggttcg gcacttgacg ctggtaaaat tggtcggttc   1740
ttgtacgaat actcgacacg ccatgaagga attttagaag atgacgaggc gattaaagat   1800
ctattcttag aactacaaca aaagtttatg gatattcgta agcgaatcgt taagttttac   1860
cacgcacgtt tgacacaaat ggttgcgatt ccaacaactt caggtactgg atcagaagtc   1920
acaccatttg ccgttattac agatgatgaa acacatgtaa agtatccact agccgattat   1980
gaattgacac cggaagttgc tattgttgat ccagaatttg ttatgaccgt accacaacac   2040
acggtatctt ggtcaggatt agatgctttg tcacatgctt tggaatcgta tgtctcagtg   2100
atggcttctg aattcacacg tccttgggca ttacaagcta ttaagttgat ttttgataac   2160
ttaacaaatt catacaatta tgatcctaaa cacccaacta aggaaggtca gaatgcacgc   2220
acaaagatgc actatgcgtc aacattggct ggtatgtcat ttgcgaatgc cttcttggga   2280
cttaaccact cactagcaca caaaactggt ggagaattcg gactacctca cggtatggca   2340
atcgctattg caatgccaca tgtgattaag tttaatgcgg taacaggaaa tgtaaagcgc   2400
acaccatacc cacgttacga aacctataca gcacaaaaag attatgctga tattgcacgt   2460
tacttaggtt tgaaaggtga aacagatgct gaattggtcg atgtattgat tgcagaaatc   2520
aagaagttgg ctgcatcagt gggtgtcaat caaacactat ctggcaacgg tgtttcaaag   2580
```

```
catgactttg atacaaagtt agaaaagatg attgacttag tttacaatga ccaatgcacg   2640

ccgggaaacc ctcgccaacc aagcttggca gaaattcgtc aattgttgaa agatcagttt   2700

taa                                                                 2703


<210> SEQ ID NO 15
<211> LENGTH: 900
<212> TYPE: PRT
<213> ORGANISM: Leuconostoc mesenteroides

<400> SEQUENCE: 15

Met Ala Glu Ala Ile Ala Lys Lys Pro Ala Lys Arg Val Leu Thr Pro
1               5                   10                  15

Glu Glu Lys Ala Glu Leu Gln Thr Gln Ala Glu Lys Met Thr Glu Val
            20                  25                  30

Leu Ile Glu Lys Ser Gln Lys Ala Leu Ser Glu Phe Ser Thr Phe Ser
        35                  40                  45

Gln Glu Gln Val Asp Lys Ile Val Ala Ala Met Ala Leu Ala Gly Ser
    50                  55                  60

Glu Asn Ser Leu Leu Leu Ala His Ala Ala His Asp Glu Thr Gly Arg
65                  70                  75                  80

Gly Val Val Glu Asp Lys Asp Thr Lys Asn Arg Phe Ala Ser Glu Ser
                85                  90                  95

Val Tyr Asn Ala Ile Lys Phe Asp Lys Thr Val Gly Val Ile Ser Glu
            100                 105                 110

Asp Lys Ile Gln Gly Lys Val Glu Leu Ala Ala Pro Leu Gly Ile Leu
        115                 120                 125

Ala Gly Ile Val Pro Thr Thr Asn Pro Thr Ser Thr Thr Ile Phe Lys
    130                 135                 140

Ser Met Leu Thr Ala Lys Thr Arg Asn Thr Ile Ile Phe Ala Phe His
145                 150                 155                 160

Pro Gln Ala Gln Lys Ala Ser Val Leu Ala Ala Lys Ile Val Tyr Asp
                165                 170                 175

Ala Ala Val Lys Ala Gly Ala Pro Glu Asn Phe Ile Gln Trp Ile Glu
            180                 185                 190

Lys Pro Ser Leu Tyr Ala Thr Ser Ala Leu Ile Gln Asn Pro His Ile
        195                 200                 205

Ala Ser Ile Leu Ala Thr Gly Gly Pro Ser Met Val Asn Ala Ala Leu
    210                 215                 220

Lys Ser Gly Asn Pro Ser Met Gly Val Gly Ala Gly Asn Gly Ala Val
225                 230                 235                 240

Tyr Ile Asp Ala Thr Val Asp Thr Asp Arg Ala Val Ser Asp Leu Leu
                245                 250                 255

Leu Ser Lys Arg Phe Asp Asn Gly Met Ile Cys Ala Thr Glu Asn Ser
            260                 265                 270

Ala Val Ile Gln Ala Pro Ile Tyr Asp Glu Ile Leu Thr Lys Leu Gln
        275                 280                 285

Glu Gln Gly Ala Tyr Leu Val Pro Lys Lys Asp Tyr Lys Lys Ile Ala
    290                 295                 300

Asp Tyr Val Phe Lys Pro Asn Ala Glu Gly Phe Gly Ile Ala Gly Pro
305                 310                 315                 320

Val Ala Gly Met Ser Gly Arg Trp Ile Ala Glu Gln Ala Gly Val Lys
                325                 330                 335

Ile Pro Asp Gly Lys Asp Val Leu Leu Phe Glu Leu Asp Gln Lys Asn
            340                 345                 350
```

```
Ile Gly Glu Ala Leu Ser Ser Glu Lys Leu Ser Pro Leu Leu Ser Ile
        355                 360                 365

Tyr Lys Val Glu Lys Arg Glu Glu Ala Ile Glu Thr Val Gln Ser Leu
    370                 375                 380

Leu Asn Tyr Gln Gly Ala Gly His Asn Ala Ala Ile Gln Ile Gly Ser
385                 390                 395                 400

Gln Asp Asp Pro Phe Ile Lys Glu Tyr Ala Asp Ala Ile Gly Ala Ser
                405                 410                 415

Arg Ile Leu Val Asn Gln Pro Asp Ser Ile Gly Gly Val Gly Asp Ile
            420                 425                 430

Tyr Thr Asp Ala Met Arg Pro Ser Leu Thr Leu Gly Thr Gly Ser Trp
        435                 440                 445

Gly Lys Asn Ser Leu Ser His Asn Leu Ser Thr Tyr Asp Leu Leu Asn
    450                 455                 460

Ile Lys Thr Val Ala Arg Arg Arg Asn Arg Pro Gln Trp Val Arg Leu
465                 470                 475                 480

Pro Lys Glu Val Tyr Tyr Glu Ala Asn Ala Ile Thr Tyr Leu Gln Asp
                485                 490                 495

Leu Pro Thr Ile Asn Arg Ala Phe Ile Val Ala Asp Pro Gly Met Val
            500                 505                 510

Gln Phe Gly Phe Val Gly Arg Val Leu Gly Gln Leu Glu Leu Arg Gln
        515                 520                 525

Glu Gln Val Glu Thr Asn Ile Tyr Gly Ser Val Lys Pro Asp Pro Thr
    530                 535                 540

Leu Ser Gln Ala Val Glu Ile Ala Arg Gln Met Ala Asp Phe Lys Pro
545                 550                 555                 560

Asp Thr Val Ile Leu Leu Gly Gly Gly Ser Ala Leu Asp Ala Gly Lys
                565                 570                 575

Ile Gly Arg Phe Leu Tyr Glu Tyr Ser Thr Arg His Glu Gly Ile Leu
            580                 585                 590

Glu Asp Asp Glu Ala Ile Lys Asp Leu Phe Leu Glu Leu Gln Gln Lys
        595                 600                 605

Phe Met Asp Ile Arg Lys Arg Ile Val Lys Phe Tyr His Ala Arg Leu
    610                 615                 620

Thr Gln Met Val Ala Ile Pro Thr Thr Ser Gly Thr Gly Ser Glu Val
625                 630                 635                 640

Thr Pro Phe Ala Val Ile Thr Asp Asp Glu Thr His Val Lys Tyr Pro
                645                 650                 655

Leu Ala Asp Tyr Glu Leu Thr Pro Glu Val Ala Ile Val Asp Pro Glu
            660                 665                 670

Phe Val Met Thr Val Pro Gln His Thr Val Ser Trp Ser Gly Leu Asp
        675                 680                 685

Ala Leu Ser His Ala Leu Glu Ser Tyr Val Ser Val Met Ala Ser Glu
    690                 695                 700

Phe Thr Arg Pro Trp Ala Leu Gln Ala Ile Lys Leu Ile Phe Asp Asn
705                 710                 715                 720

Leu Thr Asn Ser Tyr Asn Tyr Asp Pro Lys His Pro Thr Lys Glu Gly
                725                 730                 735

Gln Asn Ala Arg Thr Lys Met His Tyr Ala Ser Thr Leu Ala Gly Met
            740                 745                 750

Ser Phe Ala Asn Ala Phe Leu Gly Leu Asn His Ser Leu Ala His Lys
        755                 760                 765
```

```
Thr Gly Gly Glu Phe Gly Leu Pro His Gly Met Ala Ile Ala Ile Ala
    770                 775                 780

Met Pro His Val Ile Lys Phe Asn Ala Val Thr Gly Asn Val Lys Arg
785                 790                 795                 800

Thr Pro Tyr Pro Arg Tyr Glu Thr Tyr Thr Ala Gln Lys Asp Tyr Ala
                805                 810                 815

Asp Ile Ala Arg Tyr Leu Gly Leu Lys Gly Glu Thr Asp Ala Glu Leu
            820                 825                 830

Val Asp Val Leu Ile Ala Glu Ile Lys Lys Leu Ala Ala Ser Val Gly
        835                 840                 845

Val Asn Gln Thr Leu Ser Gly Asn Gly Val Ser Lys His Asp Phe Asp
    850                 855                 860

Thr Lys Leu Glu Lys Met Ile Asp Leu Val Tyr Asn Asp Gln Cys Thr
865                 870                 875                 880

Pro Gly Asn Pro Arg Gln Pro Ser Leu Ala Glu Ile Arg Gln Leu Leu
                885                 890                 895

Lys Asp Gln Phe
            900
```

<210> SEQ ID NO 16
<211> LENGTH: 2697
<212> TYPE: DNA
<213> ORGANISM: Oenococcus oenii

<400> SEQUENCE: 16

```
atggcagttg aaacgaagaa gattactaaa aagatactga cttccgacga acttaaagac     60

aaaaaggaga cagcaaaaaa atacattgga gaattagtcg ataaatcaag acaggcatta    120

ttagaattct ctcaatatag tcaatcacaa gttgacaaaa ttgttgccgc aatggcttta    180

gccggttccg aacattcttt ggaattagca cactttgctc gaaatgaaac tggaagagga    240

gttgttgaag acaaagatac gaaaaatcgt tttgcctcgg aatctgtata taacacgatt    300

aaaaatgaca aaacagttgg cgtaattgat gaagacccaa tcactggcaa agttcagtta    360

gctgcaccac ttgggatttt agccggaatt gttccaacga caaatccaac gtctaccacg    420

atttttaaat cattgttaac cgctaagaca cgtaatacga tcatttttgc ttttcacccg    480

caagcacaaa aatcgtctgt agcggctgcg aaaattgttt accaggcggc tagaaaagct    540

ggagcaccga aagatttcat tcagtggatc gaaacgcctt ccttggaaaa tacgactgct    600

ttgatgcaaa atcctgaaat agcttcaatt ttggctactg gaggcccttc tatggttcat    660

gccgcattaa catcgggaaa cccttcaatg ggtgttgggg caggaaatgg agctgttttc    720

attgaccata cggctcgtgt tcgtcgagcg gcagaagact tgttgctatc aaaacgtttt    780

gataatggaa tgatttgcgc tacagagaat tccgcagtta tcgaagcttc ggtttatgac    840

gaatttatga aattaatgca ggaaaagggt acttatctcg ttccgaagga tgattacaaa    900

aagatcgctg attttgtttt cagcgataaa catgcagtta atggtccggt tgccgggatg    960

agtggccgtt ggattgctga acatgccggt gttactttgc cgaagggcaa agatgttttg   1020

ttgtttgagt tggatcaaga cgacattggc gaaaaacttt cctcggaaaa acttagcccc   1080

ttgctttcgg tctataaagc tgctgatcgt aaagaagcga taaaagttgt tcaaagactt   1140

ttgaactatc aaggagctgg tcataatgcg gcaatccaga ttggcgctca agacgatccc   1200

tttgttaaag aatatgccga tgcagtttct gcatctagaa ttttggttaa ccagcccgat   1260

tcaataggtg gagtcggcga tatttataca gatgcattgc gtccaagtat gacgcttggt   1320
```

```
actggttcat gggggaagaa ttcattgtca cataatttat caacttacga tttgttgaat   1380

gtcaaaacgg ttgcccgcag acgtaatcgt cctcaatggg ttcgtcttcc aaaagatatc   1440

tactatgaga aaatgccat tacctatctg caggaattac cgaacgtcaa tcgggctttc   1500

gttattaccg atcattcgtt ggtcaaatat ggattcgtcg atcggattct tgagcaattc   1560

gaattgcgtc ccgaccaggt taaaacaagt atttacagtt ctgttcaacc ggatccttat   1620

ttgagtcagg ctgttgaaat tgcaaaacaa atgcaggagt tcgaaccgga tacagtaatt   1680

gctcttggag gaggttcctc tttggatgtt gccaagattt cccgttttct ttatgaatat   1740

tctcaagaac cggaccacat tggttttttg gaaaacattg acgatattaa agaattgttt   1800

aaaggattgc agcaaaagtt tatggatatt cggaaacgga ttgttaaatt cgaacatcag   1860

aatttgactc aactggttgc tattccaaca acttcgggta ccggttcgga agtaacaccg   1920

ttttcggtta tcaccgatga tgaaactcac gttaaatacc ctttggccga ttatgaatta   1980

actccgcaag ttgcaatcgt tgatcctgaa ttggttatga ctgtaccaaa acggaccctg   2040

gcttggtctg gactggacgc cttatctcac tcgcttgaat cctacgtgtc ggttatgagt   2100

tctgaattta cacggccgtg ggctttacag gcaatcaaac tgatttttga aaacatcgtt   2160

gattcctata attacgatcc aaagcaccca actaatcggg gcgccgaggc acgtgaaaaa   2220

atgcattatg ctgcaacttt ggccggcatg tctttcggaa acgccttctt gggtataaac   2280

cattcactgg cccataaaac cggtggagag ttcggtcttc ctcatggttt ggcaatcagc   2340

atcgcgatgc cacatgtaat tcgatttaat gcggttaccg gaaacgtcaa acggactcct   2400

tttcctcgtt atgaggttta tacagcccaa aaagattatg ccgatattgc gcgccatatt   2460

ggcctcagcg gtaagaacga tgccgaattg gttgaaaaac ttatcgccaa aatcaaggaa   2520

ttaaccgatg ccttggatgt caatattact ttgagcggca atggagtcga taaaaagagc   2580

tttgaacatt ctttggatca actggttgat cttgtttacg atgaccagtg cacgccagga   2640

aatccgcgac aaccgaattt agctgaaatt aggcagttat tgatcgacca attttaa      2697
```

<210> SEQ ID NO 17
<211> LENGTH: 898
<212> TYPE: PRT
<213> ORGANISM: Oenococcus oenii

<400> SEQUENCE: 17

```
Met Ala Val Glu Thr Lys Lys Ile Thr Lys Lys Ile Leu Thr Ser Asp
1               5                   10                  15

Glu Leu Lys Asp Lys Lys Glu Thr Ala Lys Lys Tyr Ile Gly Glu Leu
            20                  25                  30

Val Asp Lys Ser Arg Gln Ala Leu Leu Glu Phe Ser Gln Tyr Ser Gln
        35                  40                  45

Ser Gln Val Asp Lys Ile Val Ala Ala Met Ala Leu Ala Gly Ser Glu
    50                  55                  60

His Ser Leu Glu Leu Ala His Phe Ala Arg Asn Glu Thr Gly Arg Gly
65                  70                  75                  80

Val Val Glu Asp Lys Asp Thr Lys Asn Arg Phe Ala Ser Glu Ser Val
                85                  90                  95

Tyr Asn Thr Ile Lys Asn Asp Lys Thr Val Gly Val Ile Asp Glu Asp
            100                 105                 110

Pro Ile Thr Gly Lys Val Gln Leu Ala Ala Pro Leu Gly Ile Leu Ala
        115                 120                 125

Gly Ile Val Pro Thr Thr Asn Pro Thr Ser Thr Thr Ile Phe Lys Ser
```

```
    130                 135                 140

Leu Leu Thr Ala Lys Thr Arg Asn Thr Ile Ile Phe Ala Phe His Pro
145                 150                 155                 160

Gln Ala Gln Lys Ser Ser Val Ala Ala Ala Lys Ile Val Tyr Gln Ala
                165                 170                 175

Ala Arg Lys Ala Gly Ala Pro Lys Asp Phe Ile Gln Trp Ile Glu Thr
            180                 185                 190

Pro Ser Leu Glu Asn Thr Thr Ala Leu Met Gln Asn Pro Glu Ile Ala
        195                 200                 205

Ser Ile Leu Ala Thr Gly Gly Pro Ser Met Val His Ala Ala Leu Thr
    210                 215                 220

Ser Gly Asn Pro Ser Met Gly Val Gly Ala Gly Asn Gly Ala Val Phe
225                 230                 235                 240

Ile Asp His Thr Ala Arg Val Arg Arg Ala Ala Glu Asp Leu Leu Leu
                245                 250                 255

Ser Lys Arg Phe Asp Asn Gly Met Ile Cys Ala Thr Glu Asn Ser Ala
            260                 265                 270

Val Ile Glu Ala Ser Val Tyr Asp Glu Phe Met Lys Leu Met Gln Glu
        275                 280                 285

Lys Gly Thr Tyr Leu Val Pro Lys Asp Asp Tyr Lys Lys Ile Ala Asp
    290                 295                 300

Phe Val Phe Ser Asp Lys His Ala Val Asn Gly Pro Val Ala Gly Met
305                 310                 315                 320

Ser Gly Arg Trp Ile Ala Glu His Ala Gly Val Thr Leu Pro Lys Gly
                325                 330                 335

Lys Asp Val Leu Leu Phe Glu Leu Asp Gln Asp Asp Ile Gly Glu Lys
            340                 345                 350

Leu Ser Ser Glu Lys Leu Ser Pro Leu Leu Ser Val Tyr Lys Ala Ala
        355                 360                 365

Asp Arg Lys Glu Ala Ile Lys Val Val Gln Arg Leu Leu Asn Tyr Gln
    370                 375                 380

Gly Ala Gly His Asn Ala Ala Ile Gln Ile Gly Ala Gln Asp Asp Pro
385                 390                 395                 400

Phe Val Lys Glu Tyr Ala Asp Ala Val Ser Ala Ser Arg Ile Leu Val
                405                 410                 415

Asn Gln Pro Asp Ser Ile Gly Gly Val Gly Asp Ile Tyr Thr Asp Ala
            420                 425                 430

Leu Arg Pro Ser Met Thr Leu Gly Thr Gly Ser Trp Gly Lys Asn Ser
        435                 440                 445

Leu Ser His Asn Leu Ser Thr Tyr Asp Leu Leu Asn Val Lys Thr Val
    450                 455                 460

Ala Arg Arg Arg Asn Arg Pro Gln Trp Val Arg Leu Pro Lys Asp Ile
465                 470                 475                 480

Tyr Tyr Glu Lys Asn Ala Ile Thr Tyr Leu Gln Glu Leu Pro Asn Val
                485                 490                 495

Asn Arg Ala Phe Val Ile Thr Asp His Ser Leu Val Lys Tyr Gly Phe
            500                 505                 510

Val Asp Arg Ile Leu Glu Gln Phe Glu Leu Arg Pro Asp Gln Val Lys
        515                 520                 525

Thr Ser Ile Tyr Ser Ser Val Gln Pro Asp Pro Tyr Leu Ser Gln Ala
    530                 535                 540

Val Glu Ile Ala Lys Gln Met Gln Glu Phe Glu Pro Asp Thr Val Ile
545                 550                 555                 560
```

```
Ala Leu Gly Gly Gly Ser Ser Leu Asp Val Ala Lys Ile Ser Arg Phe
                565                 570                 575

Leu Tyr Glu Tyr Ser Gln Glu Pro Asp His Ile Gly Phe Leu Glu Asn
            580                 585                 590

Ile Asp Asp Ile Lys Glu Leu Phe Lys Gly Leu Gln Gln Lys Phe Met
        595                 600                 605

Asp Ile Arg Lys Arg Ile Val Lys Phe Glu His Gln Asn Leu Thr Gln
    610                 615                 620

Leu Val Ala Ile Pro Thr Thr Ser Gly Thr Gly Ser Glu Val Thr Pro
625                 630                 635                 640

Phe Ser Val Ile Thr Asp Asp Glu Thr His Val Lys Tyr Pro Leu Ala
                645                 650                 655

Asp Tyr Glu Leu Thr Pro Gln Val Ala Ile Val Asp Pro Glu Leu Val
            660                 665                 670

Met Thr Val Pro Lys Arg Thr Leu Ala Trp Ser Gly Leu Asp Ala Leu
        675                 680                 685

Ser His Ser Leu Glu Ser Tyr Val Ser Val Met Ser Ser Glu Phe Thr
    690                 695                 700

Arg Pro Trp Ala Leu Gln Ala Ile Lys Leu Ile Phe Glu Asn Ile Val
705                 710                 715                 720

Asp Ser Tyr Asn Tyr Asp Pro Lys His Pro Thr Asn Arg Gly Ala Glu
                725                 730                 735

Ala Arg Glu Lys Met His Tyr Ala Ala Thr Leu Ala Gly Met Ser Phe
            740                 745                 750

Gly Asn Ala Phe Leu Gly Ile Asn His Ser Leu Ala His Lys Thr Gly
        755                 760                 765

Gly Glu Phe Gly Leu Pro His Gly Leu Ala Ile Ser Ile Ala Met Pro
    770                 775                 780

His Val Ile Arg Phe Asn Ala Val Thr Gly Asn Val Lys Arg Thr Pro
785                 790                 795                 800

Phe Pro Arg Tyr Glu Val Tyr Thr Ala Gln Lys Asp Tyr Ala Asp Ile
                805                 810                 815

Ala Arg His Ile Gly Leu Ser Gly Lys Asn Asp Ala Glu Leu Val Glu
            820                 825                 830

Lys Leu Ile Ala Lys Ile Lys Glu Leu Thr Asp Ala Leu Asp Val Asn
        835                 840                 845

Ile Thr Leu Ser Gly Asn Gly Val Asp Lys Lys Ser Phe Glu His Ser
    850                 855                 860

Leu Asp Gln Leu Val Asp Leu Val Tyr Asp Asp Gln Cys Thr Pro Gly
865                 870                 875                 880

Asn Pro Arg Gln Pro Asn Leu Ala Glu Ile Arg Gln Leu Leu Ile Asp
                885                 890                 895

Gln Phe
```

<210> SEQ ID NO 18
<211> LENGTH: 1476
<212> TYPE: DNA
<213> ORGANISM: Saccharomyces cerevisiae

<400> SEQUENCE: 18

```
atggagagtc gaactacagg gcctttaacg actgaaacct acgatggccc cactgtggcc      60

ttcatgatat taggtgccgc cctagtattt tttatggtgc ccggattggg attcttgtac     120

tccggattgg caagaaggaa gtctgcacta gcactaatct gggttgtatt aatggcgact     180
```

```
ttggtcggta tactgcaatg gtatttctgg ggttactctc tagctttttc aaagtccgct    240

ccgaataata aattcattgg gaatctagat tcgtttggct ttagaaacgt gtacggaaaa    300

aaattcgatg aagatgccta ccctgagctc gcgtatgcaa ccttccaaat gatgttttcg    360

tgcgtcaact taagtattat cgctggcgcc actgccgaaa gaggcaggct gctaccgcac    420

atggtttttc tctttattct agctaccatt ggatattgtc cagtgacgta ttggatttgg    480

tcaccaggtg gttgggcata ccaatgggga gtcctcgatt gggcaggcgg cggcaacatt    540

gaaatattaa gcgctgtttc cgggtttgtt tactcttggt tttgggcaa aagaaatgaa    600

aagttactga taaatttcag gcctcataat gtttcattgg tcactctagg cacatccata    660

ctgtggtttg gctggctgct atttaattct gcatcctcat tatccccaaa tttgaggtca    720

gtttatgcat tcatgaatac atgtctcagt gccattactg gtgggatgac gtggtgtctt    780

ctggattaca gatcggagaa gaaatggtcg acagttggtc tgtgctccgg tatcatttct    840

gggctggtgg ctgcaacgcc aagctcaggc tgtataaccc tttacggttc acttattcaa    900

ggcattgtgg cgggggtagt gtgtaacttt gcgacgaagt tgaaatacta cgctaaagta    960

gatgatgcca tggacattct agctgagcac ggggttgcag gcgtaatagg actaattttc   1020

aatgcccttt ttggagcaga ctgggtcatt ggtatggatg gcactacaga gcacgagggc   1080

ggctgggtaa ctcacaatta caagcaaatg tataagcaga tcgcttacat tgccgcatcc   1140

attgggtaca ctgctgctgt aactgcaata atctgctttg tgctcggcta catacccggt   1200

atgaggctaa gaatatcaga agaggcagag gaggcgggta tggacgaaga tcaaattggc   1260

gaatttgcgt acgattatgt ggaagtgaga agagattact atctatgggg tgtagacgaa   1320

gattcacaac gctctgatgt aaatcaccgg gtgaacaacg ctcatttggc cgctgaacgt   1380

agcagtagcg gtactaatag ttcctcggat gggaatggag aaatgattca atccgaaaag   1440

atcctaccaa ttcatcaaga agatcctgcc aatagg                              1476
```

```
<210> SEQ ID NO 19
<211> LENGTH: 492
<212> TYPE: PRT
<213> ORGANISM: Saccharomyces cerevisiae

<400> SEQUENCE: 19

Met Glu Ser Arg Thr Thr Gly Pro Leu Thr Thr Glu Thr Tyr Asp Gly
1               5                   10                  15

Pro Thr Val Ala Phe Met Ile Leu Gly Ala Ala Leu Val Phe Phe Met
            20                  25                  30

Val Pro Gly Leu Gly Phe Leu Tyr Ser Gly Leu Ala Arg Arg Lys Ser
        35                  40                  45

Ala Leu Ala Leu Ile Trp Val Val Leu Met Ala Thr Leu Val Gly Ile
    50                  55                  60

Leu Gln Trp Tyr Phe Trp Gly Tyr Ser Leu Ala Phe Ser Lys Ser Ala
65                  70                  75                  80

Pro Asn Asn Lys Phe Ile Gly Asn Leu Asp Ser Phe Gly Phe Arg Asn
                85                  90                  95

Val Tyr Gly Lys Lys Phe Asp Glu Asp Ala Tyr Pro Glu Leu Ala Tyr
            100                 105                 110

Ala Thr Phe Gln Met Met Phe Ser Cys Val Asn Leu Ser Ile Ile Ala
        115                 120                 125

Gly Ala Thr Ala Glu Arg Gly Arg Leu Leu Pro His Met Val Phe Leu
    130                 135                 140
```

```
Phe Ile Leu Ala Thr Ile Gly Tyr Cys Pro Val Thr Tyr Trp Ile Trp
145                 150                 155                 160

Ser Pro Gly Gly Trp Ala Tyr Gln Trp Gly Val Leu Asp Trp Ala Gly
                165                 170                 175

Gly Gly Asn Ile Glu Ile Leu Ser Ala Val Ser Gly Phe Val Tyr Ser
            180                 185                 190

Trp Phe Leu Gly Lys Arg Asn Glu Lys Leu Leu Ile Asn Phe Arg Pro
        195                 200                 205

His Asn Val Ser Leu Val Thr Leu Gly Thr Ser Ile Leu Trp Phe Gly
    210                 215                 220

Trp Leu Leu Phe Asn Ser Ala Ser Ser Leu Ser Pro Asn Leu Arg Ser
225                 230                 235                 240

Val Tyr Ala Phe Met Asn Thr Cys Leu Ser Ala Ile Thr Gly Gly Met
                245                 250                 255

Thr Trp Cys Leu Leu Asp Tyr Arg Ser Glu Lys Lys Trp Ser Thr Val
            260                 265                 270

Gly Leu Cys Ser Gly Ile Ile Ser Gly Leu Val Ala Ala Thr Pro Ser
        275                 280                 285

Ser Gly Cys Ile Thr Leu Tyr Gly Ser Leu Ile Gln Gly Ile Val Ala
    290                 295                 300

Gly Val Val Cys Asn Phe Ala Thr Lys Leu Lys Tyr Tyr Ala Lys Val
305                 310                 315                 320

Asp Asp Ala Met Asp Ile Leu Ala Glu His Gly Val Ala Gly Val Ile
                325                 330                 335

Gly Leu Ile Phe Asn Ala Leu Phe Gly Ala Asp Trp Val Ile Gly Met
            340                 345                 350

Asp Gly Thr Thr Glu His Glu Gly Gly Trp Val Thr His Asn Tyr Lys
        355                 360                 365

Gln Met Tyr Lys Gln Ile Ala Tyr Ile Ala Ala Ser Ile Gly Tyr Thr
    370                 375                 380

Ala Ala Val Thr Ala Ile Ile Cys Phe Val Leu Gly Tyr Ile Pro Gly
385                 390                 395                 400

Met Arg Leu Arg Ile Ser Glu Glu Ala Glu Glu Ala Gly Met Asp Glu
                405                 410                 415

Asp Gln Ile Gly Glu Phe Ala Tyr Asp Tyr Val Glu Val Arg Arg Asp
            420                 425                 430

Tyr Tyr Leu Trp Gly Val Asp Glu Asp Ser Gln Arg Ser Asp Val Asn
        435                 440                 445

His Arg Val Asn Asn Ala His Leu Ala Ala Glu Arg Ser Ser Ser Gly
    450                 455                 460

Thr Asn Ser Ser Ser Asp Gly Asn Gly Glu Met Ile Gln Ser Glu Lys
465                 470                 475                 480

Ile Leu Pro Ile His Gln Glu Asp Pro Ala Asn Arg
                485                 490
```

```
<210> SEQ ID NO 20
<211> LENGTH: 1497
<212> TYPE: DNA
<213> ORGANISM: Saccharomyces cerevisiae

<400> SEQUENCE: 20

atgtcttaca attttacagg tacgcctaca ggcgaaggaa cgggtggtaa ctcgttgaca     60

acagatttga atacacaatt tgacttggcc aacatgggat ggatcggtgt ggcttcagca    120
```

-continued

```
ggtgtgtgga ttatggtccc aggtatcggt ttattatatt ctggtttatc caggaaaaag    180

catgctttat ccttgctttg ggcctcgatg atggcttccg ccgtgtgtat tttccaatgg    240

tttttctggg gatactcatt agctttctca cacaacacta gaggtaacgg ttttattggt    300

accttggaat tctttgggtt tcgtaacgtt ttaggagccc catctagtgt cagttctctt    360

cccgatatac tgtttgccgt ttaccaaggt atgtttgccg cagtcaccgg tgccctaatg    420

ctaggtggtg cctgcgagag ggcaaggttg tttcctatga tggtgttctt gtttttatgg    480

atgactattg tttattgtcc tattgcatgc tgggtctgga atgccgaggg ttggttggtc    540

aaattgggta gcttggacta tgcaggtggt ttatgtgtcc atttaacatc tggacatggt    600

ggtctagttt acgctttgat actgggtaag cgtaatgacc ctgttacacg taaagggatg    660

cccaagtaca aaccacattc cgtcacctcg gtggttttag gcacagtgtt cttatggttt    720

ggttggatgt tctttaacgg aggctctgca ggtaatgcaa ctatacgagc atggtactct    780

attatgtcca caaacttagc tgctgcttgc ggtggcttga catggatggt tatcgattat    840

ttcagatgcg gaagaaagtg gactacagtt ggtttgtgtt caggtatcat cgctggccta    900

gtgggtatca ccccagccgc cgggttcgtg ccaatctggt cagccgttgt cattggtgtg    960

gttactggtg caggatgtaa ccttgctgtt gacttaaaga gtctattgcg catcgatgat   1020

ggtctagatt gttactctat ccatggtgtg ggtggttgta ttggttctgt attaactggt   1080

atctttgctg cagactatgt aaatgccact gcaggctctt acattagtcc aattgatggt   1140

ggctggatca atcatcacta taaacaagtt ggttatcaat tagcaggtat atgcgctgca   1200

ctagcctgga ctgttactgt cacatctatc ttgcttctaa ctatgaatgc cattccattt   1260

ttaaaactaa gattaagtgc tgatgaggaa gaattaggta ccgacgctgc tcaaattggt   1320

gaatttacat acgaggaatc cactgcttac atcccagaac caatcagatc taaaacatcg   1380

gcacaaatgc cacctcctca tgaaaacatt gatgataaga ttgtgggtaa cacagacgca   1440

gaaaagaatt ctacgccttc cgacgcttct tctactaaga acactgacca tatagta      1497
```

<210> SEQ ID NO 21
<211> LENGTH: 499
<212> TYPE: PRT
<213> ORGANISM: Saccharomyces cerevisiae

<400> SEQUENCE: 21

```
Met Ser Tyr Asn Phe Thr Gly Thr Pro Thr Gly Glu Gly Thr Gly Gly
1               5                   10                  15

Asn Ser Leu Thr Thr Asp Leu Asn Thr Gln Phe Asp Leu Ala Asn Met
            20                  25                  30

Gly Trp Ile Gly Val Ala Ser Ala Gly Val Trp Ile Met Val Pro Gly
        35                  40                  45

Ile Gly Leu Leu Tyr Ser Gly Leu Ser Arg Lys Lys His Ala Leu Ser
    50                  55                  60

Leu Leu Trp Ala Ser Met Met Ala Ser Ala Val Cys Ile Phe Gln Trp
65                  70                  75                  80

Phe Phe Trp Gly Tyr Ser Leu Ala Phe Ser His Asn Thr Arg Gly Asn
                85                  90                  95

Gly Phe Ile Gly Thr Leu Glu Phe Phe Gly Phe Arg Asn Val Leu Gly
            100                 105                 110

Ala Pro Ser Ser Val Ser Ser Leu Pro Asp Ile Leu Phe Ala Val Tyr
        115                 120                 125

Gln Gly Met Phe Ala Ala Val Thr Gly Ala Leu Met Leu Gly Gly Ala
```

```
    130                 135                 140

Cys Glu Arg Ala Arg Leu Phe Pro Met Met Val Phe Leu Phe Leu Trp
145                 150                 155                 160

Met Thr Ile Val Tyr Cys Pro Ile Ala Cys Trp Val Trp Asn Ala Glu
                165                 170                 175

Gly Trp Leu Val Lys Leu Gly Ser Leu Asp Tyr Ala Gly Gly Leu Cys
            180                 185                 190

Val His Leu Thr Ser Gly His Gly Gly Leu Val Tyr Ala Leu Ile Leu
        195                 200                 205

Gly Lys Arg Asn Asp Pro Val Thr Arg Lys Gly Met Pro Lys Tyr Lys
    210                 215                 220

Pro His Ser Val Thr Ser Val Val Leu Gly Thr Val Phe Leu Trp Phe
225                 230                 235                 240

Gly Trp Met Phe Phe Asn Gly Gly Ser Ala Gly Asn Ala Thr Ile Arg
                245                 250                 255

Ala Trp Tyr Ser Ile Met Ser Thr Asn Leu Ala Ala Ala Cys Gly Gly
            260                 265                 270

Leu Thr Trp Met Val Ile Asp Tyr Phe Arg Cys Gly Arg Lys Trp Thr
        275                 280                 285

Thr Val Gly Leu Cys Ser Gly Ile Ile Ala Gly Leu Val Gly Ile Thr
    290                 295                 300

Pro Ala Ala Gly Phe Val Pro Ile Trp Ser Ala Val Val Ile Gly Val
305                 310                 315                 320

Val Thr Gly Ala Gly Cys Asn Leu Ala Val Asp Leu Lys Ser Leu Leu
                325                 330                 335

Arg Ile Asp Asp Gly Leu Asp Cys Tyr Ser Ile His Gly Val Gly Gly
            340                 345                 350

Cys Ile Gly Ser Val Leu Thr Gly Ile Phe Ala Ala Asp Tyr Val Asn
        355                 360                 365

Ala Thr Ala Gly Ser Tyr Ile Ser Pro Ile Asp Gly Gly Trp Ile Asn
    370                 375                 380

His His Tyr Lys Gln Val Gly Tyr Gln Leu Ala Gly Ile Cys Ala Ala
385                 390                 395                 400

Leu Ala Trp Thr Val Thr Val Thr Ser Ile Leu Leu Leu Thr Met Asn
                405                 410                 415

Ala Ile Pro Phe Leu Lys Leu Arg Leu Ser Ala Asp Glu Glu Glu Leu
            420                 425                 430

Gly Thr Asp Ala Ala Gln Ile Gly Glu Phe Thr Tyr Glu Glu Ser Thr
        435                 440                 445

Ala Tyr Ile Pro Glu Pro Ile Arg Ser Lys Thr Ser Ala Gln Met Pro
    450                 455                 460

Pro Pro His Glu Asn Ile Asp Asp Lys Ile Val Gly Asn Thr Asp Ala
465                 470                 475                 480

Glu Lys Asn Ser Thr Pro Ser Asp Ala Ser Ser Thr Lys Asn Thr Asp
                485                 490                 495

His Ile Val
```

<210> SEQ ID NO 22
<211> LENGTH: 1467
<212> TYPE: DNA
<213> ORGANISM: Saccharomyces cerevisiae

<400> SEQUENCE: 22

```
atggctcggg gtgacggaca tctatggaca gagacatatg atagttccac agtcgctttt      60
```

```
atgattttag gtgccgccct ggttttcttc atggtaccag ggctgggctt tctttttttcc    120

ggtttagcaa gaagaaaatc tgctctggct ttgatttggg tagtgataat ggctacctta    180

gtaggtatac tgcaatggta tttttggggc tattctttag cattctctaa gactgcgacg    240

aacaacaaat ttatcggcaa cttggattca tttgggttta gaaacgtcta tggcaaaatt    300

tcggatgatt ccacgtatcc tgaactgatt tatgccattt tccaaatgat gttcatgtgt    360

gtcgcattga gtattatagc tggtgccact gcggaaagag gtaagctttt tccacatatg    420

gtttttcttt ttgtttttgc gactttggtt tactgtccca tcacttattg gatttgggcc    480

ccaggtggct gggcctacca atggggggta ttagactggg ctggcggtgg gaatattgaa    540

atcctaagtg ctgtggctgg tttcgtttat tcttattttc taggaagaag aaaagaaaac    600

ctcctgatca actttagacc acataatgtt tccatggtga ctttaggtac ttctatactt    660

tggtttggtt ggttgctttt caatgctgca agctcactgt caccaaatat gaggtccgta    720

tatgcgttca tgaacacttg tctcagcgcc accacgggtg gaatgacgtg gtgtttatta    780

gattatcgat ctgaaaaaaa atggtccact gttgggttat gctccggcat tatctgtggt    840

ttagttgctg ccacgcctag ctcgggttgt attactctat atggctcttt gatccaaggt    900

ataatagcgg gtgttgtttg taattttgca acaaaaataa agtattattt aaaagtggat    960

gattccttag atctattagc tgaacacggt atcgccggtg tggtgggatt gatttttaac   1020

gctctatttg cagctgattg ggttattgga atggacggca caacaaagca taagggtggt   1080

tggttgacgc ataactggaa acaaatgtat attcaaattg cctatatcgg tgcctctgcc   1140

ggctattgtg ctgtggtcac ggccatcatt tgcttcgtat taggtaaaat tccgggtgtc   1200

catctaagag tcactgagga agccgaagca ttggggttgg atgaagatca aataggcgaa   1260

ttcgcttacg attacgtgga ggttaggaga gattattacc agtggggtgt agatacagat   1320

gcacttcata ctacatgcaa tggcgctaat tctgcgtctg agacaaatcc tactgaggac   1380

agccaaaact cctcattgtc atcagctaca gtaagcggcc aaaacgaaaa aagtaataat   1440

cctaaattgc atcacgcaaa agaagca                                        1467
```

```
<210> SEQ ID NO 23
<211> LENGTH: 489
<212> TYPE: PRT
<213> ORGANISM: Saccharomyces cerevisiae

<400> SEQUENCE: 23

Met Ala Arg Gly Asp Gly His Leu Trp Thr Glu Thr Tyr Asp Ser Ser
1               5                   10                  15

Thr Val Ala Phe Met Ile Leu Gly Ala Ala Leu Val Phe Phe Met Val
            20                  25                  30

Pro Gly Leu Gly Phe Leu Tyr Ser Gly Leu Ala Arg Arg Lys Ser Ala
        35                  40                  45

Leu Ala Leu Ile Trp Val Val Ile Met Ala Thr Leu Val Gly Ile Leu
    50                  55                  60

Gln Trp Tyr Phe Trp Gly Tyr Ser Leu Ala Phe Ser Lys Thr Ala Thr
65                  70                  75                  80

Asn Asn Lys Phe Ile Gly Asn Leu Asp Ser Phe Gly Phe Arg Asn Val
                85                  90                  95

Tyr Gly Lys Ile Ser Asp Asp Ser Thr Tyr Pro Glu Leu Ile Tyr Ala
            100                 105                 110

Ile Phe Gln Met Met Phe Met Cys Val Ala Leu Ser Ile Ile Ala Gly
```

```
        115                 120                 125

Ala Thr Ala Glu Arg Gly Lys Leu Phe Pro His Met Val Phe Leu Phe
    130                 135                 140

Val Phe Ala Thr Leu Val Tyr Cys Pro Ile Thr Tyr Trp Ile Trp Ala
145                 150                 155                 160

Pro Gly Gly Trp Ala Tyr Gln Trp Gly Val Leu Asp Trp Ala Gly Gly
                165                 170                 175

Gly Asn Ile Glu Ile Leu Ser Ala Val Ala Gly Phe Val Tyr Ser Tyr
            180                 185                 190

Phe Leu Gly Arg Arg Lys Glu Asn Leu Leu Ile Asn Phe Arg Pro His
        195                 200                 205

Asn Val Ser Met Val Thr Leu Gly Thr Ser Ile Leu Trp Phe Gly Trp
    210                 215                 220

Leu Leu Phe Asn Ala Ala Ser Ser Leu Ser Pro Asn Met Arg Ser Val
225                 230                 235                 240

Tyr Ala Phe Met Asn Thr Cys Leu Ser Ala Thr Thr Gly Gly Met Thr
                245                 250                 255

Trp Cys Leu Leu Asp Tyr Arg Ser Glu Lys Lys Trp Ser Thr Val Gly
            260                 265                 270

Leu Cys Ser Gly Ile Ile Cys Gly Leu Val Ala Ala Thr Pro Ser Ser
        275                 280                 285

Gly Cys Ile Thr Leu Tyr Gly Ser Leu Ile Gln Gly Ile Ile Ala Gly
    290                 295                 300

Val Val Cys Asn Phe Ala Thr Lys Ile Lys Tyr Tyr Leu Lys Val Asp
305                 310                 315                 320

Asp Ser Leu Asp Leu Leu Ala Glu His Gly Ile Ala Gly Val Val Gly
                325                 330                 335

Leu Ile Phe Asn Ala Leu Phe Ala Ala Asp Trp Val Ile Gly Met Asp
            340                 345                 350

Gly Thr Thr Lys His Lys Gly Gly Trp Leu Thr His Asn Trp Lys Gln
        355                 360                 365

Met Tyr Ile Gln Ile Ala Tyr Ile Gly Ala Ser Ala Gly Tyr Cys Ala
    370                 375                 380

Val Val Thr Ala Ile Ile Cys Phe Val Leu Gly Lys Ile Pro Gly Val
385                 390                 395                 400

His Leu Arg Val Thr Glu Glu Ala Glu Ala Leu Gly Leu Asp Glu Asp
                405                 410                 415

Gln Ile Gly Glu Phe Ala Tyr Asp Tyr Val Glu Val Arg Arg Asp Tyr
            420                 425                 430

Tyr Gln Trp Gly Val Asp Thr Asp Ala Leu His Thr Thr Cys Asn Gly
        435                 440                 445

Ala Asn Ser Ala Ser Glu Thr Asn Pro Thr Glu Asp Ser Gln Asn Ser
    450                 455                 460

Ser Leu Ser Ser Ala Thr Val Ser Gly Gln Asn Glu Lys Ser Asn Asn
465                 470                 475                 480

Pro Lys Leu His His Ala Lys Glu Ala
                485
```

<210> SEQ ID NO 24
<211> LENGTH: 1362
<212> TYPE: DNA
<213> ORGANISM: Saccharomyces cerevisiae

<400> SEQUENCE: 24

```
atgtcagagc cagaatttca acaagcttac gaagaagttg tctcctcttt ggaagactct      60
actcttttcg aacaacaccc agaatacaga aaggttttgc caattgtttc tgttccagaa     120
agaatcatac aattcagagt cacctgggaa aatgacaagg gtgaacaaga agttgctcaa     180
ggttacagag tgcaatataa ctccgccaag ggtccataca agggtggtct acgtttccat     240
ccttccgtga acttgtctat cttgaaattc ttgggtttcg aacaaatctt caagaactcc     300
ttgaccggcc tagacatggg tggtggtaaa ggtggtctat gtgtggactt gaagggaaga     360
tctaataacg aaatcagaag aatctgttac gctttcatga gagaattgag cagacacatt     420
ggtcaagaca ctgacgtgcc agctggtgat atcggtgttg gtggtcgtga aattggttac     480
ctgttcggtg cttacagatc atacaagaac tcctgggaag gtgtcttaac cggtaagggt     540
ttgaactggg gtggttcttt gatcagacca gaagccactg gttacggttt agtttactat     600
acccaagcta tgatcgacta tgccacaaac ggtaaggaat ctttcgaagg taagcgcgtc     660
accatctctg gtagtggtaa cgttgctcaa tacgctgcct tgaaggttat tgagctaggt     720
ggtactgtcg tttccctatc tgactccaag ggttgtatca tctctgaaac tggtatcacc     780
tccgaacaag tcgctgatat ttccagtgct aaggtcaact tcaagtcctt ggaacaaatc     840
gtcaacgaat actctacttt ctccgaaaac aaagtgcaat acattgctgg tgctcgtcca     900
tggacccacg tccaaaaggt cgacattgct ttgccatgtg ccacccaaaa tgaagtcagc     960
ggtgaagaag ccaaggcctt ggttgctcaa ggtgtcaagt ttattgccga aggttccaac    1020
atgggttcca ctccagaagc tattgccgtc tttgaaactg ctcgttccac cgccactgga    1080
ccaagcgaag ctgtttggta cggtccacca aaggctgcta acttgggtgg tgttgctgtt    1140
tctggtttag aaatggcaca aaactctcaa agaatcacat ggactagcga aagagttgac    1200
caagagttga agagaattat gatcaactgt ttcaatgaat gtatcgacta tgccaagaag    1260
tacactaagg acggtaaggt cttgccatct ttggtcaaag gtgctaatat cgcaagtttc    1320
atcaaggtct ctgatgctat gtttgaccaa ggtgatgtat tt                       1362
```

```
<210> SEQ ID NO 25
<211> LENGTH: 454
<212> TYPE: PRT
<213> ORGANISM: Saccharomyces cerevisiae

<400> SEQUENCE: 25

Met Ser Glu Pro Glu Phe Gln Gln Ala Tyr Glu Glu Val Val Ser Ser
1               5                   10                  15

Leu Glu Asp Ser Thr Leu Phe Glu Gln His Pro Glu Tyr Arg Lys Val
            20                  25                  30

Leu Pro Ile Val Ser Val Pro Glu Arg Ile Ile Gln Phe Arg Val Thr
        35                  40                  45

Trp Glu Asn Asp Lys Gly Glu Gln Glu Val Ala Gln Gly Tyr Arg Val
    50                  55                  60

Gln Tyr Asn Ser Ala Lys Gly Pro Tyr Lys Gly Gly Leu Arg Phe His
65                  70                  75                  80

Pro Ser Val Asn Leu Ser Ile Leu Lys Phe Leu Gly Phe Glu Gln Ile
                85                  90                  95

Phe Lys Asn Ser Leu Thr Gly Leu Asp Met Gly Gly Gly Lys Gly Gly
            100                 105                 110

Leu Cys Val Asp Leu Lys Gly Arg Ser Asn Asn Glu Ile Arg Arg Ile
        115                 120                 125

Cys Tyr Ala Phe Met Arg Glu Leu Ser Arg His Ile Gly Gln Asp Thr
```

```
    130                 135                 140

Asp Val Pro Ala Gly Asp Ile Gly Val Gly Gly Arg Glu Ile Gly Tyr
145                 150                 155                 160

Leu Phe Gly Ala Tyr Arg Ser Tyr Lys Asn Ser Trp Glu Gly Val Leu
                165                 170                 175

Thr Gly Lys Gly Leu Asn Trp Gly Gly Ser Leu Ile Arg Pro Glu Ala
            180                 185                 190

Thr Gly Tyr Gly Leu Val Tyr Tyr Thr Gln Ala Met Ile Asp Tyr Ala
        195                 200                 205

Thr Asn Gly Lys Glu Ser Phe Glu Gly Lys Arg Val Thr Ile Ser Gly
    210                 215                 220

Ser Gly Asn Val Ala Gln Tyr Ala Ala Leu Lys Val Ile Glu Leu Gly
225                 230                 235                 240

Gly Thr Val Val Ser Leu Ser Asp Ser Lys Gly Cys Ile Ile Ser Glu
                245                 250                 255

Thr Gly Ile Thr Ser Glu Gln Val Ala Asp Ile Ser Ser Ala Lys Val
            260                 265                 270

Asn Phe Lys Ser Leu Glu Gln Ile Val Asn Glu Tyr Ser Thr Phe Ser
        275                 280                 285

Glu Asn Lys Val Gln Tyr Ile Ala Gly Ala Arg Pro Trp Thr His Val
    290                 295                 300

Gln Lys Val Asp Ile Ala Leu Pro Cys Ala Thr Gln Asn Glu Val Ser
305                 310                 315                 320

Gly Glu Glu Ala Lys Ala Leu Val Ala Gln Gly Val Lys Phe Ile Ala
                325                 330                 335

Glu Gly Ser Asn Met Gly Ser Thr Pro Glu Ala Ile Ala Val Phe Glu
            340                 345                 350

Thr Ala Arg Ser Thr Ala Thr Gly Pro Ser Glu Ala Val Trp Tyr Gly
        355                 360                 365

Pro Pro Lys Ala Ala Asn Leu Gly Gly Val Ala Val Ser Gly Leu Glu
    370                 375                 380

Met Ala Gln Asn Ser Gln Arg Ile Thr Trp Thr Ser Glu Arg Val Asp
385                 390                 395                 400

Gln Glu Leu Lys Arg Ile Met Ile Asn Cys Phe Asn Glu Cys Ile Asp
                405                 410                 415

Tyr Ala Lys Lys Tyr Thr Lys Asp Gly Lys Val Leu Pro Ser Leu Val
            420                 425                 430

Lys Gly Ala Asn Ile Ala Ser Phe Ile Lys Val Ser Asp Ala Met Phe
        435                 440                 445

Asp Gln Gly Asp Val Phe
    450
```

<210> SEQ ID NO 26
<211> LENGTH: 3276
<212> TYPE: DNA
<213> ORGANISM: Saccharomyces cerevisiae

<400> SEQUENCE: 26

```
atgctttttg ataacaaaaa tcgcggtgct ttaaactcac tgaacacacc agatattgct      60

tctttatcaa tatcatccat gtcggactat cacgtgtttg attttcccgg taaggacctg     120

cagagagagg aagtgataga tttgctagat cagcaagggt ttattcccga cgatttgatc     180

gaacaagaag tagattggtt ttataactca ttgggtattg acgatttgtt cttctcgaga     240

gaatctcccc aattaatctc gaatatcata cattctttgt atgcttcaaa gctagatttc     300
```

```
tttgcgaagt ccaaattcaa cggaattcag ccaaggctat tcagcattaa aaacaaaatt    360
ataactaatg ataatcatgc catctttatg gaatctaata ctggtgtcag cataagcgat    420
tctcagcaaa aaaactttaa atttgctagt gacgccgtcg gaaacgatac tttggagcat    480
ggtaaggata ccatcaaaaa aaataggatt gaaatggatg attcttgtcc accttatgaa    540
ttagattccg aaattgatga ccttttcctg gataacaagt ctcaaaaaaa ctgcagatta    600
gtttcttttt gggctccaga aagcgaatta aagctaactt ttgtttatga gagtgtttac    660
cctaatgatg atccagccgg cgtagatatt tcctctcagg atttgctgaa aggtgatatt    720
gaatcgatta gtgataagac catgtacaaa gtttcgtcga acgaaaataa aaaactatac    780
ggtctcttac ttaagttggt taaagaaaga gaaggtcctg tcattaagac tactcgctcc    840
gtagaaaata aggatgaaat taggttatta gtcgcttaca agcgattcac cactaagcgt    900
tattactctg ctttgaactc tttgttccac tattacaagt tgaaaccttc taagttctat    960
ttagagtcgt ttaatgttaa ggatgatgac atcattatct tttccgttta tttgaacgag   1020
aaccagcaat tggaagatgt tctacttcac gatgtggagg cagcattgaa acaggttgaa   1080
agagaagctt cattgctata cgctatccca aacaattctt tccatgaggt ttaccagaga   1140
cgtcaattct cgcccaaaga agctatatat gctcatattg gtgctatatt cattaaccat   1200
tttgttaatc gtttaggctc tgattatcaa aaccttttat ctcaaatcac cattaagcgt   1260
aatgatacta ctcttttgga gattgtagaa aacctaaaaa gaaagttaag aaatgaaacc   1320
ttaactcagc aaactattat caacatcatg tcgaagcatt acactataat ttccaagttg   1380
tataaaaatt ttgctcaaat tcactattat cataatagta ctaaagatat ggagaagaca   1440
ttatcttttc aaagactgga aaaagtggag ccttttaaga atgaccaaga gttcgaagct   1500
tacttgaata aattcattcc aaatgattca cctgatttgt tgatcctgaa aacactgaac   1560
atcttcaaca agtctatttt gaagacaaat ttctttatta caagaaaagt agcaatatca   1620
ttcagattag atccttccct ggtgatgaca aaattcgaat atccagagac accctatggt   1680
atattttttg tcgttggtaa tactttcaaa gggttccata tcaggttcag agatatcgca   1740
aggggcggta ttcgtatagt ctgttccagg aatcaggata tttatgattt gaattccaag   1800
aacgttattg atgagaacta tcaattggcc tctactcagc aacgtaaaaa taaggatatt   1860
ccagagggtg gctctaaagg tgtcatctta ttgaacccag gattggtaga acatgaccag   1920
acatttgtcg ccttttccca atatgtggat gcaatgattg acattctaat caacgatcca   1980
ttaaaggaaa actatgtcaa ccttttacca aaggaggaaa tattattttt tggcccagat   2040
gaaggaactg ctggtttcgt ggattgggca actaaccatg ctcgtgtgag gaactgccca   2100
tggtggaaat catttttgac tggaaaatcc ccatctttgg gtggtattcc ccatgacgaa   2160
tatggtatga cttctctggg tgttcgtgct tatgttaata aaatttacga aactttaaac   2220
ttgacaaatt ctactgttta caaattccaa actggtggtc cggatggtga tttgggatcc   2280
aatgaaattc ttttatcttc gccaaacgaa tgttatttgg caattctgga cggttcaggt   2340
gtcctgtgtg atcctaaagg tttagataaa gatgaattat gccgcttggc acatgaaagg   2400
aaaatgattt ccgatttcga cacttccaaa ttatcaaaca acggattttt tgtttctgtg   2460
gatgcaatgg atatcatgct accaaatggt acaattgtag ctaacggcac aaccttcaga   2520
aacacctttc atactcaaat tttcaaattt gtggatcatg tcgacatttt tgttccatgc   2580
ggtggtagac caaactcaat tactctaaat aatctacatt attttgttga cgaaaagact   2640
```

```
gggaaatgta aaattccata tattgtggag ggtgccaatc tatttataac gcaacctgct   2700

aaaaatgctt tggaggaaca tggctgtatt ctgttcaaag atgcttctgc aaacaaaggt   2760

ggtgtcacat cttcatcaat ggaagtgttg gcctcactag cgcttaacga taacgacttc   2820

gtgcacaaat ttattggaga tgttagtggt gagaggtctg cgttgtacaa gtcgtacgtt   2880

gtagaagtgc agtcaagaat tcagaaaaat gctgaattag agtttggtca gttatggaat   2940

ttgaatcaac taaatggaac ccacatttca gaaatttcaa accaattgtc cttcactata   3000

aacaaattga acgacgatct agttgcttct caagagttgt ggctcaatga tctaaaatta   3060

agaaactacc tattgttgga taaaataatt ccaaaaattc tgattgatgt tgctgggcct   3120

cagtccgtat tggaaaacat tccagagagc tatttgaaag ttcttctgtc gagttactta   3180

tcaagcactt ttgtttacca gaacggtatc gatgttaaca ttggaaaatt cttggaattt   3240

attggtgggt taaaaagaga agcggaggca agtgct                             3276
```

<210> SEQ ID NO 27
<211> LENGTH: 1092
<212> TYPE: PRT
<213> ORGANISM: Saccharomyces cerevisiae

<400> SEQUENCE: 27

```
Met Leu Phe Asp Asn Lys Asn Arg Gly Ala Leu Asn Ser Leu Asn Thr
1               5                   10                  15

Pro Asp Ile Ala Ser Leu Ser Ile Ser Ser Met Ser Asp Tyr His Val
            20                  25                  30

Phe Asp Phe Pro Gly Lys Asp Leu Gln Arg Glu Glu Val Ile Asp Leu
        35                  40                  45

Leu Asp Gln Gln Gly Phe Ile Pro Asp Asp Leu Ile Glu Gln Glu Val
    50                  55                  60

Asp Trp Phe Tyr Asn Ser Leu Gly Ile Asp Asp Leu Phe Phe Ser Arg
65                  70                  75                  80

Glu Ser Pro Gln Leu Ile Ser Asn Ile Ile His Ser Leu Tyr Ala Ser
                85                  90                  95

Lys Leu Asp Phe Phe Ala Lys Ser Lys Phe Asn Gly Ile Gln Pro Arg
            100                 105                 110

Leu Phe Ser Ile Lys Asn Lys Ile Ile Thr Asn Asp Asn His Ala Ile
        115                 120                 125

Phe Met Glu Ser Asn Thr Gly Val Ser Ile Ser Asp Ser Gln Gln Lys
    130                 135                 140

Asn Phe Lys Phe Ala Ser Asp Ala Val Gly Asn Asp Thr Leu Glu His
145                 150                 155                 160

Gly Lys Asp Thr Ile Lys Lys Asn Arg Ile Glu Met Asp Asp Ser Cys
                165                 170                 175

Pro Pro Tyr Glu Leu Asp Ser Glu Ile Asp Asp Leu Phe Leu Asp Asn
            180                 185                 190

Lys Ser Gln Lys Asn Cys Arg Leu Val Ser Phe Trp Ala Pro Glu Ser
        195                 200                 205

Glu Leu Lys Leu Thr Phe Val Tyr Glu Ser Val Tyr Pro Asn Asp Asp
    210                 215                 220

Pro Ala Gly Val Asp Ile Ser Ser Gln Asp Leu Leu Lys Gly Asp Ile
225                 230                 235                 240

Glu Ser Ile Ser Asp Lys Thr Met Tyr Lys Val Ser Ser Asn Glu Asn
                245                 250                 255

Lys Lys Leu Tyr Gly Leu Leu Leu Lys Leu Val Lys Glu Arg Glu Gly
```

```
            260                 265                 270

Pro Val Ile Lys Thr Thr Arg Ser Val Glu Asn Lys Asp Glu Ile Arg
        275                 280                 285

Leu Leu Val Ala Tyr Lys Arg Phe Thr Thr Lys Arg Tyr Tyr Ser Ala
    290                 295                 300

Leu Asn Ser Leu Phe His Tyr Tyr Lys Leu Lys Pro Ser Lys Phe Tyr
305                 310                 315                 320

Leu Glu Ser Phe Asn Val Lys Asp Asp Asp Ile Ile Ile Phe Ser Val
            325                 330                 335

Tyr Leu Asn Glu Asn Gln Gln Leu Glu Asp Val Leu Leu His Asp Val
            340                 345                 350

Glu Ala Ala Leu Lys Gln Val Glu Arg Glu Ala Ser Leu Leu Tyr Ala
        355                 360                 365

Ile Pro Asn Asn Ser Phe His Glu Val Tyr Gln Arg Arg Gln Phe Ser
    370                 375                 380

Pro Lys Glu Ala Ile Tyr Ala His Ile Gly Ala Ile Phe Ile Asn His
385                 390                 395                 400

Phe Val Asn Arg Leu Gly Ser Asp Tyr Gln Asn Leu Leu Ser Gln Ile
            405                 410                 415

Thr Ile Lys Arg Asn Asp Thr Thr Leu Leu Glu Ile Val Glu Asn Leu
            420                 425                 430

Lys Arg Lys Leu Arg Asn Glu Thr Leu Thr Gln Gln Thr Ile Ile Asn
        435                 440                 445

Ile Met Ser Lys His Tyr Thr Ile Ile Ser Lys Leu Tyr Lys Asn Phe
    450                 455                 460

Ala Gln Ile His Tyr Tyr His Asn Ser Thr Lys Asp Met Glu Lys Thr
465                 470                 475                 480

Leu Ser Phe Gln Arg Leu Glu Lys Val Glu Pro Phe Lys Asn Asp Gln
            485                 490                 495

Glu Phe Glu Ala Tyr Leu Asn Lys Phe Ile Pro Asn Asp Ser Pro Asp
            500                 505                 510

Leu Leu Ile Leu Lys Thr Leu Asn Ile Phe Asn Lys Ser Ile Leu Lys
        515                 520                 525

Thr Asn Phe Phe Ile Thr Arg Lys Val Ala Ile Ser Phe Arg Leu Asp
    530                 535                 540

Pro Ser Leu Val Met Thr Lys Phe Glu Tyr Pro Glu Thr Pro Tyr Gly
545                 550                 555                 560

Ile Phe Phe Val Val Gly Asn Thr Phe Lys Gly Phe His Ile Arg Phe
            565                 570                 575

Arg Asp Ile Ala Arg Gly Gly Ile Arg Ile Val Cys Ser Arg Asn Gln
            580                 585                 590

Asp Ile Tyr Asp Leu Asn Ser Lys Asn Val Ile Asp Glu Asn Tyr Gln
        595                 600                 605

Leu Ala Ser Thr Gln Gln Arg Lys Asn Lys Asp Ile Pro Glu Gly Gly
    610                 615                 620

Ser Lys Gly Val Ile Leu Leu Asn Pro Gly Leu Val Glu His Asp Gln
625                 630                 635                 640

Thr Phe Val Ala Phe Ser Gln Tyr Val Asp Ala Met Ile Asp Ile Leu
            645                 650                 655

Ile Asn Asp Pro Leu Lys Glu Asn Tyr Val Asn Leu Leu Pro Lys Glu
            660                 665                 670

Glu Ile Leu Phe Phe Gly Pro Asp Glu Gly Thr Ala Gly Phe Val Asp
        675                 680                 685
```

```
Trp Ala Thr Asn His Ala Arg Val Arg Asn Cys Pro Trp Trp Lys Ser
    690                 695                 700

Phe Leu Thr Gly Lys Ser Pro Ser Leu Gly Gly Ile Pro His Asp Glu
705                 710                 715                 720

Tyr Gly Met Thr Ser Leu Gly Val Arg Ala Tyr Val Asn Lys Ile Tyr
                725                 730                 735

Glu Thr Leu Asn Leu Thr Asn Ser Thr Val Tyr Lys Phe Gln Thr Gly
            740                 745                 750

Gly Pro Asp Gly Asp Leu Gly Ser Asn Glu Ile Leu Leu Ser Ser Pro
        755                 760                 765

Asn Glu Cys Tyr Leu Ala Ile Leu Asp Gly Ser Gly Val Leu Cys Asp
    770                 775                 780

Pro Lys Gly Leu Asp Lys Asp Glu Leu Cys Arg Leu Ala His Glu Arg
785                 790                 795                 800

Lys Met Ile Ser Asp Phe Asp Thr Ser Lys Leu Ser Asn Asn Gly Phe
                805                 810                 815

Phe Val Ser Val Asp Ala Met Asp Ile Met Leu Pro Asn Gly Thr Ile
            820                 825                 830

Val Ala Asn Gly Thr Thr Phe Arg Asn Thr Phe His Thr Gln Ile Phe
        835                 840                 845

Lys Phe Val Asp His Val Asp Ile Phe Val Pro Cys Gly Gly Arg Pro
    850                 855                 860

Asn Ser Ile Thr Leu Asn Asn Leu His Tyr Phe Val Asp Glu Lys Thr
865                 870                 875                 880

Gly Lys Cys Lys Ile Pro Tyr Ile Val Glu Gly Ala Asn Leu Phe Ile
                885                 890                 895

Thr Gln Pro Ala Lys Asn Ala Leu Glu Glu His Gly Cys Ile Leu Phe
            900                 905                 910

Lys Asp Ala Ser Ala Asn Lys Gly Gly Val Thr Ser Ser Ser Met Glu
        915                 920                 925

Val Leu Ala Ser Leu Ala Leu Asn Asp Asn Asp Phe Val His Lys Phe
    930                 935                 940

Ile Gly Asp Val Ser Gly Glu Arg Ser Ala Leu Tyr Lys Ser Tyr Val
945                 950                 955                 960

Val Glu Val Gln Ser Arg Ile Gln Lys Asn Ala Glu Leu Glu Phe Gly
                965                 970                 975

Gln Leu Trp Asn Leu Asn Gln Leu Asn Gly Thr His Ile Ser Glu Ile
            980                 985                 990

Ser Asn Gln Leu Ser Phe Thr Ile  Asn Lys Leu Asn Asp  Asp Leu Val
        995                 1000                1005

Ala Ser  Gln Glu Leu Trp Leu  Asn Asp Leu Lys Leu  Arg Asn Tyr
    1010                1015                1020

Leu Leu  Leu Asp Lys Ile Ile  Pro Lys Ile Leu Ile  Asp Val Ala
    1025                1030                1035

Gly Pro  Gln Ser Val Leu Glu  Asn Ile Pro Glu Ser  Tyr Leu Lys
    1040                1045                1050

Val Leu  Leu Ser Ser Tyr Leu  Ser Ser Thr Phe Val  Tyr Gln Asn
    1055                1060                1065

Gly Ile  Asp Val Asn Ile Gly  Lys Phe Leu Glu Phe  Ile Gly Gly
    1070                1075                1080

Leu Lys  Arg Glu Ala Glu Ala  Ser Ala
    1085                1090
```

<210> SEQ ID NO 28
<211> LENGTH: 3153
<212> TYPE: DNA
<213> ORGANISM: Neurospora crassa

<400> SEQUENCE: 28
atggattctc cttcagcccc ggtcccagcc cacaagttgg ttgatcgcct caaagatcag 60
acgcccagac atccttctcc tcagccgaca catgtcagct atcccaaggt gaacggcaac 120
gggcacaggg tgctccgctc cgcaactgtt ggatatgttg cccctgtctt ccagggaaag 180
gcagagcaga tgaagcaagt caagaatatc attgtccagg gcggctggat tcccgagact 240
ctggttgacg gtcagattgc gtggttctat aatgagcttg gcatcgacga cgtctacttc 300
caactagaaa accctcaggc ggttgcaaat catatcacat ctctctatgc ggccaaagtt 360
gctgctttct ctcgcgagga caagcgggaa gagatcagac tggatatgga agcctcggac 420
cacgccattt acatcgacac aagcgaaccc ggcatgacct ccttcgacgg tccgcgatat 480
gagcacagac tcgagtccaa gtacttggat ggcgacgata cttcgaagcg tttccgtgtc 540
gagactttca gatcccccgg tgtcctgggg cagaaggaga actccaaggc agctcttcgt 600
tgctactttg tctatcagtg tctctttgtt gattctaacg ccgatcccaa ggaaactcgc 660
ctggaagtga tcagcgaccg catgttcctt gccaaggcta ccaagaacac caagcagatc 720
taccaggaca tcatccaggt tgccgtgagc cgacatggtc ccgtcattga ggttttcgac 780
atcgagggct cggaggaaat gagactggta gttgccttcc gctctcgaac agcaaagggt 840
atcttcagcg ccctcagcga cctttaccac tactacggcg tcacaagctc tcgtaagtac 900
gttgagcagt tctccaatgg tattaccgtc atgagtatct atctgcgccc tgctgcgaac 960
atcgacggca agcaccctcc tcttgagcaa tctattcacc agatcaccaa ggagatttcc 1020
ttgctgtact gccttcccca gaacaagttt cacaacatgt ttgcctctgg tgaactcagt 1080
ctgcaggaga ccatctatgc ccactgcgtc tgggtgtttg ttcagcattt cttgaaccgt 1140
cttgggacag agtacacttc gctcattgca gccctggacc ccaagaacaa ctcgcatgtt 1200
gagattctct ccaagatgaa gaagcgtctg cgtaccgaga cctttacacc tgactacatt 1260
cttgaaatca tcagctccca cccgcaactt gtgcgcgctc tctacgcctc attcgccagc 1320
gttcaccttc gggtcggcag cgattatgat cgccatctca ttgcgcctac gccggtcatg 1380
gaggtccttt ctgatgccag gcttaaggag aagatcacca aggacgtttc taacgagcac 1440
gaggaaatgg ttatgactgc cttccgtgta ttcaacaatg cagtcctcaa gacgaacttc 1500
ttcactccca ccaaagtcgc tttgagcttc cggcttaatc cctcgttcct tccggaagtc 1560
gagtatccca agccgctgta cggaatgttc ctcgtcatca cttccgagtc gcgaggtttc 1620
cacctccgct tcaaggatat tgcacggggt ggtattcgta ttgtcaagtc tcgaagtaag 1680
gaggcttacc agatcaatgc ccgcaatctc tttgatgaga actacggtct tgccagcacc 1740
cagcagcgca agaacaagga tattccggag ggcggatcga agggtgtcat tctccttgac 1800
cccaagcagc aagacaggca ccgcgaggcc tttgagaagt acatcgatag tatccttgac 1860
cttcttctga aggctgagac gcctggcatc aagaacccca ttgtcgacct ctacggcaag 1920
gaggagattt tgttcatggg accggatgag aacactgctg accttgtcga ctgggccact 1980
gagcatgccc gggctcgcgg cgctccttgg tggaaatcct tcttcactgg taaatcacca 2040
cgtcttggtg gcatccctca cgactcctat ggcatgacaa ccttgtcggt tcgtgagtat 2100
gtcaagggta tttaccgcaa gcttgagctt gatccctcca agatcagaaa gatgcagact 2160

```
ggtggtcccg atggtgatct gggaagcaac gagattctgc tcagcaacga gacttacact   2220

gctatcgttg acggatccgg tgtcctctgc gaccccaacg gcattgacaa ggatgagtta   2280

cgccgtcttg ccaaggctcg tgctatgatc tcaaactttg atatcgccaa gctttccaag   2340

gatggttatc gtgtgctttg tgacgatacc aacgtcacac tccccaacgg agaggttgtg   2400

cacaatggca ctgcattccg taacacgtac catcttcgcg acaacggcat cactgatatg   2460

ttcgtgcctt gcggtggccg tcccgagtcg atcgacctct cctcagtcaa caagcttatc   2520

aaggatggaa agtcaaccat cccatatatt gttgagggtg ccaacctgtt catcactcaa   2580

gatgccaagc tcagactgga ggaagccggc tgcatcgttt acaaggatgc cagtgccaac   2640

aaaggcggtg taaccagctc atcgctcgag gtccttgcct ccctcagctt tgacgacaag   2700

ggcttcgtta cccacatgtg ccacgattcc cgcggcaatg cgcccgagtt ctaccaggcc   2760

tatgtcaagg aagtgcaaaa caagatccag gacaatgccc gcctcgagtt cgaggccatc   2820

tggcgggaac atgagcagac tggccttcct cgatctgttc tctctgacaa gttgtcattg   2880

gccatcacct ctcttgacga ggatctccag cgttcggagc tctgggacaa cgagaagatt   2940

cgcaggtccg tccttgccga tgccttgccc aaccttctca ttaacaagat cggcctcgat   3000

accatcatcg agcgtgttcc cgattcgtat ctgagggcca tctttggcag ctacctcgcc   3060

agtcgcttcg tctatgagtt tggtagctcg cccagccagt ttgctttcta tgatttcatg   3120

tcaaagagaa tgggaaacat caataaggag taa                                 3153
```

<210> SEQ ID NO 29
<211> LENGTH: 454
<212> TYPE: PRT
<213> ORGANISM: Neurospora crassa

<400> SEQUENCE: 29

```
Met Ser Asn Leu Pro Ser Glu Pro Glu Phe Glu Gln Ala Tyr Lys Glu
1               5                   10                  15

Leu Ala Tyr Thr Leu Glu Asn Ser Ser Leu Phe Gln Lys His Pro Glu
            20                  25                  30

Tyr Arg Thr Ala Leu Thr Val Ala Ser Ile Pro Glu Arg Val Ile Gln
        35                  40                  45

Phe Arg Val Val Trp Glu Asp Asp Asn Gly Asn Val Gln Val Asn Arg
    50                  55                  60

Gly Tyr Arg Val Gln Phe Asn Ser Ala Leu Gly Pro Tyr Lys Gly Gly
65                  70                  75                  80

Leu Arg Leu His Pro Ser Val Asn Leu Ser Ile Leu Lys Phe Leu Gly
                85                  90                  95

Phe Glu Gln Ile Phe Lys Asn Ala Leu Thr Gly Leu Ser Met Gly Gly
            100                 105                 110

Gly Lys Gly Gly Ala Asp Phe Asp Pro Lys Gly Lys Ser Asp Ala Glu
        115                 120                 125

Ile Arg Arg Phe Cys Cys Ala Phe Met Ala Glu Leu His Lys His Ile
    130                 135                 140

Gly Ala Asp Thr Asp Val Pro Ala Gly Asp Ile Gly Val Gly Gly Arg
145                 150                 155                 160

Glu Ile Gly Tyr Met Phe Gly Ala Tyr Arg Lys Ala Ala Asn Arg Phe
                165                 170                 175

Glu Gly Val Leu Thr Gly Lys Gly Leu Ser Trp Gly Gly Ser Leu Ile
            180                 185                 190
```

```
Arg Pro Glu Ala Thr Gly Tyr Gly Leu Val Tyr Tyr Val Gly His Met
        195                 200                 205

Leu Glu Tyr Ser Gly Ala Gly Ser Tyr Ala Gly Lys Arg Val Ala Leu
    210                 215                 220

Ser Gly Ser Gly Asn Val Ala Gln Tyr Ala Ala Leu Lys Leu Ile Glu
225                 230                 235                 240

Leu Gly Ala Thr Val Val Ser Leu Ser Asp Ser Lys Gly Ala Leu Val
                245                 250                 255

Ala Thr Gly Glu Ser Gly Ile Thr Val Glu Asp Ile Asn Ala Val Met
            260                 265                 270

Ala Ile Lys Glu Ala Arg Gln Ser Leu Thr Ser Phe Gln His Ala Gly
        275                 280                 285

His Leu Lys Trp Ile Glu Gly Ala Arg Pro Trp Leu His Val Gly Lys
    290                 295                 300

Val Asp Ile Ala Leu Pro Cys Ala Thr Gln Asn Glu Val Ser Lys Glu
305                 310                 315                 320

Glu Ala Glu Gly Leu Leu Ala Ala Gly Cys Lys Phe Val Ala Glu Gly
                325                 330                 335

Ser Asn Met Gly Cys Thr Leu Glu Ala Ile Glu Val Phe Glu Asn Asn
            340                 345                 350

Arg Lys Glu Lys Lys Gly Glu Ala Val Trp Tyr Ala Pro Gly Lys Ala
        355                 360                 365

Ala Asn Cys Gly Gly Val Ala Val Ser Gly Leu Glu Met Ala Gln Asn
    370                 375                 380

Ser Gln Arg Leu Asn Trp Thr Gln Ala Glu Val Asp Glu Lys Leu Lys
385                 390                 395                 400

Asp Ile Met Lys Asn Ala Phe Phe Asn Gly Leu Asn Thr Ala Lys Thr
                405                 410                 415

Tyr Val Glu Ala Ala Glu Gly Glu Leu Pro Ser Leu Val Ala Gly Ser
            420                 425                 430

Asn Ile Ala Gly Phe Val Lys Val Ala Gln Ala Met His Asp Gln Gly
        435                 440                 445

Asp Trp Trp Ser Lys Asn
    450
```

<210> SEQ ID NO 30
<211> LENGTH: 1371
<212> TYPE: DNA
<213> ORGANISM: Saccharomyces cerevisiae

<400> SEQUENCE: 30

```
atgacaagcg aaccagagtt tcagcaggct tacgatgaga tcgtttcttc tgtggaggat     60

tccaaaattt ttgaaaaatt cccacagtat aaaaaagtgt tacctattgt ttctgtcccg    120

gagaggatca ttcaattcag ggtcacgtgg gaaaatgata atggcgagca agaagtggct    180

caaggataca gggtgcagtt caattcagcc aagggccctt acaagggtgg cctacgcttc    240

cacccatcag tgaacctgtc tatcctaaaa tttttgggtt ttgaacagat cttcaagaat    300

gcgctcactg ggctagatat gggcggtggt aagggtggcc tgtgtgtgga cttgaaaggc    360

aagtctgaca acgagatcag aaggatttgt tatgcgttca tgagagaact gagcaggcat    420

attggtaagg acacagacgt gcccgcagga gatattggtg tcggtggccg tgaaattggc    480

tacctattcg gcgcttacag atcatacaag aactcctggg aaggtgtgtt gactggtaag    540

ggtttaaact ggggtggctc acttatcagg ccggaggcca ccgggttcgg cttagtttac    600
```

```
tatacgcaag caatgatcga ttatgcaaca aacggcaagg agtcgtttga gggcaaacgt    660

gtgacaatct ccggaagtgg caatgttgcg caatatgcag ctttgaaagt gatcgagctg    720

ggtggtattg tggtgtcttt atccgattcg aaggggtgca tcatctctga gacgggcatt    780

acttctgagc aaattcacga tatcgcttcc gccaagatcc gtttcaagtc gttagaggaa    840

atcgttgatg aatactctac tttcagcgaa agtaagatga agtacgttgc aggagcacgc    900

ccatggacgc atgtgagcaa cgtcgacatt gccttgccct gtgccaccca aaacgaggtc    960

agtggtgacg aagccaaggc cctagtggca tctggcgtta agttcgttgc cgaaggtgct   1020

aacatgggtt ctacacccga ggctatttct gttttcgaaa cagcgcgtag cactgcaacc   1080

aatgcaaagg atgcagtttg gtttgggcca ccaaaggcag ctaacctggg cggcgtggca   1140

gtatccggtc tggaaatggc tcagaattct caaaaagtaa cttggactgc cgagcgggtc   1200

gatcaagaac taaagaagat aatgatcaac tgcttcaacg actgcataca ggccgcacaa   1260

gagtactcta cggaaaaaaa tacaaacacc ttgccatcat tggtcaaggg ggccaacatt   1320

gccagcttcg tcatggtggc tgacgcaatg cttgaccagg gagacgtttt t            1371
```

<210> SEQ ID NO 31
<211> LENGTH: 457
<212> TYPE: PRT
<213> ORGANISM: Saccharomyces cerevisiae

<400> SEQUENCE: 31

```
Met Thr Ser Glu Pro Glu Phe Gln Gln Ala Tyr Asp Glu Ile Val Ser
1               5                   10                  15

Ser Val Glu Asp Ser Lys Ile Phe Glu Lys Phe Pro Gln Tyr Lys Lys
            20                  25                  30

Val Leu Pro Ile Val Ser Val Pro Glu Arg Ile Ile Gln Phe Arg Val
        35                  40                  45

Thr Trp Glu Asn Asp Asn Gly Glu Gln Glu Val Ala Gln Gly Tyr Arg
    50                  55                  60

Val Gln Phe Asn Ser Ala Lys Gly Pro Tyr Lys Gly Gly Leu Arg Phe
65                  70                  75                  80

His Pro Ser Val Asn Leu Ser Ile Leu Lys Phe Leu Gly Phe Glu Gln
                85                  90                  95

Ile Phe Lys Asn Ala Leu Thr Gly Leu Asp Met Gly Gly Gly Lys Gly
            100                 105                 110

Gly Leu Cys Val Asp Leu Lys Gly Lys Ser Asp Asn Glu Ile Arg Arg
        115                 120                 125

Ile Cys Tyr Ala Phe Met Arg Glu Leu Ser Arg His Ile Gly Lys Asp
    130                 135                 140

Thr Asp Val Pro Ala Gly Asp Ile Gly Val Gly Gly Arg Glu Ile Gly
145                 150                 155                 160

Tyr Leu Phe Gly Ala Tyr Arg Ser Tyr Lys Asn Ser Trp Glu Gly Val
                165                 170                 175

Leu Thr Gly Lys Gly Leu Asn Trp Gly Gly Ser Leu Ile Arg Pro Glu
            180                 185                 190

Ala Thr Gly Phe Gly Leu Val Tyr Tyr Thr Gln Ala Met Ile Asp Tyr
        195                 200                 205

Ala Thr Asn Gly Lys Glu Ser Phe Glu Gly Lys Arg Val Thr Ile Ser
    210                 215                 220

Gly Ser Gly Asn Val Ala Gln Tyr Ala Ala Leu Lys Val Ile Glu Leu
225                 230                 235                 240
```

```
Gly Gly Ile Val Val Ser Leu Ser Asp Ser Lys Gly Cys Ile Ile Ser
                245                 250                 255

Glu Thr Gly Ile Thr Ser Glu Gln Ile His Asp Ile Ala Ser Ala Lys
            260                 265                 270

Ile Arg Phe Lys Ser Leu Glu Glu Ile Val Asp Glu Tyr Ser Thr Phe
        275                 280                 285

Ser Glu Ser Lys Met Lys Tyr Val Ala Gly Ala Arg Pro Trp Thr His
    290                 295                 300

Val Ser Asn Val Asp Ile Ala Leu Pro Cys Ala Thr Gln Asn Glu Val
305                 310                 315                 320

Ser Gly Asp Glu Ala Lys Ala Leu Val Ala Ser Gly Val Lys Phe Val
                325                 330                 335

Ala Glu Gly Ala Asn Met Gly Ser Thr Pro Glu Ala Ile Ser Val Phe
            340                 345                 350

Glu Thr Ala Arg Ser Thr Ala Thr Asn Ala Lys Asp Ala Val Trp Phe
        355                 360                 365

Gly Pro Pro Lys Ala Ala Asn Leu Gly Gly Val Ala Val Ser Gly Leu
    370                 375                 380

Glu Met Ala Gln Asn Ser Gln Lys Val Thr Trp Thr Ala Glu Arg Val
385                 390                 395                 400

Asp Gln Glu Leu Lys Lys Ile Met Ile Asn Cys Phe Asn Asp Cys Ile
                405                 410                 415

Gln Ala Ala Gln Glu Tyr Ser Thr Glu Lys Asn Thr Asn Thr Leu Pro
            420                 425                 430

Ser Leu Val Lys Gly Ala Asn Ile Ala Ser Phe Val Met Val Ala Asp
        435                 440                 445

Ala Met Leu Asp Gln Gly Asp Val Phe
    450                 455
```

<210> SEQ ID NO 32
<211> LENGTH: 6435
<212> TYPE: DNA
<213> ORGANISM: Saccharomyces cerevisiae

<400> SEQUENCE: 32

```
atgccagtgt tgaaatcaga caatttcgat ccattggaag aagcttacga aggtgggaca     60

attcaaaact ataacgatga acaccatctt cataaatctt gggcaaatgt gattccggac    120

aaacgaggac tttacgaccc tgattatgaa catgacgctt gtggtgtcgg tttcgtagca    180

aataagcatg gtgaacagtc tcacaagatt gttactgacg ctagatatct tttagtgaat    240

atgacacatc gtggtgccgt ctcatctgat gggaacggtg acggtgccgg tattctgcta    300

ggtattcctc acgaatttat gaaaagagaa ttcaagttag atcttgatct agacatacct    360

gagatgggca aatacgccgt aggtaacgtc ttcttcaaga agaacgaaaa aaataacaag    420

aaaaatttaa ttaagtgtca gaagattttc gaggatttag ctgcatcctt caacttatcc    480

gtattaggtt ggagaaacgt ccccgtagat tctactattt taggagacgt tgcattatct    540

cgtgaaccta ctattctaca gccattattg gttccattgt atgatgaaaa acaaccggag    600

tttaatgaaa ctaaatttag aactcaattg tatcttttaa ggaaggaggc ctctcttcaa    660

ataggactgg aaaactggtt ctatgtttgt tccctaaaca ataccaccat tgtttacaag    720

ggtcaattga cgccagctca agtgtataac tactatcccg acttgactaa tgcgcatttc    780

aaatcccaca tggcgttggt ccattcaaga ttttccacta atactttccc ctcttgggat    840

agagctcaac ctttacgttg gctagctcat aatggtgaaa ttaacacctt aagaggtaac    900
```

```
aagaattgga tgcgctccag agaaggtgtg atgaattcag caactttcaa agatgagtta    960
gacaaactat acccaattat cgaagaaggt ggttctgatt cagctgcatt ggataacgtt   1020
ttagaactat tgactattaa tggcacatta tctctacctg aagctgttat gatgatggtt   1080
cctgaagcgt atcataagga tatggattct gacctaaaag catggtacga ctgggctgca   1140
tgtctgatgg aaccttggga tggtccagct ttgttaactt tcactgatgg acgttactgt   1200
ggtgctatat tggatagaaa tggtttaaga ccttgtcgtt attacatcac tagtgatgac   1260
agagttatct gtgcttcaga ggtaggtgtc attcctatcg aaaattcatt ggttgttcaa   1320
aaaggtaaac tgaagccagg tgatttattc ctagtggata ctcaattggg tgaaatggtc   1380
gatactaaaa agttaaaatc tcaaatctca aaaagacaag attttaagtc ttggttatcc   1440
aaagtcatca agttagacga cttgttatca aaaaccgcta atttggttcc taaagaattt   1500
atatcacagg attcattgtc tttgaaagtt caaagtgacc cacgtctatt ggccaatggt   1560
tataccttcg aacaagtcac atttctgtta actccaatgg ctttaacagg taaagaagct   1620
ttaggttcga tgggtaacga tgcgccactg gcttgtttaa atgaaaatcc tgtcttactt   1680
tatgattatt tcagacaatt gtttgctcaa gtgaccaatc ctccaattga cccaattcgt   1740
gaagcaaatg ttatgtcgtt agaatgttat gtcggacctc aaggcaacct tttggaaatg   1800
cattcatctc aatgtgatcg tttattattg aaatctccta ttttgcattg gaatgagttc   1860
caagctttga aaaacattga agctgcttac ccatcatggt ctgtagcaga aattgatatc   1920
acattcgaca agagtgaggg tctattgggc tataccgaca caattgataa aatcactaag   1980
ttagcgagcg aagcaattga tgatggtaaa aagatcttaa taattactga caggaaaatg   2040
ggtgccaacc gtgtttccat ctcctctttg attgcaattt catgtattca tcatcaccta   2100
atcagaaaca agcagcgttc ccaagttgct ttgattttgg aaacaggtga agccagagaa   2160
attcaccatt tctgtgtcct actaggttat ggttgtgatg gtgtttatcc atacttagcc   2220
atggaaactt tggtcagaat gaatagagaa ggtctacttc gtaatgtcaa caatgacaat   2280
gatacacttg aggaagggca aatactagaa aattacaagc acgctattga tgcaggtatc   2340
ttgaaggtta tgtctaaaat gggtatctcc actctagcat cctacaaagg tgctcaaatt   2400
tttgaagccc taggtttaga taactctatt gttgatttgt gtttcacagg tacttcttcc   2460
agaattagag gtgtaacttt cgagtatttg gctcaagatg ccttttcttt acatgagcgt   2520
ggttatccat ccagacaaac cattagtaaa tctgttaact taccagaaag tggtgaatac   2580
cactttaggg atggtggtta caaacacgtc aacgaaccaa ccgcaattgc ttcgttacaa   2640
gatactgtca gaaacaaaaa tgatgtctct tggcaattat atgtaaagaa ggaaatggaa   2700
gcaattagag actgtacact aagaggactg ttagaattag attttgaaaa ttctgtcagt   2760
atccctctag aacaagttga accatggact gaaattgcca gaagatttgc gtcaggtgca   2820
atgtcttatg gttctatttc tatggaagct cactctacat tggctattgc catgaatcgt   2880
ttaggggcca aatccaattg tggtgaaggt ggtgaagacg cagaacgttc tgctgttcaa   2940
gaaaacggtg atactatgag atctgctatc aaacaagttg cttccgctag attcggtgta   3000
acttcatact acttgtcaga tgctgatgaa atccaaatta agattgctca gggtgctaag   3060
ccgggtgaag gtggtgaact accagcccac aaagtgtcta aggatatcgc aaaaaccagg   3120
cactccaccc ctaatgttgg gttaatctct cctcctcctc atcacgatat ttattccatt   3180
gaagatttga aacaactgat ttatgatttg aaatgtgcta atccaagagc gggaatttct   3240
```

```
gtaaagttgg tttccgaagt tggtgttggt attgttgcct ctggtgtagc taaggctaaa   3300
gccgatcata tcttagtttc tggtcatgat ggtggtacag gtgctgcaag atggacgagt   3360
gtcaaatatg cgggtttgcc atgggaatta ggtctagctg aaactcacca gactttagtc   3420
ttgaatgatt taagacgtaa tgttgttgtc caaaccgatg gtcaattgag aactgggttt   3480
gatattgctg ttgcagtttt attaggggca gaatctttta ccttggcaac agttccatta   3540
attgctatgg gttgtgttat gttaagaaga tgtcacttga actcttgtgc tgttggtatt   3600
gccacacaag atccatattt gagaagtaag tttaagggtc agcccgaaca tgttatcaac   3660
ttcttctatt acttgatcca agatttaaga caaatcatgg ccaagttagg attccgtacc   3720
attgacgaaa tggtgggtca ttctgaaaaa ttaaagaaaa gggacgacgt aaatgccaaa   3780
gccataaata tcgatttatc tcctattttg accccagcac atgttattcg tccaggtgtt   3840
ccaaccaagt tcactaagaa acaagaccac aaactccaca cccgtctaga taataagtta   3900
atcgatgagg ctgaagttac tttggatcgt ggcttaccag tgaatattga cgcctctata   3960
atcaatactg atcgtgcact cggttctact ttatcttaca gagtctcgaa gaaatttggt   4020
gaagatggtt tgccaaagga caccgttgtc gttaacatag aaggttcagc gggtcaatct   4080
tttggtgctt tcctagcttc tggtatcact tttatcttga atggtgatgc taatgattat   4140
gttggtaaag gtttatccgg tggtattatt gtcattaaac caccaaagga ttctaaattc   4200
aagagtgatg aaaatgtaat tgttggtaac acttgtttct atggtgctac ttctggtact   4260
gcattcattt caggtagtgc cggtgagcgt ttcggtgtca gaaactctgg tgccaccatc   4320
gttgttgaga gaattaaggg taacaatgcc tttgagtata tgactggtgg tcgtgccatt   4380
gtcttatcac aaatggaatc cctaaacgcc ttctctggtg ctactggtgg tattgcatac   4440
tgtttaactt ccgattacga cgattttgtt ggaaagatta acaaagatac tgttgagtta   4500
gaatcattat gtgacccggt cgagattgcg tttgttaaga atttgatcca ggagcattgg   4560
aactacacac aatctgatct agcagccagg attctcggta atttcaacca ttatttgaaa   4620
gatttcgtta aagtcattcc aactgattat aagaaagttt tgttgaagga gaaagcagaa   4680
gctgccaagg caaaggctaa ggcaacttca gaatacttaa agaagtttag atcgaaccaa   4740
gaagttgatg acgaagtcaa tactctattg attgctaatc aaaaagctaa agagcaagaa   4800
aaaaagaaga gtattactat ttcaaataag gccactttga aggagcctaa ggttgttgat   4860
ttagaagatg cagttccaga ttccaaacag ctagagaaga atagcgaaag gattgaaaaa   4920
acacgtggtt ttatgatcca caaacgtcgt catgagacac acagagatcc aagaaccaga   4980
gttaatgact ggaaagaatt tactaaccct attaccaaga aggatgccaa atatcaaact   5040
gcgagatgta tggattgtgg tacaccattc tgtttatctg ataccggttg tcccctatct   5100
aacattatcc ccaagtttaa tgaattgtta ttcaagaacc aatggaagtt ggcactggac   5160
aaattgctag agacaaacaa tttcccagaa ttcactggaa gagtatgtcc agcaccctgt   5220
gagggagctt gtacactagg tattattgaa gacccagtcg gcataaaatc ggttgaaaga   5280
attatcattg acaatgcttt caaggaagga tggattaagc cttgtccacc aagtacacgc   5340
actggcttta cagtgggtgt cattggttct ggtccagcag gtttagcgtg tgctgatatg   5400
ttgaaccgtg ccggacatac ggtcactgtt tatgaaagat ccgaccgttg tggtgggtta   5460
ttgatgtatg gtattccaaa catgaagttg gataaggcta tagtgcaacg tcgtattgat   5520
ctattgagtg ccgaaggtat tgactttgtt accaacaccg aaattggtaa aaccataagc   5580
atggatgagc taaagaacaa gcacaatgca gtagtgtatg ctatcggttc taccattcca   5640
```

```
cgtgacttac ctattaaggg tcgtgaattg aagaatattg attttgccat gcagttgttg   5700

gaatctaaca caaaagcttt attgaacaaa gatctggaaa tcattcgtga aaagatccaa   5760

ggtaagaaag taattgttgt cggtggtggt gacacaggta acgattgttt aggtacatct   5820

gtaagacacg gtgcagcatc agttttgaat ttcgaattgt tgcctgagcc accagtggaa   5880

cgtgccaaag acaatccatg gcctcaatgg ccgcgtgtca tgagagtgga ctacggtcat   5940

gctgaagtga aagagcatta tggtagagac cctcgtgaat actgcatctt gtccaaggaa   6000

tttatcggta acgatgaggg tgaagtcact gccatcagaa ctgtgcgcgt agaatggaag   6060

aagtcacaaa gtggcgtatg gcaaatggta gaaattccca acagtgaaga gatctttgaa   6120

gccgatatca ttttgttgtc tatgggtttc gtgggtcctg aattgatcaa tggcaacgat   6180

aacgaagtta agaagacaag acgtggtacg attgccacac tcgacgactc ctcatactct   6240

attgatggag gaaagacttt tgcatgtggt gactgtagaa gagggcaatc tttgattgtc   6300

tgggccatcc aagaaggtag aaaatgtgct gcctctgtcg ataagttcct aatggacggc   6360

actacgtatc taccaagtaa tggtggtatc gttcaacgtg attacaaact attgaaagaa   6420

ttagctagtc aagtc                                                      6435
```

<210> SEQ ID NO 33
<211> LENGTH: 2145
<212> TYPE: PRT
<213> ORGANISM: Saccharomyces cerevisiae

<400> SEQUENCE: 33

```
Met Pro Val Leu Lys Ser Asp Asn Phe Asp Pro Leu Glu Glu Ala Tyr
1               5                   10                  15

Glu Gly Gly Thr Ile Gln Asn Tyr Asn Asp Glu His His Leu His Lys
            20                  25                  30

Ser Trp Ala Asn Val Ile Pro Asp Lys Arg Gly Leu Tyr Asp Pro Asp
        35                  40                  45

Tyr Glu His Asp Ala Cys Gly Val Gly Phe Val Ala Asn Lys His Gly
    50                  55                  60

Glu Gln Ser His Lys Ile Val Thr Asp Ala Arg Tyr Leu Leu Val Asn
65                  70                  75                  80

Met Thr His Arg Gly Ala Val Ser Ser Asp Gly Asn Gly Asp Gly Ala
                85                  90                  95

Gly Ile Leu Leu Gly Ile Pro His Glu Phe Met Lys Arg Glu Phe Lys
            100                 105                 110

Leu Asp Leu Asp Leu Asp Ile Pro Glu Met Gly Lys Tyr Ala Val Gly
        115                 120                 125

Asn Val Phe Phe Lys Lys Asn Glu Lys Asn Asn Lys Lys Asn Leu Ile
    130                 135                 140

Lys Cys Gln Lys Ile Phe Glu Asp Leu Ala Ala Ser Phe Asn Leu Ser
145                 150                 155                 160

Val Leu Gly Trp Arg Asn Val Pro Val Asp Ser Thr Ile Leu Gly Asp
                165                 170                 175

Val Ala Leu Ser Arg Glu Pro Thr Ile Leu Gln Pro Leu Leu Val Pro
            180                 185                 190

Leu Tyr Asp Glu Lys Gln Pro Glu Phe Asn Glu Thr Lys Phe Arg Thr
        195                 200                 205

Gln Leu Tyr Leu Leu Arg Lys Glu Ala Ser Leu Gln Ile Gly Leu Glu
    210                 215                 220
```

```
Asn Trp Phe Tyr Val Cys Ser Leu Asn Asn Thr Thr Ile Val Tyr Lys
225                 230                 235                 240

Gly Gln Leu Thr Pro Ala Gln Val Tyr Asn Tyr Tyr Pro Asp Leu Thr
                245                 250                 255

Asn Ala His Phe Lys Ser His Met Ala Leu Val His Ser Arg Phe Ser
            260                 265                 270

Thr Asn Thr Phe Pro Ser Trp Asp Arg Ala Gln Pro Leu Arg Trp Leu
        275                 280                 285

Ala His Asn Gly Glu Ile Asn Thr Leu Arg Gly Asn Lys Asn Trp Met
    290                 295                 300

Arg Ser Arg Glu Gly Val Met Asn Ser Ala Thr Phe Lys Asp Glu Leu
305                 310                 315                 320

Asp Lys Leu Tyr Pro Ile Ile Glu Glu Gly Gly Ser Asp Ser Ala Ala
                325                 330                 335

Leu Asp Asn Val Leu Glu Leu Leu Thr Ile Asn Gly Thr Leu Ser Leu
            340                 345                 350

Pro Glu Ala Val Met Met Met Val Pro Glu Ala Tyr His Lys Asp Met
        355                 360                 365

Asp Ser Asp Leu Lys Ala Trp Tyr Asp Trp Ala Ala Cys Leu Met Glu
    370                 375                 380

Pro Trp Asp Gly Pro Ala Leu Leu Thr Phe Thr Asp Gly Arg Tyr Cys
385                 390                 395                 400

Gly Ala Ile Leu Asp Arg Asn Gly Leu Arg Pro Cys Arg Tyr Tyr Ile
                405                 410                 415

Thr Ser Asp Asp Arg Val Ile Cys Ala Ser Glu Val Gly Val Ile Pro
            420                 425                 430

Ile Glu Asn Ser Leu Val Val Gln Lys Gly Lys Leu Lys Pro Gly Asp
        435                 440                 445

Leu Phe Leu Val Asp Thr Gln Leu Gly Glu Met Val Asp Thr Lys Lys
    450                 455                 460

Leu Lys Ser Gln Ile Ser Lys Arg Gln Asp Phe Lys Ser Trp Leu Ser
465                 470                 475                 480

Lys Val Ile Lys Leu Asp Asp Leu Leu Ser Lys Thr Ala Asn Leu Val
                485                 490                 495

Pro Lys Glu Phe Ile Ser Gln Asp Ser Leu Ser Leu Lys Val Gln Ser
            500                 505                 510

Asp Pro Arg Leu Leu Ala Asn Gly Tyr Thr Phe Glu Gln Val Thr Phe
        515                 520                 525

Leu Leu Thr Pro Met Ala Leu Thr Gly Lys Glu Ala Leu Gly Ser Met
    530                 535                 540

Gly Asn Asp Ala Pro Leu Ala Cys Leu Asn Glu Asn Pro Val Leu Leu
545                 550                 555                 560

Tyr Asp Tyr Phe Arg Gln Leu Phe Ala Gln Val Thr Asn Pro Pro Ile
                565                 570                 575

Asp Pro Ile Arg Glu Ala Asn Val Met Ser Leu Glu Cys Tyr Val Gly
            580                 585                 590

Pro Gln Gly Asn Leu Leu Glu Met His Ser Ser Gln Cys Asp Arg Leu
        595                 600                 605

Leu Leu Lys Ser Pro Ile Leu His Trp Asn Glu Phe Gln Ala Leu Lys
    610                 615                 620

Asn Ile Glu Ala Ala Tyr Pro Ser Trp Ser Val Ala Glu Ile Asp Ile
625                 630                 635                 640

Thr Phe Asp Lys Ser Glu Gly Leu Leu Gly Tyr Thr Asp Thr Ile Asp
```

```
                645                 650                 655

Lys Ile Thr Lys Leu Ala Ser Glu Ala Ile Asp Asp Gly Lys Lys Ile
            660                 665                 670

Leu Ile Ile Thr Asp Arg Lys Met Gly Ala Asn Arg Val Ser Ile Ser
        675                 680                 685

Ser Leu Ile Ala Ile Ser Cys Ile His His His Leu Ile Arg Asn Lys
    690                 695                 700

Gln Arg Ser Gln Val Ala Leu Ile Leu Glu Thr Gly Glu Ala Arg Glu
705                 710                 715                 720

Ile His His Phe Cys Val Leu Leu Gly Tyr Gly Cys Asp Gly Val Tyr
                725                 730                 735

Pro Tyr Leu Ala Met Glu Thr Leu Val Arg Met Asn Arg Glu Gly Leu
            740                 745                 750

Leu Arg Asn Val Asn Asn Asp Asn Asp Thr Leu Glu Glu Gly Gln Ile
        755                 760                 765

Leu Glu Asn Tyr Lys His Ala Ile Asp Ala Gly Ile Leu Lys Val Met
    770                 775                 780

Ser Lys Met Gly Ile Ser Thr Leu Ala Ser Tyr Lys Gly Ala Gln Ile
785                 790                 795                 800

Phe Glu Ala Leu Gly Leu Asp Asn Ser Ile Val Asp Leu Cys Phe Thr
                805                 810                 815

Gly Thr Ser Ser Arg Ile Arg Gly Val Thr Phe Glu Tyr Leu Ala Gln
            820                 825                 830

Asp Ala Phe Ser Leu His Glu Arg Gly Tyr Pro Ser Arg Gln Thr Ile
        835                 840                 845

Ser Lys Ser Val Asn Leu Pro Glu Ser Gly Glu Tyr His Phe Arg Asp
    850                 855                 860

Gly Gly Tyr Lys His Val Asn Glu Pro Thr Ala Ile Ala Ser Leu Gln
865                 870                 875                 880

Asp Thr Val Arg Asn Lys Asn Asp Val Ser Trp Gln Leu Tyr Val Lys
                885                 890                 895

Lys Glu Met Glu Ala Ile Arg Asp Cys Thr Leu Arg Gly Leu Leu Glu
            900                 905                 910

Leu Asp Phe Glu Asn Ser Val Ser Ile Pro Leu Glu Gln Val Glu Pro
        915                 920                 925

Trp Thr Glu Ile Ala Arg Arg Phe Ala Ser Gly Ala Met Ser Tyr Gly
    930                 935                 940

Ser Ile Ser Met Glu Ala His Ser Thr Leu Ala Ile Ala Met Asn Arg
945                 950                 955                 960

Leu Gly Ala Lys Ser Asn Cys Gly Glu Gly Gly Glu Asp Ala Glu Arg
                965                 970                 975

Ser Ala Val Gln Glu Asn Gly Asp Thr Met Arg Ser Ala Ile Lys Gln
            980                 985                 990

Val Ala Ser Ala Arg Phe Gly Val  Thr Ser Tyr Tyr Leu  Ser Asp Ala
        995                 1000                1005

Asp Glu  Ile Gln Ile Lys Ile  Ala Gln Gly Ala Lys  Pro Gly Glu
    1010                1015                1020

Gly Gly  Glu Leu Pro Ala His  Lys Val Ser Lys Asp  Ile Ala Lys
    1025                1030                1035

Thr Arg  His Ser Thr Pro Asn  Val Gly Leu Ile Ser  Pro Pro Pro
    1040                1045                1050

His His  Asp Ile Tyr Ser Ile  Glu Asp Leu Lys Gln  Leu Ile Tyr
    1055                1060                1065
```

```
Asp Leu  Lys Cys Ala Asn Pro  Arg Ala Gly Ile Ser  Val Lys Leu
    1070                 1075                 1080

Val Ser  Glu Val Gly Val Gly  Ile Val Ala Ser Gly  Val Ala Lys
    1085                 1090                 1095

Ala Lys  Ala Asp His Ile Leu  Val Ser Gly His Asp  Gly Gly Thr
    1100                 1105                 1110

Gly Ala  Ala Arg Trp Thr Ser  Val Lys Tyr Ala Gly  Leu Pro Trp
    1115                 1120                 1125

Glu Leu  Gly Leu Ala Glu Thr  His Gln Thr Leu Val  Leu Asn Asp
    1130                 1135                 1140

Leu Arg  Arg Asn Val Val Val  Gln Thr Asp Gly Gln  Leu Arg Thr
    1145                 1150                 1155

Gly Phe  Asp Ile Ala Val Ala  Val Leu Leu Gly Ala  Glu Ser Phe
    1160                 1165                 1170

Thr Leu  Ala Thr Val Pro Leu  Ile Ala Met Gly Cys  Val Met Leu
    1175                 1180                 1185

Arg Arg  Cys His Leu Asn Ser  Cys Ala Val Gly Ile  Ala Thr Gln
    1190                 1195                 1200

Asp Pro  Tyr Leu Arg Ser Lys  Phe Lys Gly Gln Pro  Glu His Val
    1205                 1210                 1215

Ile Asn  Phe Phe Tyr Tyr Leu  Ile Gln Asp Leu Arg  Gln Ile Met
    1220                 1225                 1230

Ala Lys  Leu Gly Phe Arg Thr  Ile Asp Glu Met Val  Gly His Ser
    1235                 1240                 1245

Glu Lys  Leu Lys Lys Arg Asp  Asp Val Asn Ala Lys  Ala Ile Asn
    1250                 1255                 1260

Ile Asp  Leu Ser Pro Ile Leu  Thr Pro Ala His Val  Ile Arg Pro
    1265                 1270                 1275

Gly Val  Pro Thr Lys Phe Thr  Lys Lys Gln Asp His  Lys Leu His
    1280                 1285                 1290

Thr Arg  Leu Asp Asn Lys Leu  Ile Asp Glu Ala Glu  Val Thr Leu
    1295                 1300                 1305

Asp Arg  Gly Leu Pro Val Asn  Ile Asp Ala Ser Ile  Ile Asn Thr
    1310                 1315                 1320

Asp Arg  Ala Leu Gly Ser Thr  Leu Ser Tyr Arg Val  Ser Lys Lys
    1325                 1330                 1335

Phe Gly  Glu Asp Gly Leu Pro  Lys Asp Thr Val Val  Val Asn Ile
    1340                 1345                 1350

Glu Gly  Ser Ala Gly Gln Ser  Phe Gly Ala Phe Leu  Ala Ser Gly
    1355                 1360                 1365

Ile Thr  Phe Ile Leu Asn Gly  Asp Ala Asn Asp Tyr  Val Gly Lys
    1370                 1375                 1380

Gly Leu  Ser Gly Gly Ile Ile  Val Ile Lys Pro Pro  Lys Asp Ser
    1385                 1390                 1395

Lys Phe  Lys Ser Asp Glu Asn  Val Ile Val Gly Asn  Thr Cys Phe
    1400                 1405                 1410

Tyr Gly  Ala Thr Ser Gly Thr  Ala Phe Ile Ser Gly  Ser Ala Gly
    1415                 1420                 1425

Glu Arg  Phe Gly Val Arg Asn  Ser Gly Ala Thr Ile  Val Val Glu
    1430                 1435                 1440

Arg Ile  Lys Gly Asn Asn Ala  Phe Glu Tyr Met Thr  Gly Gly Arg
    1445                 1450                 1455
```

```
Ala Ile  Val Leu Ser Gln Met  Glu Ser Leu Asn Ala  Phe Ser Gly
    1460                 1465                 1470

Ala Thr  Gly Gly Ile Ala Tyr  Cys Leu Thr Ser Asp  Tyr Asp Asp
    1475                 1480                 1485

Phe Val  Gly Lys Ile Asn Lys  Asp Thr Val Glu Leu  Glu Ser Leu
    1490                 1495                 1500

Cys Asp  Pro Val Glu Ile Ala  Phe Val Lys Asn Leu  Ile Gln Glu
    1505                 1510                 1515

His Trp  Asn Tyr Thr Gln Ser  Asp Leu Ala Ala Arg  Ile Leu Gly
    1520                 1525                 1530

Asn Phe  Asn His Tyr Leu Lys  Asp Phe Val Lys Val  Ile Pro Thr
    1535                 1540                 1545

Asp Tyr  Lys Lys Val Leu Leu  Lys Glu Lys Ala Glu  Ala Ala Lys
    1550                 1555                 1560

Ala Lys  Ala Lys Ala Thr Ser  Glu Tyr Leu Lys Lys  Phe Arg Ser
    1565                 1570                 1575

Asn Gln  Glu Val Asp Asp Glu  Val Asn Thr Leu Leu  Ile Ala Asn
    1580                 1585                 1590

Gln Lys  Ala Lys Glu Gln Glu  Lys Lys Lys Ser Ile  Thr Ile Ser
    1595                 1600                 1605

Asn Lys  Ala Thr Leu Lys Glu  Pro Lys Val Val Asp  Leu Glu Asp
    1610                 1615                 1620

Ala Val  Pro Asp Ser Lys Gln  Leu Glu Lys Asn Ser  Glu Arg Ile
    1625                 1630                 1635

Glu Lys  Thr Arg Gly Phe Met  Ile His Lys Arg Arg  His Glu Thr
    1640                 1645                 1650

His Arg  Asp Pro Arg Thr Arg  Val Asn Asp Trp Lys  Glu Phe Thr
    1655                 1660                 1665

Asn Pro  Ile Thr Lys Lys Asp  Ala Lys Tyr Gln Thr  Ala Arg Cys
    1670                 1675                 1680

Met Asp  Cys Gly Thr Pro Phe  Cys Leu Ser Asp Thr  Gly Cys Pro
    1685                 1690                 1695

Leu Ser  Asn Ile Ile Pro Lys  Phe Asn Glu Leu Leu  Phe Lys Asn
    1700                 1705                 1710

Gln Trp  Lys Leu Ala Leu Asp  Lys Leu Leu Glu Thr  Asn Asn Phe
    1715                 1720                 1725

Pro Glu  Phe Thr Gly Arg Val  Cys Pro Ala Pro Cys  Glu Gly Ala
    1730                 1735                 1740

Cys Thr  Leu Gly Ile Ile Glu  Asp Pro Val Gly Ile  Lys Ser Val
    1745                 1750                 1755

Glu Arg  Ile Ile Ile Asp Asn  Ala Phe Lys Glu Gly  Trp Ile Lys
    1760                 1765                 1770

Pro Cys  Pro Pro Ser Thr Arg  Thr Gly Phe Thr Val  Gly Val Ile
    1775                 1780                 1785

Gly Ser  Gly Pro Ala Gly Leu  Ala Cys Ala Asp Met  Leu Asn Arg
    1790                 1795                 1800

Ala Gly  His Thr Val Thr Val  Tyr Glu Arg Ser Asp  Arg Cys Gly
    1805                 1810                 1815

Gly Leu  Leu Met Tyr Gly Ile  Pro Asn Met Lys Leu  Asp Lys Ala
    1820                 1825                 1830

Ile Val  Gln Arg Arg Ile Asp  Leu Leu Ser Ala Glu  Gly Ile Asp
    1835                 1840                 1845

Phe Val  Thr Asn Thr Glu Ile  Gly Lys Thr Ile Ser  Met Asp Glu
```

```
    1850                1855                1860

Leu Lys  Asn Lys His Asn Ala  Val Val Tyr Ala Ile  Gly Ser Thr
    1865                1870                1875

Ile Pro  Arg Asp Leu Pro Ile  Lys Gly Arg Glu Leu  Lys Asn Ile
    1880                1885                1890

Asp Phe  Ala Met Gln Leu Leu  Glu Ser Asn Thr Lys  Ala Leu Leu
    1895                1900                1905

Asn Lys  Asp Leu Glu Ile Ile  Arg Glu Lys Ile Gln  Gly Lys Lys
    1910                1915                1920

Val Ile  Val Val Gly Gly Gly  Asp Thr Gly Asn Asp  Cys Leu Gly
    1925                1930                1935

Thr Ser  Val Arg His Gly Ala  Ala Ser Val Leu Asn  Phe Glu Leu
    1940                1945                1950

Leu Pro  Glu Pro Pro Val Glu  Arg Ala Lys Asp Asn  Pro Trp Pro
    1955                1960                1965

Gln Trp  Pro Arg Val Met Arg  Val Asp Tyr Gly His  Ala Glu Val
    1970                1975                1980

Lys Glu  His Tyr Gly Arg Asp  Pro Arg Glu Tyr Cys  Ile Leu Ser
    1985                1990                1995

Lys Glu  Phe Ile Gly Asn Asp  Glu Gly Glu Val Thr  Ala Ile Arg
    2000                2005                2010

Thr Val  Arg Val Glu Trp Lys  Lys Ser Gln Ser Gly  Val Trp Gln
    2015                2020                2025

Met Val  Glu Ile Pro Asn Ser  Glu Glu Ile Phe Glu  Ala Asp Ile
    2030                2035                2040

Ile Leu  Leu Ser Met Gly Phe  Val Gly Pro Glu Leu  Ile Asn Gly
    2045                2050                2055

Asn Asp  Asn Glu Val Lys Lys  Thr Arg Arg Gly Thr  Ile Ala Thr
    2060                2065                2070

Leu Asp  Asp Ser Ser Tyr Ser  Ile Asp Gly Gly Lys  Thr Phe Ala
    2075                2080                2085

Cys Gly  Asp Cys Arg Arg Gly  Gln Ser Leu Ile Val  Trp Ala Ile
    2090                2095                2100

Gln Glu  Gly Arg Lys Cys Ala  Ala Ser Val Asp Lys  Phe Leu Met
    2105                2110                2115

Asp Gly  Thr Thr Tyr Leu Pro  Ser Asn Gly Gly Ile  Val Gln Arg
    2120                2125                2130

Asp Tyr  Lys Leu Leu Lys Glu  Leu Ala Ser Gln Val
    2135                2140                2145
```

<210> SEQ ID NO 34
<211> LENGTH: 1110
<212> TYPE: DNA
<213> ORGANISM: Saccharomyces cerevisiae

<400> SEQUENCE: 34

```
atggctgaag caagcatcga aaagactcaa attttacaaa aatatctaga actggaccaa      60

agaggtagaa taattgccga atacgtttgg atcgatggta ctggtaactt acgttccaaa     120

ggtagaactt tgaagaagag aatcacatcc attgaccaat tgccagaatg gaacttcgac     180

ggttcttcta ccaaccaagc gccaggccac gactctgaca tctatttgaa acccgttgct     240

tactacccag atcccttcag gagaggtgac aacattgttg tcttggccgc atgttacaac     300

aatgacggta ctccaaacaa gttcaaccac agacacgaag ctgccaagct atttgctgct     360
```

```
cataaggatg aagaaatctg gtttggtcta gaacaagaat acactctatt tgacatgtat    420

gacgatgttt acggatggcc aaagggtggg tacccagctc cacaaggtcc ttactactgt    480

ggtgttggtg ccggtaaggt ttatgccaga gacatgatcg aagctcacta cagagcttgt    540

ttgtatgccg gattagaaat ttctggtatt aacgctgaag tcatgccatc tcaatgggaa    600

ttccaagtcg gtccatgtac cggtattgac atgggtgacc aattatggat ggccagatac    660

tttttgcaca gagtggcaga agagtttggt atcaagatct cattccatcc aaagccattg    720

aagggtgact ggaacggtgc cggttgtcac actaacgttt ccaccaagga aatgagacaa    780

ccaggtggta tgaaatacat cgaacaagcc atcgagaagt tatccaagag acacgctgaa    840

cacattaagt tgtacggtag cgataacgac atgagattaa ctggtagaca tgaaaccgct    900

tccatgactg cctttcttc tggtgtcgcc aacagaggta gctcaattag aatcccaaga     960

tccgtcgcca aggaaggtta cggttacttt gaagaccgta gaccagcttc caacatcgac   1020

ccatacttgg ttacaggtat catgtgtgaa actgtttgcg gtgctattga caatgctgac   1080

atgacgaagg aatttgaaag agaatcttca                                    1110
```

```
<210> SEQ ID NO 35
<211> LENGTH: 370
<212> TYPE: PRT
<213> ORGANISM: Saccharomyces cerevisiae

<400> SEQUENCE: 35

Met Ala Glu Ala Ser Ile Glu Lys Thr Gln Ile Leu Gln Lys Tyr Leu
1               5                   10                  15

Glu Leu Asp Gln Arg Gly Arg Ile Ile Ala Glu Tyr Val Trp Ile Asp
            20                  25                  30

Gly Thr Gly Asn Leu Arg Ser Lys Gly Arg Thr Leu Lys Lys Arg Ile
        35                  40                  45

Thr Ser Ile Asp Gln Leu Pro Glu Trp Asn Phe Asp Gly Ser Ser Thr
    50                  55                  60

Asn Gln Ala Pro Gly His Asp Ser Asp Ile Tyr Leu Lys Pro Val Ala
65                  70                  75                  80

Tyr Tyr Pro Asp Pro Phe Arg Arg Gly Asp Asn Ile Val Val Leu Ala
                85                  90                  95

Ala Cys Tyr Asn Asn Asp Gly Thr Pro Asn Lys Phe Asn His Arg His
            100                 105                 110

Glu Ala Ala Lys Leu Phe Ala Ala His Lys Asp Glu Glu Ile Trp Phe
        115                 120                 125

Gly Leu Glu Gln Glu Tyr Thr Leu Phe Asp Met Tyr Asp Asp Val Tyr
    130                 135                 140

Gly Trp Pro Lys Gly Gly Tyr Pro Ala Pro Gln Gly Pro Tyr Tyr Cys
145                 150                 155                 160

Gly Val Gly Ala Gly Lys Val Tyr Ala Arg Asp Met Ile Glu Ala His
                165                 170                 175

Tyr Arg Ala Cys Leu Tyr Ala Gly Leu Glu Ile Ser Gly Ile Asn Ala
            180                 185                 190

Glu Val Met Pro Ser Gln Trp Glu Phe Gln Val Gly Pro Cys Thr Gly
        195                 200                 205

Ile Asp Met Gly Asp Gln Leu Trp Met Ala Arg Tyr Phe Leu His Arg
    210                 215                 220

Val Ala Glu Glu Phe Gly Ile Lys Ile Ser Phe His Pro Lys Pro Leu
225                 230                 235                 240
```

```
Lys Gly Asp Trp Asn Gly Ala Gly Cys His Thr Asn Val Ser Thr Lys
            245                 250                 255

Glu Met Arg Gln Pro Gly Gly Met Lys Tyr Ile Glu Gln Ala Ile Glu
            260                 265                 270

Lys Leu Ser Lys Arg His Ala Glu His Ile Lys Leu Tyr Gly Ser Asp
        275                 280                 285

Asn Asp Met Arg Leu Thr Gly Arg His Glu Thr Ala Ser Met Thr Ala
    290                 295                 300

Phe Ser Ser Gly Val Ala Asn Arg Gly Ser Ser Ile Arg Ile Pro Arg
305                 310                 315                 320

Ser Val Ala Lys Glu Gly Tyr Gly Tyr Phe Glu Asp Arg Arg Pro Ala
            325                 330                 335

Ser Asn Ile Asp Pro Tyr Leu Val Thr Gly Ile Met Cys Glu Thr Val
            340                 345                 350

Cys Gly Ala Ile Asp Asn Ala Asp Met Thr Lys Glu Phe Glu Arg Glu
        355                 360                 365

Ser Ser
    370
```

<210> SEQ ID NO 36
<211> LENGTH: 5505
<212> TYPE: DNA
<213> ORGANISM: Saccharomyces cerevisiae

<400> SEQUENCE: 36

```
atgacagtta gttccgatac aactgctgaa atatcgttag gttggtcaat ccaagactgg     60

attgatttcc acaagtcatc aagctcccag gcttcactaa ggcttcttga atcactacta    120

gactctcaaa atgttgcgcc agtcgataat gcgtggatat cgctaatttc aaaggaaaat    180

ttactgcacc aattccaaat tttaaagagc agagaaaata aagaaactct acctctctac    240

ggtgtcccta ttgctgttaa ggacaacatc gacgttagag gtctacccac caccgctgca    300

tgtccatcct ttgcatatga gccttccaaa gactctaaag tagtagaact actaagaaat    360

gcaggtgcga taatcgtggg taagacaaac ttggaccaat ttgccacagg attagtcggc    420

acacggtctc catatgggaa aacaccttgc gcttttagca aagagcatgt atctggtggt    480

tcctccgctg ggtcagcatc ggtggtcgcc agaggtatcg taccaattgc attgggtact    540

gatacagcag gttctggtag agtcccagcc gccttgaaca acctgattgg cctaaagcca    600

acaaagggcg tcttttcctg tcaaggtgta gttcccgctt gtaaatcttt agactgcgtc    660

tccatctttg cattaaacct aagtgatgct gaacgctgct tccgcatcat gtgccagcca    720

gatcctgata atgatgaata ttctagaccc tatgtttcca accctttgaa aaaattttca    780

agcaatgtaa cgattgctat tcctaaaaat atcccatggt atggtgaaac caagaatcct    840

gtactgtttt ccaatgctgt cgaaaatcta tcaagaacgg gcgctaacgt catagaaatt    900

gattttgagc ctcttttaga gttagctcgc tgtttatacg aaggtacttg ggtggccgag    960

cgttatcaag ctattcaatc gtttttggac agtaaaccac caaaggaatc tttggaccct   1020

actgttattt caattataga aggggccaag aaatacagtg cagtagactg cttcagtttt   1080

gaatacaaaa gacaaggcat cttgcaaaaa gtgagacgac ttctcgaatc agtcgatgtc   1140

ttgtgtgtgc ccacatgtcc tttaaatcct actatgcaac aagttgcgga tgaaccagtc   1200

ctagtcaatt caagacaagg cacatggact aattttgtca acttggcaga tttggcagcc   1260

cttgctgttc ccgcagggtt ccgagacgat ggtttgccaa atggtattac tttaatcggt   1320
```

-continued

```
aaaaaattca cagattacgc actattagag ttggctaacc gctatttcca aaatatattc   1380
cccaacggtt ccagaacata cggtactttt acctcttctt cagtaaagcc agcaaacgat   1440
caattagtgg gaccagacta tgacccatct acgtccataa aattggctgt tgtcggtgca   1500
catcttaagg gtctgcctct acattggcaa ttggaaaagg tcaatgcaac atatttatgt   1560
acaacaaaaa catcaaaagc ttaccagctt tttgctttgc ccaaaaatgg accagtttta   1620
aaacctggtt tgagaagagt tcaagatagc aatggctctc aaatcgaatt agaagtgtac   1680
agtgttccaa aagaactgtt cggtgctttt atttccatgg ttcctgaacc attaggaata   1740
ggttcagtgg agttagaatc tggtgaatgg atcaaatcct ttatttgtga agaatctggt   1800
tacaaagcca aaggtacagt tgatatcaca aagtatggtg gatttagagc atattttgaa   1860
atgttgaaga aaaaagagtc ccaaaagaag aagttatttg ataccgtgtt aattgccaat   1920
agaggtgaaa ttgccgttcg tattatcaag acattaaaaa aattgggtat tagatcagtt   1980
gcagtttatt ccgaccctga taaatattct caacacgtta ctgatgcaga tgtttctgta   2040
ccccttcatg gcacaaccgc agcccaaact tatttagaca tgaataagat catagatgcc   2100
gctaagcaaa ctaatgcaca ggccattatt cctggttatg gtttcttgtc ggaaaatgcg   2160
gatttttctg atgcgtgcac cagtgctggc attacctttg ttggtccttc gggagatatt   2220
atcagaggtt tagggttaaa acattctgct agacagattg cacagaaggc tggcgttcct   2280
ctagtgccag gctctttgct tatcacatca gttgaagagg ctaagaaagt cgcagcggaa   2340
ttggaatacc cagttatggt gaagtcaact gctggtggcg gtggtattgg tttgcagaaa   2400
gtcgattctg aagaggacat cgagcatatt tttgagactg tgaaacatca aggtgaaaca   2460
tttttcggtg acgctggtgt atttctggaa cggtttatcg aaaatgccag gcatgttgaa   2520
gtccaactta tgggagatgg ttttggtaag gccattgctt tgggcgaacg tgattgttct   2580
ttacagcgtc gtaaccaaaa agttatcgaa gaaactcctg caccaaattt gccagaaaag   2640
acgaggttgg cgttaagaaa ggcagctgaa agtttgggat ctttattgaa ttacaagtgt   2700
gctggtacgg ttgaatttat ttacgatgag aaaaaggacg agttttactt tttagaagtt   2760
aatacaagat tacaagttga acatccaata acagaaatgg ttacagggtt agacttggtc   2820
gagtggatga tcaggattgc cgctaatgat gcacctgatt ttgattctac aaaggtagaa   2880
gtcaatgggg tttcaatgga ggcacgttta tatgctgaaa atccattgaa aaatttcaga   2940
ccttctccag gtttacttgt cgatgtgaaa tttcctgatt gggcaagagt ggatacttgg   3000
gttaagaaag gtactaatat ttctcccgaa tatgatccaa cattggccaa aattatcgtt   3060
catgggaaag accgtgatga tgcaatttcc aagttaaatc aagcgttaga agaaacaaaa   3120
gtttacggat gtattactaa cattgactac ctgaagtcta tcattaccag tgatttcttt   3180
gctaaagcaa aagtttctac aaacattttg aactcttatc aatatgagcc taccgccatc   3240
gaaattactt tgcccggtgc acacactagt attcaggatt accccggtag agttgggtac   3300
tggagaattg gtgttccgcc ctctggtcca acggacgcat attcgtttag attggcgaac   3360
agaattgttg gtaatgacta caggactcct gccattgaag taacgttgac tggtccatcc   3420
atcgttttcc attgtgaaac tgtcattgcc attactggtg gtaccgctct atgtacatta   3480
gacggccaag aaattcccca acacaaaccg gtcgaagtta agaggggatc tactttatcc   3540
attggcaagt tgacaagcgg ctgtagagca tacttaggta tcaggggtgg cattgatgtg   3600
cctaaatact tgggctctta ttctactttc actctaggaa atgtcggtgg atacaatgga   3660
agggtgctaa aacttggaga cgtactattc ttaccaagca atgaagaaaa taaatcagtt   3720
```

```
gagtgccttc cacagaatat tcctcaatca ttaattcctc aaatttccga aactaaggaa   3780
tggagaattg gtgtaacatg tggtccccat gggtctccag atttttttaa acctgagtcc   3840
atcgaagaat ttttcagtga gaagtggaag gttcattaca actccaatag atttggtgtc   3900
cgtttgattg gacctaaacc taagtgggca agaagtaatg gtggtgaagg tggtatgcat   3960
ccttcaaaca ctcacgatta cgtttattct ctgggtgcaa ttaatttcac gggtgatgag   4020
ccagttatta ttacttgcga tggtccttcc ttaggtggtt ttgtgtgtca agctgttgtc   4080
ccagaagcag aactgtggaa ggttggacag gttaaacccg gtgattccat tcagtttgtg   4140
ccactttctt acgaaagctc gagatcctta aaggaatctc aggatgttgc aattaaatca   4200
ttggatggta ctaagttaag gcgcttagac tctgtttcaa ttttaccatc attcgaaacg   4260
cctattcttg cacaaatgga aaaagtgaat gagctttcac caaaggttgt atacagacaa   4320
gcaggtgatc gttatgtttt ggtggaatac ggtgataatg aaatgaattt taatatttcc   4380
tatagaattg aatgcctgat ctcccttgtg aaaaagaata agactattgg tattgttgaa   4440
atgtcccaag gtgttagatc tgtattgata gaatttgatg gttacaaagt cactcaaaaa   4500
gaattgctta aagtattggt ggcatatgaa acagaaatcc agtttgatga aaattggaag   4560
ataacttcta atataataag attaccgatg gctttcgaag actcgaagac tttggcatgt   4620
gttcaaaggt atcaagaaac aattcgttcg tctgctccat ggttgccaaa taacgttgat   4680
ttcattgcca atgtaaatgg aatttcaagg aatgaagttt atgatatgtt gtattctgcc   4740
agatttatgg ttttaggttt aggtgatgtc ttcctagggt cgccttgtgc tgttccatta   4800
gatcctcgtc acagattttt gggaagcaag tacaacccaa gtagaacata tacagaaaga   4860
ggtgcagtcg gtattggcgg tatgtatatg tgcatatatg ctgctaacag tcctggtggg   4920
taccaattag tgggtagaac aataccaatt tgggacaaac tatgtctggc cgcatcttct   4980
gaggttccgt ggttgatgaa cccatttgac caagtcgaat tttacccagt ttctgaagaa   5040
gatttggata aaatgactga agattgtgat aatggtgttt ataaagtcaa tatcgaaaag   5100
agtgtttttg atcatcaaga atacttgaga tggatcaacg caaacaaaga ttccatcaca   5160
gcattccagg agggccagct tggtgaaaga gcagaggaat ttgccaaatt gattcaaaat   5220
gcaaactctg aactaaaaga aagtgtcaca gtcaaacctg acgaggaaga agacttccca   5280
gaaggtgcag aaattgtata ttctgagtat tctgggcgtt tttggaaatc catagcatct   5340
gttggagatg ttattgaagc aggtcaaggg ctactaatta ttgaagccat gaaagcggaa   5400
atgattatat ccgctcctaa atcgggtaag attatcaaga tttgccatgg caatggtgat   5460
atggttgatt ctggtgacat agtggccgtc atagagacat tggca                   5505
```

<210> SEQ ID NO 37
<211> LENGTH: 1835
<212> TYPE: PRT
<213> ORGANISM: Saccharomyces cerevisiae

<400> SEQUENCE: 37

```
Met Thr Val Ser Ser Asp Thr Thr Ala Glu Ile Ser Leu Gly Trp Ser
1               5                   10                  15

Ile Gln Asp Trp Ile Asp Phe His Lys Ser Ser Ser Ser Gln Ala Ser
            20                  25                  30

Leu Arg Leu Leu Glu Ser Leu Leu Asp Ser Gln Asn Val Ala Pro Val
        35                  40                  45

Asp Asn Ala Trp Ile Ser Leu Ile Ser Lys Glu Asn Leu Leu His Gln
```

```
    50                  55                  60

Phe Gln Ile Leu Lys Ser Arg Glu Asn Lys Glu Thr Leu Pro Leu Tyr
65                  70                  75                  80

Gly Val Pro Ile Ala Val Lys Asp Asn Ile Asp Val Arg Gly Leu Pro
                85                  90                  95

Thr Thr Ala Ala Cys Pro Ser Phe Ala Tyr Glu Pro Ser Lys Asp Ser
            100                 105                 110

Lys Val Val Glu Leu Leu Arg Asn Ala Gly Ala Ile Ile Val Gly Lys
        115                 120                 125

Thr Asn Leu Asp Gln Phe Ala Thr Gly Leu Val Gly Thr Arg Ser Pro
    130                 135                 140

Tyr Gly Lys Thr Pro Cys Ala Phe Ser Lys Glu His Val Ser Gly Gly
145                 150                 155                 160

Ser Ser Ala Gly Ser Ala Ser Val Val Ala Arg Gly Ile Val Pro Ile
                165                 170                 175

Ala Leu Gly Thr Asp Thr Ala Gly Ser Gly Arg Val Pro Ala Ala Leu
            180                 185                 190

Asn Asn Leu Ile Gly Leu Lys Pro Thr Lys Gly Val Phe Ser Cys Gln
        195                 200                 205

Gly Val Val Pro Ala Cys Lys Ser Leu Asp Cys Val Ser Ile Phe Ala
    210                 215                 220

Leu Asn Leu Ser Asp Ala Glu Arg Cys Phe Arg Ile Met Cys Gln Pro
225                 230                 235                 240

Asp Pro Asp Asn Asp Glu Tyr Ser Arg Pro Tyr Val Ser Asn Pro Leu
                245                 250                 255

Lys Lys Phe Ser Ser Asn Val Thr Ile Ala Ile Pro Lys Asn Ile Pro
            260                 265                 270

Trp Tyr Gly Glu Thr Lys Asn Pro Val Leu Phe Ser Asn Ala Val Glu
        275                 280                 285

Asn Leu Ser Arg Thr Gly Ala Asn Val Ile Glu Ile Asp Phe Glu Pro
    290                 295                 300

Leu Leu Glu Leu Ala Arg Cys Leu Tyr Glu Gly Thr Trp Val Ala Glu
305                 310                 315                 320

Arg Tyr Gln Ala Ile Gln Ser Phe Leu Asp Ser Lys Pro Pro Lys Glu
                325                 330                 335

Ser Leu Asp Pro Thr Val Ile Ser Ile Ile Glu Gly Ala Lys Lys Tyr
            340                 345                 350

Ser Ala Val Asp Cys Phe Ser Phe Glu Tyr Lys Arg Gln Gly Ile Leu
        355                 360                 365

Gln Lys Val Arg Arg Leu Leu Glu Ser Val Asp Val Leu Cys Val Pro
    370                 375                 380

Thr Cys Pro Leu Asn Pro Thr Met Gln Gln Val Ala Asp Glu Pro Val
385                 390                 395                 400

Leu Val Asn Ser Arg Gln Gly Thr Trp Thr Asn Phe Val Asn Leu Ala
                405                 410                 415

Asp Leu Ala Ala Leu Ala Val Pro Ala Gly Phe Arg Asp Asp Gly Leu
            420                 425                 430

Pro Asn Gly Ile Thr Leu Ile Gly Lys Lys Phe Thr Asp Tyr Ala Leu
        435                 440                 445

Leu Glu Leu Ala Asn Arg Tyr Phe Gln Asn Ile Phe Pro Asn Gly Ser
    450                 455                 460

Arg Thr Tyr Gly Thr Phe Thr Ser Ser Ser Val Lys Pro Ala Asn Asp
465                 470                 475                 480
```

```
Gln Leu Val Gly Pro Asp Tyr Asp Pro Ser Thr Ser Ile Lys Leu Ala
                485                 490                 495

Val Val Gly Ala His Leu Lys Gly Leu Pro Leu His Trp Gln Leu Glu
            500                 505                 510

Lys Val Asn Ala Thr Tyr Leu Cys Thr Thr Lys Thr Ser Lys Ala Tyr
        515                 520                 525

Gln Leu Phe Ala Leu Pro Lys Asn Gly Pro Val Leu Lys Pro Gly Leu
    530                 535                 540

Arg Arg Val Gln Asp Ser Asn Gly Ser Gln Ile Glu Leu Glu Val Tyr
545                 550                 555                 560

Ser Val Pro Lys Glu Leu Phe Gly Ala Phe Ile Ser Met Val Pro Glu
                565                 570                 575

Pro Leu Gly Ile Gly Ser Val Glu Leu Glu Ser Gly Glu Trp Ile Lys
            580                 585                 590

Ser Phe Ile Cys Glu Glu Ser Gly Tyr Lys Ala Lys Gly Thr Val Asp
        595                 600                 605

Ile Thr Lys Tyr Gly Gly Phe Arg Ala Tyr Phe Glu Met Leu Lys Lys
    610                 615                 620

Lys Glu Ser Gln Lys Lys Lys Leu Phe Asp Thr Val Leu Ile Ala Asn
625                 630                 635                 640

Arg Gly Glu Ile Ala Val Arg Ile Ile Lys Thr Leu Lys Lys Leu Gly
                645                 650                 655

Ile Arg Ser Val Ala Val Tyr Ser Asp Pro Asp Lys Tyr Ser Gln His
            660                 665                 670

Val Thr Asp Ala Asp Val Ser Val Pro Leu His Gly Thr Thr Ala Ala
        675                 680                 685

Gln Thr Tyr Leu Asp Met Asn Lys Ile Ile Asp Ala Ala Lys Gln Thr
    690                 695                 700

Asn Ala Gln Ala Ile Ile Pro Gly Tyr Gly Phe Leu Ser Glu Asn Ala
705                 710                 715                 720

Asp Phe Ser Asp Ala Cys Thr Ser Ala Gly Ile Thr Phe Val Gly Pro
                725                 730                 735

Ser Gly Asp Ile Ile Arg Gly Leu Gly Leu Lys His Ser Ala Arg Gln
            740                 745                 750

Ile Ala Gln Lys Ala Gly Val Pro Leu Val Pro Gly Ser Leu Leu Ile
        755                 760                 765

Thr Ser Val Glu Glu Ala Lys Lys Val Ala Ala Glu Leu Glu Tyr Pro
    770                 775                 780

Val Met Val Lys Ser Thr Ala Gly Gly Gly Gly Ile Gly Leu Gln Lys
785                 790                 795                 800

Val Asp Ser Glu Glu Asp Ile Glu His Ile Phe Glu Thr Val Lys His
                805                 810                 815

Gln Gly Glu Thr Phe Phe Gly Asp Ala Gly Val Phe Leu Glu Arg Phe
            820                 825                 830

Ile Glu Asn Ala Arg His Val Glu Val Gln Leu Met Gly Asp Gly Phe
        835                 840                 845

Gly Lys Ala Ile Ala Leu Gly Glu Arg Asp Cys Ser Leu Gln Arg Arg
    850                 855                 860

Asn Gln Lys Val Ile Glu Glu Thr Pro Ala Pro Asn Leu Pro Glu Lys
865                 870                 875                 880

Thr Arg Leu Ala Leu Arg Lys Ala Ala Glu Ser Leu Gly Ser Leu Leu
                885                 890                 895
```

```
Asn Tyr Lys Cys Ala Gly Thr Val Glu Phe Ile Tyr Asp Glu Lys Lys
            900                 905                 910

Asp Glu Phe Tyr Phe Leu Glu Val Asn Thr Arg Leu Gln Val Glu His
        915                 920                 925

Pro Ile Thr Glu Met Val Thr Gly Leu Asp Leu Val Glu Trp Met Ile
    930                 935                 940

Arg Ile Ala Ala Asn Asp Ala Pro Asp Phe Asp Ser Thr Lys Val Glu
945                 950                 955                 960

Val Asn Gly Val Ser Met Glu Ala Arg Leu Tyr Ala Glu Asn Pro Leu
                965                 970                 975

Lys Asn Phe Arg Pro Ser Pro Gly Leu Leu Val Asp Val Lys Phe Pro
            980                 985                 990

Asp Trp Ala Arg Val Asp Thr Trp  Val Lys Lys Gly Thr  Asn Ile Ser
        995                 1000                1005

Pro Glu  Tyr Asp Pro Thr Leu  Ala Lys Ile Ile Val  His Gly Lys
    1010                 1015                1020

Asp Arg  Asp Asp Ala Ile Ser  Lys Leu Asn Gln Ala  Leu Glu Glu
    1025                 1030                1035

Thr Lys  Val Tyr Gly Cys Ile  Thr Asn Ile Asp Tyr  Leu Lys Ser
    1040                 1045                1050

Ile Ile  Thr Ser Asp Phe Phe  Ala Lys Ala Lys Val  Ser Thr Asn
    1055                 1060                1065

Ile Leu  Asn Ser Tyr Gln Tyr  Glu Pro Thr Ala Ile  Glu Ile Thr
    1070                 1075                1080

Leu Pro  Gly Ala His Thr Ser  Ile Gln Asp Tyr Pro  Gly Arg Val
    1085                 1090                1095

Gly Tyr  Trp Arg Ile Gly Val  Pro Pro Ser Gly Pro  Met Asp Ala
    1100                 1105                1110

Tyr Ser  Phe Arg Leu Ala Asn  Arg Ile Val Gly Asn  Asp Tyr Arg
    1115                 1120                1125

Thr Pro  Ala Ile Glu Val Thr  Leu Thr Gly Pro Ser  Ile Val Phe
    1130                 1135                1140

His Cys  Glu Thr Val Ile Ala  Ile Thr Gly Gly Thr  Ala Leu Cys
    1145                 1150                1155

Thr Leu  Asp Gly Gln Glu Ile  Pro Gln His Lys Pro  Val Glu Val
    1160                 1165                1170

Lys Arg  Gly Ser Thr Leu Ser  Ile Gly Lys Leu Thr  Ser Gly Cys
    1175                 1180                1185

Arg Ala  Tyr Leu Gly Ile Arg  Gly Gly Ile Asp Val  Pro Lys Tyr
    1190                 1195                1200

Leu Gly  Ser Tyr Ser Thr Phe  Thr Leu Gly Asn Val  Gly Gly Tyr
    1205                 1210                1215

Asn Gly  Arg Val Leu Lys Leu  Gly Asp Val Leu Phe  Leu Pro Ser
    1220                 1225                1230

Asn Glu  Glu Asn Lys Ser Val  Glu Cys Leu Pro Gln  Asn Ile Pro
    1235                 1240                1245

Gln Ser  Leu Ile Pro Gln Ile  Ser Glu Thr Lys Glu  Trp Arg Ile
    1250                 1255                1260

Gly Val  Thr Cys Gly Pro His  Gly Ser Pro Asp Phe  Phe Lys Pro
    1265                 1270                1275

Glu Ser  Ile Glu Glu Phe Phe  Ser Glu Lys Trp Lys  Val His Tyr
    1280                 1285                1290

Asn Ser  Asn Arg Phe Gly Val  Arg Leu Ile Gly Pro  Lys Pro Lys
```

```
    1295                1300                1305

Trp Ala  Arg Ser Asn Gly Gly  Glu Gly Gly Met His  Pro Ser Asn
    1310                1315                1320

Thr His  Asp Tyr Val Tyr Ser  Leu Gly Ala Ile Asn  Phe Thr Gly
    1325                1330                1335

Asp Glu  Pro Val Ile Ile Thr  Cys Asp Gly Pro Ser  Leu Gly Gly
    1340                1345                1350

Phe Val  Cys Gln Ala Val Val  Pro Glu Ala Glu Leu  Trp Lys Val
    1355                1360                1365

Gly Gln  Val Lys Pro Gly Asp  Ser Ile Gln Phe Val  Pro Leu Ser
    1370                1375                1380

Tyr Glu  Ser Ser Arg Ser Leu  Lys Glu Ser Gln Asp  Val Ala Ile
    1385                1390                1395

Lys Ser  Leu Asp Gly Thr Lys  Leu Arg Arg Leu Asp  Ser Val Ser
    1400                1405                1410

Ile Leu  Pro Ser Phe Glu Thr  Pro Ile Leu Ala Gln  Met Glu Lys
    1415                1420                1425

Val Asn  Glu Leu Ser Pro Lys  Val Val Tyr Arg Gln  Ala Gly Asp
    1430                1435                1440

Arg Tyr  Val Leu Val Glu Tyr  Gly Asp Asn Glu Met  Asn Phe Asn
    1445                1450                1455

Ile Ser  Tyr Arg Ile Glu Cys  Leu Ile Ser Leu Val  Lys Lys Asn
    1460                1465                1470

Lys Thr  Ile Gly Ile Val Glu  Met Ser Gln Gly Val  Arg Ser Val
    1475                1480                1485

Leu Ile  Glu Phe Asp Gly Tyr  Lys Val Thr Gln Lys  Glu Leu Leu
    1490                1495                1500

Lys Val  Leu Val Ala Tyr Glu  Thr Glu Ile Gln Phe  Asp Glu Asn
    1505                1510                1515

Trp Lys  Ile Thr Ser Asn Ile  Ile Arg Leu Pro Met  Ala Phe Glu
    1520                1525                1530

Asp Ser  Lys Thr Leu Ala Cys  Val Gln Arg Tyr Gln  Glu Thr Ile
    1535                1540                1545

Arg Ser  Ser Ala Pro Trp Leu  Pro Asn Asn Val Asp  Phe Ile Ala
    1550                1555                1560

Asn Val  Asn Gly Ile Ser Arg  Asn Glu Val Tyr Asp  Met Leu Tyr
    1565                1570                1575

Ser Ala  Arg Phe Met Val Leu  Gly Leu Gly Asp Val  Phe Leu Gly
    1580                1585                1590

Ser Pro  Cys Ala Val Pro Leu  Asp Pro Arg His Arg  Phe Leu Gly
    1595                1600                1605

Ser Lys  Tyr Asn Pro Ser Arg  Thr Tyr Thr Glu Arg  Gly Ala Val
    1610                1615                1620

Gly Ile  Gly Gly Met Tyr Met  Cys Ile Tyr Ala Ala  Asn Ser Pro
    1625                1630                1635

Gly Gly  Tyr Gln Leu Val Gly  Arg Thr Ile Pro Ile  Trp Asp Lys
    1640                1645                1650

Leu Cys  Leu Ala Ala Ser Ser  Glu Val Pro Trp Leu  Met Asn Pro
    1655                1660                1665

Phe Asp  Gln Val Glu Phe Tyr  Pro Val Ser Glu Glu  Asp Leu Asp
    1670                1675                1680

Lys Met  Thr Glu Asp Cys Asp  Asn Gly Val Tyr Lys  Val Asn Ile
    1685                1690                1695
```

```
Glu Lys  Ser Val Phe Asp His  Gln Glu Tyr Leu Arg  Trp Ile Asn
    1700                 1705                 1710

Ala Asn  Lys Asp Ser Ile Thr  Ala Phe Gln Glu Gly  Gln Leu Gly
    1715                 1720                 1725

Glu Arg  Ala Glu Glu Phe Ala  Lys Leu Ile Gln Asn  Ala Asn Ser
    1730                 1735                 1740

Glu Leu  Lys Glu Ser Val Thr  Val Lys Pro Asp Glu  Glu Glu Asp
    1745                 1750                 1755

Phe Pro  Glu Gly Ala Glu Ile  Val Tyr Ser Glu Tyr  Ser Gly Arg
    1760                 1765                 1770

Phe Trp  Lys Ser Ile Ala Ser  Val Gly Asp Val Ile  Glu Ala Gly
    1775                 1780                 1785

Gln Gly  Leu Leu Ile Ile Glu  Ala Met Lys Ala Glu  Met Ile Ile
    1790                 1795                 1800

Ser Ala  Pro Lys Ser Gly Lys  Ile Ile Lys Ile Cys  His Gly Asn
    1805                 1810                 1815

Gly Asp  Met Val Asp Ser Gly  Asp Ile Val Ala Val  Ile Glu Thr
    1820                 1825                 1830

Leu Ala
    1835
```

<210> SEQ ID NO 38
<211> LENGTH: 2205
<212> TYPE: DNA
<213> ORGANISM: Saccharomyces cerevisiae

<400> SEQUENCE: 38

```
atgggagaat ttaaacctcc gctacctcaa ggcgctgggt acgctattgt attgggccta     60

ggggccgtat ttgcaggaat gatggttttg accacttatt tactgaaacg ttatcaaaag    120

gaaatcatca cagcagaaga attcaccacc gccggtagat ctgtaaaaac cggcttagtg    180

gctgcagccg tggtttctag ttggatctgg tgttctacat tgttaacgtc gtcaacaaag    240

gaatatgcag acggtatatt tggcggttat gcgtacgctg ctggcgcatg cttccaaatt    300

attgcattcg caattttggc aattaaaacc aagcaaatgg ctcccaatgc gcacacatat    360

ttagaattag tgagaacaag atatggtaag atcggccatg gttgctactt gttttatgcc    420

atcgcgacga atattttagt cacttcaatg cttttaactt caggttctgc tgtctttagt    480

gatttaaccg ggatgaacac tatcgcatca tgtttttttac tgcctgtggg tgttgttgtt    540

tatactctat ttggtgggat taaagcaact ttcttaacgg actatatgca cacatgtgtc    600

attatcatca ttgtcctcgt atttgccttt aaagtttatg cgactagtga tgttttaggc    660

tcaccgggaa aagtttatga cttagttcgt gaagccgcca agaggcatcc agtagacggt    720

aactatcagg gtgaatatat gaccatgaca tccaaatccg ctggtatttt attaattatt    780

aacctgattg gaaatttcgg caccgttttc cttgataatg gttattggaa taaagcgatt    840

tctgctagtc ccgcagcgag tttgaaagca tatgccatcg gtgggttagc atggtttgca    900

gtaccttctt tgatttcatt gaccatggga ttagcatgtc ttgcggtgga aacgtctccg    960

aacttcccca cctatcctga tccacttact tcgttccagg caaattctgg gttagtcttg   1020

ccggcagctg caattgctat catgggtaag gggggtgctg tggcatcgct gctaatgatt   1080

ttcatggccg tcacatctgc tatgtctgct gaactaattg ccgtttcatc tgttttcact   1140

tacgatatct atagagaata tattgatcct cgtgcaagcg gtaagaaatt gatttacaca   1200
```

-continued

```
tcacacgttg cttgtatctt ttttggtctt gccatgagtg gattttcggt tggtttatac   1260

tatggtggta tttctatggg ttatatctat gaaatgatgg gtataattat tagtagtgca   1320

gtattacctg tcgttttgac cttatgttcc aaagacatga atttggtggc cgctgtagtg   1380

tcgcctattt tgggcacagg actggctata atgtcatggc ttgtctgtac caaatccctt   1440

tataaagaat tgaccgtgga tactacgttc atggattatc caatgttaac aggtaacttg   1500

gtggctttgc tatcaccagc catttttatt cctattttaa cgtatgtgtt taagccacaa   1560

aattttgact gggagaaaat gaaagatatt actagagttg acgaaactgc agagttagtt   1620

caggctgacc ctgatatcca gctttacgat gctgaagcta acgataagga acaagaagaa   1680

gaaacaaatt ctctggtctc agatagtgaa aaaaacgatg ttagagtaaa taatgaaaaa   1740

ttgattgagc ctaaccttgg tgttgtaata agtaatgcca tttttcaaga agatgacaca   1800

cagttacaaa atgaattaga cgaagaacaa agagaactag cacgtggttt aaaaattgca   1860

tacttcctat gtgttttttt cgctttggca tttttggtag tttggcccat gcccatgtat   1920

ggttccaaat atatcttcag taaaaaattc tttaccggtt gggttgttgt gatgatcatc   1980

tggctttttt tcagtgcgtt tgccgtttgt atttatccac tctgggaagg taggcatggt   2040

atatatacca ctttgcgagg cctttactgg gatctatctg gtcaaactta taaattaagg   2100

gaatggcaaa attcgaaccc acaagatctg catgtagtaa caagccaaat tagtgcgaga   2160

gcacatagac aatcatcaca tttcggacaa gttgatgaaa taatt                   2205
```

<210> SEQ ID NO 39
<211> LENGTH: 735
<212> TYPE: PRT
<213> ORGANISM: Saccharomyces cerevisiae

<400> SEQUENCE: 39

```
Met Gly Glu Phe Lys Pro Pro Leu Pro Gln Gly Ala Gly Tyr Ala Ile
1               5                   10                  15

Val Leu Gly Leu Gly Ala Val Phe Ala Gly Met Met Val Leu Thr Thr
            20                  25                  30

Tyr Leu Leu Lys Arg Tyr Gln Lys Glu Ile Ile Thr Ala Glu Glu Phe
        35                  40                  45

Thr Thr Ala Gly Arg Ser Val Lys Thr Gly Leu Val Ala Ala Ala Val
    50                  55                  60

Val Ser Ser Trp Ile Trp Cys Ser Thr Leu Leu Thr Ser Ser Thr Lys
65                  70                  75                  80

Glu Tyr Ala Asp Gly Ile Phe Gly Gly Tyr Ala Tyr Ala Ala Gly Ala
                85                  90                  95

Cys Phe Gln Ile Ile Ala Phe Ala Ile Leu Ala Ile Lys Thr Lys Gln
            100                 105                 110

Met Ala Pro Asn Ala His Thr Tyr Leu Glu Leu Val Arg Thr Arg Tyr
        115                 120                 125

Gly Lys Ile Gly His Gly Cys Tyr Leu Phe Tyr Ala Ile Ala Thr Asn
    130                 135                 140

Ile Leu Val Thr Ser Met Leu Leu Thr Ser Gly Ser Ala Val Phe Ser
145                 150                 155                 160

Asp Leu Thr Gly Met Asn Thr Ile Ala Ser Cys Phe Leu Leu Pro Val
                165                 170                 175

Gly Val Val Val Tyr Thr Leu Phe Gly Gly Ile Lys Ala Thr Phe Leu
            180                 185                 190

Thr Asp Tyr Met His Thr Cys Val Ile Ile Ile Ile Val Leu Val Phe
```

```
        195                 200                 205

Ala Phe Lys Val Tyr Ala Thr Ser Asp Val Leu Gly Ser Pro Gly Lys
    210                 215                 220

Val Tyr Asp Leu Val Arg Glu Ala Ala Lys Arg His Pro Val Asp Gly
225                 230                 235                 240

Asn Tyr Gln Gly Glu Tyr Met Thr Met Thr Ser Lys Ser Ala Gly Ile
                245                 250                 255

Leu Leu Ile Ile Asn Leu Ile Gly Asn Phe Gly Thr Val Phe Leu Asp
            260                 265                 270

Asn Gly Tyr Trp Asn Lys Ala Ile Ser Ala Ser Pro Ala Ala Ser Leu
        275                 280                 285

Lys Ala Tyr Ala Ile Gly Gly Leu Ala Trp Phe Ala Val Pro Ser Leu
    290                 295                 300

Ile Ser Leu Thr Met Gly Leu Ala Cys Leu Ala Val Glu Thr Ser Pro
305                 310                 315                 320

Asn Phe Pro Thr Tyr Pro Asp Pro Leu Thr Ser Phe Gln Ala Asn Ser
                325                 330                 335

Gly Leu Val Leu Pro Ala Ala Ala Ile Ala Ile Met Gly Lys Gly Gly
            340                 345                 350

Ala Val Ala Ser Leu Leu Met Ile Phe Met Ala Val Thr Ser Ala Met
        355                 360                 365

Ser Ala Glu Leu Ile Ala Val Ser Ser Val Phe Thr Tyr Asp Ile Tyr
    370                 375                 380

Arg Glu Tyr Ile Asp Pro Arg Ala Ser Gly Lys Lys Leu Ile Tyr Thr
385                 390                 395                 400

Ser His Val Ala Cys Ile Phe Phe Gly Leu Ala Met Ser Gly Phe Ser
                405                 410                 415

Val Gly Leu Tyr Tyr Gly Gly Ile Ser Met Gly Tyr Ile Tyr Glu Met
            420                 425                 430

Met Gly Ile Ile Ile Ser Ser Ala Val Leu Pro Val Val Leu Thr Leu
        435                 440                 445

Cys Ser Lys Asp Met Asn Leu Val Ala Ala Val Val Ser Pro Ile Leu
    450                 455                 460

Gly Thr Gly Leu Ala Ile Met Ser Trp Leu Val Cys Thr Lys Ser Leu
465                 470                 475                 480

Tyr Lys Glu Leu Thr Val Asp Thr Thr Phe Met Asp Tyr Pro Met Leu
                485                 490                 495

Thr Gly Asn Leu Val Ala Leu Leu Ser Pro Ala Ile Phe Ile Pro Ile
            500                 505                 510

Leu Thr Tyr Val Phe Lys Pro Gln Asn Phe Asp Trp Glu Lys Met Lys
        515                 520                 525

Asp Ile Thr Arg Val Asp Glu Thr Ala Glu Leu Val Gln Ala Asp Pro
    530                 535                 540

Asp Ile Gln Leu Tyr Asp Ala Glu Ala Asn Asp Lys Glu Gln Glu Glu
545                 550                 555                 560

Glu Thr Asn Ser Leu Val Ser Asp Ser Glu Lys Asn Asp Val Arg Val
                565                 570                 575

Asn Asn Glu Lys Leu Ile Glu Pro Asn Leu Gly Val Val Ile Ser Asn
            580                 585                 590

Ala Ile Phe Gln Glu Asp Asp Thr Gln Leu Gln Asn Glu Leu Asp Glu
        595                 600                 605

Glu Gln Arg Glu Leu Ala Arg Gly Leu Lys Ile Ala Tyr Phe Leu Cys
    610                 615                 620
```

```
Val Phe Phe Ala Leu Ala Phe Leu Val Val Trp Pro Met Pro Met Tyr
625                 630                 635                 640

Gly Ser Lys Tyr Ile Phe Ser Lys Lys Phe Phe Thr Gly Trp Val Val
                645                 650                 655

Val Met Ile Ile Trp Leu Phe Phe Ser Ala Phe Ala Val Cys Ile Tyr
            660                 665                 670

Pro Leu Trp Glu Gly Arg His Gly Ile Tyr Thr Thr Leu Arg Gly Leu
        675                 680                 685

Tyr Trp Asp Leu Ser Gly Gln Thr Tyr Lys Leu Arg Glu Trp Gln Asn
    690                 695                 700

Ser Asn Pro Gln Asp Leu His Val Val Thr Ser Gln Ile Ser Ala Arg
705                 710                 715                 720

Ala His Arg Gln Ser Ser His Phe Gly Gln Val Asp Glu Ile Ile
                725                 730                 735


<210> SEQ ID NO 40
<211> LENGTH: 1134
<212> TYPE: DNA
<213> ORGANISM: Zea mays

<400> SEQUENCE: 40

atggcgagag cgctgccgct ggtgctcgcg gcgtccgtcc tgctggcggc cgccgcgctg      60

ctgctggccg cggcgccggc gccggcggcc gcaggtcgac ttcggcgcgg aggacctggc     120

gtcgagagga ggcgctgtgg gcgctgtacg agcgctggcg cggccgccac gcggtggcgc     180

gggacctggg cgacaaggcg cgccgtcttc aacgtcttca aggccaacgt gcgcctcatc     240

cacgagttca accgccggga cgagccctac aagctccgcc tcaaccgctt cggcgacatg     300

accgccgacg agttccgacg ccactacgcg ggctccaggg tcgcgcacca ccgcatgttc     360

cgcggcgaca ggcagggctc ctcggcgtcg gcgtcgttca tgtacgccga cgcgcgcgac     420

gtcccggcct ccgtcgactg gaggcagaag ggcgccgtca ccgacgtcaa ggaccagggc     480

cagtgcggta gctgctgggc gttctcgacg atcgccgccg tggagggcat caacgcgatc     540

aagaccaaga acctgacgtc gctgtcggag cagcagctgg tggactgcga caccaaggcc     600

aacgccggct gcaacggggg cctcatggac tacgcgttcc agtacatcgc caagcacggc     660

ggggtggcgg cggaggacgc gtacccgtac agagcgcgcc aggcgtcctg caagaagtcg     720

ccggccccgg tcgtcaccat cgacggctac gaggacgtgc cggccaacga cgagtcggcg     780

ctcaagaagg cggtggcgca ccagcccgtg tccgtcgcca tcgaggccag tggctcgcac     840

ttccagttct actccgaggg ggtcttctcc ggcaggtgcg ggacggagct ggaccacggc     900

gtcgcggcgg tcggctacgg ggtcaccgcg gacggcacca agtactggct ggtcaagaac     960

tcgtggggcc ccgagtgggg cgagaagggg tacatccgca tggcgcgcga cgtggccgcc    1020

aaggagggac actgcggcat cgccatggag gcatcctacc ccgtcaagac ctcgcccaac    1080

cccaaggtcc acgccgtcgt cgacgaggac ggctccagcc acgacgagct ctga          1134


<210> SEQ ID NO 41
<211> LENGTH: 376
<212> TYPE: PRT
<213> ORGANISM: Zea mays

<400> SEQUENCE: 41

Met Ala Arg Ala Leu Pro Leu Val Leu Ala Ala Ser Val Leu Leu Ala
1               5                   10                  15
```

```
Ala Ala Leu Leu Leu Leu Ala Phe Ala Pro Ala Pro Ala Ala Ala Val
            20                  25                  30

Asp Phe Gly Ala Glu Asp Leu Ala Ser Glu Glu Ala Leu Trp Ala Leu
        35                  40                  45

Tyr Glu Arg Trp Arg Gly Arg His Ala Leu Ala Arg Asp Leu Gly Asp
    50                  55                  60

Lys Ala Arg Arg Phe Asn Val Phe Lys Ala Asn Val Arg Leu Ile His
65                  70                  75                  80

Glu Phe Asn Arg Arg Asp Glu Pro Tyr Lys Leu Arg Leu Asn Arg Phe
                85                  90                  95

Gly Asp Met Thr Ala Asp Glu Phe Arg Arg His Tyr Ala Gly Ser Arg
            100                 105                 110

Val Ala His His Arg Met Phe Arg Gly Asp Arg Gln Gly Ser Ser Ala
        115                 120                 125

Ser Ala Ser Phe Met Tyr Ala Asp Ala Arg Asp Val Pro Ala Ser Val
    130                 135                 140

Asp Trp Arg Gln Lys Gly Ala Val Thr Asp Val Lys Asp Gln Gly Gln
145                 150                 155                 160

Cys Gly Ser Cys Trp Ala Phe Ser Thr Ile Ala Ala Val Glu Gly Ile
                165                 170                 175

Asn Ala Ile Lys Thr Lys Asn Leu Thr Ser Leu Ser Glu Gln Gln Leu
            180                 185                 190

Val Asp Cys Asp Thr Lys Ala Asn Ala Gly Cys Asn Gly Gly Leu Met
        195                 200                 205

Asp Tyr Ala Phe Gln Tyr Ile Ala Lys His Gly Gly Val Ala Ala Glu
    210                 215                 220

Asp Ala Tyr Pro Tyr Arg Ala Arg Gln Ala Ser Cys Lys Lys Ser Pro
225                 230                 235                 240

Ala Pro Val Val Thr Ile Asp Gly Tyr Glu Asp Val Pro Ala Asn Asp
                245                 250                 255

Glu Ser Ala Leu Lys Lys Ala Val Ala His Gln Pro Val Ser Val Ala
            260                 265                 270

Ile Glu Ala Ser Gly Ser His Phe Gln Phe Tyr Ser Glu Gly Val Phe
        275                 280                 285

Ser Gly Arg Cys Gly Thr Glu Leu Asp His Gly Val Thr Ala Val Gly
    290                 295                 300

Tyr Gly Val Thr Ala Asp Gly Thr Lys Tyr Trp Leu Val Lys Asn Ser
305                 310                 315                 320

Trp Gly Pro Glu Trp Gly Glu Lys Gly Tyr Ile Arg Met Ala Arg Asp
                325                 330                 335

Val Ala Ala Lys Glu Gly His Cys Gly Ile Ala Met Glu Ala Ser Tyr
            340                 345                 350

Pro Val Lys Thr Ser Pro Asn Pro Lys Val His Ala Val Val Asp Glu
        355                 360                 365

Asp Gly Ser Ser His Asp Glu Leu
    370                 375
```

<210> SEQ ID NO 42
<211> LENGTH: 1413
<212> TYPE: DNA
<213> ORGANISM: Zea mays

<400> SEQUENCE: 42

```
atggctgctc tgggccgtgg cctgcccctc ctcctcctgc tcctcctcct cgccgtatcg      60
```

```
ggggccgcca acgccgcggc ggcgcccggc ggcatgtcca tcatcaccta caacgaggag    120

cacggcgcgc gggggctgga gcggacggag ccggaggtgc gggccatgta cgacctctgg    180

ctcgcggagc acggccgcgc ctacaacgcg ctgggcgagg gcgagggcga gcgcgaccgc    240

cgcttcctcg tcttctggga caacctccgc ttcgtcgacg cgcacaacga gcgcgccggc    300

gcccgcggct tccgcctcgg gatgaaccag ttcgccgacc tcaccaacga cgagttccgc    360

gccgcgtacc tcggcgccat ggtccccgcc gcccgccggg gagccgtcgt gggggagagg    420

taccgccacg acggcgccgc cgaggagctg ccggagagcg tcgactggag ggagaagggc    480

gccgtcgcgc ccgtcaagaa ccagggkcaa tgcggaagtt gctgggcttt ctctgcagta    540

agctcagtgg aaagcgttaa ccagatcgtc accggtgaga tggtgacact gtctgaacag    600

gagctcgtag agtgctcgac tgacggaggg aacagcggct gcaacggcgg gctcatggac    660

gccgctttcg atttcatcat aaagaacggg ggcatcgata ccgaagatga ctacccttac    720

agagccgtgg acgggaagtg cgacatgaac aggaaaaatg ccagggttgt gagcatcgat    780

ggctttgaag acgtgcctga gaacgacgag aagtcgctgc agaaggcggt tgctcaccag    840

ccagttagcg ttgccattga ggccggaggc cgggagttcc agctctacaa atcgggtgtc    900

ttcagcggaa gctgcaccac gaaccttgac catggtgtcg tcgcggtcgg ctacggcgcc    960

gagaacggga aggactactg gatcgtccgc aactcgtggg gcccgaagtg gggcgaggct   1020

ggttacatcc gtatggagag gaacgtcaac gccagcactg ggaagtgcgg gatcgcgatg   1080

atggcgtcct acccgacgaa gaagggcgcg aaccctccca ggccgtctcc aaccccgcca   1140

acaccgccgg ctgcccctga caatgtctgc gacgagaact tctcgtgctc cgcgggcagc   1200

acctgctgct gcgcgtttgg cttcaggaac gtctgcttgg tctggggctg ctgcccggtc   1260

gagggcgcca cctgctgcaa ggatcacgcc agctgctgcc cgccgggcta ccctgtctgc   1320

aacgtcagag ctggaacttg ctcggtgagc aagaacagcc cactgagcgt caaggccttg   1380

aagcgcactc tcgccaagct gagcaccgca tga                                1413
```

<210> SEQ ID NO 43
<211> LENGTH: 470
<212> TYPE: PRT
<213> ORGANISM: Zea mays

<400> SEQUENCE: 43

```
Met Ala Ala Leu Gly Arg Gly Leu Pro Leu Leu Leu Leu Leu Leu Leu
1               5                   10                  15

Leu Ala Val Ser Gly Ala Ala Asn Ala Ala Ala Ala Pro Gly Gly Met
            20                  25                  30

Ser Ile Ile Thr Tyr Asn Glu Glu His Gly Ala Arg Gly Leu Glu Arg
        35                  40                  45

Thr Glu Pro Glu Val Arg Ala Met Tyr Asp Leu Trp Leu Ala Glu His
    50                  55                  60

Gly Arg Ala Tyr Asn Ala Leu Gly Glu Gly Glu Gly Glu Arg Asp Arg
65                  70                  75                  80

Arg Phe Leu Val Phe Trp Asp Asn Leu Arg Phe Val Asp Ala His Asn
                85                  90                  95

Glu Arg Ala Gly Ala Arg Gly Phe Arg Leu Gly Met Asn Gln Phe Ala
            100                 105                 110

Asp Leu Thr Asn Asp Glu Phe Arg Ala Ala Tyr Leu Gly Ala Met Val
        115                 120                 125

Pro Ala Ala Arg Arg Gly Ala Val Val Gly Glu Arg Tyr Arg His Asp
```

```
    130                 135                 140

Gly Ala Ala Glu Glu Leu Pro Glu Ser Val Asp Trp Arg Glu Lys Gly
145                 150                 155                 160

Ala Val Ala Pro Val Lys Asn Gln Gly Gln Cys Gly Ser Cys Trp Ala
                165                 170                 175

Phe Ser Ala Val Ser Ser Val Glu Ser Val Asn Gln Ile Val Thr Gly
            180                 185                 190

Glu Met Val Thr Leu Ser Glu Gln Glu Leu Val Glu Cys Ser Thr Asp
        195                 200                 205

Gly Gly Asn Ser Gly Cys Asn Gly Gly Leu Met Asp Ala Ala Phe Asp
    210                 215                 220

Phe Ile Ile Lys Asn Gly Gly Ile Asp Thr Glu Asp Asp Tyr Pro Tyr
225                 230                 235                 240

Arg Ala Val Asp Gly Lys Cys Asp Met Asn Arg Lys Asn Ala Arg Val
                245                 250                 255

Val Ser Ile Asp Gly Phe Glu Asp Val Pro Glu Asn Asp Glu Lys Ser
            260                 265                 270

Leu Gln Lys Ala Val Ala His Gln Pro Val Ser Val Ala Ile Glu Ala
        275                 280                 285

Gly Gly Arg Glu Phe Gln Leu Tyr Lys Ser Gly Val Phe Ser Gly Ser
    290                 295                 300

Cys Thr Thr Asn Leu Asp His Gly Val Val Ala Val Gly Tyr Gly Ala
305                 310                 315                 320

Glu Asn Gly Lys Asp Tyr Trp Ile Val Arg Asn Ser Trp Gly Pro Lys
                325                 330                 335

Trp Gly Glu Ala Gly Tyr Ile Arg Met Glu Arg Asn Val Asn Ala Ser
            340                 345                 350

Thr Gly Lys Cys Gly Ile Ala Met Met Ala Ser Tyr Pro Thr Lys Lys
        355                 360                 365

Gly Ala Asn Pro Pro Arg Pro Ser Pro Thr Pro Pro Thr Pro Pro Ala
    370                 375                 380

Ala Pro Asp Asn Val Cys Asp Glu Asn Phe Ser Cys Ser Ala Gly Ser
385                 390                 395                 400

Thr Cys Cys Cys Ala Phe Gly Phe Arg Asn Val Cys Leu Val Trp Gly
                405                 410                 415

Cys Cys Pro Val Glu Gly Ala Thr Cys Cys Lys Asp His Ala Ser Cys
            420                 425                 430

Cys Pro Pro Gly Tyr Pro Val Cys Asn Val Arg Ala Gly Thr Cys Ser
        435                 440                 445

Val Ser Lys Asn Ser Pro Leu Ser Val Lys Ala Leu Lys Arg Thr Leu
    450                 455                 460

Ala Lys Leu Ser Thr Ala
465                 470


<210> SEQ ID NO 44
<211> LENGTH: 1512
<212> TYPE: DNA
<213> ORGANISM: Zea mays

<400> SEQUENCE: 44

atggctgcct ccaccacggc ggcggcggcg ctgctgctgc tcctcctgtc gctcgccgcg      60

gcggcggaca tgtcgatcgt gtcctacggg gagcgcagck wcgaggaggc gcggcggatg     120

tacgcggagt ggatggcggc gcacggccgg acctacaacg ccgtcggcga ggaggagcgg     180
```

```
cggtaccagg tgttccggga caacctccgc tacatcgacg cgcacaacgc cgccgccgac    240

gcgggcgtcc actccttccg cctcggcctc aaccgcttcg ccgacctcac caacgacgag    300

taccgcgcca cctacctcgg cgccaggacc aggccgcaga gggagaggaa gctcggcgcc    360

aggtaccacg ccgccgacaa cgaggacctg ccggagtccg tcgactggag ggccaagggc    420

gccgtcgccg aggtcaagga ccagggcagc tgcgggagct gttgggcttt ctcaacaata    480

gcagctgtgg aaggcatcaa ccagattgtt acaggcgact tgatctcctt gtctgagcaa    540

gagcttgtcg actgtgacac ttcgtacaat caggggtgca atggaggtct gatggactat    600

gcgtttgagt tcatcatcaa caatggcgga atcgacaccg agaaggatta cccttacaaa    660

ggcacggacg gacgatgtga tgtcaacagg aaaaacgcga aggttgtcac tattgacagc    720

tacgaagatg taccagcgaa cgatgagaag agtctgcaga aggcagttgc aaaccagcct    780

gtcagtgtcg caattgaggc tgctggcaca gcatttcagc tctacagctc gggtatcttc    840

actggaagct gtggaacagc gctagaccat ggtgtcacgg ccgtcggcta cggcacagag    900

aacggcaagg actactggat cgtgaagaac tcatggggca gcagctgggg cgagtccggg    960

tacgtgagga tggagcgcaa catcaaggcg tccagcggca agtgcggtat cgcggttgag   1020

ccgtcatacc cgttgaagga gggcgctaac ccgccgaacc ctggccccag cccgccgtcc   1080

ccgaccccgg cgcccgccgt ctgcgacaac tactactcgt gccctgacag caccacctgc   1140

tgctgcatct acgagtacgg caagtactgc ttcgcctggg gctgctgccc gctcgagggc   1200

gccacctgct gcgacgatca ctacagctgc tgcccccatg actaccccat ctgcaacgtc   1260

aggcagggaa cctgcctcat gggcaaggac agcccactgt cactgtcagt gaaggctacg   1320

aagcgaaccc tggccaagcc gcactgggct ttctccggca acacagctga cggcatgaag   1380

agcagcgcat gagaaaacgt gggcaaggac agcccactgt cactgtcagt gaaggctacg   1440

aagcgaaccc tggccaagcc gcactgggct ttctccggca acacagctga cggcatgaag   1500

agcagcgcat ga                                                       1512
```

```
<210> SEQ ID NO 45
<211> LENGTH: 463
<212> TYPE: PRT
<213> ORGANISM: Zea mays
<220> FEATURE:
<221> NAME/KEY: misc_feature
<222> LOCATION: (34)..(34)
<223> OTHER INFORMATION: Xaa can be any naturally occurring amino acid

<400> SEQUENCE: 45

Met Ala Ala Ser Thr Thr Ala Ala Ala Ala Leu Leu Leu Leu Leu Leu
1               5                   10                  15

Ser Leu Ala Ala Ala Ala Asp Met Ser Ile Val Ser Tyr Gly Glu Arg
            20                  25                  30

Ser Xaa Glu Glu Ala Arg Arg Met Tyr Ala Glu Trp Met Ala Ala His
        35                  40                  45

Gly Arg Thr Tyr Asn Ala Val Gly Glu Glu Glu Arg Arg Tyr Gln Val
    50                  55                  60

Phe Arg Asp Asn Leu Arg Tyr Ile Asp Ala His Asn Ala Ala Ala Asp
65                  70                  75                  80

Ala Gly Val His Ser Phe Arg Leu Gly Leu Asn Arg Phe Ala Asp Leu
                85                  90                  95

Thr Asn Asp Glu Tyr Arg Ala Thr Tyr Leu Gly Ala Arg Thr Arg Pro
            100                 105                 110
```

```
Gln Arg Glu Arg Lys Leu Gly Ala Arg Tyr His Ala Ala Asp Asn Glu
        115                 120                 125

Asp Leu Pro Glu Ser Val Asp Trp Arg Ala Lys Gly Ala Val Ala Glu
    130                 135                 140

Val Lys Asp Gln Gly Ser Cys Gly Ser Cys Trp Ala Phe Ser Thr Ile
145                 150                 155                 160

Ala Ala Val Glu Gly Ile Asn Gln Ile Val Thr Gly Asp Leu Ile Ser
                165                 170                 175

Leu Ser Glu Gln Glu Leu Val Asp Cys Asp Thr Ser Tyr Asn Gln Gly
            180                 185                 190

Cys Asn Gly Gly Leu Met Asp Tyr Ala Phe Glu Phe Ile Ile Asn Asn
        195                 200                 205

Gly Gly Ile Asp Thr Glu Lys Asp Tyr Pro Tyr Lys Gly Thr Asp Gly
    210                 215                 220

Arg Cys Asp Val Asn Arg Lys Asn Ala Lys Val Val Thr Ile Asp Ser
225                 230                 235                 240

Tyr Glu Asp Val Pro Ala Asn Asp Glu Lys Ser Leu Gln Lys Ala Val
                245                 250                 255

Ala Asn Gln Pro Val Ser Val Ala Ile Glu Ala Ala Gly Thr Ala Phe
            260                 265                 270

Gln Leu Tyr Ser Ser Gly Ile Phe Thr Gly Ser Cys Gly Thr Ala Leu
        275                 280                 285

Asp His Gly Val Thr Ala Val Gly Tyr Gly Thr Glu Asn Gly Lys Asp
    290                 295                 300

Tyr Trp Ile Val Lys Asn Ser Trp Gly Ser Ser Trp Gly Glu Ser Gly
305                 310                 315                 320

Tyr Val Arg Met Glu Arg Asn Ile Lys Ala Ser Ser Gly Lys Cys Gly
                325                 330                 335

Ile Ala Val Glu Pro Ser Tyr Pro Leu Lys Glu Gly Ala Asn Pro Pro
            340                 345                 350

Asn Pro Gly Pro Ser Pro Pro Ser Pro Thr Pro Ala Pro Ala Val Cys
        355                 360                 365

Asp Asn Tyr Tyr Ser Cys Pro Asp Ser Thr Thr Cys Cys Cys Ile Tyr
    370                 375                 380

Glu Tyr Gly Lys Tyr Cys Phe Ala Trp Gly Cys Cys Pro Leu Glu Gly
385                 390                 395                 400

Ala Thr Cys Cys Asp Asp His Tyr Ser Cys Cys Pro His Asp Tyr Pro
                405                 410                 415

Ile Cys Asn Val Arg Gln Gly Thr Cys Leu Met Gly Lys Asp Ser Pro
            420                 425                 430

Leu Ser Leu Ser Val Lys Ala Thr Lys Arg Thr Leu Ala Lys Pro His
        435                 440                 445

Trp Ala Phe Ser Gly Asn Thr Ala Asp Gly Met Lys Ser Ser Ala
    450                 455                 460


<210> SEQ ID NO 46
<211> LENGTH: 1359
<212> TYPE: DNA
<213> ORGANISM: Neurospora crassa

<400> SEQUENCE: 46

atggatcttg acggcatccc ttctctcaac aacggaagcc ttcgccattc gacaaaagca      60

agatgcagat accccaaaga tggtggatac tatgtcaatg tgaccattgg tacacccgga     120

aggaatcttt ccctacatct cgacacaggc tcaagtgata cttgggtgaa ttctcccagt     180
```

```
tcgattcttt gtcaagatga agacaaacca tgcgaatact ccggcaccta cctagccaat    240

gactcgtcta cttatgagta catcagcaat catttcgaca tcaagtatgt ggatgggtct    300

ggcgccagag ggactatgc ctccgatact ttcacaatcg gcaacaccaa actgaaccgg     360

ctgcagtttg gcattggcta ctcttcaact aacgcgcagg gactgctcgg tatagggtac    420

accctgagcg aagtgcaaac ccgtgccggg ttgccagcct ataacaacct tccggcgcaa    480

atggtcgccg acggcttgat caactccaac gcctactcca tctggctcaa tgacctcgat    540

gccctcacgg gtaccattct cttcggcggc gtcgacgccg ccaagtacga gggcgacctg    600

ctcaccctac ccgttcaaac cccagaaaag ggcacgtaca agaacctcat ggtcaccatg    660

accggcctgt ctctatctca gtcccagtcc tcctccagcg acaagggcaa cggtgatgac    720

accacccaga tctccaaaga caacctcgcc cttgccgttc tcttggacac cggctcaacc    780

ctcagttatc tccccagtga gctcgtcaaa ccgctctacg acgcgatcgg tatcgaatac    840

ataacagacc ccgacggcaa agtagatggc tacgcgccct gccatctcat gtcctcgtcg    900

caatccgtca tgttctcctt ctcctccccg cttcagattg ccgtgcccat gaacgagctc    960

atcgtcaacc ggaccttcca cggaaaactc ccacgcatgc cggacggcgt cacagacgcc   1020

tgcatctttg gcatccaaga acgtaatggc acgggagcaa acaccttggg cgacacgttc   1080

ctgcgcagcg cgtatgttgt gtttgatttg gacaacaacg agatctcgat ggcgcagacg   1140

aggtttaatg ccacggcgac ggacctgaag gagattaaga agggcaaagg tggggtgccg   1200

ggcgcgaagg cggtggaaaa tcctgtggag gccacgagcg gcctgtctgg taatgaaggg   1260

gggatatatg tgaatggggc ggcgtgtgaa ttgaatgtgg gtatgggaat ggcttggggt   1320

ttgttggttg gtgctacgat ggtggttttg gggttgtga                          1359
```

<210> SEQ ID NO 47
<211> LENGTH: 452
<212> TYPE: PRT
<213> ORGANISM: Neurospora crassa

<400> SEQUENCE: 47

```
Met Asp Leu Asp Gly Ile Pro Ser Leu Asn Asn Gly Ser Leu Arg His
1               5                   10                  15

Ser Thr Lys Ala Arg Cys Arg Tyr Pro Lys Asp Gly Gly Tyr Tyr Val
            20                  25                  30

Asn Val Thr Ile Gly Thr Pro Gly Arg Asn Leu Ser Leu His Leu Asp
        35                  40                  45

Thr Gly Ser Ser Asp Thr Trp Val Asn Ser Pro Ser Ser Ile Leu Cys
    50                  55                  60

Gln Asp Glu Asp Lys Pro Cys Glu Tyr Ser Gly Thr Tyr Leu Ala Asn
65                  70                  75                  80

Asp Ser Ser Thr Tyr Glu Tyr Ile Ser Asn His Phe Asp Ile Lys Tyr
                85                  90                  95

Val Asp Gly Ser Gly Ala Arg Gly Asp Tyr Ala Ser Asp Thr Phe Thr
            100                 105                 110

Ile Gly Asn Thr Lys Leu Asn Arg Leu Gln Phe Gly Ile Gly Tyr Ser
        115                 120                 125

Ser Thr Asn Ala Gln Gly Leu Leu Gly Ile Gly Tyr Thr Leu Ser Glu
    130                 135                 140

Val Gln Thr Arg Ala Gly Leu Pro Ala Tyr Asn Asn Leu Pro Ala Gln
145                 150                 155                 160
```

```
Met Val Ala Asp Gly Leu Ile Asn Ser Asn Ala Tyr Ser Ile Trp Leu
                165                 170                 175

Asn Asp Leu Asp Ala Leu Thr Gly Thr Ile Leu Phe Gly Gly Val Asp
            180                 185                 190

Ala Ala Lys Tyr Glu Gly Asp Leu Leu Thr Leu Pro Val Gln Thr Pro
        195                 200                 205

Glu Lys Gly Thr Tyr Lys Asn Leu Met Val Thr Met Thr Gly Leu Ser
    210                 215                 220

Leu Ser Gln Ser Gln Ser Ser Ser Ser Asp Lys Gly Asn Gly Asp Asp
225                 230                 235                 240

Thr Thr Gln Ile Ser Lys Asp Asn Leu Ala Leu Ala Val Leu Leu Asp
                245                 250                 255

Thr Gly Ser Thr Leu Ser Tyr Leu Pro Ser Glu Leu Val Lys Pro Leu
            260                 265                 270

Tyr Asp Ala Ile Gly Ile Glu Tyr Ile Thr Asp Pro Asp Gly Lys Val
        275                 280                 285

Asp Gly Tyr Ala Pro Cys His Leu Met Ser Ser Ser Gln Ser Val Met
    290                 295                 300

Phe Ser Phe Ser Ser Pro Leu Gln Ile Ala Val Pro Met Asn Glu Leu
305                 310                 315                 320

Ile Val Asn Arg Thr Phe His Gly Lys Leu Pro Arg Met Pro Asp Gly
                325                 330                 335

Val Thr Asp Ala Cys Ile Phe Gly Ile Gln Glu Arg Asn Gly Thr Gly
            340                 345                 350

Ala Asn Thr Leu Gly Asp Thr Phe Leu Arg Ser Ala Tyr Val Val Phe
        355                 360                 365

Asp Leu Asp Asn Asn Glu Ile Ser Met Ala Gln Thr Arg Phe Asn Ala
    370                 375                 380

Thr Ala Thr Asp Leu Lys Glu Ile Lys Lys Gly Lys Gly Gly Val Pro
385                 390                 395                 400

Gly Ala Lys Ala Val Glu Asn Pro Val Glu Ala Thr Ser Gly Leu Ser
                405                 410                 415

Gly Asn Glu Gly Gly Ile Tyr Val Asn Gly Ala Ala Cys Glu Leu Asn
            420                 425                 430

Val Gly Met Gly Met Ala Trp Gly Leu Leu Val Gly Ala Thr Met Val
        435                 440                 445

Val Leu Gly Leu
    450
```

<210> SEQ ID NO 48
<211> LENGTH: 1443
<212> TYPE: DNA
<213> ORGANISM: Podospora anserina

<400> SEQUENCE: 48

```
atgaagacag ccacttctct tttggttgtt gcagcctcgc ttgcgggtca gacgatagac      60

gctctctctt tgccatcgac gacgccaaca caacaacaac aacgaagaga tggaagtgga     120

ccgagggttg tggggatgga tattcagagg aggacgccca aaaacccatt acatcgagat     180

catctaagaa agagagggag cgtggaggtc gatttggaca atcaggaaac cctctacttc     240

atcaacggca caatcggcac cccaccaaaa tccctccgtc tacacctcga caccggctcg     300

tccgacctct gggtcaacac cccatcctcc tccctatgca cccagtcctc agcgccctgt     360

aaatacgccg gcacttactc ggccaacggc tcaagcacgt acgagtacat cggctcctgg     420
```

```
ttcaacatct cctacgtcga cggctccggc gcctcggggg attacgtttc cgacaccgtc     480

acctttggcg acgccacgct ggacaggttg cagtttggca taggatactc gtccaacaac     540

gcccagggca tcctcgggat agggtacccg atcaacgaag tccaagtcgg cagggcagga     600

atgagacctt acaacaacct ccccgcgcaa atggtggccg acgggctgat ccaaacaaac     660

gcttattccc tgtggctgaa cgacctcgac gctgacacgg ggaatattct gtttggcggt     720

gtcgacacgg aaaagtttgt tcccccgttg atgtccctcc cggtggaatc cgaggcgggg     780

gtgtacgccg agtttatgat cacgttgacg aaagtcgagc tcggctcggc gcaggtaggc     840

ggcgatctcg ccttggctgt gctgttggat accggcagca gcttgacgta cctccccgac     900

cggatggtgc aagatatttt cgaccttgtc gacgcgcagt acgatcctga ggctaacgcg     960

gcgtatgttc cttgctcgct tgccgacaat gagactgctg ttttgtcgtt tacgtttacg    1020

gagccgacga tcaatgtggg gatggatgag cttgtgctcg accttgtgac gagctcgggg    1080

aggaggccgg tttttagtga cgggacggag gcgtgcctgt ttgggattgc gccggcgggg    1140

gaggggacga atgtgctggg ggatacgttt ttgaggagtg cgtatgtggt ttatgacttg    1200

gagaataacg agatttcgtt ggcggcgacg aggttcaaca gtacggggac gagggttgag    1260

gagataggga agggggaggg gggggtgccg ggggcgacga aggtggagaa tccgaccaag    1320

gcgacggagg ggttggatgg gccgaatggt ttggggggga taagtgctgg gaataagagg    1380

ggtttggagg ttggggtggt gtggttggtg gcgggtatgg tgggagtttt gctggtggtc    1440

taa                                                                  1443
```

<210> SEQ ID NO 49
<211> LENGTH: 480
<212> TYPE: PRT
<213> ORGANISM: Podospora anserina

<400> SEQUENCE: 49

```
Met Lys Thr Ala Thr Ser Leu Leu Val Val Ala Ala Ser Leu Ala Gly
1               5                   10                  15

Gln Thr Ile Asp Ala Leu Ser Leu Pro Ser Thr Thr Pro Thr Gln Gln
            20                  25                  30

Gln Gln Arg Arg Asp Gly Ser Gly Pro Arg Val Val Gly Met Asp Ile
        35                  40                  45

Gln Arg Arg Thr Pro Lys Asn Pro Leu His Arg Asp His Leu Arg Lys
    50                  55                  60

Arg Gly Ser Val Glu Val Asp Leu Asp Asn Gln Glu Thr Leu Tyr Phe
65                  70                  75                  80

Ile Asn Gly Thr Ile Gly Thr Pro Pro Lys Ser Leu Arg Leu His Leu
                85                  90                  95

Asp Thr Gly Ser Ser Asp Leu Trp Val Asn Thr Pro Ser Ser Ser Leu
            100                 105                 110

Cys Thr Gln Ser Ser Ala Pro Cys Lys Tyr Ala Gly Thr Tyr Ser Ala
        115                 120                 125

Asn Gly Ser Ser Thr Tyr Glu Tyr Ile Gly Ser Trp Phe Asn Ile Ser
    130                 135                 140

Tyr Val Asp Gly Ser Gly Ala Ser Gly Asp Tyr Val Ser Asp Thr Val
145                 150                 155                 160

Thr Phe Gly Asp Ala Thr Leu Asp Arg Leu Gln Phe Gly Ile Gly Tyr
                165                 170                 175

Ser Ser Asn Asn Ala Gln Gly Ile Leu Gly Ile Gly Tyr Pro Ile Asn
            180                 185                 190
```

```
Glu Val Gln Val Gly Arg Ala Gly Met Arg Pro Tyr Asn Asn Leu Pro
        195                 200                 205

Ala Gln Met Val Ala Asp Gly Leu Ile Gln Thr Asn Ala Tyr Ser Leu
    210                 215                 220

Trp Leu Asn Asp Leu Asp Ala Asp Thr Gly Asn Ile Leu Phe Gly Gly
225                 230                 235                 240

Val Asp Thr Glu Lys Phe Val Pro Pro Leu Met Ser Leu Pro Val Glu
                245                 250                 255

Ser Glu Ala Gly Val Tyr Ala Glu Phe Met Ile Thr Leu Thr Lys Val
            260                 265                 270

Glu Leu Gly Ser Ala Gln Val Gly Gly Asp Leu Ala Leu Ala Val Leu
        275                 280                 285

Leu Asp Thr Gly Ser Ser Leu Thr Tyr Leu Pro Asp Arg Met Val Gln
    290                 295                 300

Asp Ile Phe Asp Leu Val Asp Ala Gln Tyr Asp Pro Glu Ala Asn Ala
305                 310                 315                 320

Ala Tyr Val Pro Cys Ser Leu Ala Asp Asn Glu Thr Ala Val Leu Ser
                325                 330                 335

Phe Thr Phe Thr Glu Pro Thr Ile Asn Val Gly Met Asp Glu Leu Val
            340                 345                 350

Leu Asp Leu Val Thr Ser Ser Gly Arg Arg Pro Val Phe Ser Asp Gly
        355                 360                 365

Thr Glu Ala Cys Leu Phe Gly Ile Ala Pro Ala Gly Glu Gly Thr Asn
    370                 375                 380

Val Leu Gly Asp Thr Phe Leu Arg Ser Ala Tyr Val Val Tyr Asp Leu
385                 390                 395                 400

Glu Asn Asn Glu Ile Ser Leu Ala Ala Thr Arg Phe Asn Ser Thr Gly
                405                 410                 415

Thr Arg Val Glu Glu Ile Gly Lys Gly Glu Gly Gly Val Pro Gly Ala
            420                 425                 430

Thr Lys Val Glu Asn Pro Thr Lys Ala Thr Glu Gly Leu Asp Gly Pro
        435                 440                 445

Asn Gly Leu Gly Gly Ile Ser Ala Gly Asn Lys Arg Gly Leu Glu Val
    450                 455                 460

Gly Val Val Trp Leu Val Ala Gly Met Val Gly Val Leu Leu Val Val
465                 470                 475                 480
```

<210> SEQ ID NO 50
<211> LENGTH: 1425
<212> TYPE: DNA
<213> ORGANISM: Magnaporthe oryzae

<400> SEQUENCE: 50

```
atgaggttaa tagcatcact ggccttggcg gcatcactgg cctcttcaat cacaaatgga      60

tcaacgatac cgaggagggc ctcgggcaca ccagctgcgc cgagggtaat tggcctggag     120

acggaaaggc agcacatccc gaatcccttg gagcgggaca ggttaaggag gagagccgcc     180

gtcatggcta ctctcgacaa cgagcagacg ctgtactttg tcaacgtctc catcggcacg     240

ccaccgcaga agctacgtct tcaccttgac accggcagca gtgacctgtg ggtcaacacg     300

cccgactcga aactctgttc cgtctcgtcg cagccgtgca gatttgccgg aacctttagc     360

gcaaacagct cctctacata tcaatacatc aacagtgtct tcaacatctc gtacgttgac     420

ggctcaggcg ccaatggcga ctatgtctcc gatatggtca cggtgggcaa caccaagatc     480
```

```
gaccgcctcc agttcggaat cggatacacg agcagttcgg cgcagggaat tctgggcgtc    540

ggttatgagg ccaacgaggt gcaggtcgga cgtgctcagc tcaagccgta ccgcaacctc    600

ccctcgcgca tggtcgagga gggcctgatc gcttccaacg cctacagcct ttacctcaat    660

gacctgcagt ccaacaaggg cagcatcctg tttggtggca tcgacacgga gcagtacacg    720

ggaacgctgc agaccgtccc gatccagccc aacggtggcc gcatggccga gtttctcatc    780

accttgacct ctgtctcctt gacctcggca agcattggcg gtgacaagct ggccctggcc    840

gtgctgctcg actcgggttc ctcgctcacc tacctgcccg acgacatcgt aaagaacatg    900

tacagcgccg tgggcgccca gtacgacagc aacgagggcg ccgcatacgt cccctgctcc    960

ctcgccaggg accaggccaa ctcgttgacc tttagctttt ccggcatccc catcgtcgtg   1020

cccatgaacg agctcgtctt ggacctggta acttccaacg gccgccggcc ctcgttccgc   1080

aacggcgtcc ccgcctgcct gtttggcgtc gccccggccg gcaagggcac caatgttcta   1140

ggtgacacgt tcctccgctc cgcctacgtc gtctacgacc tcgaaaacaa cgccatctcg   1200

ctcgctcaga ccagcttcaa cgctaccaag agcaacgtca aggagatcgg caagggcagc   1260

aaccctgttc ccggcgccgt tgccgtctcg cagcccgtcg ctgccacttc gggcctgtcg   1320

cagaacggcg gcaacaggtc tggctctggc gccatcgccc gggccgttcc gactctcttg   1380

ctcgtcggag gaatcttctc cggttcgttg ttgactctgt tctag                   1425


<210> SEQ ID NO 51
<211> LENGTH: 474
<212> TYPE: PRT
<213> ORGANISM: Magnaporthe oryzae

<400> SEQUENCE: 51

Met Arg Leu Ile Ala Ser Leu Ala Leu Ala Ala Ser Leu Ala Ser Ser
1               5                   10                  15

Ile Thr Asn Gly Ser Thr Ile Pro Arg Arg Ala Ser Gly Thr Pro Ala
            20                  25                  30

Ala Pro Arg Val Ile Gly Leu Glu Thr Glu Arg Gln His Ile Pro Asn
        35                  40                  45

Pro Leu Glu Arg Asp Arg Leu Arg Arg Arg Ala Ala Val Met Ala Thr
    50                  55                  60

Leu Asp Asn Glu Gln Thr Leu Tyr Phe Val Asn Val Ser Ile Gly Thr
65                  70                  75                  80

Pro Pro Gln Lys Leu Arg Leu His Leu Asp Thr Gly Ser Ser Asp Leu
                85                  90                  95

Trp Val Asn Thr Pro Asp Ser Lys Leu Cys Ser Val Ser Ser Gln Pro
            100                 105                 110

Cys Arg Phe Ala Gly Thr Phe Ser Ala Asn Ser Ser Ser Thr Tyr Gln
        115                 120                 125

Tyr Ile Asn Ser Val Phe Asn Ile Ser Tyr Val Asp Gly Ser Gly Ala
    130                 135                 140

Asn Gly Asp Tyr Val Ser Asp Met Val Thr Val Gly Asn Thr Lys Ile
145                 150                 155                 160

Asp Arg Leu Gln Phe Gly Ile Gly Tyr Thr Ser Ser Ser Ala Gln Gly
                165                 170                 175

Ile Leu Gly Val Gly Tyr Glu Ala Asn Glu Val Gln Val Gly Arg Ala
            180                 185                 190

Gln Leu Lys Pro Tyr Arg Asn Leu Pro Ser Arg Met Val Glu Glu Gly
        195                 200                 205
```

```
Leu Ile Ala Ser Asn Ala Tyr Ser Leu Tyr Leu Asn Asp Leu Gln Ser
    210                 215                 220

Asn Lys Gly Ser Ile Leu Phe Gly Gly Ile Asp Thr Glu Gln Tyr Thr
225                 230                 235                 240

Gly Thr Leu Gln Thr Val Pro Ile Gln Pro Asn Gly Gly Arg Met Ala
                245                 250                 255

Glu Phe Leu Ile Thr Leu Thr Ser Val Ser Leu Thr Ser Ala Ser Ile
            260                 265                 270

Gly Gly Asp Lys Leu Ala Leu Ala Val Leu Leu Asp Ser Gly Ser Ser
        275                 280                 285

Leu Thr Tyr Leu Pro Asp Asp Ile Val Lys Asn Met Tyr Ser Ala Val
    290                 295                 300

Gly Ala Gln Tyr Asp Ser Asn Glu Gly Ala Ala Tyr Val Pro Cys Ser
305                 310                 315                 320

Leu Ala Arg Asp Gln Ala Asn Ser Leu Thr Phe Ser Phe Ser Gly Ile
                325                 330                 335

Pro Ile Val Val Pro Met Asn Glu Leu Val Leu Asp Leu Val Thr Ser
            340                 345                 350

Asn Gly Arg Arg Pro Ser Phe Arg Asn Gly Val Pro Ala Cys Leu Phe
        355                 360                 365

Gly Val Ala Pro Ala Gly Lys Gly Thr Asn Val Leu Gly Asp Thr Phe
    370                 375                 380

Leu Arg Ser Ala Tyr Val Val Tyr Asp Leu Glu Asn Asn Ala Ile Ser
385                 390                 395                 400

Leu Ala Gln Thr Ser Phe Asn Ala Thr Lys Ser Asn Val Lys Glu Ile
                405                 410                 415

Gly Lys Gly Ser Asn Pro Val Pro Gly Ala Val Ala Val Ser Gln Pro
            420                 425                 430

Val Ala Ala Thr Ser Gly Leu Ser Gln Asn Gly Gly Asn Arg Ser Gly
        435                 440                 445

Ser Gly Ala Ile Ala Arg Ala Val Pro Thr Leu Leu Leu Val Gly Gly
    450                 455                 460

Ile Phe Ser Gly Ser Leu Leu Thr Leu Phe
465                 470
```

<210> SEQ ID NO 52
<211> LENGTH: 1806
<212> TYPE: DNA
<213> ORGANISM: Saccharomyces cerevisiae

<400> SEQUENCE: 52

```
atgagtaata cttcttcgta cgagaagaat aatccagata atctgaaaca caatggtatt      60

accatagatt ctgagtttct aactcaggag ccaataacca ttccctcaaa tggctccgct     120

gtttctattg acgaaacagg ttcagggtcc aaatggcaag actttaaaga ttctttcaaa     180

agggtaaaac ctattgaagt tgatcctaat ctttcagaag ctgaaaaagt ggctatcatc     240

actgcccaaa ctccattgaa gcaccacttg aagaatagac atttgcaaat gattgccatc     300

ggtggtgcca tcggtactgg tctgctggtt gggtcaggta ctgcactaag aacaggtggt     360

cccgcttcgc tactgattgg atgggggtct acaggtacca tgatttacgc tatggttatg     420

gctctgggtg agttggctgt tatcttccct atttcgggtg ggttcaccac gtacgctacc     480

agatttattg atgagtcctt tggttacgct aataatttca attatatgtt acaatggttg     540

gttgtgctac cattggaaat tgtctctgca tctattactg taaatttctg ggtacagat      600
```

```
ccaaagtata gagatgggtt tgttgcgttg ttttggcttg caattgttat catcaatatg    660
tttggtgtca aaggttatgg tgaagcagaa ttcgtctttt catttatcaa ggtcatcact    720
gttgttgggt tcatcatctt aggtatcatt ctaaactgtg gtggtggtcc aacaggtggt    780
tacattgggg gcaagtactg gcatgatcct ggtgcctttg ctggtgacac tccaggtgct    840
aaattcaaag gtgtttgttc tgtcttcgtc accgctgcct tttcttttgc cggttcagaa    900
ttggttggtc ttgctgccag tgaatccgta gagcctagaa agtccgttcc taaggctgct    960
aaacaagttt tctggagaat caccctattt tatattctgt cgctattaat gattggtctt   1020
ttagtcccat acaacgataa aagtttgatt ggtgcctcct ctgtggatgc tgctgcttca   1080
cccttcgtca ttgccattaa gactcacggt atcaagggtt tgccaagtgt tgtcaacgtc   1140
gttatcttga ttgccgtgtt atctgtcggt aactctgcca tttatgcatg ttccagaaca   1200
atggttgccc tagctgaaca gagatttctg ccagaaatct tttcctacgt tgaccgtaag   1260
ggtagaccat tggtgggaat tgctgtcaca tctgcattcg gtcttattgc gtttgttgcc   1320
gcctccaaaa aggaaggtga agttttcaac tggttactag ccttgtctgg gttgtcatct   1380
ctattcacat ggggtggtat ctgtatttgt cacattcgtt tcagaaaggc attggccgcc   1440
caaggaagag gcttggatga attgtctttc aagtctccta ccggtgtttg gggttcctac   1500
tggggggttat ttatggttat tattatgttc attgcccaat tctacgttgc tgtattcccc   1560
gtgggagatt ctccaagtgc ggaaggtttc ttcgaagctt atctatcctt cccacttgtt   1620
atggttatgt acatcggaca caagatctat aagaggaatt ggaagctttt catcccagca   1680
gaaaagatgg acattgatac gggtagaaga gaagtcgatt tagatttgtt gaaacaagaa   1740
attgcagaag aaaaggcaat tatggccaca aagccaagat ggtatagaat ctggaatttc   1800
tggtgt                                                              1806
```

<210> SEQ ID NO 53
<211> LENGTH: 602
<212> TYPE: PRT
<213> ORGANISM: Saccharomyces cerevisiae

<400> SEQUENCE: 53

```
Met Ser Asn Thr Ser Ser Tyr Glu Lys Asn Asn Pro Asp Asn Leu Lys
1               5                   10                  15

His Asn Gly Ile Thr Ile Asp Ser Glu Phe Leu Thr Gln Glu Pro Ile
            20                  25                  30

Thr Ile Pro Ser Asn Gly Ser Ala Val Ser Ile Asp Glu Thr Gly Ser
        35                  40                  45

Gly Ser Lys Trp Gln Asp Phe Lys Asp Ser Phe Lys Arg Val Lys Pro
    50                  55                  60

Ile Glu Val Asp Pro Asn Leu Ser Glu Ala Glu Lys Val Ala Ile Ile
65                  70                  75                  80

Thr Ala Gln Thr Pro Leu Lys His His Leu Lys Asn Arg His Leu Gln
                85                  90                  95

Met Ile Ala Ile Gly Gly Ala Ile Gly Thr Gly Leu Leu Val Gly Ser
            100                 105                 110

Gly Thr Ala Leu Arg Thr Gly Gly Pro Ala Ser Leu Leu Ile Gly Trp
        115                 120                 125

Gly Ser Thr Gly Thr Met Ile Tyr Ala Met Val Met Ala Leu Gly Glu
    130                 135                 140

Leu Ala Val Ile Phe Pro Ile Ser Gly Gly Phe Thr Thr Tyr Ala Thr
145                 150                 155                 160
```

```
Arg Phe Ile Asp Glu Ser Phe Gly Tyr Ala Asn Asn Phe Asn Tyr Met
                165                 170                 175

Leu Gln Trp Leu Val Val Leu Pro Leu Glu Ile Val Ser Ala Ser Ile
            180                 185                 190

Thr Val Asn Phe Trp Gly Thr Asp Pro Lys Tyr Arg Asp Gly Phe Val
        195                 200                 205

Ala Leu Phe Trp Leu Ala Ile Val Ile Ile Asn Met Phe Gly Val Lys
    210                 215                 220

Gly Tyr Gly Glu Ala Glu Phe Val Phe Ser Phe Ile Lys Val Ile Thr
225                 230                 235                 240

Val Val Gly Phe Ile Ile Leu Gly Ile Ile Leu Asn Cys Gly Gly Gly
                245                 250                 255

Pro Thr Gly Gly Tyr Ile Gly Gly Lys Tyr Trp His Asp Pro Gly Ala
            260                 265                 270

Phe Ala Gly Asp Thr Pro Gly Ala Lys Phe Lys Gly Val Cys Ser Val
        275                 280                 285

Phe Val Thr Ala Ala Phe Ser Phe Ala Gly Ser Glu Leu Val Gly Leu
    290                 295                 300

Ala Ala Ser Glu Ser Val Glu Pro Arg Lys Ser Val Pro Lys Ala Ala
305                 310                 315                 320

Lys Gln Val Phe Trp Arg Ile Thr Leu Phe Tyr Ile Leu Ser Leu Leu
                325                 330                 335

Met Ile Gly Leu Leu Val Pro Tyr Asn Asp Lys Ser Leu Ile Gly Ala
            340                 345                 350

Ser Ser Val Asp Ala Ala Ala Ser Pro Phe Val Ile Ala Ile Lys Thr
        355                 360                 365

His Gly Ile Lys Gly Leu Pro Ser Val Val Asn Val Val Ile Leu Ile
    370                 375                 380

Ala Val Leu Ser Val Gly Asn Ser Ala Ile Tyr Ala Cys Ser Arg Thr
385                 390                 395                 400

Met Val Ala Leu Ala Glu Gln Arg Phe Leu Pro Glu Ile Phe Ser Tyr
                405                 410                 415

Val Asp Arg Lys Gly Arg Pro Leu Val Gly Ile Ala Val Thr Ser Ala
            420                 425                 430

Phe Gly Leu Ile Ala Phe Val Ala Ala Ser Lys Lys Glu Gly Glu Val
        435                 440                 445

Phe Asn Trp Leu Leu Ala Leu Ser Gly Leu Ser Ser Leu Phe Thr Trp
    450                 455                 460

Gly Gly Ile Cys Ile Cys His Ile Arg Phe Arg Lys Ala Leu Ala Ala
465                 470                 475                 480

Gln Gly Arg Gly Leu Asp Glu Leu Ser Phe Lys Ser Pro Thr Gly Val
                485                 490                 495

Trp Gly Ser Tyr Trp Gly Leu Phe Met Val Ile Ile Met Phe Ile Ala
            500                 505                 510

Gln Phe Tyr Val Ala Val Phe Pro Val Gly Asp Ser Pro Ser Ala Glu
        515                 520                 525

Gly Phe Phe Glu Ala Tyr Leu Ser Phe Pro Leu Val Met Val Met Tyr
    530                 535                 540

Ile Gly His Lys Ile Tyr Lys Arg Asn Trp Lys Leu Phe Ile Pro Ala
545                 550                 555                 560

Glu Lys Met Asp Ile Asp Thr Gly Arg Arg Glu Val Asp Leu Asp Leu
                565                 570                 575
```

```
Leu Lys Gln Glu Ile Ala Glu Glu Lys Ala Ile Met Ala Thr Lys Pro
            580                 585                 590

Arg Trp Tyr Arg Ile Trp Asn Phe Trp Cys
        595                 600


<210> SEQ ID NO 54
<211> LENGTH: 1062
<212> TYPE: DNA
<213> ORGANISM: Saccharomyces cerevisiae

<400> SEQUENCE: 54

atgatgaata acaacggcaa ccaagtgtcg aatctctcca atgcgctccg tcaagtaaac      60

ataggaaaca ggaacagtaa tacaaccacc gatcaaagta atataaattt tgaattttca     120

acaggtgtaa ataataataa taataacaat agcagtagta ataacaataa tgttcaaaac     180

aataacagcg gccgcaatgg tagccaaaat aatgataacg agaataatat caagaatacc     240

ttagaacaac atcgacaaca acaacaggca ttttcggata tgagtcacgt ggagtattcc     300

agaattacaa aatttttca agaacaacca ctggagggat ataccctttt ctctcacagg     360

tctgcgccta atggattcaa agttgctata gtactaagtg aacttggatt tcattataac     420

acaatcttcc tagatttcaa tcttggcgaa catagggccc ccgaatttgt gtctgtgaac     480

cctaatgcaa gagttccagc tttaatcgat catggtatgg acaacttgtc tatttgggaa     540

tcaggggcga ttttattaca tttggtaaat aaatattaca aagagactgg taatccatta     600

ctctggtccg atgatttagc tgaccaatca caaatcaacg catggttgtt cttccaaacg     660

tcagggcatg cgccaatgat tggacaagct ttacatttca gatacttcca ttcacaaaag     720

atagcaagtg ctgtagaaag atatacggat gaggttagaa gagtttacgg tgtagtggag     780

atggccttgg ctgaacgtag agaagcgctg gtgatggaat tagacacgga aaatgcggct     840

gcatactcag ctggtacaac accaatgtca caaagtcgtt tctttgatta tcccgtatgg     900

cttgtaggag ataaattaac tatagcagat ttggcctttg tcccatggaa taatgtcgtg     960

gatagaattg gcattaatat caaaattgaa tttccagaag tttacaaatg gacgaagcat    1020

atgatgagaa gacccgcggt catcaaggca ttgcgtggtg aa                      1062


<210> SEQ ID NO 55
<211> LENGTH: 354
<212> TYPE: PRT
<213> ORGANISM: Saccharomyces cerevisiae

<400> SEQUENCE: 55

Met Met Asn Asn Asn Gly Asn Gln Val Ser Asn Leu Ser Asn Ala Leu
1               5                   10                  15

Arg Gln Val Asn Ile Gly Asn Arg Asn Ser Asn Thr Thr Thr Asp Gln
            20                  25                  30

Ser Asn Ile Asn Phe Glu Phe Ser Thr Gly Val Asn Asn Asn Asn Asn
        35                  40                  45

Asn Asn Ser Ser Ser Asn Asn Asn Asn Val Gln Asn Asn Asn Ser Gly
    50                  55                  60

Arg Asn Gly Ser Gln Asn Asn Asp Asn Glu Asn Asn Ile Lys Asn Thr
65                  70                  75                  80

Leu Glu Gln His Arg Gln Gln Gln Gln Ala Phe Ser Asp Met Ser His
                85                  90                  95

Val Glu Tyr Ser Arg Ile Thr Lys Phe Phe Gln Glu Gln Pro Leu Glu
            100                 105                 110
```

```
Gly Tyr Thr Leu Phe Ser His Arg Ser Ala Pro Asn Gly Phe Lys Val
        115                 120                 125

Ala Ile Val Leu Ser Glu Leu Gly Phe His Tyr Asn Thr Ile Phe Leu
    130                 135                 140

Asp Phe Asn Leu Gly Glu His Arg Ala Pro Glu Phe Val Ser Val Asn
145                 150                 155                 160

Pro Asn Ala Arg Val Pro Ala Leu Ile Asp His Gly Met Asp Asn Leu
                165                 170                 175

Ser Ile Trp Glu Ser Gly Ala Ile Leu Leu His Leu Val Asn Lys Tyr
            180                 185                 190

Tyr Lys Glu Thr Gly Asn Pro Leu Leu Trp Ser Asp Asp Leu Ala Asp
        195                 200                 205

Gln Ser Gln Ile Asn Ala Trp Leu Phe Phe Gln Thr Ser Gly His Ala
    210                 215                 220

Pro Met Ile Gly Gln Ala Leu His Phe Arg Tyr Phe His Ser Gln Lys
225                 230                 235                 240

Ile Ala Ser Ala Val Glu Arg Tyr Thr Asp Glu Val Arg Arg Val Tyr
                245                 250                 255

Gly Val Val Glu Met Ala Leu Ala Glu Arg Arg Glu Ala Leu Val Met
            260                 265                 270

Glu Leu Asp Thr Glu Asn Ala Ala Ala Tyr Ser Ala Gly Thr Thr Pro
        275                 280                 285

Met Ser Gln Ser Arg Phe Phe Asp Tyr Pro Val Trp Leu Val Gly Asp
    290                 295                 300

Lys Leu Thr Ile Ala Asp Leu Ala Phe Val Pro Trp Asn Asn Val Val
305                 310                 315                 320

Asp Arg Ile Gly Ile Asn Ile Lys Ile Glu Phe Pro Glu Val Tyr Lys
                325                 330                 335

Trp Thr Lys His Met Met Arg Arg Pro Ala Val Ile Lys Ala Leu Arg
            340                 345                 350

Gly Glu
```

<210> SEQ ID NO 56
<211> LENGTH: 282
<212> TYPE: DNA
<213> ORGANISM: Saccharomyces cerevisiae

<400> SEQUENCE: 56

```
atggaccgat ctttgcaagt atatatctgt atgtatccat atttagatgg cagcaagcaa     60

tatagatttg atgagcttat atcattttat cgtccttgtc caaaaagtct tgataacatt    120

aaaagtcact accgtcaaat ccatcatcaa atccgccgtc gaacccacca gcatcatcaa    180

atccgccgtc ggacccacca gcatcatcac cgtagtaatt gttctcgaca acgacagtgt    240

ctggtccgtc atagttgtgg tcgtcaaatg cgtgttctag ca                       282
```

<210> SEQ ID NO 57
<211> LENGTH: 94
<212> TYPE: PRT
<213> ORGANISM: Saccharomyces cerevisiae

<400> SEQUENCE: 57

```
Met Asp Arg Ser Leu Gln Val Tyr Ile Cys Met Tyr Pro Tyr Leu Asp
1               5                   10                  15

Gly Ser Lys Gln Tyr Arg Phe Asp Glu Leu Ile Ser Phe Tyr Arg Pro
            20                  25                  30
```

```
Cys Pro Lys Ser Leu Asp Asn Ile Lys Ser His Tyr Arg Gln Ile His
        35                  40                  45

His Gln Ile Arg Arg Arg Thr His Gln His His Gln Ile Arg Arg Arg
    50                  55                  60

Thr His Gln His His His Arg Ser Asn Cys Ser Arg Gln Arg Gln Cys
65                  70                  75                  80

Leu Val Arg His Ser Cys Gly Arg Gln Met Arg Val Leu Ala
                85                  90


<210> SEQ ID NO 58
<211> LENGTH: 499
<212> TYPE: DNA
<213> ORGANISM: Saccharomyces cerevisiae

<400> SEQUENCE: 58

gggcgccata accaaggtat ctatagaccg ccaatcagca aactacctcc gtacattcct     60

gttgcaccca cacatttata cacccagacc gcgacaaatt acccataagg ttgtttgtga    120

cggcgtcgta caagagaacg tgggaacttt ttaggctcac caaaaaagaa aggaaaaata    180

cgagttgctg acagaagcct caagaaaaaa aaaattcttc ttcgactatg ctggagccag    240

agatgatcga gccggtagtt aactatatat agctaaattg gttccatcac cttctttttct   300

ggtgtcgctc cttctagtgc tatttctggc ttttcctatt tttttttttc catttttctt    360

tctctctttc taatatataa attctcttgc attttctatt tttctctcta tctattctac    420

ttgtttattc ccttcaaggt tttttttaag gactacttgt ttttagaata tacggtcaac    480

gaactataat taactaaac                                                 499


<210> SEQ ID NO 59
<211> LENGTH: 449
<212> TYPE: DNA
<213> ORGANISM: Saccharomyces cerevisiae

<400> SEQUENCE: 59

ccagaaaggc aacgcaaaat tttttttcca gggaataaac tttctatgac ccactacttc     60

tcgtaggaac aatttcgggc ccctgcgtgt tcttctgagg ttcatctttt acatttgctt    120

ctgctggata attttcagag gcaacaagga aaaattagat ggcaaaaagt cgtctttcaa    180

ggaaaaatcc ccaccatcct tcgagatccc ctgtaactta ttggcaactg aaagaatgaa    240

aaggaggaaa atacaaaata tactagaact gaaaaaaaaa agtataaata gagacgatat    300

atgccaatac ttcacaatgt tcgaatccat tcttcatttg cagctattgt aaaataataa    360

aacatcaaga acaaacaagc tcaacttgtc ttttctaaga acaaagaata aacacaaaaa    420

caaaaagttt ttttaatttt aatcaaaaa                                      449


<210> SEQ ID NO 60
<211> LENGTH: 749
<212> TYPE: DNA
<213> ORGANISM: Saccharomyces cerevisiae

<400> SEQUENCE: 60

cgattttttt ctaaaccgtg gaatatttcg gatatccttt tgttgtttcc gggtgtacaa     60

tatggacttc ctcttttctg gcaaccaaac ccatacatcg ggattcctat aataccttcg    120

ttggtctccc taacatgtag gtggcggagg ggagatatac aatagaacag ataccagaca    180

agacataatg ggctaaacaa gactacacca attacactgc ctcattgatg gtggtacata    240

acgaactaat actgtagccc tagacttgat agccatcatc atatcgaagt ttcactaccc    300
```

```
tttttccatt tgccatctat tgaagtaata ataggcgcat gcaacttctt ttcttttttt    360

ttcttttctc tctcccccgt tgttgtctca ccatatccgc aatgacaaaa aaatgatgga    420

agacactaaa ggaaaaaatt aacgacaaag acagcaccaa cagatgtcgt tgttccagag    480

ctgatgaggg gtatctcgaa gcacacgaaa ctttttcctt ccttcattca cgcacactac    540

tctctaatga gcaacggtat acggccttcc ttccagttac ttgaatttga aataaaaaaa    600

gtttgctgtc ttgctatcaa gtataaatag acctgcaatt attaatcttt tgtttcctcg    660

tcattgttct cgttcccttt cttccttgtt tctttttctg cacaatattt caagctatac    720

caagcataca atcaactatc tcatataca                                       749


<210> SEQ ID NO 61
<211> LENGTH: 450
<212> TYPE: DNA
<213> ORGANISM: Saccharomyces cerevisiae

<400> SEQUENCE: 61

ctacttattc ccttcgagat tatatctagg aacccatcag gttggtggaa gattacccgt     60

tctaagactt ttcagcttcc tctattgatg ttacacctgg acaccccttt tctggcatcc    120

agtttttaat cttcagtggc atgtgagatt ctccgaaatt aattaaagca atcacacaat    180

tctctcggat gccacctcgg ttgaaactga caggtggttt gttacgcatg ctaatgcaaa    240

ggagcctata tacctttggc tcggctgctg taacagggaa tataaagggc agcataattt    300

aggagtttag tgaacttgca acatttacta ttttcccttc ttacgtaaat atttttcttt    360

ttaattctaa atcaatcttt ttcaattttt tgtttgtatt cttttcttgc ttaaatctat    420

aactacaaaa aacacataca taaactaaag                                      450


<210> SEQ ID NO 62
<211> LENGTH: 500
<212> TYPE: DNA
<213> ORGANISM: Saccharomyces cerevisiae
<220> FEATURE:
<221> NAME/KEY: misc_feature
<222> LOCATION: (368)..(368)
<223> OTHER INFORMATION: n is a, c, g, or t
<220> FEATURE:
<221> NAME/KEY: misc_feature
<222> LOCATION: (452)..(453)
<223> OTHER INFORMATION: n is a, c, g, or t

<400> SEQUENCE: 62

gttaattcaa attaattgat atagtttttt aatgagtatt gaatctgttt agaaataatg     60

gaatattatt tttatttatt tatttatatt attggtcggc tcttttcttc tgaaggtcaa    120

tgacaaaatg atatgaagga aataatgatt tctaaaatta tacaacgtaa gatattttta    180

caagagccta gctcatcttt tgtcatgcac tattttactc acgcttgaaa ttaacggcca    240

gttcactgcg gagtcatttc aaagtcatcc taatcgatct atcgtttttg atagctcatt    300

ttggagttcg cgattgtctt ctgttattca caactgtttt aatttttatt tcattctgga    360

actcttcnag ttctttgtaa agtctttcat agtagcttac tttatcctcc aacatattta    420

acttcatgtc aatttcggct cttaaatttt cnncatcatc aagttcaaca tcatctttta    480

acttgaattt attctctagc                                                 500


<210> SEQ ID NO 63
<211> LENGTH: 491
<212> TYPE: DNA
```

<213> ORGANISM: Saccharomyces cerevisiae

<400> SEQUENCE: 63

```
gcgatttaat ctctaattat tagttaaagt tttataagca tttttatgta acgaaaaata     60
aattggttca tattattact gcactgtcac ttaccatgga aagaccagac aagaagttgc    120
cgacagtctg ttgaattggc ttaagtctgg gtccgctcct ttctaaattt gaagaatttc    180
tcttaaacga tatgtatatt cttttcgttg gaaaagatgt cttccaaaaa aaaaaaaccg    240
atgaattagt ggaaccaagg aaaaaaaaga ggtatccttg attaaggaac actgtttaaa    300
cagtgtggtt tccaaaaacc tgaaactgca ttagcgtaat agaagactag acacctcgat    360
acaaataatg gttactcaat tcaaaactgc cagcgaattc gactctgcaa ttgctcaaga    420
caagctagtt gtcgtagatt tctacgccac ttggtgcggt ccatgtaaaa tgattgctcc    480
aatgattgaa a                                                         491
```

<210> SEQ ID NO 64
<211> LENGTH: 504
<212> TYPE: DNA
<213> ORGANISM: Saccharomyces cerevisiae

<400> SEQUENCE: 64

```
tcctgttgaa gtagcattta atcataattt ttgtcacatt ttaatcaact tgatttttct     60
ggtttaattt ttctaatttt aattttaatt tttttatcaa tgggaactga tacactaaaa    120
agaattagga gccaacaaga ataagccgct tatttcctac tagagtttac ttaaaatttc    180
atctcgaatt gtcattctaa tattttatcc acacacacac acaccttaaa atttttagat    240
taaatggcat caactcttag cttcacacac acacacacac cgaagctggt tgttttattt    300
gatttgatat aattggtttc tctggatggt actttttctt tcttggttat ttcctatttt    360
aaaatatgaa acgcacacaa gtcataatta ttctaataga gcacaattca caacacgcac    420
atttcaactt taatattttt ttagaaacac tttatttagt ctaattctta atttttaata    480
tatataatgc acacacacta attt                                           504
```

<210> SEQ ID NO 65
<211> LENGTH: 500
<212> TYPE: DNA
<213> ORGANISM: Saccharomyces cerevisiae

<400> SEQUENCE: 65

```
tagcgtgtta cgcacccaaa ctttttatga aagtctttgt ttataatgat gaggtttata     60
aatatatagt ggagcaaaga ttaatcacta aatcaagaag cagtaccagt atttttttta    120
tatcaagtag tgataatgga aatagcccaa atttggcttc cgtcggcaca tagcacgttt    180
gagagacatt atcaccatca agcatcgagc cgcccaaacc taactgtata agtttttttca   240
cgtttttgat ttttccttgc acacttcgat attactctca cgataaaagg gccgaagaga    300
atatttttct tgaacatcca gaattttaat tcggagaaat ttcacaagcc gccgatttaa    360
gggtcctgtg ttcttaataa tcagcctctc tcaaagcagg taagaggcag tctttctttt    420
aacaatagga gacattcgaa ctaaaacatc agccccaaaa atgcgcttga aggtcattag    480
gatttggatt tcttcctcat                                                500
```

<210> SEQ ID NO 66
<211> LENGTH: 23
<212> TYPE: DNA
<213> ORGANISM: Artificial Sequence

<220> FEATURE:
<223> OTHER INFORMATION: X14961

<400> SEQUENCE: 66
gcagttacct tttagcaccc aac 23

<210> SEQ ID NO 67
<211> LENGTH: 24
<212> TYPE: DNA
<213> ORGANISM: Artificial Sequence
<220> FEATURE:
<223> OTHER INFORMATION: X14966

<400> SEQUENCE: 67
ggtgtaggta agcagaatga ggag 24

<210> SEQ ID NO 68
<211> LENGTH: 59
<212> TYPE: DNA
<213> ORGANISM: Artificial Sequence
<220> FEATURE:
<223> OTHER INFORMATION: X15464

<400> SEQUENCE: 68
gtccatgtaa aatgattgct ccaatgattg aaagaggttt agacattggc tcttcattg 59

<210> SEQ ID NO 69
<211> LENGTH: 59
<212> TYPE: DNA
<213> ORGANISM: Artificial Sequence
<220> FEATURE:
<223> OTHER INFORMATION: X15465

<400> SEQUENCE: 69
ctaagctcaa tgaagagcca atgtctaaac ctctttcaat cattggagca atcatttta 59

<210> SEQ ID NO 70
<211> LENGTH: 60
<212> TYPE: DNA
<213> ORGANISM: Artificial Sequence
<220> FEATURE:
<223> OTHER INFORMATION: X18846

<400> SEQUENCE: 70
gtccatgtaa aatgattgct ccaatgattg aaaagcacgc agcacgctgt atttacgtat 60

<210> SEQ ID NO 71
<211> LENGTH: 59
<212> TYPE: DNA
<213> ORGANISM: Artificial Sequence
<220> FEATURE:
<223> OTHER INFORMATION: X18847

<400> SEQUENCE: 71
aattaaatac gtaaatacag cgtgctgcgt gcttttcaat cattggagca atcatttta 59

<210> SEQ ID NO 72
<211> LENGTH: 60
<212> TYPE: DNA
<213> ORGANISM: Artificial Sequence
<220> FEATURE:
<223> OTHER INFORMATION: X18858

<400> SEQUENCE: 72
agccagctta aagagttaaa aatttcatag ctactactta ttcccttcga gattatatct 60

<210> SEQ ID NO 73
<211> LENGTH: 59
<212> TYPE: DNA
<213> ORGANISM: Artificial Sequence
<220> FEATURE:
<223> OTHER INFORMATION: X18859

<400> SEQUENCE: 73
gttcctagat ataatctcga agggaataag tagtagctat gaaattttta actctttaa 59

<210> SEQ ID NO 74
<211> LENGTH: 60
<212> TYPE: DNA
<213> ORGANISM: Artificial Sequence
<220> FEATURE:
<223> OTHER INFORMATION: X18860

<400> SEQUENCE: 74
acatcatctt ttaacttgaa tttattctct agcagcacgc agcacgctgt atttacgtat 60

<210> SEQ ID NO 75
<211> LENGTH: 59
<212> TYPE: DNA
<213> ORGANISM: Artificial Sequence
<220> FEATURE:
<223> OTHER INFORMATION: X18861

<400> SEQUENCE: 75
aattaaatac gtaaatacag cgtgctgcgt gctgctagag aataaattca agttaaaag 59

<210> SEQ ID NO 76
<211> LENGTH: 30
<212> TYPE: DNA
<213> ORGANISM: Artificial Sequence
<220> FEATURE:
<223> OTHER INFORMATION: X18869

<400> SEQUENCE: 76
agatcctgtg gtagtgctgt ctgaacagaa 30

<210> SEQ ID NO 77
<211> LENGTH: 59
<212> TYPE: DNA
<213> ORGANISM: Artificial Sequence
<220> FEATURE:
<223> OTHER INFORMATION: X18955

<400> SEQUENCE: 77
ataaaattaa atacgtaaat acagcgtgct gcgtgctcga tttttttcta aaccgtgga 59

<210> SEQ ID NO 78
<211> LENGTH: 60
<212> TYPE: DNA
<213> ORGANISM: Artificial Sequence
<220> FEATURE:
<223> OTHER INFORMATION: X19513

<400> SEQUENCE: 78
acttggtgcg gtccatgtaa aatgattgct ccaatgattg aaaatgagga agaaatccaa 60

<210> SEQ ID NO 79
<211> LENGTH: 60
<212> TYPE: DNA
<213> ORGANISM: Artificial Sequence
<220> FEATURE:
<223> OTHER INFORMATION: X19514

<400> SEQUENCE: 79
tgaaggtcat taggatttgg atttcttcct cattttcaat cattggagca atcattttac 60

<210> SEQ ID NO 80
<211> LENGTH: 59
<212> TYPE: DNA
<213> ORGANISM: Artificial Sequence
<220> FEATURE:
<223> OTHER INFORMATION: X19551

<400> SEQUENCE: 80
agccagctta aagagttaaa aatttcatag ctagggcgcc ataaccaagg tatctatag 59

<210> SEQ ID NO 81
<211> LENGTH: 60
<212> TYPE: DNA
<213> ORGANISM: Artificial Sequence
<220> FEATURE:
<223> OTHER INFORMATION: X19552

<400> SEQUENCE: 81
tggcggtcta tagatacctt ggttatggcg ccctagctat gaaattttta actctttaag 60

<210> SEQ ID NO 82
<211> LENGTH: 59
<212> TYPE: DNA
<213> ORGANISM: Artificial Sequence
<220> FEATURE:
<223> OTHER INFORMATION: X19721

<400> SEQUENCE: 82
aaagaaatgt cagagccaga atttcaacaa gctaagcttt ctaactgatc tatccaaaa 59

<210> SEQ ID NO 83
<211> LENGTH: 60
<212> TYPE: DNA
<213> ORGANISM: Artificial Sequence
<220> FEATURE:
<223> OTHER INFORMATION: X19722

<400> SEQUENCE: 83
ttttcagttt tggatagatc agttagaaag cttagcttgt tgaaattctg gctctgacat 60

<210> SEQ ID NO 84
<211> LENGTH: 60
<212> TYPE: DNA
<213> ORGANISM: Artificial Sequence
<220> FEATURE:
<223> OTHER INFORMATION: X19726

<400> SEQUENCE: 84
atccgaaata ttccacggtt tagaaaaaaa tcggatgcta tgtttgacca aggtgatgta 60

<210> SEQ ID NO 85
<211> LENGTH: 60
<212> TYPE: DNA
<213> ORGANISM: Artificial Sequence
<220> FEATURE:
<223> OTHER INFORMATION: X19727

<400> SEQUENCE: 85
ttaaaataca tcaccttggt caaacatagc atccgatttt tttctaaacc gtggaatatt 60

<210> SEQ ID NO 86

<211> LENGTH: 60
<212> TYPE: DNA
<213> ORGANISM: Artificial Sequence
<220> FEATURE:
<223> OTHER INFORMATION: X19948

<400> SEQUENCE: 86
aaagaaatgt cagagccaga atttcaacaa gctgatgcta tgtttgacca aggtgatgta 60

<210> SEQ ID NO 87
<211> LENGTH: 60
<212> TYPE: DNA
<213> ORGANISM: Artificial Sequence
<220> FEATURE:
<223> OTHER INFORMATION: X19949

<400> SEQUENCE: 87
ttaaaataca tcaccttggt caaacatagc atcagcttgt tgaaattctg gctctgacat 60

<210> SEQ ID NO 88
<211> LENGTH: 60
<212> TYPE: DNA
<213> ORGANISM: Artificial Sequence
<220> FEATURE:
<223> OTHER INFORMATION: X19950

<400> SEQUENCE: 88
atccgaaata ttccacggtt tagaaaaaaa tcgagcacgc agcacgctgt atttacgtat 60

<210> SEQ ID NO 89
<211> LENGTH: 60
<212> TYPE: DNA
<213> ORGANISM: Artificial Sequence
<220> FEATURE:
<223> OTHER INFORMATION: X19967

<400> SEQUENCE: 89
tgaaggtcat taggatttgg atttcttcct cataaattag tgtgtgtgca ttatatatat 60

<210> SEQ ID NO 90
<211> LENGTH: 60
<212> TYPE: DNA
<213> ORGANISM: Artificial Sequence
<220> FEATURE:
<223> OTHER INFORMATION: X19968

<400> SEQUENCE: 90
tttttaatat atataatgca cacacactaa tttatgagga agaaatccaa atcctaatga 60

<210> SEQ ID NO 91
<211> LENGTH: 59
<212> TYPE: DNA
<213> ORGANISM: Artificial Sequence
<220> FEATURE:
<223> OTHER INFORMATION: X19969

<400> SEQUENCE: 91
aattaaatac gtaaatacag cgtgctgcgt gctccagaaa ggcaacgcaa aattttttt 59

<210> SEQ ID NO 92
<211> LENGTH: 60
<212> TYPE: DNA
<213> ORGANISM: Artificial Sequence
<220> FEATURE:
<223> OTHER INFORMATION: X19970

<400> SEQUENCE: 92
ccctggaaaa aaaattttgc gttgcctttc tggagcacgc agcacgctgt atttacgtat 60

<210> SEQ ID NO 93
<211> LENGTH: 32
<212> TYPE: DNA
<213> ORGANISM: Artificial Sequence
<220> FEATURE:
<223> OTHER INFORMATION: X20022

<400> SEQUENCE: 93
aggtagacgc tacagtcaca ggtgtcacaa ct 32

<210> SEQ ID NO 94
<211> LENGTH: 60
<212> TYPE: DNA
<213> ORGANISM: Artificial Sequence
<220> FEATURE:
<223> OTHER INFORMATION: X20023

<400> SEQUENCE: 94
ggacgaggca agctaaacag atctctagac ctattggtgt acaacttaat ttgcagctta 60

<210> SEQ ID NO 95
<211> LENGTH: 60
<212> TYPE: DNA
<213> ORGANISM: Artificial Sequence
<220> FEATURE:
<223> OTHER INFORMATION: X20024

<400> SEQUENCE: 95
ccgtttcttt tctttggact atcatgtagt ctcaggctgc tttaaaaaca agaaagaaag 60

<210> SEQ ID NO 96
<211> LENGTH: 32
<212> TYPE: DNA
<213> ORGANISM: Artificial Sequence
<220> FEATURE:
<223> OTHER INFORMATION: X20025

<400> SEQUENCE: 96
gagtgggatg cgcatatagt gcatgaacct at 32

<210> SEQ ID NO 97
<211> LENGTH: 60
<212> TYPE: DNA
<213> ORGANISM: Artificial Sequence
<220> FEATURE:
<223> OTHER INFORMATION: X20026

<400> SEQUENCE: 97
ttgttttaag ctgcaaatta agttgtacac caaaggctgc tttaaaaaca agaaagaaag 60

<210> SEQ ID NO 98
<211> LENGTH: 60
<212> TYPE: DNA
<213> ORGANISM: Artificial Sequence
<220> FEATURE:
<223> OTHER INFORMATION: X20027

<400> SEQUENCE: 98
cttcttcttt ctttcttgtt tttaaagcag cctttggtgt acaacttaat ttgcagctta 60

<210> SEQ ID NO 99
<211> LENGTH: 60
<212> TYPE: DNA

<213> ORGANISM: Artificial Sequence
<220> FEATURE:
<223> OTHER INFORMATION: X20028

<400> SEQUENCE: 99
ttgttttaag ctgcaaatta agttgtacac caataggtct agagatctgt ttagcttgcc 60

<210> SEQ ID NO 100
<211> LENGTH: 60
<212> TYPE: DNA
<213> ORGANISM: Artificial Sequence
<220> FEATURE:
<223> OTHER INFORMATION: X20029

<400> SEQUENCE: 100
cttcttcttt ctttcttgtt tttaaagcag cctgagacta catgatagtc caaagaaaag 60

<210> SEQ ID NO 101
<211> LENGTH: 59
<212> TYPE: DNA
<213> ORGANISM: Artificial Sequence
<220> FEATURE:
<223> OTHER INFORMATION: X20043

<400> SEQUENCE: 101
ataaaattaa atacgtaaat acagcgtgct gcgtgctatg aggaagaaat ccaaatcct 59

<210> SEQ ID NO 102
<211> LENGTH: 59
<212> TYPE: DNA
<213> ORGANISM: Artificial Sequence
<220> FEATURE:
<223> OTHER INFORMATION: X20044

<400> SEQUENCE: 102
tgaaggtcat taggatttgg atttcttcct catagcacgc agcacgctgt atttacgta 59

<210> SEQ ID NO 103
<211> LENGTH: 60
<212> TYPE: DNA
<213> ORGANISM: Artificial Sequence
<220> FEATURE:
<223> OTHER INFORMATION: X20282

<400> SEQUENCE: 103
agccagctta aagagttaaa aatttcatag ctaccagaaa ggcaacgcaa aatttttttt 60

<210> SEQ ID NO 104
<211> LENGTH: 60
<212> TYPE: DNA
<213> ORGANISM: Artificial Sequence
<220> FEATURE:
<223> OTHER INFORMATION: X20283

<400> SEQUENCE: 104
ccctggaaaa aaaattttgc gttgcctttc tggtagctat gaaattttta actctttaag 60

<210> SEQ ID NO 105
<211> LENGTH: 60
<212> TYPE: DNA
<213> ORGANISM: Artificial Sequence
<220> FEATURE:
<223> OTHER INFORMATION: X20284

<400> SEQUENCE: 105
tttttaatat atataatgca cacacactaa tttagcacgc agcacgctgt atttacgtat 60

<210> SEQ ID NO 106
<211> LENGTH: 60
<212> TYPE: DNA
<213> ORGANISM: Artificial Sequence
<220> FEATURE:
<223> OTHER INFORMATION: X20285

<400> SEQUENCE: 106
aattaaatac gtaaatacag cgtgctgcgt gctaaattag tgtgtgtgca ttatatatat 60

<210> SEQ ID NO 107
<211> LENGTH: 60
<212> TYPE: DNA
<213> ORGANISM: Artificial Sequence
<220> FEATURE:
<223> OTHER INFORMATION: X20286

<400> SEQUENCE: 107
agccagctta aagagttaaa aatttcatag ctatgtggta gaattcaaaa gactatgtga 60

<210> SEQ ID NO 108
<211> LENGTH: 60
<212> TYPE: DNA
<213> ORGANISM: Artificial Sequence
<220> FEATURE:
<223> OTHER INFORMATION: X20287

<400> SEQUENCE: 108
atggcatcac atagtctttt gaattctacc acatagctat gaaattttta actctttaag 60

<210> SEQ ID NO 109
<211> LENGTH: 60
<212> TYPE: DNA
<213> ORGANISM: Artificial Sequence
<220> FEATURE:
<223> OTHER INFORMATION: X20288

<400> SEQUENCE: 109
ttttaatatt gcttttcaat tactgttatt aaaagcacgc agcacgctgt atttacgtat 60

<210> SEQ ID NO 110
<211> LENGTH: 60
<212> TYPE: DNA
<213> ORGANISM: Artificial Sequence
<220> FEATURE:
<223> OTHER INFORMATION: X20289

<400> SEQUENCE: 110
aattaaatac gtaaatacag cgtgctgcgt gcttttaata acagtaattg aaaagcaata 60

<210> SEQ ID NO 111
<211> LENGTH: 32
<212> TYPE: DNA
<213> ORGANISM: Artificial Sequence
<220> FEATURE:
<223> OTHER INFORMATION: X20620

<400> SEQUENCE: 111
ggtgattgga atggttatgg ttccggaatc gc 32

<210> SEQ ID NO 112
<211> LENGTH: 60
<212> TYPE: DNA
<213> ORGANISM: Artificial Sequence
<220> FEATURE:

<223> OTHER INFORMATION: X20621

<400> SEQUENCE: 112
ggacgaggca agctaaacag atctctagac ctatatacta catagaaagc aattaaaaga 60

<210> SEQ ID NO 113
<211> LENGTH: 60
<212> TYPE: DNA
<213> ORGANISM: Artificial Sequence
<220> FEATURE:
<223> OTHER INFORMATION: X20622

<400> SEQUENCE: 113
ccgtttcttt tctttggact atcatgtagt ctcctccacc taacaaaccc gcaccaacac 60

<210> SEQ ID NO 114
<211> LENGTH: 32
<212> TYPE: DNA
<213> ORGANISM: Artificial Sequence
<220> FEATURE:
<223> OTHER INFORMATION: X20623

<400> SEQUENCE: 114
gtcatatggc ctcttaacgt ggtcctttgt gg 32

<210> SEQ ID NO 115
<211> LENGTH: 60
<212> TYPE: DNA
<213> ORGANISM: Artificial Sequence
<220> FEATURE:
<223> OTHER INFORMATION: X20630

<400> SEQUENCE: 115
tttttatctt ttaattgctt tctatgtagt atataggtct agagatctgt ttagcttgcc 60

<210> SEQ ID NO 116
<211> LENGTH: 60
<212> TYPE: DNA
<213> ORGANISM: Artificial Sequence
<220> FEATURE:
<223> OTHER INFORMATION: X20631

<400> SEQUENCE: 116
tacttggtgt tggtgcgggt ttgttaggtg gaggagacta catgatagtc caaagaaaag 60

<210> SEQ ID NO 117
<211> LENGTH: 60
<212> TYPE: DNA
<213> ORGANISM: Artificial Sequence
<220> FEATURE:
<223> OTHER INFORMATION: X20632

<400> SEQUENCE: 117
tttttatctt ttaattgctt tctatgtagt atactccacc taacaaaccc gcaccaacac 60

<210> SEQ ID NO 118
<211> LENGTH: 60
<212> TYPE: DNA
<213> ORGANISM: Artificial Sequence
<220> FEATURE:
<223> OTHER INFORMATION: X20633

<400> SEQUENCE: 118
tacttggtgt tggtgcgggt ttgttaggtg gagtatacta catagaaagc aattaaaaga 60

<210> SEQ ID NO 119
<211> LENGTH: 36
<212> TYPE: DNA
<213> ORGANISM: Artificial Sequence
<220> FEATURE:
<223> OTHER INFORMATION: X21123

<400> SEQUENCE: 119
gcgacatgtg atgagattgc atgcacctcc acagaa 36

<210> SEQ ID NO 120
<211> LENGTH: 60
<212> TYPE: DNA
<213> ORGANISM: Artificial Sequence
<220> FEATURE:
<223> OTHER INFORMATION: X21124

<400> SEQUENCE: 120
ggacgaggca agctaaacag atctctagac ctatctttat tctttttatt gttgtgaatt 60

<210> SEQ ID NO 121
<211> LENGTH: 60
<212> TYPE: DNA
<213> ORGANISM: Artificial Sequence
<220> FEATURE:
<223> OTHER INFORMATION: X21125

<400> SEQUENCE: 121
ccgtttcttt tctttggact atcatgtagt ctcgcttcaa taaaattgtt ttgtataaat 60

<210> SEQ ID NO 122
<211> LENGTH: 35
<212> TYPE: DNA
<213> ORGANISM: Artificial Sequence
<220> FEATURE:
<223> OTHER INFORMATION: X21126

<400> SEQUENCE: 122
ggcagctatc tctactatcc cgtttagtac tatcc 35

<210> SEQ ID NO 123
<211> LENGTH: 60
<212> TYPE: DNA
<213> ORGANISM: Artificial Sequence
<220> FEATURE:
<223> OTHER INFORMATION: X21127

<400> SEQUENCE: 123
atattaaatt cacaacaata aaaagaataa agataggtct agagatctgt ttagcttgcc 60

<210> SEQ ID NO 124
<211> LENGTH: 60
<212> TYPE: DNA
<213> ORGANISM: Artificial Sequence
<220> FEATURE:
<223> OTHER INFORMATION: X21128

<400> SEQUENCE: 124
gaactaattt atacaaaaca attttattga agcgagacta catgatagtc caaagaaaag 60

<210> SEQ ID NO 125
<211> LENGTH: 59
<212> TYPE: DNA
<213> ORGANISM: Artificial Sequence
<220> FEATURE:
<223> OTHER INFORMATION: X21133

<400> SEQUENCE: 125
atattaaatt cacaacaata aaaagaataa agagcttcaa taaaattgtt ttgtataaa 59

<210> SEQ ID NO 126
<211> LENGTH: 34
<212> TYPE: DNA
<213> ORGANISM: Artificial Sequence
<220> FEATURE:
<223> OTHER INFORMATION: X21135

<400> SEQUENCE: 126
gcattgattg tctatcagag catatcaagg tggt 34

<210> SEQ ID NO 127
<211> LENGTH: 60
<212> TYPE: DNA
<213> ORGANISM: Artificial Sequence
<220> FEATURE:
<223> OTHER INFORMATION: X21136

<400> SEQUENCE: 127
ggacgaggca agctaaacag atctctagac ctacggtgac tgttgctact tccctatata 60

<210> SEQ ID NO 128
<211> LENGTH: 60
<212> TYPE: DNA
<213> ORGANISM: Artificial Sequence
<220> FEATURE:
<223> OTHER INFORMATION: X21137

<400> SEQUENCE: 128
ccgtttcttt tctttggact atcatgtagt ctcccgtaag cgctattttc tttttgttcg 60

<210> SEQ ID NO 129
<211> LENGTH: 35
<212> TYPE: DNA
<213> ORGANISM: Artificial Sequence
<220> FEATURE:
<223> OTHER INFORMATION: X21138

<400> SEQUENCE: 129
ggctaggacc ccgtaaggag gaaagaatag gcaag 35

<210> SEQ ID NO 130
<211> LENGTH: 60
<212> TYPE: DNA
<213> ORGANISM: Artificial Sequence
<220> FEATURE:
<223> OTHER INFORMATION: X21139

<400> SEQUENCE: 130
tatatatata tagggaagta gcaacagtca ccgtaggtct agagatctgt ttagcttgcc 60

<210> SEQ ID NO 131
<211> LENGTH: 60
<212> TYPE: DNA
<213> ORGANISM: Artificial Sequence
<220> FEATURE:
<223> OTHER INFORMATION: X21140

<400> SEQUENCE: 131
tagttacgaa caaaaagaaa atagcgctta cgggagacta catgatagtc caaagaaaag 60

<210> SEQ ID NO 132
<211> LENGTH: 60

<212> TYPE: DNA
<213> ORGANISM: Artificial Sequence
<220> FEATURE:
<223> OTHER INFORMATION: X21147

<400> SEQUENCE: 132
tatatatata tagggaagta gcaacagtca ccgccgtaag cgctattttc tttttgttcg 60

<210> SEQ ID NO 133
<211> LENGTH: 60
<212> TYPE: DNA
<213> ORGANISM: Artificial Sequence
<220> FEATURE:
<223> OTHER INFORMATION: X21148

<400> SEQUENCE: 133
tagttacgaa caaaaagaaa atagcgctta cggcggtgac tgttgctact tccctatata 60

<210> SEQ ID NO 134
<211> LENGTH: 60
<212> TYPE: DNA
<213> ORGANISM: Artificial Sequence
<220> FEATURE:
<223> OTHER INFORMATION: X21179

<400> SEQUENCE: 134
ttgttttaag ctgcaaatta agttgtacac caagggcgcc ataaccaagg tatctataga 60

<210> SEQ ID NO 135
<211> LENGTH: 60
<212> TYPE: DNA
<213> ORGANISM: Artificial Sequence
<220> FEATURE:
<223> OTHER INFORMATION: X21180

<400> SEQUENCE: 135
tggcggtcta tagatacctt ggttatggcg cccttggtgt acaacttaat ttgcagctta 60

<210> SEQ ID NO 136
<211> LENGTH: 60
<212> TYPE: DNA
<213> ORGANISM: Artificial Sequence
<220> FEATURE:
<223> OTHER INFORMATION: X21181

<400> SEQUENCE: 136
cttcttcttt ctttcttgtt tttaaagcag cctcgatttt tttctaaacc gtggaatatt 60

<210> SEQ ID NO 137
<211> LENGTH: 60
<212> TYPE: DNA
<213> ORGANISM: Artificial Sequence
<220> FEATURE:
<223> OTHER INFORMATION: X21182

<400> SEQUENCE: 137
atccgaaata ttccacggtt tagaaaaaaa tcgaggctgc tttaaaaaca agaaagaaag 60

<210> SEQ ID NO 138
<211> LENGTH: 60
<212> TYPE: DNA
<213> ORGANISM: Artificial Sequence
<220> FEATURE:
<223> OTHER INFORMATION: X21289

<400> SEQUENCE: 138
aaagaaatgt cagagccaga atttcaacaa gctaggtcta gagatctgtt tagcttgcct 60

<210> SEQ ID NO 139
<211> LENGTH: 60
<212> TYPE: DNA
<213> ORGANISM: Artificial Sequence
<220> FEATURE:
<223> OTHER INFORMATION: X21290

<400> SEQUENCE: 139
ttaaaataca tcaccttggt caaacatagc atcgagacta catgatagtc caaagaaaag 60

<210> SEQ ID NO 140
<211> LENGTH: 60
<212> TYPE: DNA
<213> ORGANISM: Artificial Sequence
<220> FEATURE:
<223> OTHER INFORMATION: X21291

<400> SEQUENCE: 140
gggacgaggc aagctaaaca gatctctaga cctagcttgt tgaaattctg gctctgacat 60

<210> SEQ ID NO 141
<211> LENGTH: 59
<212> TYPE: DNA
<213> ORGANISM: Artificial Sequence
<220> FEATURE:
<223> OTHER INFORMATION: X21292

<400> SEQUENCE: 141
ccgtttcttt tctttggact atcatgtagt ctcgatgcta tgtttgacca aggtgatgt 59

<210> SEQ ID NO 142
<211> LENGTH: 60
<212> TYPE: DNA
<213> ORGANISM: Artificial Sequence
<220> FEATURE:
<223> OTHER INFORMATION: X21319

<400> SEQUENCE: 142
ttgttttaag ctgcaaatta agttgtacac caacgatttt tttctaaacc gtggaatatt 60

<210> SEQ ID NO 143
<211> LENGTH: 60
<212> TYPE: DNA
<213> ORGANISM: Artificial Sequence
<220> FEATURE:
<223> OTHER INFORMATION: X21320

<400> SEQUENCE: 143
atccgaaata ttccacggtt tagaaaaaaa tcgttggtgt acaacttaat ttgcagctta 60

<210> SEQ ID NO 144
<211> LENGTH: 60
<212> TYPE: DNA
<213> ORGANISM: Artificial Sequence
<220> FEATURE:
<223> OTHER INFORMATION: X21321

<400> SEQUENCE: 144
ttttcagttt tggatagatc agttagaaag cttaggctgc tttaaaaaca agaaagaaag 60

<210> SEQ ID NO 145
<211> LENGTH: 60
<212> TYPE: DNA
<213> ORGANISM: Artificial Sequence

<220> FEATURE:
<223> OTHER INFORMATION: X21322

<400> SEQUENCE: 145
cttcttcttt ctttcttgtt tttaaagcag cctaagcttt ctaactgatc tatccaaaac 60

<210> SEQ ID NO 146
<211> LENGTH: 60
<212> TYPE: DNA
<213> ORGANISM: Artificial Sequence
<220> FEATURE:
<223> OTHER INFORMATION: X21507

<400> SEQUENCE: 146
gaactaattt atacaaaaca attttattga agctctttat tctttttatt gttgtgaatt 60

<210> SEQ ID NO 147
<211> LENGTH: 60
<212> TYPE: DNA
<213> ORGANISM: Artificial Sequence
<220> FEATURE:
<223> OTHER INFORMATION: X21735

<400> SEQUENCE: 147
agccagctta aagagttaaa aatttcatag ctacgatttt tttctaaacc gtggaatatt 60

<210> SEQ ID NO 148
<211> LENGTH: 60
<212> TYPE: DNA
<213> ORGANISM: Artificial Sequence
<220> FEATURE:
<223> OTHER INFORMATION: X21736

<400> SEQUENCE: 148
atccgaaata ttccacggtt tagaaaaaaa tcgtagctat gaaattttta actctttaag 60

<210> SEQ ID NO 149
<211> LENGTH: 31
<212> TYPE: DNA
<213> ORGANISM: Artificial Sequence
<220> FEATURE:
<223> OTHER INFORMATION: X21754

<400> SEQUENCE: 149
gccaaagtgg attctcctac tcaagctttg c 31

<210> SEQ ID NO 150
<211> LENGTH: 60
<212> TYPE: DNA
<213> ORGANISM: Artificial Sequence
<220> FEATURE:
<223> OTHER INFORMATION: X23319

<400> SEQUENCE: 150
aaagaaatgt cagagccaga atttcaacaa gctcgatttt tttctaaacc gtggaatatt 60

<210> SEQ ID NO 151
<211> LENGTH: 60
<212> TYPE: DNA
<213> ORGANISM: Artificial Sequence
<220> FEATURE:
<223> OTHER INFORMATION: X23320

<400> SEQUENCE: 151
atccgaaata ttccacggtt tagaaaaaaa tcgagcttgt tgaaattctg gctctgacat 60

<210> SEQ ID NO 152
<211> LENGTH: 60
<212> TYPE: DNA
<213> ORGANISM: Artificial Sequence
<220> FEATURE:
<223> OTHER INFORMATION: X23321

<400> SEQUENCE: 152
gtccatgtaa aatgattgct ccaatgattg aaagatgcta tgtttgacca aggtgatgta 60

<210> SEQ ID NO 153
<211> LENGTH: 60
<212> TYPE: DNA
<213> ORGANISM: Artificial Sequence
<220> FEATURE:
<223> OTHER INFORMATION: X23322

<400> SEQUENCE: 153
ttaaaataca tcaccttggt caaacatagc atctttcaat cattggagca atcattttac 60

<210> SEQ ID NO 154
<211> LENGTH: 60
<212> TYPE: DNA
<213> ORGANISM: Artificial Sequence
<220> FEATURE:
<223> OTHER INFORMATION: X23408

<400> SEQUENCE: 154
ttttcagttt tggatagatc agttagaaag ctttagctat gaaattttta actctttaag 60

<210> SEQ ID NO 155
<211> LENGTH: 60
<212> TYPE: DNA
<213> ORGANISM: Artificial Sequence
<220> FEATURE:
<223> OTHER INFORMATION: X23409

<400> SEQUENCE: 155
agccagctta aagagttaaa aatttcatag ctaaagcttt ctaactgatc tatccaaaac 60

<210> SEQ ID NO 156
<211> LENGTH: 730
<212> TYPE: PRT
<213> ORGANISM: Saccharomyces cerevisiae

<400> SEQUENCE: 156

```
Met Gln Asp Asp Pro Glu Asn Ser Lys Leu Tyr Asp Leu Leu Asn Ser
1               5                   10                  15

His Leu Asp Val His Gly Arg Ser Asn Glu Glu Pro Arg Gln Thr Gly
            20                  25                  30

Asp Ser Arg Ser Gln Ser Ser Gly Asn Thr Gly Glu Asn Glu Glu Asp
        35                  40                  45

Ile Ala Phe Ala Ser Gly Leu Asn Gly Gly Thr Phe Asp Ser Met Leu
    50                  55                  60

Glu Ala Leu Pro Asp Asp Leu Tyr Phe Thr Asp Phe Val Ser Pro Phe
65                  70                  75                  80

Thr Ala Ala Ala Thr Thr Ser Val Thr Thr Lys Thr Val Lys Asp Thr
                85                  90                  95

Thr Pro Ala Thr Asn His Met Asp Asp Asp Ile Ala Met Phe Asp Ser
            100                 105                 110

Leu Ala Thr Thr Gln Pro Ile Asp Ile Ala Ala Ser Asn Gln Gln Asn
        115                 120                 125
```

```
Gly Glu Ile Ala Gln Leu Trp Asp Phe Asn Val Asp Gln Phe Asn Met
    130                 135                 140

Thr Pro Ser Asn Ser Ser Gly Ser Ala Thr Ile Ser Ala Pro Asn Ser
145                 150                 155                 160

Phe Thr Ser Asp Ile Pro Gln Tyr Asn His Gly Ser Leu Gly Asn Ser
                165                 170                 175

Val Ser Lys Ser Ser Leu Phe Pro Tyr Asn Ser Ser Thr Ser Asn Ser
            180                 185                 190

Asn Ile Asn Gln Pro Ser Ile Asn Asn Asn Ser Asn Thr Asn Ala Gln
        195                 200                 205

Ser His His Ser Phe Asn Ile Tyr Lys Leu Gln Asn Asn Asn Ser Ser
    210                 215                 220

Ser Ser Ala Met Asn Ile Thr Asn Asn Asn Asn Ser Asn Asn Ser Asn
225                 230                 235                 240

Ile Gln His Pro Phe Leu Lys Lys Ser Asp Ser Ile Gly Leu Ser Ser
                245                 250                 255

Ser Asn Thr Thr Asn Ser Val Arg Lys Asn Ser Leu Ile Lys Pro Met
            260                 265                 270

Ser Ser Thr Ser Leu Ala Asn Phe Lys Arg Ala Ala Ser Val Ser Ser
        275                 280                 285

Ser Ile Ser Asn Met Glu Pro Ser Gly Gln Asn Lys Lys Pro Leu Ile
    290                 295                 300

Gln Cys Phe Asn Cys Lys Thr Phe Lys Thr Pro Leu Trp Arg Arg Ser
305                 310                 315                 320

Pro Glu Gly Asn Thr Leu Cys Asn Ala Cys Gly Leu Phe Gln Lys Leu
                325                 330                 335

His Gly Thr Met Arg Pro Leu Ser Leu Lys Ser Asp Val Ile Lys Lys
            340                 345                 350

Arg Ile Ser Lys Lys Arg Ala Lys Gln Thr Asp Pro Asn Ile Ala Gln
        355                 360                 365

Asn Thr Pro Ser Ala Pro Ala Thr Ala Ser Thr Ser Val Thr Thr Thr
    370                 375                 380

Asn Ala Lys Pro Ile Arg Ser Arg Lys Lys Ser Leu Gln Gln Asn Ser
385                 390                 395                 400

Leu Ser Arg Val Ile Pro Glu Glu Ile Ile Arg Asp Asn Ile Gly Asn
                405                 410                 415

Thr Asn Asn Ile Leu Asn Val Asn Arg Gly Gly Tyr Asn Phe Asn Ser
            420                 425                 430

Val Pro Ser Pro Val Leu Met Asn Ser Gln Ser Tyr Asn Ser Ser Asn
        435                 440                 445

Ala Asn Phe Asn Gly Ala Ser Asn Ala Asn Leu Asn Ser Asn Asn Leu
    450                 455                 460

Met Arg His Asn Ser Asn Thr Val Thr Pro Asn Phe Arg Arg Ser Ser
465                 470                 475                 480

Arg Arg Ser Ser Thr Ser Ser Asn Thr Ser Ser Ser Ser Lys Ser Ser
                485                 490                 495

Ser Arg Ser Val Val Pro Ile Leu Pro Lys Pro Ser Pro Asn Ser Ala
            500                 505                 510

Asn Ser Gln Gln Phe Asn Met Asn Met Asn Leu Met Asn Thr Thr Asn
        515                 520                 525

Asn Val Ser Ala Gly Asn Ser Val Ala Ser Ser Pro Arg Ile Ile Ser
    530                 535                 540
```

```
Ser Ala Asn Phe Asn Ser Asn Ser Pro Leu Gln Gln Asn Leu Leu Ser
545                 550                 555                 560

Asn Ser Phe Gln Arg Gln Gly Met Asn Ile Pro Arg Arg Lys Met Ser
                565                 570                 575

Arg Asn Ala Ser Tyr Ser Ser Ser Phe Met Ala Ala Ser Leu Gln Gln
            580                 585                 590

Leu His Glu Gln Gln Gln Val Asp Val Asn Ser Asn Thr Asn Thr Asn
        595                 600                 605

Ser Asn Arg Gln Asn Trp Asn Ser Ser Asn Ser Val Ser Thr Asn Ser
    610                 615                 620

Arg Ser Ser Asn Phe Val Ser Gln Lys Pro Asn Phe Asp Ile Phe Asn
625                 630                 635                 640

Thr Pro Val Asp Ser Pro Ser Val Ser Arg Pro Ser Ser Arg Lys Ser
                645                 650                 655

His Thr Ser Leu Leu Ser Gln Gln Leu Gln Asn Ser Glu Ser Asn Ser
            660                 665                 670

Phe Ile Ser Asn His Lys Phe Asn Asn Arg Leu Ser Ser Asp Ser Thr
        675                 680                 685

Ser Pro Ile Lys Tyr Glu Ala Asp Val Ser Ala Gly Gly Lys Ile Ser
    690                 695                 700

Glu Asp Asn Ser Thr Lys Gly Ser Ser Lys Glu Ser Ser Ala Ile Ala
705                 710                 715                 720

Asp Glu Leu Asp Trp Leu Lys Phe Gly Ile
                725                 730
```

<210> SEQ ID NO 157
<211> LENGTH: 2193
<212> TYPE: DNA
<213> ORGANISM: Saccharomyces cerevisiae

<400> SEQUENCE: 157

```
atgcaagacg accccgaaaa ttcgaagctg tacgacctgc tgaatagtca tctggacgtg     60

catggtcgaa gtaatgaaga gccgagacaa actggtgaca gtaggagcca gagtagtggc    120

aacaccggtg aaaacgagga ggatatagca tttgccagtg gattaaacgg cggcacattc    180

gactcaatgc tggaggcact gcccgatgat ttatatttta cggacttcgt gtctcctttt    240

acagcagctg ccacgaccag cgtgactact aagacggtca aggacaccac accagctacc    300

aatcatatgg atgatgatat tgcgatgttt gattcacttg ccacaactca gcccatcgac    360

atagccgcat ccaaccaaca aaatggtgaa attgcacaac tttgggactt taacgtggac    420

caattcaaca tgacgcccag caactcgagc ggttcagcta ctattagtgc tcctaacagc    480

tttacttccg acataccgca atacaaccac ggttccctcg gcaacagcgt ctccaaatcc    540

tcactgttcc cgtataattc cagcacgtcc aacagcaaca tcaaccagcc atctatcaat    600

aacaactcaa atactaatgc gcagtcccac cattccttca acatctacaa actacaaaac    660

aacaactcat cttcatccgc tatgaacatt accaataata ataatagcaa caatagtaat    720

atccagcatc cttttctgaa gaagagcgat tcgataggat tatcttcatc caacacaaca    780

aattctgtaa gaaaaaactc acttatcaag ccaatgtcgt ccacgtccct ggccaatttc    840

aaaagagctg cctcagtatc ttccagtata tccaatatgg aaccatcagg acaaaataaa    900

aaacctctga tacaatgttt caattgtaaa actttcaaga caccgctttg gaggagaagc    960

ccagagggga atactctttg caatgcctgc ggtcttttcc agaaattaca tggtaccatg   1020

aggccattat ccttaaaatc ggacgttatc aaaaagagga tttcaaagaa gagagccaaa   1080
```

caaacggacc caaacattgc acaaaatact ccaagtgcac ctgcaactgc ctcaacttca 1140
gtaaccacta caaatgctaa acccatacga tcgaggaaaa aatcactaca acaaaactct 1200
ttatctagag tgatacctga agaaatcatt agagacaaca tcggtaatac taataatatc 1260
cttaatgtaa ataggggagg ctataacttc aactcagtcc cctccccggt cctcatgaac 1320
agccaatcgt ataatagtag taacgcaaat tttaatggag caagcaatgc aaatttgaat 1380
tctaataact taatgcgtca caattcgaac actgttactc ctaattttag aaggtcttca 1440
agacgaagta gtacttcatc gaacacctca agttccagta aatcttcatc cagatctgtt 1500
gttccgatat taccaaaacc ttcacctaat agcgctaatt cacagcagtt caacatgaac 1560
atgaacctaa tgaacacaac aaataatgta agtgcaggaa atagtgtcgc atcctcacca 1620
agaattatat cgtccgcaaa ctttaactca aatagtcctc tacagcagaa tctattatca 1680
aattctttcc aacgtcaagg aatgaatata ccaagaagaa agatgtcgcg caatgcatcg 1740
tactcctcat cgtttatggc tgcgtctttg caacaactgc acgaacagca acaagtggac 1800
gtgaattcca acacaaacac gaattcgaat agacagaatt ggaattcaag caatagcgtt 1860
tcaacaaatt caagatcatc aaattttgtc tctcaaaagc caaattttga tatttttaat 1920
actcctgtag attcaccgag tgtctcaaga ccttcttcaa gaaaatcaca tacctcattg 1980
ttatcacaac aattgcagaa ctcggagtcg aattcgttta tctcaaatca caaatttaac 2040
aatagattat caagtgactc tacttcacct ataaaatatg aagcagatgt gagtgcaggc 2100
ggaaagatca gtgaggataa ttccacaaaa ggatcttcta aagaaagttc agcaattgct 2160
gacgaattgg attggttaaa atttggtata tga 2193

<210> SEQ ID NO 158
<211> LENGTH: 753
<212> TYPE: DNA
<213> ORGANISM: Saccharomyces cerevisiae

<400> SEQUENCE: 158
atgcctttga ccacaaaacc tttatctttg aaaatcaacg ccgctctatt cgatgttgac 60
ggtaccatca tcatctctca accagccatt gctgctttct ggagagattt cggtaaagac 120
aagccttact tcgatgccga acacgttatt cacatctctc acggttggag aacttacgat 180
gccattgcca agttcgctcc agactttgct gatgaagaat acgttaacaa gctagaaggt 240
gaaatcccag aaaagtacgg tgaacactcc atcgaagttc caggtgctgt caagttgtgt 300
aatgctttga acgccttgcc aaaggaaaaa tgggctgtcg ccacctctgg tacccgtgac 360
atggccaaga aatggttcga cattttgaag atcaagagac cagaatactt catcaccgcc 420
aatgatgtca agcaaggtaa gcctcaccca gaaccatact taaagggtag aaacggtttg 480
ggtttcccaa ttaatgaaca agacccatcc aaatctaagg ttgttgtctt tgaagacgca 540
ccagctggta ttgctgctgg taaggctgct ggctgtaaaa tcgttggtat tgctaccact 600
ttcgatttgg acttcttgaa ggaaaagggt tgtgacatca ttgtcaagaa ccacgaatct 660
atcagagtcg gtgaatacaa cgctgaaacc gatgaagtcg aattgatctt tgatgactac 720
ttatacgcta aggatgactt gttgaaatgg taa 753

<210> SEQ ID NO 159
<211> LENGTH: 250
<212> TYPE: PRT
<213> ORGANISM: Saccharomyces cerevisiae

<400> SEQUENCE: 159

```
Met Pro Leu Thr Thr Lys Pro Leu Ser Leu Lys Ile Asn Ala Ala Leu
1               5                   10                  15

Phe Asp Val Asp Gly Thr Ile Ile Ile Ser Gln Pro Ala Ile Ala Ala
            20                  25                  30

Phe Trp Arg Asp Phe Gly Lys Asp Lys Pro Tyr Phe Asp Ala Glu His
        35                  40                  45

Val Ile His Ile Ser His Gly Trp Arg Thr Tyr Asp Ala Ile Ala Lys
    50                  55                  60

Phe Ala Pro Asp Phe Ala Asp Glu Glu Tyr Val Asn Lys Leu Glu Gly
65                  70                  75                  80

Glu Ile Pro Glu Lys Tyr Gly Glu His Ser Ile Glu Val Pro Gly Ala
                85                  90                  95

Val Lys Leu Cys Asn Ala Leu Asn Ala Leu Pro Lys Glu Lys Trp Ala
            100                 105                 110

Val Ala Thr Ser Gly Thr Arg Asp Met Ala Lys Lys Trp Phe Asp Ile
        115                 120                 125

Leu Lys Ile Lys Arg Pro Glu Tyr Phe Ile Thr Ala Asn Asp Val Lys
    130                 135                 140

Gln Gly Lys Pro His Pro Glu Pro Tyr Leu Lys Gly Arg Asn Gly Leu
145                 150                 155                 160

Gly Phe Pro Ile Asn Glu Gln Asp Pro Ser Lys Ser Lys Val Val Val
                165                 170                 175

Phe Glu Asp Ala Pro Ala Gly Ile Ala Ala Gly Lys Ala Ala Gly Cys
            180                 185                 190

Lys Ile Val Gly Ile Ala Thr Thr Phe Asp Leu Asp Phe Leu Lys Glu
        195                 200                 205

Lys Gly Cys Asp Ile Ile Val Lys Asn His Glu Ser Ile Arg Val Gly
    210                 215                 220

Glu Tyr Asn Ala Glu Thr Asp Glu Val Glu Leu Ile Phe Asp Asp Tyr
225                 230                 235                 240

Leu Tyr Ala Lys Asp Asp Leu Leu Lys Trp
                245                 250
```

<210> SEQ ID NO 160
<211> LENGTH: 753
<212> TYPE: DNA
<213> ORGANISM: Saccharomyces cerevisiae

<400> SEQUENCE: 160

```
atgggattga ctactaaacc tctatctttg aaagttaacg ccgctttgtt cgacgtcgac     60

ggtaccatta tcatctctca accagccatt gctgcattct ggagggattt cggtaaggac    120

aaaccttatt tcgatgctga acacgttatc caagtctcgc atggttggag aacgtttgat    180

gccattgcta agttcgctcc agactttgcc aatgaagagt atgttaacaa attagaagct    240

gaaattccgg tcaagtacgg tgaaaaatcc attgaagtcc caggtgcagt taagctgtgc    300

aacgctttga acgctctacc aaaagagaaa tgggctgtgg caacttccgg tacccgtgat    360

atggcacaaa aatggttcga gcatctggga atcaggagac caaagtactt cattaccgct    420

aatgatgtca aacagggtaa gcctcatcca gaaccatatc tgaagggcag gaatggctta    480

ggatatccga tcaatgagca agacccttcc aaatctaagg tagtagtatt tgaagacgct    540

ccagcaggta ttgccgccgg aaaagccgcc ggttgtaaga tcattggtat tgccactact    600

ttcgacttgg acttcctaaa ggaaaaaggc tgtgacatca ttgtcaaaaa ccacgaatcc    660
```

atcagagttg gcggctacaa tgccgaaaca gacgaagttg aattcatttt tgacgactac 720
ttatatgcta aggacgatct gttgaaatgg taa 753

<210> SEQ ID NO 161
<211> LENGTH: 250
<212> TYPE: PRT
<213> ORGANISM: Saccharomyces cerevisiae

<400> SEQUENCE: 161

Met Gly Leu Thr Thr Lys Pro Leu Ser Leu Lys Val Asn Ala Ala Leu
1 5 10 15

Phe Asp Val Asp Gly Thr Ile Ile Ile Ser Gln Pro Ala Ile Ala Ala
20 25 30

Phe Trp Arg Asp Phe Gly Lys Asp Lys Pro Tyr Phe Asp Ala Glu His
35 40 45

Val Ile Gln Val Ser His Gly Trp Arg Thr Phe Asp Ala Ile Ala Lys
50 55 60

Phe Ala Pro Asp Phe Ala Asn Glu Glu Tyr Val Asn Lys Leu Glu Ala
65 70 75 80

Glu Ile Pro Val Lys Tyr Gly Glu Lys Ser Ile Glu Val Pro Gly Ala
85 90 95

Val Lys Leu Cys Asn Ala Leu Asn Ala Leu Pro Lys Glu Lys Trp Ala
100 105 110

Val Ala Thr Ser Gly Thr Arg Asp Met Ala Gln Lys Trp Phe Glu His
115 120 125

Leu Gly Ile Arg Arg Pro Lys Tyr Phe Ile Thr Ala Asn Asp Val Lys
130 135 140

Gln Gly Lys Pro His Pro Glu Pro Tyr Leu Lys Gly Arg Asn Gly Leu
145 150 155 160

Gly Tyr Pro Ile Asn Glu Gln Asp Pro Ser Lys Ser Lys Val Val Val
165 170 175

Phe Glu Asp Ala Pro Ala Gly Ile Ala Ala Gly Lys Ala Ala Gly Cys
180 185 190

Lys Ile Ile Gly Ile Ala Thr Thr Phe Asp Leu Asp Phe Leu Lys Glu
195 200 205

Lys Gly Cys Asp Ile Ile Val Lys Asn His Glu Ser Ile Arg Val Gly
210 215 220

Gly Tyr Asn Ala Glu Thr Asp Glu Val Glu Phe Ile Phe Asp Asp Tyr
225 230 235 240

Leu Tyr Ala Lys Asp Asp Leu Leu Lys Trp
245 250

<210> SEQ ID NO 162
<211> LENGTH: 1548
<212> TYPE: DNA
<213> ORGANISM: Saccharomycopsis fibuligera

<400> SEQUENCE: 162
atgatcagat tgaccgtttt cttgaccgct gtttttgctg ctgttgcttc ttgtgttcca 60
gttgaattgg ataagagaaa caccggtcat ttccaagctt attctggtta taccgttgct 120
agatctaact tcacccaatg gattcatgaa caaccagctg tttcttggta ctacttgttg 180
caaaacatcg attacccaga aggtcaattc aaatctgcta aaccaggtgt tgttgttgct 240
tctccatcta catctgaacc agattacttc taccaatgga ctagagatac cgctattacc 300

```
ttcttgtcct tgattgctga agttgaagat cattctttct ccaacactac cttggctaag    360

gttgtcgaat attacatttc caacacctac accttgcaaa gagtttctaa tccatccggt    420

aacttcgatt ctccaaatca tgatggtttg ggtgaaccta agttcaacgt tgatgatact    480

gcttatacag cttcttgggg tagaccacaa aatgatggtc cagctttgag agcttacgct    540

atttctagat acttgaacgc tgttgctaag cacaacaacg gtaaattatt attggccggt    600

caaaacggta ttccttattc ttctgcttcc gatatctact ggaagattat taagccagac    660

ttgcaacatg tttctactca ttggtctacc tctggttttg atttgtggga agaaaatcaa    720

ggtactcatt tcttcaccgc tttggttcaa ttgaaggctt tgtcttacgg tattccattg    780

tctaagacct acaatgatcc aggtttcact tcttggttgg aaaaacaaaa ggatgccttg    840

aactcctaca ttaactcttc cggtttcgtt aactctggta aaaagcacat cgttgaatct    900

ccacaattgt catctagagg tggtttggat tctgctactt atattgctgc cttgatcacc    960

catgatatcg gtgatgatga tacttacacc ccattcaatg ttgataactc ctacgttttg   1020

aactccttgt attacctatt ggtcgacaac aagaacagat acaagatcaa cggtaactac   1080

aaagctggtg ctgctgttgg tagatatcct gaagatgttt acaacggtgt tggtacttct   1140

gaaggtaatc catggcaatt ggctactgct tatgctggtc aaacttttta caccttggcc   1200

tacaattcct tgaagaacaa gaagaacttg gtcatcgaaa agttgaacta cgacttgtac   1260

aactccttca ttgctgattt gtccaagatt gattcttcct acgcttctaa ggattctttg   1320

actttgacct acggttccga taactacaag aacgttatca agtccttgtt gcaattcggt   1380

gactcattct tgaaggtttt gttggatcac atcgatgaca acggtcaatt gactgaagaa   1440

atcaacagat acaccggttt tcaagctggt gcagtttctt tgacttggtc atctggttct   1500

ttgttgtctg ctaatagagc cagaaacaag ttgatcgaat tattgtaa                1548
```

<210> SEQ ID NO 163
<211> LENGTH: 515
<212> TYPE: PRT
<213> ORGANISM: Saccharomycopsis fibuligera

<400> SEQUENCE: 163

```
Met Ile Arg Leu Thr Val Phe Leu Thr Ala Val Phe Ala Ala Val Ala
1               5                   10                  15

Ser Cys Val Pro Val Glu Leu Asp Lys Arg Asn Thr Gly His Phe Gln
            20                  25                  30

Ala Tyr Ser Gly Tyr Thr Val Ala Arg Ser Asn Phe Thr Gln Trp Ile
        35                  40                  45

His Glu Gln Pro Ala Val Ser Trp Tyr Tyr Leu Leu Gln Asn Ile Asp
    50                  55                  60

Tyr Pro Glu Gly Gln Phe Lys Ser Ala Lys Pro Gly Val Val Val Ala
65                  70                  75                  80

Ser Pro Ser Thr Ser Glu Pro Asp Tyr Phe Tyr Gln Trp Thr Arg Asp
                85                  90                  95

Thr Ala Ile Thr Phe Leu Ser Leu Ile Ala Glu Val Glu Asp His Ser
            100                 105                 110

Phe Ser Asn Thr Thr Leu Ala Lys Val Val Glu Tyr Tyr Ile Ser Asn
        115                 120                 125

Thr Tyr Thr Leu Gln Arg Val Ser Asn Pro Ser Gly Asn Phe Asp Ser
    130                 135                 140
```

```
Pro Asn His Asp Gly Leu Gly Glu Pro Lys Phe Asn Val Asp Asp Thr
145                 150                 155                 160

Ala Tyr Thr Ala Ser Trp Gly Arg Pro Gln Asn Asp Gly Pro Ala Leu
                165                 170                 175

Arg Ala Tyr Ala Ile Ser Arg Tyr Leu Asn Ala Val Ala Lys His Asn
            180                 185                 190

Asn Gly Lys Leu Leu Leu Ala Gly Gln Asn Gly Ile Pro Tyr Ser Ser
        195                 200                 205

Ala Ser Asp Ile Tyr Trp Lys Ile Ile Lys Pro Asp Leu Gln His Val
    210                 215                 220

Ser Thr His Trp Ser Thr Ser Gly Phe Asp Leu Trp Glu Glu Asn Gln
225                 230                 235                 240

Gly Thr His Phe Phe Thr Ala Leu Val Gln Leu Lys Ala Leu Ser Tyr
                245                 250                 255

Gly Ile Pro Leu Ser Lys Thr Tyr Asn Asp Pro Gly Phe Thr Ser Trp
            260                 265                 270

Leu Glu Lys Gln Lys Asp Ala Leu Asn Ser Tyr Ile Asn Ser Ser Gly
        275                 280                 285

Phe Val Asn Ser Gly Lys Lys His Ile Val Glu Ser Pro Gln Leu Ser
    290                 295                 300

Ser Arg Gly Gly Leu Asp Ser Ala Thr Tyr Ile Ala Ala Leu Ile Thr
305                 310                 315                 320

His Asp Ile Gly Asp Asp Asp Thr Tyr Thr Pro Phe Asn Val Asp Asn
                325                 330                 335

Ser Tyr Val Leu Asn Ser Leu Tyr Tyr Leu Leu Val Asp Asn Lys Asn
            340                 345                 350

Arg Tyr Lys Ile Asn Gly Asn Tyr Lys Ala Gly Ala Ala Val Gly Arg
        355                 360                 365

Tyr Pro Glu Asp Val Tyr Asn Gly Val Gly Thr Ser Glu Gly Asn Pro
    370                 375                 380

Trp Gln Leu Ala Thr Ala Tyr Ala Gly Gln Thr Phe Tyr Thr Leu Ala
385                 390                 395                 400

Tyr Asn Ser Leu Lys Asn Lys Lys Asn Leu Val Ile Glu Lys Leu Asn
                405                 410                 415

Tyr Asp Leu Tyr Asn Ser Phe Ile Ala Asp Leu Ser Lys Ile Asp Ser
            420                 425                 430

Ser Tyr Ala Ser Lys Asp Ser Leu Thr Leu Thr Tyr Gly Ser Asp Asn
        435                 440                 445

Tyr Lys Asn Val Ile Lys Ser Leu Leu Gln Phe Gly Asp Ser Phe Leu
    450                 455                 460

Lys Val Leu Leu Asp His Ile Asp Asp Asn Gly Gln Leu Thr Glu Glu
465                 470                 475                 480

Ile Asn Arg Tyr Thr Gly Phe Gln Ala Gly Ala Val Ser Leu Thr Trp
                485                 490                 495

Ser Ser Gly Ser Leu Leu Ser Ala Asn Arg Ala Arg Asn Lys Leu Ile
            500                 505                 510

Glu Leu Leu
        515
```